United States Patent
Danaher et al.

(10) Patent No.: US 12,054,782 B2
(45) Date of Patent: Aug. 6, 2024

(54) GENE EXPRESSION ASSAY FOR MEASUREMENT OF DNA MISMATCH REPAIR DEFICIENCY

(71) Applicant: Bruker Spatial Biology, Inc., Billerica, MA (US)

(72) Inventors: Patrick Danaher, Seattle, WA (US); Sarah Warren, Seattle, WA (US)

(73) Assignee: Bruker Spatial Biology, Inc., Billerica, MA (US)

( * ) Notice: Subject to any disclaimer, the term of this patent is extended or adjusted under 35 U.S.C. 154(b) by 836 days.

(21) Appl. No.: 17/086,842

(22) Filed: Nov. 2, 2020

(65) Prior Publication Data

US 2021/0198748 A1    Jul. 1, 2021

Related U.S. Application Data

(63) Continuation of application No. PCT/US2019/030537, filed on May 3, 2019.

(60) Provisional application No. 62/666,870, filed on May 4, 2018.

(51) Int. Cl.
*C12Q 1/6886* (2018.01)
*G16B 20/20* (2019.01)

(52) U.S. Cl.
CPC ........... *C12Q 1/6886* (2013.01); *G16B 20/20* (2019.02); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2003/0013091 A1 | 1/2003 | Dimitrov |
| 2007/0166708 A1 | 7/2007 | Dimitrov et al. |
| 2010/0015607 A1 | 1/2010 | Geiss et al. |
| 2010/0047924 A1 | 2/2010 | Webster et al. |
| 2010/0112710 A1 | 5/2010 | Geiss et al. |
| 2010/0261026 A1 | 10/2010 | Ferree et al. |
| 2010/0262374 A1 | 10/2010 | Hwang et al. |
| 2011/0086774 A1 | 4/2011 | Dunaway et al. |
| 2014/0017688 A1 | 1/2014 | Webster et al. |
| 2014/0371088 A1 | 12/2014 | Webster |

FOREIGN PATENT DOCUMENTS

| | | |
|---|---|---|
| EP | 3 133 165 A1 | 2/2017 |
| WO | WO 2016/094377 A1 | 6/2016 |

OTHER PUBLICATIONS

Whitehead (Genome Biology 2005 vol. 6 Issue 2 Article R13).*
Ayers, M. et al., "IFN-γ-related mRNA profile predicts clinical response to PD-1 blockade," J Clin Invest., 127(8):2930-2940 (2017); https://doi.org/10.1172/JCI91190.
Castro, M. P. & Goldstein, N., "Mismatch repair deficiency associated with complete remission to combination programmed cell death ligand immune therapy in a patient with sporadic urothelial carcinoma: immunotheranostic considerations," Journal for ImmunoTherapy of Cancer, 3:58 (2015), doi: 10.1186/s40425-015-0104-y, 6 pages.
Cohen, R. et al., "Clinical and molecular characterisation of hereditary and sporadic metastatic colorectal cancers harbouring microsatellite instability/DNA mismatch repair deficiency," European Journal of Cancer, 86:266-274 (2017).
Cortes-Ciriano, I. et al., "A molecular portrait of microsatellite instability across mutliple cancers," Nature Communications, 8:15180 (2017), doi: 10.1038/ncomms15180, 12 pages.
Danaher, P. et al., "A gene expression assay for simultaneous measurement of microsatellite instability and anti-tumor immune activity," Journal for ImmunoTherapy of Cancer, 7:15 (2019), https://doi.org/10.1186/s40425-018-0472-1, 12 pages.
Danaher, P. et al., "Development of a gene expression signatures characterizing the tumor-immune interaction,"Journal of Clinical Oncology, 36(5): Suppl 205-205, Abstract, 1 page.
Esteller, M. et al., "hMLH1 Promoter Hypermethylation Is an Early Event in Human Endometrial Tumorigenesis," American Journal of Pathology, 155(5): 1767-1772 (1999).
Fehrenbacher, L. et al., "Atezolizumab versus docetaxel for patients with previously treated non-small-cell lung cancer (POPLAR): a multicentre, open-label, phase 2 randomised controlled trial," Lancet, 387:1837-1846 (2016).
Geiss, G. K. et al., "Direct multiplexed measurement of gene expression with color-coded probe pairs," Nature Biotechnology, 26(6):317-325 (2008).
Heald, B. et al., "Implementation of Universal Microsatellite Instability and Immunohistochemistry Screening for Diagnosing Lynch Syndrome in a Large Academic Medical Center," J Clin Oncol, 31(10): 1336-1340 (2013).
Hirsch, F. R. et al., "PD-L1 Immunohistochemistry Assays for Lung Cancer: Results from Phase 1 of the Blueprint PD-L1 IHC Assay Comparison Project," Journal of Thoracic Oncology, 12(2):208-222 (2016).
Hughes, L. A. E. et al., "The CpG Island Methylator Phenotype: What's in a Name?" Cancer Res, 73(19): 5858-5868 (2013).
Kane, M. F. et al., "Methylation of the hMLH1 Promoter correlates with Lack of Expression of hMLH1 in Sporadic colon Tumors and Mismatch Repair-defective Human Tumor Cell Lines," Cancer Research, 57(5):808-811 (1997).
Krause, L. et al., "Identification of the CIMP-like subtype and aberrant methylation of members of the chromosomal segregation and spindle assembly pathways in esophageal adenocarcinoma," Carcinogenics, 37(4):356-365 (2016).
Le Gallo, M. & Bell, D. W., "The Emerging Genomic Landscape of Endometrial Cancer," Clinical Chemistry, 60:198-110 (2014).
Le, D. T. et al., "Mismatch repair deficiency predicts response of solid tumors to PD-1 blockade," Science, 357:409-413 (2017).

(Continued)

*Primary Examiner* — Amanda Haney
(74) *Attorney, Agent, or Firm* — COOLEY LLP

(57) ABSTRACT

The present disclosure relates to methods using gene expression measurements to identify mismatch repair deficiency, microsatellite instability and hypermutation in a subject.

12 Claims, 6 Drawing Sheets
Specification includes a Sequence Listing.

(56) References Cited

OTHER PUBLICATIONS

Mensenkamp, A. R. et al., "Somatic Mutations in MLH1 and MSH2 Are a Frequent Cause of Mismatch-Repair Deficiency in Lynch Syndrome-Like Tumors," Gastroenterology, 146:643-646 (2014), including Supplementary Materials and Methods, pp. 646.e1-646.e7.

Rizvi, N. A. et al., "Mutational landscape determines sensitivity to PD-1 blockade in non-small cell lung cancer," Science, 348(6230): 124-128 (2015).

Schlesner, M. & Eils, R., "Hypermutation takes the driver's seat," Genome Medicine, 7:31 (2015), doi: 10.1186/s13073-015-0159-x, 3 pages.

Simpkins, S. B. et al., "MLH1 promoter methylation and gene silencing is the primary cause of microsatellite instability in sporadic endometrial cancers," Human Molecular Genetics, 8(4):661-666 (1999).

The Cancer Genome Atlas Research Network, Analysis Working Group: Dana-Farber Cancer Institute., Bass, A. et al., "Comprehensive molecular characterization of gastric adenocarcinoma," Nature, 513:202-209 (2014); https://doi.org/10.1038/nature13480.

The Cancer Genome Atlas Network, Genome Sequencing Center Baylor College of Medicine, Muzny, D. et al. "Comprehensive molecular characterization of human colon and rectal cancer," Nature, 487:330-337 (2012); https://doi.org/10.1038/nature11252.

Umar, A. et al., "Revised Bethesda Guidelines for Hereditary Nonpolyposis Colorectal Cancer (Lynch Syndrome) and Microsatellite Instability," J Natl Cancer Inst, 96:261-268 (2004).

Valeri, N. et al., "MicroRNA-21 induces resistance to 5-fluorouracil by down-regulating human DNA MutS homolog 2 (hMSH2)," PNAS, 107(49):21098-21103 (2010).

Westdorp, H. et al., "Opportunities for immunotherapy in microsatellite instable colorectal cancer," Cancer Immunol Immunother, 65:1249-1259 (2016).

Wright, G. et al., "A gene expression-based method to diagnose clinically distinct subgroups of diffuse large B cell lymphoma," PNAS, 100(17):9991-9996 (2003).

Zhang, Q.-Y. et al., "Status and Significance of CpG Island Methylator Phenotype in Endometrial Cancer," Gynecol Obstet Invest, 72:183-191 (2011).

\* cited by examiner

GENE EXPRESSION ASSAY FOR MEASUREMENT OF DNA MISMATCH REPAIR DEFICIENCY

CROSS-REFERENCE TO RELATED APPLICATIONS

This application is a continuation of International Patent Application No. PCT/US2019/030537, filed May 3, 2019, which claims priority to, and the benefit of, U.S. Provisional Application No. 62/666,870, filed May 4, 2018. The contents of each of the aforementioned patent applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Nov. 2, 2020, is named "NATE-038_C01US_SeqList.txt" and is about 168 KB in size.

BACKGROUND OF THE INVENTION

There are currently a variety of methods for identifying mismatch repair deficiency, microsatellite instability and hypermutation in tumor samples from a subject. Current methods rely on PCR and immunohistochemistry. These methods require a large tumor sample, are costly, and are time-intensive. Importantly, whether a subject will respond to and receive a clinical benefit from checkpoint inhibitors, e.g. drugs that target PD-1 or PD-L1, can be predicted based on the presence of mismatch repair deficiency, microsatellite instability and hypermutation. Thus, there is a need in the art for methods of identifying mismatch repair deficiency, microsatellite instability and hypermutation that are rapid, specific, and accurate, and that require smaller tumor samples. The present disclosure addresses these needs.

SUMMARY OF THE INVENTION

The present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three gene are used, or $c_1$ is 1.03 and $c_2$ is 0.70 when four genes are used; d) comparing the MLS score with a predetermined cutoff value, wherein the cutoff value identifies mismatch repair deficiency in a subject with at least 95% specificity; and e) producing a report identifying the presence of mismatch repair deficiency in the subject when the MLS score is equal to or greater than the predetermined cutoff value or producing a report identifying the absence of mismatch repair deficiency in the subject when the MLS score is less than the predetermined cutoff value.

The present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three gene are used, or $c_1$ is 1.03 and $c_2$ is 0.70 when four genes are used; d) comparing the MLS score with a predetermined cutoff value, wherein the cutoff value identifies mismatch repair deficiency in a subject with at least 95% specificity; and e) identifying the presence of mismatch repair deficiency in the subject when the MLS score is equal to or greater than the predetermined cutoff value or identifying the absence of mismatch repair deficiency in the subject when the MLS score is less than the predetermined cutoff value.

The predetermined cutoff value that identifies mismatch repair deficiency in a subject can have a specificity of 99%. Alternatively, the cutoff value that identifies mismatch repair deficiency in a subject can have a specificity of 99.5%. The predetermined cutoff value can be 1.645, 2.326, or 2.576.

The at least one gene in step (a) can comprise MLH1. Alternatively, the at least one gene in step (a) can comprise each of MLH1, MSH2, MSH6 and PMS2.

The present disclosure provides a method of identifying mismatch repair deficiency in a subject comprising: a) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; b) determining a score HPS, wherein $HPS=(y-\mu_2)/\sigma_2$, wherein $y=\Sigma_{i=1}^{10} y_i w_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and $\sigma_2$ is the standard deviation of the linear combination of the log-transformed normalized expression of the at least one gene in non-hypermutated samples; c) comparing the HPS score with a predetermined cutoff value, wherein the cutoff value identifies mismatch repair deficiency in a subject with at least 95% specificity; and d) producing a report identifying the presence of mismatch repair deficiency in the subject when the HPS score is equal to or greater than the predetermined cutoff value or producing a report identifying the absence of mismatch repair deficiency in the subject when the HPS score is less than the predetermined cutoff value.

The present disclosure provides a method of identifying mismatch repair deficiency in a subject comprising: a) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; b) determining a score HPS, wherein $HPS=(y-\mu_2)/\sigma_2$, wherein $y=\Sigma_{i=1}^{10} y_i w_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and $\sigma_2$ is the standard deviation of the linear combination of the log-transformed normalized expression of the at least one gene in non-hypermutated samples; c) comparing the HPS score with a predetermined cutoff value, wherein the cutoff value identifies mismatch repair deficiency in a subject with at least 95% specificity; and d) identifying the presence of mismatch repair deficiency in the subject when the HPS score is equal to or greater than the predetermined cutoff value or identifying the absence of mismatch repair deficiency in the subject when the HPS score is less than the predetermined cutoff value.

The prespecified weight for gene i, $w_i$, in step (b) can be:

| Gene | Weight |
|---|---|
| EPM2AIP1 | −0.31218 |
| TTC30A | −0.19894 |
| SMAP1 | −0.1835 |
| RNLS | −0.19023 |
| WNT11 | −0.11515 |
| SFXN1 | 0.214676 |
| SREBF1 | 0.194835 |
| TYMS | 0.206972 |
| EIF5AL1 | 0.194935 |
| WDR76 | 0.188582 |

The predetermined cutoff value that identifies mismatch repair deficiency in a subject can have a specificity of 99%. Alternatively, the cutoff value that identifies mismatch repair deficiency in a subject can have a specificity of 99.5%. The cutoff value can be 1.645, 2.326, or 2.576.

The at least one gene in step (a) can comprise each of EPM2AIP1, TTC30A, SMAP1, RNLS, WNT11, SFXN1, SREBF1, TYMS, EIF5AL1, and WDR76.

The present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three genes are used, or $c_1$ is 1.03 and $c_2$ is 0.70 when four genes are used; d) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; e) determining a score HPS, wherein $HPS=(y-\mu_2)/\sigma_2$, wherein $y=\Sigma_{i=1}^{10} y_i w_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and $\sigma_2$ is the standard deviation of the linear combination of the log-transformed normalized expression of the at least one gene in non-hypermutated samples; f) determining a score MPS wherein $MPS=(\max(HPS,0)^2+\min(MLS,0)^2)^{1/2}$; g) comparing the MPS score with a predetermined cutoff value, wherein the cutoff value identifies mismatch repair deficiency in a subject with at least 95% specificity; and h) producing a report identifying the presence of mismatch repair deficiency in the subject when the MPS score is equal to or greater than the predetermined cutoff value or producing a report identifying the absence of mismatch repair deficiency in the subject when the MPS score is less than the predetermined cutoff value.

The present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three genes are used, or $c_1$ is 1.03 and $c_2$ is 0.70 when four genes are used; d) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; e) determining a score HPS, wherein $HPS=(y-\mu_2)/\sigma_2$, wherein $y=\Sigma_{i=1}^{10} y_i w_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and $\sigma_2$ is the standard deviation of the linear combination of the log-transformed normalized expression of the at least one gene in non-hypermutated samples; f) determining a score MPS wherein $MPS=(\max(HPS,0)^2+\min(MLS,0)^2)^{1/2}$; g) comparing the MPS score with a predetermined cutoff value, wherein the cutoff value identifies mismatch repair deficiency in a subject with at least 95% specificity; and h) identifying the presence of mismatch repair deficiency in the subject when the MPS score is equal to or greater than the predetermined cutoff value or identifying the absence of mismatch repair deficiency in the subject when the MPS score is less than the predetermined cutoff value.

The prespecified weight for gene i, $w_i$, in step (e) can be

| Gene | Weight |
|---|---|
| EPM2AIP1 | −0.31218 |
| TTC30A | −0.19894 |
| SMAP1 | −0.1835 |
| RNLS | −0.19023 |
| WNT11 | −0.11515 |
| SFXN1 | 0.214676 |
| SREBF1 | 0.194835 |
| TYMS | 0.206972 |
| EIF5AL1 | 0.194935 |
| WDR76 | 0.188582 |

The predetermined cutoff value that identifies mismatch repair deficiency in a subject can have a specificity of 99%. Alternatively, the cutoff value that identifies mismatch repair deficiency in a subject can have a specificity of 99.5%. The cutoff value can be 2.058, 2.699, or 2.939.

The at least one gene in step (a) can comprise MLH1. Alternatively, the at least one gene in step (a) can comprise each of MLH1, MSH2, MSH6 and PMS2.

The at least one gene in step (d) can comprise each of EPM2AIP1, TTC30A, SMAP1, RNLS, WNT11, SFXN1, SREBF1, TYMS, EIF5AL1 and WDR76.

The at least one gene in step (a) can comprise MLH1 and the at least one gene in step (d) can comprise each of EPM2AIP1, TTC30A, SMAP1, RNLS, WNT11, SFXN1, SREBF1, TYMS, EIF5AL1 and WDR76. Alternatively, the at least one gene in step (a) can comprise each of MLH1, MSH2, MSH6 and PMS2 and the at least one gene in step (d) can comprise each of EPM2AIP1, TTC30A, SMAP1, RNLS, WNT11, SFXN1, SREBF1, TYMS, EIF5AL1 and WDR76.

A subject can be diagnosed with cancer.

A report identifying mismatch repair deficiency can further identify the subject as having cancer.

A report identifying the presence of mismatch repair deficiency can further identify the subject for treatment with an anti-cancer therapy. A treatment can comprise administering to the subject immunotherapy. A treatment can comprise administering to the subject checkpoint inhibitors. A treatment can comprise administering to the subject pembrolizumab, nivolumab, atezolizumab, avelumab, durvalumab, pidilizumab, REGN2810, AMP-224, MEDI0680, PDR001, CT-001 or a combination thereof. A treatment can comprise administering to the subject a CTLA4 antibody. The CTLA4 antibody can comprise ipilimumab, tremelimumab or a combination thereof.

The methods of the present disclosure can further comprise determining a tumor inflammation signature score.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION OF THE INVENTION

Figure 1:
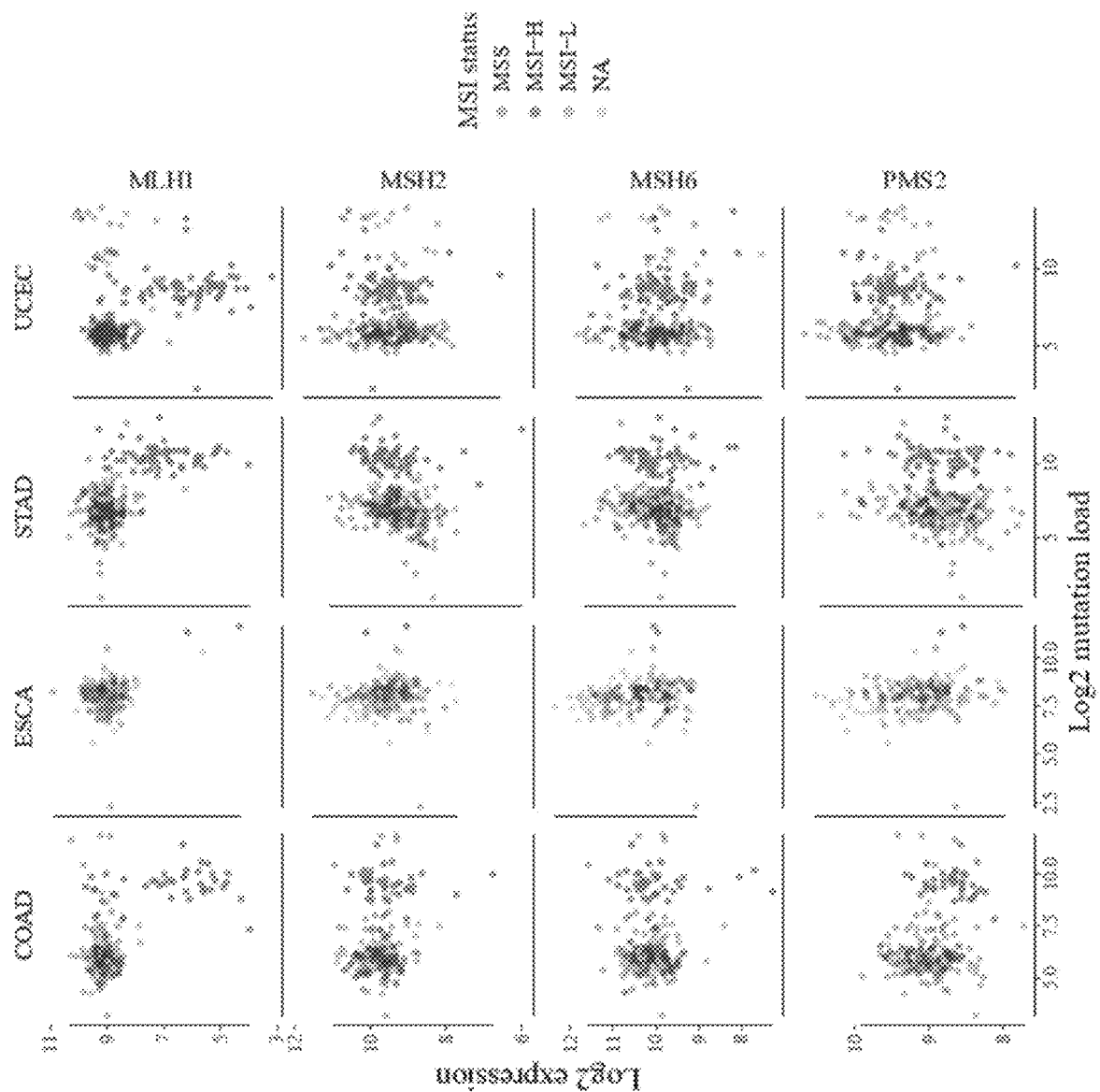
FIG. 1 is a series of graphs that shows the expression level of certain mismatch repair genes plotted against mutation load and microsatellite instability status in four different cancer types.

The present disclosure provides methods that identify mismatch repair deficiency, hypermutation, and microsatellite instability in a subject using gene expression measurements.

The clinical benefit of checkpoint inhibitors varies widely between patients and only a small subset experience durable disease remission upon treatment. Response to checkpoint inhibition is associated with two biological axes: tumor foreignness, typically measured by tumor mutation burden or microsatellite instability (MSI), and the presence of an adaptive anti-tumor immune response, typically measured by gene expression signatures of inflammation or immunohistochemistry. Because tumor foreignness and the magnitude of the adaptive immune response in the tumor microenvironment are only weakly correlated, more accurate predictions of immunotherapy response should be possible by measuring and integrating both variables together. However, in a clinical setting, performing multiple assays is often impractical due to more tissue requirement, increased turnaround time, and cost. Here, the ability of gene expression to predict tumor MSI was investigated, and a single assay that enables measurement of tumor foreignness and tumor inflammation was developed.

DNA mismatch repair deficiency (MMRd) has been observed in most cancer types in The Cancer Genome Atlas (TCGA), and occurs in more than 5% of adrenal, rectal, colon, stomach, and uterine tumors. Tumors with this phenotype develop both point and frameshift mutations at an increased rate and are often described as hypermutated. The failure of mismatch repair (MMR) to correct replication errors at short repeated DNA sequences can lead to the phenomenon of high-level MSI (MSI-H). MSI-H cancers have distinct clinical behavior, which has led to widespread MSI testing in cancers where MSI-H is common. In colorectal cancer, the MSI-H phenotype demonstrates association with proximal tumor localization, a dense local lymphocyte infiltration, and a low frequency of distant organ metastasis. Moreover, MSI-H colorectal cancers have a better prognosis than their microsatellite-stable (MSS) counterparts. Diminished responsiveness of MSI-H colorectal cancer patients towards chemotherapy has been shown in several studies. In the era of immunotherapy, MMRd has gained greater relevance as a cause of hypermutation potentiating anti-tumor immune responses which may be augmented by checkpoint inhibition. Importantly, the frameshift mutations that accrue in MMRd tumors lead to highly abnormal peptides that may be more immunogenic. Thus, the high pan-cancer clinical efficacy of checkpoint inhibitors in MMRd tumors may arise more from their high rate of frameshift mutations than from their total tumor mutation burden.

MMRd often arises from loss of protein expression of 1 of 4 genes essential for MMR: MLH1, MSH2, MSH6, and PMS2. Lost expression of these proteins can arise from mutations in their coding regions, either from acquired somatic mutations or from germline mutations associated with Lynch syndrome. In tumors with intact sequences for these genes, loss of protein expression can follow loss of mRNA expression. A common cause of lost mRNA expression in these genes is the CpG island methylator phenotype (CIMP), which is associated with widespread methylation across the genome and frequently silences DNA repair genes. Loss of MMR activity due to microRNA-induced downregulation of MSH2 has also been observed in colorectal tumors. MMRd can be detected by measuring either its cause or its effect. Immunohistochemistry (IHC) is used to measure loss of expression of proteins essential to the MMR machinery, and PCR and sequencing are used to measure MSI, the genomic "scarring" which occurs as a consequence of MMRd.

The biology underlying MMRd provides two opportunities for capturing MMRd with gene expression data. First, loss of expression of MMR genes may be used to detect cases of MMRd resulting from transcriptional silencing. Second, if it is assumed that MMRd and CIMP exert broad and consistent influence on the transcriptome, then a data-driven predictor of hypermutation based on RNA expression patterns may also be possible.

Various methods of the present disclosure are described in full detail herein.

In one aspect, the present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three gene are used, or $c_1$ is 1.03 and $c_2$ is 0.70 when four genes are used; d) comparing the MLS score with a predetermined cutoff value, wherein the cutoff value identifies mismatch repair deficiency in a subject with at least 95% specificity; and e) producing a report identifying the presence of mismatch repair deficiency in the subject when the MLS score is equal to or greater than the predetermined cutoff value or producing a report identifying the absence of mismatch repair deficiency in the subject when the MLS score is less than the predetermined cutoff value.

In one aspect, the present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three gene are used, or $c_1$ is 1.03 and $c_2$ is 0.70 when four genes are used; d) comparing the MLS score with a predetermined cutoff value, wherein the cutoff value identifies mismatch repair deficiency in a subject with at least 95% specificity; and e) identifying the presence of mismatch repair deficiency in the subject when the MLS score is equal to or greater than the predetermined cutoff value or identifying the absence of mismatch repair deficiency in the subject when the MLS score is less than the predetermined cutoff value.

In some aspects, the preceding methods can further comprise administering at least one treatment to a subject identified as having mismatch repair deficiency. A treatment can comprise anti-cancer therapy. A treatment can comprise administering to the subject immunotherapy. The at least one treatment can comprise administering to the subject at least one checkpoint inhibitor. A treatment can comprise administering to the subject pembrolizumab, nivolumab, atezolizumab, avelumab, durvalumab, pidilizumab, REGN2810, AMP-224, MEDI0680, PDR001, CT-001 or a combination thereof. A treatment can comprise administering to the subject a CTLA4 antibody. A CTLA4 antibody can comprise ipilimumab, tremelimumab or a combination thereof.

In one aspect, the present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three gene are used, or $c_1$ is 1.03 and $c_2$ is 0.70 when four genes are used; d) comparing the MLS score with a predetermined cutoff value, wherein the cutoff value identifies mismatch repair deficiency in a subject with at least 95% specificity; and e) administering at least one treatment to the subject when the MLS score is equal to or greater than the predetermined cutoff value. A treatment can comprise anti-cancer therapy. A treatment can comprise administering to the subject immunotherapy. The at least one treatment can comprise administering to the subject at least one checkpoint inhibitor.

A treatment can comprise administering to the subject pembrolizumab, nivolumab, atezolizumab, avelumab, durvalumab, pidilizumab, REGN2810, AMP-224, MEDI0680, PDR001, CT-001 or a combination thereof. A treatment can comprise administering to the subject a CTLA4 antibody. A CTLA4 antibody can comprise ipilimumab, tremelimumab or a combination thereof.

In some aspects of the preceding methods, determining $\mu_1$ in step (b), wherein $\mu_1$ is the mean of the log-transformed normalized expression of the at least one gene in non-hypermutated samples, comprises: 1) measuring the gene expression level of the at least one gene in a plurality of analogous, non-hypermutated tumor samples from at least one subject, wherein at least one sample in the plurality of analogous, non-hypermutated samples originates from the same tissue as the tumor sample in step (a) of the preceding method; 2) determining for each of the at least one gene the log-transformed normalized expression; and 3) determining for each of the at least one gene the mean of the log 2-transformed expression from step (2).

In some aspects of the preceding methods, determining $\sigma_1$ in step (b), wherein $\sigma_1$ is the standard deviation of the log-transformed normalized expression of the at least one gene in non-hypermutated samples, comprises: 1) measuring the gene expression level of the at least one gene in a plurality of analogous, non-hypermutated tumor samples from at least one subject, wherein at least one sample in the plurality of analogous, non-hypermutated samples originates from the same tissue as the tumor sample in step (a) of the preceding method; 2) determining for each of the at least one gene the log-transformed normalized expression; and 3) determining for each of the at least one gene the standard deviation of the log 2-transformed expression from step (2).

In some aspects of the preceding methods, measuring the gene expression of the at least one gene in a tumor sample from the subject and measuring the gene expression of the at least one gene in a plurality of analogous non-hypermutated tumor samples is performed using the same method. In some aspects of the preceding method, measuring the gene expression of the at least one gene in a tumor sample from the subject and measuring the gene expression of the at least one gene in a plurality of analogous non-hypermutated tumor samples is performed using the same apparatus. In preferred aspects of the preceding method, measuring the gene expression of the at least one gene in a tumor sample from the subject and measuring the gene expression of the at least one gene in a plurality of analogous non-hypermutated tumor samples is performed using the same method and apparatus.

In some aspects, the predetermined cutoff value in the preceding methods that identifies mismatch repair deficiency in a subject can have a specificity of 99%. In some aspects, the predetermined cutoff value in the preceding methods that identifies mismatch repair deficiency in a subject can have a specificity of at least 99%. In preferred aspects, the cutoff value that identifies mismatch repair deficiency in a subject can have a specificity of 99.5%. In preferred aspects, the cutoff value that identifies mismatch repair deficiency in a subject can have a specificity of at least 99.5%.

In some aspects, the predetermined cutoff value in the preceding methods that identifies mismatch repair deficiency in a subject can have a specificity of at least 70%, or at least 75%, or at least 80%, or at least 85%, or at least 90%, or at least 91%, or at least 92%, or at least 93%, or at least 94%, or at least 95%, or at least 96%, or at least 97% or at least 98%.

In some aspects of the preceding methods, the predetermined cutoff value of the preceding method that identifies mismatch repair deficiency in a subject can be 1.645. Alternatively, the predetermined cutoff value can be 2.326. Alternatively still, the predetermined cutoff value can be 2.576.

In some aspects, the at least one gene in step (a) of the preceding methods can comprise MLH1. Alternatively, the at least one gene in step (a) can comprise each of MLH1, MSH2, MSH6 and PMS2.

In some aspects, step (a) of the preceding methods can comprise measuring the gene expression level of at least two genes, or at least three genes or at least four genes comprising MLH1, MSH2, MSH6 or PMS2 in a tumor sample from the subject.

In some aspects, when the tumor sample is a colon adenocarcinoma (COAD), esophageal carcinoma (ESCA), stomach adenocarcinoma (STAD) or uterine corpus endometrial carcinoma (UCEC) tumor sample, at in step (b) of the preceding methods can be:

|      | MLH1   | MSH2   | MSH6   | PMS2   |
| ---- | ------ | ------ | ------ | ------ |
| COAD | 0.3241 | 0.4108 | 0.4198 | 0.3259 |
| ESCA | 0.5221 | 0.6602 | 0.7347 | 0.4927 |
| STAD | 0.4245 | 0.6020 | 0.4814 | 0.4314 |
| UCEC | 0.4543 | 0.7312 | 0.6158 | 0.4217 |

Table 1 shows the sequences of the at least one gene from step (a) of the preceding method.

TABLE 1

Gene sequences used in the methods of the present invention

| Gene | GenBank Accession No. | Sequence | SEQ ID NO. |
| --- | --- | --- | --- |
| MLH1 | NM_000249.2 | ATTGGCTGAAGGCACTTCCGTTGAGCATCTAGA CGTTTCCTTGGCTCTTCTGGCGCCAAAATGTCGT TCGTGGCAGGGGTTATTCGGCGGCTGGACGAG ACAGTGGTGAACCGCATCGCGGCGGGGGAAGT TATCCAGCGGCCAGCTAATGCTATCAAAGAGAT GATTGAGAACTGTTTAGATGCAAAATCCACAAG TATTCAAGTGATTGTTAAAGAGGGAGGCCTGAA GTTGATTCAGATCCAAGACAATGGCACCGGGAT CAGGAAAGAAGATCTGGATATTGTATGTGAAA GGTTCACTACTAGTAAACTGCAGTCCTTTGAGG ATTTAGCCAGTATTTCTACCTATGGCTTTCGAG GTGAGGCTTTGGCCAGCATAAGCCATGTGGCTC ATGTTACTATTACAACGAAAACAGCTGATGGAA | 1 |

TABLE 1-continued

Gene sequences used in the methods of the present invention

| Gene | GenBank Accession No. | Sequence | SEQ ID NO. |
|---|---|---|---|
| | | AGTGTGCATACAGAGCAAGTTACTCAGATGGA<br>AAACTGAAAGCCCCTCCTAAACCATGTGCTGGC<br>AATCAAGGGACCCAGATCACGGTGGAGGACCT<br>TTTTTACAACATAGCCACGAGGAGAAAAGCTTT<br>AAAAAATCCAAGTGAAGAATATGGGAAAATTT<br>TGGAAGTTGTTGGCAGGTATTCAGTACACAATG<br>CAGGCATTAGTTTCTCAGTTAAAAAACAAGGAG<br>AGACAGTAGCTGATGTTAGGACACTACCCAATG<br>CCTCAACCGTGGACAATATTCGCTCCATCTTTG<br>GAAATGCTGTTAGTCGAGAACTGATAGAAATTG<br>GATGTGAGGATAAAACCCTAGCCTTCAAAATG<br>AATGGTTACATATCCAATGCAAACTACTCAGTG<br>AAGAAGTGCATCTTCTTACTCTTCATCAACCAT<br>CGTCTGGTAGAATCAACTTCCTTGAGAAAAGCC<br>ATAGAAACAGTGTATGCAGCCTATTTGCCCAAA<br>AACACACACCCATTCCTGTACCTCAGTTTAGAA<br>ATCAGTCCCCAGAATGTGGATGTTAATGTGCAC<br>CCCACAAAGCATGAAGTTCACTTCCTGCACGAG<br>GAGAGCATCCTGGAGCGGGTGCAGCAGCACAT<br>CGAGAGCAAGCTCCTGGGCTCCAATTCCTCCAG<br>GATGTACTTCACCCAGACTTTGCTACCAGGACT<br>TGCTGGCCCCTCTGGGGAGATGGTTAAATCCAC<br>AACAAGTCTGACCTCGTCTTCTACTTCTGGAAG<br>TAGTGATAAGGTCTATGCCCACCAGATGGTTCG<br>TACAGATTCCCGGGAACAGAAGCTTGATGCATT<br>TCTGCAGCCTCTGAGCAAACCCCTGTCCAGTCA<br>GCCCCAGGCCATTGTCACAGAGGATAAGACAG<br>ATATTTCTAGTGGCAGGGCTAGGCAGCAAGATG<br>AGGAGATGCTTGAACTCCCAGCCCCTGCTGAAG<br>TGGCTGCCAAAAATCAGAGCTTGGAGGGGGAT<br>ACAACAAAGGGGACTTCAGAAATGTCAGAGAA<br>GAGAGGACCTACTTCCAGCAACCCCAGAAAGA<br>GACATCGGGAAGATTCTGATGTGGAAATGGTG<br>GAAGATGATTCCCGAAAGGAAATGACTGCAGC<br>TTGTACCCCCGGAGAAGGATCATTAACCTCAC<br>TAGTGTTTTGAGTCTCCAGGAAGAAATTAATGA<br>GCAGGGACATGAGGTTCTCCGGGAGATGTTGC<br>ATAACCACTCCTTCGTGGGCTGTGTGAATCCTC<br>AGTGGGCCTTGCACAGCATCAAACCAAGTTAT<br>ACCTTCTCAACACCACCAAGCTTAGTGAAGAAC<br>TGTTCTACCAGATACTCATTTATGATTTTGCCAA<br>TTTTGGTGTTCTCAGGTTATCGGAGCCAGCACC<br>GCTCTTTGACCTTGCCATGCTTGCCTTAGATAGT<br>CCAGAGAGTGGCTGGACAGAGGAAGATGGTCC<br>CAAAGAAGGACTTGCTGAATACATTGTTGAGTT<br>TCTGAAGAAGAAGGCTGAGATGCTTGCAGACT<br>ATTTCTCTTTGGAAATTGATGAGGAAGGGAACC<br>TGATTGGATTACCCCTTCTGATTGACAACTATG<br>TGCCCCCTTTGGAGGGACTGCCTATCTTCATTCT<br>TCGACTAGCCACTGAGGTGAATTGGGACGAAG<br>AAAAGGAATGTTTTGAAAGCCTCAGTAAAGAA<br>TGCGCTATGTTCTATTCCATCCGGAAGCAGTAC<br>ATATCTGAGGAGTCGACCCTCTCAGGCCAGCAG<br>AGTGAAGTGCCTGGCTCCATTCCAAACTCCTGG<br>AAGTGGACTGTGGAACACATTGTCTATAAAGCC<br>TTGCGCTCACACATTCTGCCTCCTAAACATTTCA<br>CAGAAGATGGAAATATCCTGCAGCTTGCTAACC<br>TGCCTGATCTATACAAAGTCTTTGAGAGGTGTT<br>AAATATGGTTATTTATGCACTGTGGGATGTGTT<br>CTTCTTTCTCTGTATTCCGATACAAAGTGTTGTA<br>TCAAAGTGTGATATACAAAGTGTACCAACATAA<br>GTGTTGGTAGCACTTAAGACTTATACTTGCCTT<br>CTGATAGTATTCCTTTATACACAGTGGATTGAT<br>TATAAATAAATAGATGTGTCTTAACATAA | |
| MSH2 | NM_000251.1 | GGCGGGAAACAGCTTAGTGGGTGTGGGGTCGC<br>GCATTTTCTTCAACCAGGAGGTGAGGAGGTTTC<br>GACATGGCGGTGCAGCCGAAGGAGACGCTGCA<br>GTTGGAGAGCGCGGCCGAGGTCGGCTTCGTGC<br>GCTTCTTTCAGGGCATGCCGGAGAAGCCGACCA<br>CCACAGTGCGCCTTTTCGACCGGGGCGACTTCT<br>ATACGGCGCACGGCGAGGACGCGCTGCTGGCC<br>GCCCGGGAGGTGTTCAAGACCCAGGGGGTGAT<br>CAAGTACATGGGGCCGGCAGGAGCAAAGAATC<br>TGCAGAGTGTTGTGCTTAGTAAAATGAATTTTG | 2 |

TABLE 1-continued

Gene sequences used in the methods of the present invention

| Gene | GenBank Accession No. | Sequence | SEQ ID NO. |
|---|---|---|---|
| | | AATCTTTTGTAAAAGATCTTCTTCTGGTTCGTCA GTATAGAGTTGAAGTTTATAAGAATAGAGCTGG AAATAAGGCATCCAAGGAGAATGATTGGTATTT GGCATATAAGGCTTCTCCTGGCAATCTCTCTCA GTTTGAAGACATTCTCTTTGGTAACAATGATAT GTCAGCTTCCATTGGTGTTGTGGGTGTTAAAAT GTCCGCAGTTGATGGCCAGAGACAGGTTGGAG TTGGGTATGTGGATTCCATACAGAGGAAACTAG GACTGTGTGAATTCCCTGATAATGATCAGTTCT CCAATCTTGAGGCTCTCCTCATCCAGATTGGAC CAAAGGAATGTGTTTTACCCGGAGGAGAGACT GCTGGAGACATGGGGAAACTGAGACAGATAAT TCAAAGAGGAGGAATTCTGATCACAGAAAGAA AAAAAGCTGACTTTTCCACAAAAGACATTTATC AGGACCTCAACCGGTTGTTGAAAGGCAAAAAG GGAGAGCAGATGAATAGTGCTGTATTGCCAGA AATGGAGAATCAGGTTGCAGTTTCATCACTGTC TGCGGTAATCAAGTTTTTAGAACTCTTATCAGA TGATTCCAACTTTGGACAGTTTGAACTGACTAC TTTTGACTTCAGCCAGTATATGAAATTGGATAT TGCAGCAGTCAGAGCCCTTAACCTTTTTCAGGG TTCTGTTGAAGATACCACTGGCTCTCAGTCTCT GGCTGCCTTGCTGAATAAGTGTAAAACCCCTCA AGGACAAAGACTTGTTAACCAGTGGATTAAGC AGCCTCTCATGGATAAGAACAGAATAGAGGAG AGATTGAATTTAGTGGAAGCTTTTGTAGAAGAT GCAGAATTGAGGCAGACTTTACAAGAAGATTT ACTTCGTCGATTCCCAGATCTTAACCGACTTGC CAAGAAGTTTCAAAGACAAGCAGCAAACTTAC AAGATTGTTACCGACTCTATCAGGGTATAAATC AACTACCTAATGTTATACAGGCTCTGGAAAAAC ATGAAGGAAAACACCAGAAATTATTGTTGGCA GTTTTTGTGACTCCTCTTACTGATCTTCGTTCTG ACTTCTCCAAGTTTCAGGAAATGATAGAAACAA CTTTAGATATGGATCAGGTGGAAAACCATGAAT TCCTTGTAAAACCTTCATTTGATCCTAATCTCAG TGAATTAAGAGAAATAATGAATGACTTGGAAA AGAAGATGCAGTCAACATTAATAAGTGCAGCC AGAGATCTTGGCTTGGACCCTGGCAAACAGATT AAACTGGATTCCAGTGCACAGTTTGGATATTAC TTTCGTGTAACCTGTAAGGAAGAAAAAGTCCTT CGTAACAATAAAAACTTTAGTACTGTAGATATC CAGAAGAATGGTGTTAAATTTACCAACAGCAA ATTGACTTCTTTAAATGAAGAGTATACCAAAAA TAAAACAGAATATGAAGAAGCCCAGGATGCCA TTGTTAAAGAAATTGTCAATATTTCTTCAGGCT ATGTAGAACCAATGCAGACACTCAATGATGTGT TAGCTCAGCTAGATGCTGTTGTCAGCTTTGCTC ACGTGTCAAATGGAGCACCTGTTCCATATGTAC GACCAGCCATTTTGGAGAAAGGACAAGGAAGA ATTATATTAAAAGCATCCAGGCATGCTTGTGTT GAAGTTCAAGATGAAATTGCATTTATTCCTAAT GACGTATACTTTGAAAAAGATAAACAGATGTTC CACATCATTACTGGCCCCAATATGGGAGGTAAA TCAACATATATTCGACAAACTGGGGTGATAGTA CTCATGGCCCAAATTGGGTGTTTTGTGCCATGT GAGTCAGCAGAAGTGTCCATTGTGGACTGCATC TTAGCCCGAGTAGGGGCTGGTGACAGTCAATTG AAAGGAGTCTCCACGTTCATGGCTGAAATGTTG GAAACTGCTTCTATCCTCAGGTCTGCAACCAAA GATTCATTAATAATCATAGATGAATTGGGAAGA GGAACTTCTACCTACGATGGATTTGGGTTAGCA TGGGCTATATCAGAATACATTGCAACAAAGATT GGTGCTTTTTGCATGTTTGCAACCCATTTTCATG AACTTACTGCCTTGGCCAATCAGATACCAACTG TTAATAATCTACATGTCACAGCACTCACCACTG AAGAGACCTTAACTATGCTTTATCAGGTGAAGA AAGGTGTCTGTGATCAAAGTTTTGGGATTCATG TTGCAGAGCTTGCTAATTTCCCTAAGCATGTAA TAGAGTGTGCTAAACAGAAAGCCCTGGAACTT GAGGAGTTTCAGTATATTGGAGAATCGCAAGG ATATGATATCATGGAACCAGCAGCAAAGAAGT GCTATCTGGAAAGAGAGCAAGGTGAAAAAATT ATTCAGGAGTTCCTGTCCAAGGTGAAACAAATG CCCTTTACTGAAATGTCAGAAGAAAACATCACA | |

TABLE 1-continued

Gene sequences used in the methods of the present invention

| Gene | GenBank Accession No. | Sequence | SEQ ID NO. |
|---|---|---|---|
| | | ATAAAGTTAAAACAGCTAAAAGCTGAAGTAAT<br>AGCAAAGAATAATAGCTTTGTAAATGAAATCAT<br>TTCACGAATAAAAGTTACTACGTGAAAAATCCC<br>AGTAATGGAATGAAGGTAATATTGATAAGCTAT<br>TGTCTGTAATAGTTTTATATTGTTTTATATTAAC<br>CCTTTTTCCATAGTGTTAACTGTCAGTGCCCATG<br>GGCTATCAACTTAATAAGATATTTAGTAATATT<br>TTACTTTGAGGACATTTTCAAAGATTTTTATTTT<br>GAAAAATGAGAGCTGTAACTGAGGACTGTTTG<br>CAATTGACATAGGCAATAATAAGTGATGTGCTG<br>AATTTTATAAATAAAATCATGTAGTTTGTGG | |
| MSH6 | NM_000179.2 | GGCGAGGCGCCTGTTGATTGGCCACTGGGGCCC<br>GGGTTCCTCCGGCGGAGCGCGCCTCCCCCCAGA<br>TTTCCCGCCAGCAGGAGCCGCGCGGTAGATGCG<br>GTGCTTTTAGGAGCTCCGTCCGACAGAACGGTT<br>GGGCCTTGCCGGCTGTCGGTATGTCGCGACAGA<br>GCACCCTGTACAGCTTCTTCCCCAAGTCTCCGG<br>CGCTGAGTGATGCCAACAAGGCCTCGGCCAGG<br>GCCTCACGCGAAGGCGGCCGTGCCGCCGCTGCC<br>CCCGGGGCCTCTCCTTCCCCAGGCGGGGATGCG<br>GCCTGGAGCGAGGCTGGGCCTGGGCCCAGGCC<br>CTTGGCGCGCTCCGCGTCACCGCCCAAGGCGAA<br>GAACCTCAACGGAGGGCTGCGGAGATCGGTAG<br>CGCCTGCTGCCCCACCAGTTGTGACTTCTCAC<br>CAGGAGATTTGGTTTGGGCCAAGATGGAGGGTT<br>ACCCCTGGTGGCCTTGTCTGGTTTACAACCACC<br>CCTTTGATGGAACATTCATCCGCGAGAAAGGGA<br>AATCAGTCCGTGTTCATGTACAGTTTTTTGATG<br>ACAGCCCAACAAGGGGCTGGGTTAGCAAAAGG<br>CTTTTAAAGCCATATACAGGTTCAAAATCAAAG<br>GAAGCCCAGAAGGGAGGTCATTTTTACAGTGC<br>AAAGCCTGAAATACTGAGAGCAATGCAACGTG<br>CAGATGAAGCCTTAAATAAAGACAAGATTAAG<br>AGGCTTGAATTGGCAGTTTGTGATGAGCCCTCA<br>GAGCCAGAAGAGGAAGAAGAGATGGAGGTAG<br>GCACAACTTACGTAACAGATAAGAGTGAAGAA<br>GATAATGAAATTGAGAGTGAAGAGGAAGTACA<br>GCCTAAGACACAAGGATCTAGGCGAAGTAGCC<br>GCCAAATAAAAAAACGAAGGGTCATATCAGAT<br>TCTGAGAGTGACATTGGTGGCTCTGATGTGGAA<br>TTTAAGCCAGACACTAAGGAGGAAGGAAGCAG<br>TGATGAAATAAGCAGTGGAGTGGGGGATAGTG<br>AGAGTGAAGGCCTGAACAGCCCTGTCAAAGTT<br>GCTCGAAAGCGGAAGAGAATGGTGACTGGAAA<br>TGGCTCTCTTAAAAGGAAAAGCTCTAGGAAGG<br>AAACGCCCTCAGCCACCAAACAAGCAACTAGC<br>ATTTCATCAGAAACCAAGAATACTTTGAGAGCT<br>TTCTCTGCCCCTCAAAATTCTGAATCCCAAGCC<br>CACGTTAGTGGAGGTGGTGATGACAGTAGTCGC<br>CCTACTGTTTGGTATCATGAAACTTTAGAATGG<br>CTTAAGGAGGAAAAGAGAAGAGATGAGCACAG<br>GAGGAGGCCTGATCACCCCGATTTTGATGCATC<br>TACACTCTATGTGCCTGAGGATTTCCTCAATTCT<br>TGTACTCCTGGGATGAGGAAGTGGTGGCAGATT<br>AAGTCTCAGAACTTTGATCTTGTCATCTGTTAC<br>AAGGTGGGAAATTTTATGAGCTGTACCACATG<br>GATGCTCTTATTGGAGTCAGTGAACTGGGGCTG<br>GTATTCATGAAAGGCAACTGGGCCCATTCTGGC<br>TTTCCTGAAATTGCATTTGGCCGTTATTCAGATT<br>CCCTGGTGCAGAAGGGCTATAAAGTAGCACGA<br>GTGGAACAGACTGAGACTCCAGAAATGATGGA<br>GGCACGATGTAGAAAGATGGCACATATATCCA<br>AGTATGATAGAGTGGTGAGGAGGGAGATCTGT<br>AGGATCATTACCAAGGGTACACAGACTTACAGT<br>GTGCTGGAAGGTGATCCCTCTGAGAACTACAGT<br>AAGTATCTTCTTAGCCTCAAAGAAAAAGAGGA<br>AGATTCTTCTGGCCATACTCGTGCATATGGTGT<br>GTGCTTTGTTGATACTTCACTGGGAAAGTTTTTC<br>ATAGGTCAGTTTTCAGATGATCGCCATTGTTCG<br>AGATTTAGGACTCTAGTGGCACACTATCCCCCA<br>GTACAAGTTTTATTTGAAAAAGGAAATCTCTCA<br>AAGGAAACTAAAACAATTCTAAAGAGTTCATT<br>GTCCTGTTCTCTTCAGGAAGGTCTGATACCCGG<br>CTCCCAGTTTTGGGATGCATCCAAAACTTTGAG | 3 |

TABLE 1-continued

Gene sequences used in the methods of the present invention

| Gene | GenBank Accession No. | Sequence | SEQ ID NO. |
|---|---|---|---|
| | | AACTCTCCTTGAGGAAGAATATTTTAGGGAAAA | |
| | | GCTAAGTGATGGCATTGGGGTGATGTTACCCCA | |
| | | GGTGCTTAAAGGTATGACTTCAGAGTCTGATTC | |
| | | CATTGGGTTGACACCAGGAGAGAAAAGTGAAT | |
| | | TGGCCCTCTCTGCTCTAGGTGGTTGTGTCTTCTA | |
| | | CCTCAAAAAATGCCTTATTGATCAGGAGCTTTT | |
| | | ATCAATGGCTAATTTTGAAGAATATATTCCCTT | |
| | | GGATTCTGACACAGTCAGCACTACAAGATCTGG | |
| | | TGCTATCTTCACCAAAGCCTATCAACGAATGGT | |
| | | GCTAGATGCAGTGACATTAAACAACTTGGAGAT | |
| | | TTTTCTGAATGGAACAAATGGTTCTACTGAAGG | |
| | | AACCCTACTAGAGAGGGTTGATACTTGCCATAC | |
| | | TCCTTTTGGTAAGCGGCTCCTAAAGCAATGGCT | |
| | | TTGTGCCCACTCTGTAACCATTATGCTATTAAT | |
| | | GATCGTCTAGATGCCATAGAAGACCTCATGGTT | |
| | | GTGCCTGACAAAATCTCCGAAGTTGTAGAGCTT | |
| | | CTAAAGAAGCTTCCAGATCTTGAGAGGCTACTC | |
| | | AGTAAAATTCATAATGTTGGGTCTCCCCTGAAG | |
| | | AGTCAGAACCACCCAGACAGCAGGGCTATAAT | |
| | | GTATGAAGAAACTACATACAGCAAGAAGAAGA | |
| | | TTATTGATTTTCTTTCTGCTCTGGAAGGATTCAA | |
| | | AGTAATGTGTAAAATTATAGGGATCATGGAAG | |
| | | AAGTTGCTGATGGTTTTAAGTCTAAAATCCTTA | |
| | | AGCAGGTCATCTCTCTGCAGACAAAAAATCCTG | |
| | | AAGGTCGTTTTCCTGATTTGACTGTAGAATTGA | |
| | | ACCGATGGGATACAGCCTTTGACCATGAAAAG | |
| | | GCTCGAAAGACTGGACTTATTACTCCCAAAGCA | |
| | | GGCTTTGACTCTGATTATGACCAAGCTCTTGCT | |
| | | GACATAAGAGAAAATGAACAGAGCCTCCTGGA | |
| | | ATACCTAGAGAAACAGCGCAACAGAATTGGCT | |
| | | GTAGGACCATAGTCTATTGGGGGATTGGTAGGA | |
| | | ACCGTTACCAGCTGGAAATTCCTGAGAATTTCA | |
| | | CCACTCGCAATTTGCCAGAAGAATACGAGTTGA | |
| | | AATCTACCAAGAAGGGCTGTAAACGATACTGG | |
| | | ACCAAAACTATTGAAAAGAAGTTGGCTAATCTC | |
| | | ATAAATGCTGAAGAACGGAGGGATGTATCATT | |
| | | GAAGGACTGCATGCGGCGACTGTTCTATAACTT | |
| | | TGATAAAAATTACAAGGACTGGCAGTCTGCTGT | |
| | | AGAGTGTATCGCAGTGTTGGATGTTTTACTGTG | |
| | | CCTGGCTAACTATAGTCGAGGGGGTGATGGTCC | |
| | | TATGTGTCGCCCAGTAATTCTGTTGCCGGAAGA | |
| | | TACCCCCCCCTTCTTAGAGCTTAAAGGATCACG | |
| | | CCATCCTTGCATTACGAAGACTTTTTTTGGAGA | |
| | | TGATTTTATTCCTAATGACATTCTAATAGGCTGT | |
| | | GAGGAAGAGGAGCAGGAAAATGGCAAAGCCTA | |
| | | TTGTGTGCTTGTTACTGGACCAAATATGGGGGG | |
| | | CAAGTCTACGCTTATGAGACAGGCTGGCTTATT | |
| | | AGCTGTAATGGCCCAGATGGGTTGTTACGTCCC | |
| | | TGCTGAAGTGTGCAGGCTCACACCAATTGATAG | |
| | | AGTGTTTACTAGACTTGGTGCCTCAGACAGAAT | |
| | | AATGTCAGGTGAAAGTACATTTTTTGTTGAATT | |
| | | AAGTGAAACTGCCAGCATACTCATGCATGCAAC | |
| | | AGCACATTCTCTGGTGCTTGTGGATGAATTAGG | |
| | | AAGAGGTACTGCAACATTTGATGGGACGGCAA | |
| | | TAGCAAATGCAGTTGTTAAAGAACTTGCTGAGA | |
| | | CTATAAAATGTCGTACATTATTTTCAACTCACT | |
| | | ACCATTCATTAGTAGAAGATTATTCTCAAAATG | |
| | | TTGCTGTGCGCCTAGGACATATGGCATGCATGG | |
| | | TAGAAAATGAATGTGAAGACCCCAGCCAGGAG | |
| | | ACTATTACGTTCCTCTATAAATTCATTAAGGGA | |
| | | GCTTGTCCTAAAAGCTATGGCTTTAATGCAGCA | |
| | | AGGCTTGCTAATCTCCCAGAGGAAGTTATTCAA | |
| | | AAGGGACATAGAAAAGCAAGAGAATTTGAGAA | |
| | | GATGAATCAGTCACTACGATTATTTCGGGAAGT | |
| | | TTGCCTGGCTAGTGAAAGGTCAACTGTAGATGC | |
| | | TGAAGCTGTCCATAAATTGCTGACTTTGATTAA | |
| | | GGAATTATAGACTGACTACATTGGAAGCTTTGA | |
| | | GTTGACTTCTGACAAAGGTGGTAAATTCAGACA | |
| | | ACATTATGATCTAATAAACTTTATTTTTTAAAA | |
| | | ATGAAAAAAAAAAAAAAAAAAAAAAAAA | |
| | | AAAAAAAAAAAAAAAAAAAAAAAAAAAA | |
| | | AAAAAAAAAAAAAAAAAAAAAAAAAAAAA | |
| | | AAAAAAAAAAAAAAAA | |

TABLE 1-continued

Gene sequences used in the methods of the present invention

| Gene | GenBank Accession No. | Sequence | SEQ ID NO. |
|---|---|---|---|
| PMS2 | NM_000535.6 | AGCCAATGGGAGTTCAGGAGGCGGAGCGCCTG TGGGAGCCCTGGAGGGAACTTTCCCAGTCCCCG AGGCGGATCGGGTGTTGCATCCATGGAGCGAG CTGAGAGCTCGAGTACAGAACCTGCTAAGGCC ATCAAACCTATTGATCGGAAGTCAGTCCATCAG ATTTGCTCTGGGCAGGTGGTACTGAGTCTAAGC ACTGCGGTAAAGGAGTTAGTAGAAAACAGTCT GGATGCTGGTGCCACTAATATTGATCTAAAGCT TAAGGACTATGGAGTGGATCTTATTGAAGTTTC AGACAATGGATGTGGGGTAGAAGAAGAAAACT TCGAAGGCTTAACTCTGAAACATCACACATCTA AGATTCAAGAGTTTGCCGACCTAACTCAGGTTG AAACTTTTGGCTTTCGGGGGGAAGCTCTGAGCT CACTTTGTGCACTGAGCGATGTCACCATTTCTA CCTGCCACGCATCGGCGAAGGTTGGAACTCGAC TGATGTTTGATCACAATGGGAAAATTATCCAGA AAACCCCTACCCCCGCCCCAGAGGGACCACA GTCAGCGTGCAGCAGTTATTTTCCACACTACCT GTGCGCCATAAGGAATTTCAAAGGAATATTAA GAAGGAGTATGCCAAATGGTCCAGGTCTTAC ATGCATACTGTATCATTTCAGCAGGCATCCGTG TAAGTTGCACCAATCAGCTTGGACAAGGAAAA CGACAGCCTGTGGTATGCACAGGTGGAAGCCC CAGCATAAAGGAAAATATCGGCTCTGTGTTTGG GCAGAAGCAGTTGCAAAGCCTCATTCCTTTTGT TCAGCTGCCCCCTAGTGACTCCGTGTGTGAAGA GTACGGTTTGAGCTGTTCCGATGCTCTGCATAA TCTTTTTTACATCTCAGGTTTCATTTCACAATGC ACGCATGGAGTTGGAAGGAGTTCAACAGACAG ACAGTTTTCTTTATCAACCGGCGGCCTTGTGA CCCAGCAAAGGTCTGCAGACTCGTGAATGAGG TCTACCACATGTATAATCGACACCAGTATCCAT TTGTTGTTCTTAACATTTCTGTTGATTCAGAATG CGTTGATATCAATGTTACTCCAGATAAAAGGCA AATTTTGCTACAAGAGGAAAAGCTTTTGTTGGC AGTTTTAAAGACCTCTTTGATAGGAATGTTTGA TAGTGATGTCAACAAGCTAAATGTCAGTCAGCA GCCACTGCTGGATGTTGAAGGTAACTTAATAAA AATGCATGCAGCGGATTTGGAAAAGCCCATGG TAGAAAAGCAGGATCAATCCCCTTCATTAAGGA CTGGGAGAAGAAAAAAAGACGTGTCCATTTCC AGACTGCGAGAGGCCTTTTCTCTTCGTCACACA ACAGAGAACAAGCCTCACAGCCCAAAGACTCC AGAACCAAGAAGGAGCCCTCTAGGACAGAAAA GGGGTATGCTGTCTTCTAGCACTTCAGGTGCCA TCTCTGACAAAGGCGTCCTGAGACCTCAGAAAG AGGCAGTGAGTTCCAGTCACGGACCCAGTGAC CCTACGGACAGAGCGGAGGTGGAGAAGGACTC GGGGCACGGCAGCACTTCCGTGGATTCTGAGG GGTTCAGCATCCCAGACACGGGCAGTCACTGCA GCAGCGAGTATGCGGCCAGCTCCCCAGGGGAC AGGGGCTCGCAGGAACATGTGGACTCTCAGGA GAAAGCGCCTAAAACTGACGACTCTTTTTCAGA TGTGGACTGCCATTCAAACCAGGAAGATACCG GATGTAAATTTCGAGTTTTGCCTCAGCCAACTA ATCTCGCAACCCCAAACACAAAGCGTTTTAAAA AAGAAGAAATTCTTTCCAGTTCTGACATTTGTC AAAAGTTAGTAAATACTCAGGACATGTCAGCCT CTCAGGTTGATGTAGCTGTGAAATTAATAAGA AAGTTGTGCCCCTGGACTTTTCTATGAGTTCTTT AGCTAAACGAATAAAGCAGTTACATCATGAAG CACAGCAAAGTGAAGGGGAACAGAATTACAGG AAGTTTAGGGCAAAGATTTGTCCTGGAGAAAAT CAAGCAGCCGAAGATGAACTAAGAAAAGAGAT AAGTAAAACGATGTTTGCAGAAATGGAAATCA TTGGTCAGTTTAACCTGGGATTTATAATAACCA AACTGAATGAGGATATCTTCATAGTGGACCAGC ATGCCACGGACGAGAAGTATAACTTCGAGATG CTGCAGCAGCACACCGTGCTCCAGGGGCAGAG GCTCATAGCACCTCAGACTCTCAACTTAACTGC TGTTAATGAAGCTGTTCTGATAGAAAATCTGGA AATATTTAGAAAGAATGGCTTTGATTTTGTTAT CGATGAAAATGCTCCAGTCACTGAAAGGGCTA AACTGATTTCCTTGCCAACTAGTAAAAACTGGA CCTTCGGACCCCAGGACGTCGATGAACTGATCT | 4 |

TABLE 1-continued

Gene sequences used in the methods of the present invention

| Gene | GenBank Accession No. | Sequence | SEQ ID NO. |
|---|---|---|---|
| | | TCATGCTGAGCGACAGCCCTGGGGTCATGTGCC | |
| | | GGCCTTCCCGAGTCAAGCAGATGTTTGCCTCCA | |
| | | GAGCCTGCCGGAAGTCGGTGATGATTGGGACT | |
| | | GCTCTTAACACAAGCGAGATGAAGAAACTGAT | |
| | | CACCCACATGGGGGAGATGGACCACCCCTGGA | |
| | | ACTGTCCCCATGGAAGGCCAACCATGAGACAC | |
| | | ATCGCCAACCTGGGTGTCATTTCTCAGAACTGA | |
| | | CCGTAGTCACTGTATGGAATAATTGGTTTTATC | |
| | | GCAGATTTTTATGTTTTGAAAGACAGAGTCTTC | |
| | | ACTAACCTTTTTTGTTTTAAAATGAACCTGCTAC | |
| | | TTAAAAAAATACACATCACACCCATTTAAAAG | |
| | | TGATCTTGAGAACCTTTTCAAACCAGATGGAGC | |
| | | ATTGCTTGCAAATTTTTTTCTCTATGTTTGCAT | |
| | | GCGCTCGTGTGTGTGTCCAGGCAAGAACACA | |
| | | TTTTATAAAAATAAGAACACTTGGGCTGGGCAT | |
| | | GGTGGCTCATGCCTGTGATCGCAGCACTTTGGG | |
| | | AGGCCGAGGCCGGCGGATCACCTGAGATCAGA | |
| | | AGTTCGAGACCAGCCTGACCAACATGGAGAAA | |
| | | CCCTGCCTCTACTAAAAATACAAAATTAGCCAG | |
| | | GTGTGCTGGCGCATGCCTGTAATCCCCGCTACC | |
| | | CAGGAGGCTGAGGCAGGAGAATCGCTTGAACC | |
| | | CGGGAGACGGAGGTTGCAGTGAACCGAGATTG | |
| | | CGCCACTGCGCTCCAGCCTGGGTGAGATAGAAC | |
| | | AAGACTGTGTCTCAAAAAACAAAACAAAACAA | |
| | | AACAAAAAAAAAAAACCAAACCACTTTGGAA | |
| | | GTTACTCAGGCCTCTGCTCTGGCTGGACATAGT | |
| | | TTAGTCTATAACTTTCAACCCTTAATGATAATTA | |
| | | AATTCATCTTTGTTTAATTTCATAAATTTAAAAG | |
| | | TAGGGTCCTTTTCAGTTAGTGATTCTCAGCCCTG | |
| | | ATTCACATTAAATTTTTAAACACGGGGATTCT | |
| | | CTGCCCGGCTGGAAGAAAATGACTGGATGGGA | |
| | | CAGGGGTCACTATTTGAAACATTCCTCTGTGCG | |
| | | GCCAAGGTCGCAAAATGCTGTCCTCGCAGGGG | |
| | | AACAAAAAGAGTTTGATTTCCCATAATTTGATG | |
| | | CTGTGATTTGGTTTCCTCAGGATGTGAACTGTA | |
| | | GAACATTCCAGTTACTGGCCTTGAATGGTTCTG | |
| | | GGAATATAAGAATCCCTGTCTGTCTTTTCAAAT | |
| | | AGTTTTCATGGAACCTTGTCCTGTTTGAACTTGG | |
| | | CTGAAAATGGAAGTAAAGATGCCCTCTTGGGG | |
| | | GCCCAGAGATGACAGATGTGGCTCCCCCTGCTG | |
| | | CCCCCACCCCTTCTCCAGACTGTGGGCGGCTCC | |
| | | CCTTCCTGCTTTAGAATCCCTCAGATGGAGGAG | |
| | | GCAGTACAGTAGTCACTGTGCCATCGTGTCTGG | |
| | | CACTGTGCTGGCGTGGTCTGCAGGATCCCACTT | |
| | | ATGAACTCTCCAGATTGGGAGCTGTGGCAGGAT | |
| | | AACAGCCCCCAAGACAGCTGTGTCCTAATCCCC | |
| | | AGAACCTGTGACCACGCTGCCTCACGTGGCAGA | |
| | | AGGGACTCGGCAGGTGTGATTGAGTGAAGGAT | |
| | | CTTTTTTTTTTTTCTTTGAGATGAAGTTTCGCT | |
| | | CTTGTTGCCCAGGCTGGAGTTCAATAGCATGAT | |
| | | CTCAGCTCACTGCAGCCTCTGCCTCCCAGGTTC | |
| | | AAGTGATTCTCCCACCTCAGCCTCCCGAGTAGC | |
| | | TGGGATTACAGGTGTCCAGAACCATACTGGCTA | |
| | | ATTTTTGTATTTTTAGTAGAGACAGGGTTTCACC | |
| | | ATGTTGACCAGGCTGGTCTCGAACTCCTGACCT | |
| | | CAGGTGATCCGACCGCCTCGGCCTCCCAAAGTG | |
| | | CTGGGATTACAGGTGTGAGCCATCATGCCTGGC | |
| | | TGAGTTAAGGATCTTGCAACAGAGAGATTATCC | |
| | | TGGATTGTCTGGGTGGGCCCAGTCCATTGGGTG | |
| | | AGTCCTTCAAAGGTGGAGACCTTTCCCTGCTGG | |
| | | CCAGAGAGAGGCTGTCTTGCTGGTTTTGGAGAT | |
| | | GGAAGGAGGTACCACTAGTCAAGGATTGCAAG | |
| | | CAGTCTCTAGAACAGGGATTCCAACACTCCGGA | |
| | | CACAGACCAGTAGTGGTCCATGGCCTATTAGGA | |
| | | AGTGGGGTGCACAGCAGGTTAGGGGCCGGCAA | |
| | | GCCAGCGAAGCTTCATCTGTATTTATAGCCACT | |
| | | CCCCGTCGCTGGCGTTACCACCCGAGCTCCGCC | |
| | | TCCTGTCACATCAGCGGTGGGCATTAGATTCTC | |
| | | ATAGCAGCACGAGCCCTATTGTGAACTGCACAC | |
| | | ACGAGGGATGTAGGTTGCACGCTCCTTATGAGA | |
| | | ATCTGATGCCTGATGATCTGTCACTGTCTCCCGT | |
| | | CACCCCAGATGGGGCTGTCTAGTTGCAGGAAA | |
| | | ACAAGCTCAGGGCTCCCACTGAGTCTCTGTGAT | |
| | | GGTGAGTTGTAGAATTATTTAATTATATGTTAC | |
| | | AATGTAATAATAGTAGAAATAAAGTGCACAAT | |

TABLE 1-continued

Gene sequences used in the methods of the present invention

| Gene | GenBank Accession No. | Sequence | SEQ ID NO. |
|---|---|---|---|
| | | AAATGCAATGCACTTGAATCGTCCTGAAACCAT CCCTCCCCGACCCCAATCCATGGAAAAATTGTG TTCCGCGAAACCGGTCTCTGGTGCCAAAAAGGT TGGGGACCGCTTCTGGAAAAGCTGGAAAAGGC AAGAAAACGCATTCTCTCCCTCAGCCTCTGGAA GGAACCAGCACTGTGGGACTAATTTACATACTG TAGGGTAATAAATTTGTGTTGCTTCGAACCACT AAAAAAAA | |
| EPM2AIP1 | NM_014805.3 | GCTTGCGCGTTAGAGATCGCTGTCCGCTCTTCC TATTGGTTCGTTTTTAGGAGCTCGGGGAATACG AAATATCCAGCCAATAGGAGCAGAGATGCCGG AACCGGGCTTGTGTGCCTCTGCTGAGGTGATCT GGCGCAGAGCGGAGGAGGTGCTTGGCGCTTCT CAGGCTCCTCCTCTCCCCTTGCGGCCTTTCTAAC GTTGGCCCTGCTCTTGTGGCCTCCCGCAGAATG TGGATGACGCCCAAAAGAAGCAAGATGGAAGT CGACGAGGCTCTAGTTTTCCGGCCCGAGTGGAC CCAGCGTTATTGGTGGTGGAGCCTCCGGAGGG CGATGGGGCCCTGTGCCTGGTCTGTCGCCGCCT CATCGTAGCTACCCGCGAACGCGACGTCAGGC GCCACTACGAGGCTGAGCACGAATACTACGAG CGGTATGTGGCGGACGGCGAGCGCGCGGCCCT GGTGGAGCGTCTGCGTCAGGGCGACTTGCCCGT GGCCTCCTTCACTCCTGAAGAGAGAGCTGCTCG TGCAGGCCTCGGGCTCTGCCGCCTCTTGGCCTT GAAGGGTCGCGGCTGGGGTGAGGGGGACTTTG TATACCAGTGCATGGAGGTGTTGCTGAGAGAG GTACTGCCCGAGCATGTAAGCGTCCTGCAAGGC GTTGACTTATCTCCAGATATCACAAGGCAGAGG ATCCTGAGCATTGACAGGAATCTACGCAACCAG CTTTTTAACCGAGCCAGGGACTTTAAAGCCTAT TCTCTTGCCTTGGACGACCAGGCTTTTGTGGCCT ATGAGAACTACCTCCTGGTCTTTATCCGCGGTG TAGGCCCTGAGTTGGAGGTGCAAGAAGATCTTC TGACCATAATCAACCTGACTCATCATTTCAGTG TTGGTGCGCTCATGTCGGCAATCCTAGAGTCCC TGCAGACAGCAGGGCTTAGCTTGCAGAGAATG GTTGGACTGACCACGACCCATACTTTGAGGATG ATTGGTGAGAACTCAGGACTCGTCTCATACATG AGAGAAAAGGCCGTAAGCCCCAACTGTTGAA TGTCATTCATTATTCAGGATTTCTTCACTTGGAA CTGTTGAGCTCCTATGATGTAGATGTTAATCAG ATCATAAATACCATATCCGAATGGATAGTTTTG ATTAAGACCAGAGGCGTTAGGCGACCTGAATTT CAGACTTTACTAACGGAATCTGAATCAGAGCAT GGTGAAAGGGTTAATGGACGATGTCTGAACAA TTGGCTTAGGAGAGGGAAAACTTTAAAACTAAT ATTCTCTCTAAGAAAAGAAATGGAAGCGTTCTT GGTTTCAGTAGGGGCAACAACAGTCCACTTCTC AGACAAACAATGGCTTTGTGACTTTGGCTTCTT GGTGGACATTATGGAACACCTTCGAGAACTCAG TGAAGAATTACGAGTTAGTAAAGTCTTTGCTGC TGCTGCCTTTGACCATATTTGTACTTTCGAAGTT AAGCTGAATTTATTTCAAAGACATATTGAGGAA AAAAATCTAACAGACTTTCCTGCCCTCAGAGAA GTTGTTGATGAGCTAAAACAGCAAATAAGGA AGATGAAAAATATTTGATCCTGATAGGTATCA AATGGTGATCTGTCGTCTCCAAAAAGAATTTGA GAGACATTTTAAGGACCTCAGGTTCATTAAAAA GGACTTAGAACTTTTTCAAATCCATTTAACTTT AAACCTGAATATGCACCTATTTCAGTGAGGGTG GAGCTAACAAAACTTCAGGCAAACACTAATCTT TGGAATGAATACAGAATCAAAGACTTGGGGCA GTTTTATGCTGGATTGTCTGCTGAATCCTACCCA ATTATCAAAGGGGTTGCCTGTAAGGTGGCATCC TTGTTTGATAGTAACCAAATCTGTGAAAAGGCT TTTTCATATTTGACTCGAAACCAACACACTTTG AGTCAGCCATTAACAGATGAGCATCTCCAAGCC CTGTTTCGGGTTGCCACAACTGAAATGGAGCCC GGTTGGGATGACCTTGTGAGAGAAAGAAATGA ATCTAATCCATAAGGCTTTGTAGTACAAGATTG AAAAACTCAACAAGAATTTAATTCTAAAAGCA AAAATTGGTTTGAGTTTTCAAGTTTACTAATTTG GATTGTGAGAAAGTACCAAGTACCAGCCGTCC | 5 |

TABLE 1-continued

Gene sequences used in the methods of the present invention

| Gene | GenBank Accession No. | Sequence | SEQ ID NO. |
|---|---|---|---|
| | | AAACTGATCACAATTAAAATTCTGACAGTTGCC | |
| | | TTTTTTTTCATCTCAAATGGCAGCATGGGACTG | |
| | | AAACATGAGAATGCCACCTTTTTTAAAACTTAG | |
| | | TTTAGTGACAAAGTCATTGTCTTTTATGATATA | |
| | | GTTAATTTTAAAGAGATTTAGTATTAATGTGAG | |
| | | TTGAATTTGCAGTCTGTTTTTAGGTGTTCTGAA | |
| | | GATAAATGCCAAAAATTTCAGCTCTTATTTTAA | |
| | | TGGAGTGTTAAAATTCTGATTCATATAGTCTTA | |
| | | AATTATCAACTCCTTAAATGTGCTTTTGAACCA | |
| | | ATTTGCAGAAGCTCACATAGCAAGTTCATAAGT | |
| | | TTCCAAAAAGGAAGCCCATACATAACAGTGGA | |
| | | GGTGTTTTGTCTAACCATCAAAATGTTTGAGAC | |
| | | TTTTTTTTAAACATTTCTGAGTTCGAAGGTAATA | |
| | | CTGACAGATTTCTTCCCTCTTCCCTCCCCATCAC | |
| | | CCACCTCAGTGATAACACATTACTGATAGAGGA | |
| | | AGTCATTAGAATCATTTTTAAGTTTCAGATATA | |
| | | GGAGACTTCATGCAATTTGGAGATAAGACTAAT | |
| | | TATTGGGGGTTTTCCTTGGATTTTTTTTTAATA | |
| | | ACTGGGGGCTATTTTATCAGCTTGCCTATTAAA | |
| | | GGACTATGGTAAGTATAGAATCTTAATGGTTGC | |
| | | CAGTTAGTAATTCTTTTTTTTTTTTTTTACTGT | |
| | | AGACACAAGTTTGGCCCTATCAAAAACGATGA | |
| | | GGAAAAAAGATTGCACTCCAGGATTAGGAGGT | |
| | | GTGAGATATTTTAGCTTTTTTGTCTTATCTGCGT | |
| | | GGGTATTGCTGCTTTATTTTAAAAAATCCTGCCT | |
| | | AAAGTAAACACTTTGTTTTAAAATGATACAGTA | |
| | | TCAGATTTTGTTAGATGCTAGAAATGGATTTAT | |
| | | TCTAAAATTTGGAACTGTCGTACACATTCTATA | |
| | | TGTAAGATAGCACACAAGTAGAAATATTTAAA | |
| | | AGCAGTCTTATTCACAGATTGCAGTAATTCTGT | |
| | | ATTTCTACTAAGATAATCTGCTTTGTGCCAAAA | |
| | | CAGTAATTTCCAAACTTCTGTTCACCATGAAAA | |
| | | GGCAATCTTAAAGTTCATTATGTAAAACTAATT | |
| | | ATAAACAGGACCCAATTTATATTCATAGATCCT | |
| | | CTCAAGTATTATACAATTTAAAAACTCTTGTTC | |
| | | CAAAGTCCTGTCTTAACTATTGAAACACCTTAA | |
| | | TCTGTGGTTACTAATCCAGCAAATTCAAGGAAC | |
| | | CAGGCTATGACTAAGAATTTAGGTGGAATTGAT | |
| | | GTCTGGGCAATTAAAATAAATGGCATAAGAGC | |
| | | TTAAAAACCAAAGTIGTGCCAGTGGCTTTCAAC | |
| | | TAGAGGCAGTAACCTGTCATTCCAGAGGATGCT | |
| | | GAGAAATGTGTAGGGGCACTTTTTTGGTTGTCA | |
| | | TATTTACTAGGGGCTTCTGTTGGCATTTAAGCCT | |
| | | AAAGACACTCACCCCTGCAGTGCATGGGACAG | |
| | | CCTGGCACAATGAAGAATTAGCCCTCCCAAAAT | |
| | | GTAGATTATTTTATTTCAAGGGATAGGGCAGAT | |
| | | TACCATTAGAAGCAAAATTAAAAGTACAAGCT | |
| | | GGGCAAACTGACAGAATACTAGATAGGAGAGA | |
| | | CTAATTCCAACCTTCTAAATTTGGCTAGTAAAG | |
| | | TGCAATAAAGGCATTGATAAGTTCTGTTAGCTC | |
| | | ACCATAGCACTTGTAAATCAGGAATTAATAATT | |
| | | GAATCAGATTTAAGGGCTCTGTCCTGTTATACA | |
| | | TATTTAAGGCAGAAAAAAAGTTACATGTCGATT | |
| | | AGGTACTTATCAAGAATGGTCAAGCTGAGATTT | |
| | | TGGTTAATAGAGTAAGCTTACATATCTAGAGAA | |
| | | ACAACATAGTGGAAAACCGAAAAAAAAAAACA | |
| | | GAAAAATCTACCGGTAATTTCCCAATAGCTTTG | |
| | | AATATTCACAGCAGAGCTTTATTACTTGAGAGA | |
| | | AAGACTGGAAGACCTGAAAGCCACTTCTGCTTT | |
| | | CTAACCCCAGTTCCTTAAATATTGAAATCTTGT | |
| | | ACATTTGTGAAATTCCAGTATGTTTTGCTTAAG | |
| | | GTGTTAATAAAATTAGTTTGCATCATGTAGTCA | |
| | | TTGAGTGAGGGGAGATATAAGCCAAGGATTT | |
| | | TAAATTGACCCTTAGCTATAGAGAATTTGCTAT | |
| | | AAGCTAGTCTTGTTTGTAAAAAAAAAAAAAA | |
| | | AAAAGAAAAGAAAAAGTGTATTTTACTGTTT | |
| | | TCTGTATTAAGTAATTCTGTAACTGCATGGCAG | |
| | | TCTTTTTTTTTTAAATAAATATAGTTGTTACTG | |
| | | GTCCTGTTGTAGCAGTGAATATAGTTAAAATAC | |
| | | GTACATTAAAAAAAAAATTATTAGGTCCTTACC | |
| | | AGTTACTGTCCTATAGCTCATTCCTACTAGTTTT | |
| | | CTTGACAGATTTGTATTCCCAGTGTCCCGTATTG | |
| | | CCACTCAAATTGCTCTACTATGCTAAGTCCTTGT | |
| | | TAATAGTCTTACCCTCCTTGAAACACTTGAACA | |
| | | CTTGATGACTTTAGCTTTGAGGAGATACCATCT | |

TABLE 1-continued

Gene sequences used in the methods of the present invention

| Gene | GenBank Accession No. | Sequence | SEQ ID NO. |
|---|---|---|---|
| | | CCAGGTGTGCTTTCTTAGTCTTTGCAGGCACCTC | |
| | | TTCCCTTCAATATCTGTTCTTCGTATTTTTAAAA | |
| | | AAATTTGTTTTAGACTGCCTTGTTCTGTGTCAGC | |
| | | TCGCTAGCTGATCTCATTTCCTTCCATGGTTTCC | |
| | | TTACCATTTATATGCAAATGACTGTCAGATTCA | |
| | | TATCTCCTTTCTAGATCTTCCCTAATTGATGTAT | |
| | | CTAATTGCTAACAAATGCTCTTTGCTGTCTCAG | |
| | | GCACTACATGTCATTGATCTTGCCCCCAATCCT | |
| | | GCTCCTCCTCTCATGTTTCCTCTTTGACTAAATG | |
| | | GCATTACCACTACCAACCATTCATTTGTCCTTTT | |
| | | TACCAATTCTCCAATGCTGCCATTTTAATTCAG | |
| | | GCCATCAACCTACCTAAATTATAGCAACAGCCT | |
| | | CCTTATTAGTCTCCCTGTTTTTTATTTTTATTCCT | |
| | | TTCTACACTACAACCAAATTGCTCCAAAAGACT | |
| | | TACTGATCATGTCACTGCATTGCTTTCACCATTG | |
| | | CTCTTAGGGTACAATACAAATTTATCTTCATCTT | |
| | | TAAGGTCTCAGTATGCCACTTCATCTAGGAAAC | |
| | | CTTCATTGATGCCCTCTAGATTAGGTGCCCTTAC | |
| | | TATCCATTCCCTATACACCCTGTTCTTTCCCAGA | |
| | | CATACACTTGGCACACTTTATTGTTACTGCTTAT | |
| | | TGATCACTGCTAGACTGTAAGCTTTGTAAGGGC | |
| | | AGGGACCATATAAGCCTTGTTCACTGTTATATC | |
| | | TCTAGTGCTTAGCACAATGCCTGGCATTTCAAT | |
| | | AAATGTTTGGACAAACGAATATTTGTGTAGTGT | |
| | | TTTACAATTTTTGAAGCTCTTTCACAGTCTTATT | |
| | | TGACCTTCACAGTCATTCTGCCTTAGACTGTCC | |
| | | ATTGGGTAACTTTTATCCACATATTACTAATTG | |
| | | AAAAATGAAGACAAGTTCTTTGTAACTAGGGA | |
| | | CCTCGTTGTATTCTCAGAATTTAGTGTAGTGCTT | |
| | | AGCATGTGACTTAAATATGTATTATGTGACTGT | |
| | | TAAACAAATTGTGGTTTTCTCTGTTGTATGAAA | |
| | | GGAGAGAAGGATAACAAATTGCGGTTTTCCCTG | |
| | | GTAAACACAGTAAGTAGTAAACTCAGGATTCA | |
| | | AAACCAAATATACACACCAAATCCACTATGTAA | |
| | | TATTAAGTTTGCATATCCATGTATAGAATCTTAT | |
| | | TTTTTTTTACCCTTTGTAAACAGTGTCATATATA | |
| | | TATATATATTTTTTTTTTTTTTTAAATTTCCAAA | |
| | | GGAACCTACATATAGAGGGAAAAGATTAGACA | |
| | | ACTACTTAGTGAACTAAAACAATATGTTTTTAC | |
| | | TAAATGTTACATTTAGTATTGGAAAAAGATAAT | |
| | | GCCGCCTAAGAGTTAATAATCATTTTTCCTTTTG | |
| | | TAGGCATCAACACTAGGAGAAAATGGCATGCT | |
| | | ATTTACTTGCTACTTTCCTTTACAGATGATTTTT | |
| | | GGCTCTTCTGGGATTTAAAAGTAAGTAAATTTA | |
| | | ACAAAGTAGAAGACTGACTCAGCCCTTCTGGTC | |
| | | ACTATATATTCAGTTCACTTGTTTTTACACCTGC | |
| | | AGAATGTCCTTATCACCCAAAGGGAGATGACCC | |
| | | AAAAGTGACATCTAGTTAATGTATACTTCTAAA | |
| | | GTTTGCTGTATTCCTTTGCCTTCTTGTTCCCATG | |
| | | CCTCTCTGAACTTAATTTCTGGGTAACTGAGGC | |
| | | TTTTCAGGCTTAGGTGGGAAAGCCACACCCTTA | |
| | | GTCTGTTTCCTTAAGCCATTTTGACCAATTTATG | |
| | | GGATTAACTAGTATAATCTTAGTTGGAGTTTTA | |
| | | GTCTGAGGCATATTAAGTCATTCAGAGATCTTA | |
| | | ACAGTAGGTGTCATAGTCATCCAGTGATTTGGT | |
| | | GCTTGCTGCAAAACTGGCTTTTTTTTTTTTTTTT | |
| | | TTTTTGAGGCGGGGTCTCACTTTGTCACCCAGG | |
| | | CTGGAGTGCAGAGGTACAATCTCAGCTCAATGC | |
| | | AATCTCTGCCTTCCTGGCTCAAGCAATTCTCCC | |
| | | ACTGCAGCCTCCTAAGTAGCTGGGAATACAGGT | |
| | | ATACACGAGTACACCCAGCTAATTTTTGTATTT | |
| | | TTATGTGGAGACAGGGTCTTGCTGTATTCCCCA | |
| | | GGCTAGTCTCGAATTCCTGGACTCAAGCAGTCC | |
| | | GCCCGCCTCGGGCTCCCAAAATGTTGGTGTTAT | |
| | | ACGTGTGAGCCTCTGCACCCGGCGGCAAAACTG | |
| | | GCTTTTAATCAACCTTTTGGCTAAAGGATTTCTC | |
| | | TTTTTATTTATTTGTAAAAGGATTTCCCATTTTT | |
| | | ATCTTTCTTTTTGATATTAAAATGTTGCCTCATC | |
| | | CTACCCAGTAAGTACTTGAATTTGAATTCTCTTC | |
| | | CTTTTCATTTTTGCCTGCAAACTGACCAGTCTTT | |
| | | TCTGAGTTCATCTCTTCTGTACGTTTTGTCAAGT | |
| | | GCAGTGAACAGCAACTACAAAATATTTTGTTTT | |
| | | TCTGTCTTTTTCTTTAGTAAAGGGTAGATGATCT | |
| | | GCCTTTCAGGTTATCTCAAGGGGCAGTTTCACC | |
| | | TTTCCATAATATAAATTACCCTTGTGTAAGTTAT | |

TABLE 1-continued

Gene sequences used in the methods of the present invention

| Gene | GenBank Accession No. | Sequence | SEQ ID NO. |
|---|---|---|---|
| | | TTCTTCCATCTTCTGATAGCAATTTCCTGAATGC<br>CTGCCAGCTAACCATTAAGCCAGTGTTCAGTAT<br>TTTAGCATTTTAAAAAACAAGGGACCAATTTCT<br>GTGTCAGCATGGGCTAGCTTGCCATTGAATAAC<br>AAAGGCAAAATCTCACTGTCTCACACAACTTTT<br>CTATTGCAACTTGCCTAGGGACTTTGGTTTAGA<br>TCATAGGTTGGCCATGATCAAACTATGGTCCAT<br>GGGCAAAATCTGTCTAGCTCCTTATTTATCTAA<br>ATAAAGTTTTACTGGAATATA | |
| TTC30A | NM_152275.3 | GCGGCGCCACAGGAACGATGCATGCCGGGACC<br>GGGAAGATTCAGTCTCTGAACGGCCCGGAGTA<br>GTCGTCTTTCCCCTTCTGACTGCCGCCACGCTGC<br>AGTCCAGAATATTTGAAGATCAAACCGAACTTG<br>AGAGACTAACGAGAACGGTCCCTTTTTATTCCT<br>AACAGATTCCTTCCGTGGCAAAGTAACCCGTCG<br>TCTTCCGTTTCCGGTTGCCCGGTTGCCCTGTTGC<br>CGTGGTAACCGCACGCATAACAGCCGTGGTGGT<br>TATGGCTGGTCTGAGCGGCGCGCAGATCCCCGA<br>CGGGGAGTTTACCGCGCTAGTGTACCGGCTCAT<br>CCGCGATGCCCGCTACGCCGAGGCGGTGCAGCT<br>GCTGGGCCGAGAACTGCAGCGGAGCCCCAGGA<br>GCCGTGCCGGCCTGTCGCTGCTAGGCTACTGCT<br>ACTACCGCCTGCAGGAGTTCGCGCTGGCGGCCG<br>AGTGCTATGAGCAGCTGGGCCAGCTGCACCCG<br>GAACTGGAGCAGTACCGCCTGTACCAGGCCCA<br>GGCCCTGTACAAGGCCTGCCTTTATCCGGAGGC<br>CACTCGGGTCGCCTTCCTTCTCCTGGATAACCC<br>CGCCTACCACAGCCGGGTCCTCCGCCTGCAAGC<br>TGCCATCAAGTATAGCGAGGGCGATCTGCCAG<br>GGTCCAGGAGCCTGGTGGAGCAGCTGCTGAGT<br>GGGGAAGGGGGAGAAGAAAGTGGAGGCGACA<br>ATGAGACCGATGGCCAGGTCAACCTGGGTTGTT<br>TGCTCTACAAGGAGGGACAGTATGAAGCTGCA<br>TGCTCCAAGTTTTCTGCCACACTGCAGGCCTCG<br>GGCTACCAGCCTGACCTTTCCTACAACCTGGCT<br>TTGGCCTATTACAGCAGCCGACAGTATGCCTCA<br>GCACTGAAGCATATCGCTGAGATTATTGAGCGT<br>GGCATCCGCCAGCATCCTGAGCTAGGTGTGGGC<br>ATGACCACCGAGGGCTTTGATGTTCGCAGTGTT<br>GGCAACACCTTAGTTCTCCATCAGACTGCTCTG<br>GTGGAAGCCTTCAACCTTAAGGCAGCCATAGA<br>ATACCAACTGAGAAACTATGAGGTAGCTCAAG<br>AAACCCTCACCGACATGCCACCCAGGGCAGAG<br>GAAGAGTTGGACCCTGTGACCCTGCACAACCA<br>GGCACTAATGAACATGGATGCCAGGCCTACAG<br>AAGGGTTTGAAAAGCTACAGTTTTTGCTCCAAC<br>AGAATCCCTTTCCTCCAGAGACTTTTGGCAACC<br>TGTTGCTGCTCTACTGTAAATATGAGTATTTTGA<br>CCTGGCAGCAGATGTCCTGGCAGAAAATGCCC<br>ATTTGACGTATAAGTTCCTCACACCCTATCTCTA<br>TGACTTCTTAGATGCCCTGATCACTTGCCAGAC<br>AGCTCCTGAAGAGGCTTTCATTAAGCTTGATGG<br>GCTAGCAGGGATGCTGACTGAGCAGCTTCGGA<br>GACTCACCAAGCAAGTACAGGAAGCAAGACAC<br>AACAGAGATGATGAAGCTATCAAAAAGGCAGT<br>GAATGAATATGATGAAACCATGGAGAAATACA<br>TTCCTGTGTTGATGGCTCAGGCAAAAATCTACT<br>GGAATCTTGAAAATTATCCAATGGTGGAAAAG<br>GTCTTCCGCAAATCTGTGGAATTCTGTAACGAC<br>CATGATGTGTGGAAGTTGAATGTGGCTCATGTT<br>CTGTTCATGCAGGAAAACAAATACAAAGAAGC<br>CATTGGTTTCTATGAACCCATAGTCAAGAAGCA<br>TTATGATAACATCCTGAATGTCAGTGCTATTGT<br>ACTGGCTAATCTCTGTGTTTCCTATATTATGACA<br>AGTCAAAATGAAGAAGCAGAGGAGTTGATGAG<br>GAAGATTGAAAAGGAGGAAGAGCAGCTCTCTT<br>ATGATGACCCAAATCGGAAAATGTACCATCTCT<br>GCATTGTGAATTTGGTGATAGGAACTCTTTATT<br>GTGCCAAAGGAAACTATGAGTTTGGTATTTCTC<br>GAGTTATCAAAAGCTTGGAGCCTTATAATAAAA<br>AGCTGGGAACAGATACCTGGTATTATGCCAAA<br>AGATGCTTCCTGTCCTTGTTAGAAAACATGTCA<br>AAACACATGATAGTCATTCATGACAGTGTTATT<br>CAAGAATGTGTCCAGTTTTTAGGACACTGTGAA | 6 |

TABLE 1-continued

Gene sequences used in the methods of the present invention

| Gene | GenBank Accession No. | Sequence | SEQ ID NO. |
|---|---|---|---|
| | | CTTTATGGCACAAACATACCTGCTGTTATTGAA<br>CAACCCCTCGAAGAAGAAAGAATGCATGTTGG<br>GAAGAATACAGTCACAGATGAGTCCAGACAAT<br>TGAAAGCTTTGATTTATGAGATTATAGGATGGA<br>ATAAGTAGTTATGACTGATAGTGGCTTTTTTCA<br>AAATGGCTTTCTTACGTACCACACTTTTTTTAT<br>CTGTATTTAGCCTTGGCATCTTTATATTTGTCTT<br>ATTTTGAATCTTATCCACTTTGTAAGAACAAGT<br>TTATGTTTGAGCAACTTTTTCATTTAATCCAGAA<br>GGGTAGGGACTATGCAGTGTAAGCTGCATCACT<br>TCTGCTTTCTTCCTACTAGTGACAATCATCTGGT<br>CTTGCCCTCAAGCAACAATTGCTAGAGTAACAT<br>CTTTGTATAAGCAAGTAACCCCAGATAGAGTTG<br>ACGTTTCAGCTTTGGGCTGTCAAAAGGGTATGT<br>CATGGACCAAAGCACTGTTAGTACGGGTATGTT<br>TGCATTTGGTCACTGATATGTAAATGACTGCTA<br>GCCCACGGCTGGACCACTTCTCAATCAGCAAAT<br>AAAGCCATGTCTATTTTGCTATCTCAGCATAGA<br>CTATGCTGTCTGATAAATCTAATTCTTAACTCTA<br>TTTCTCCAGTTTTTTAGTCCTTTAACTTTCTGGA<br>TTGCAACGAAGTCTAGTTTAGACCTCTAAGCCC<br>TTTTAGAAGTACAAGTATAATGGGAATTTCTTT<br>TCTTGGTTCTTTTCAGGTTATGAGGTTTGGTCAG<br>TGACAAAATTTTTTTCATAATTTGGTTGATTGG<br>TTGCTTCTTAAGTTTTATAATAAACGTTTTTCTT<br>CATGTTCTATTTTGATTTTACAGAAATGATTTT<br>GCCTCCTTGTGGATACTGACATATATTAAGTGT<br>GGAAGCTTATTAATATTTTGGTTTTTTAAAAAC<br>TGAAATTTTTAATTTTTACTTTTTAATTTTTTAG<br>GAAAAAATAAGCACTGAACTGAGAATGAGAAG<br>AATAAAAGTATGAGTTCCATACCTTCTAATTTT<br>AGGCTGTCAGAAATTCCTTTATTCTTTGGGATTT<br>CACAATCATTTGAACTATCAGAAGCCTTTACAA<br>TTACTTTTAGCTGTAACATCCGATTCTGTATAAG<br>CCACATAGAAAAAAGTTGCCTTTCTTTTTTTATG<br>ACCTGGATATATAAGCAAATCAGCTAGGAAAT<br>ATATAATTGTATTTTATATTAATGTTTTCTAGGA<br>TTTTGGCTTACAGTAAATGTTAACCCCTATGGT<br>AAGTGATTGTTATTGTTGGATGTTATACTGATT<br>ATTAATAAGAAATTTGGATTTTTGCCTTTTTACC<br>TGGAATTTTTGCTTACAGCCGTAGCTATGAATA<br>TATATAGGGTGGTCCCCAGTCTCTGTTATGGTT<br>GCGCATAAATTAATAATTTTATAAGTATTTAGA<br>AATGGTATAATTCTCTTAACTTCCTCTTTCAGTT<br>TTTGTACTAATGTTTGTTTTTGTTCGGGAAGAGG<br>AGATTTGCTTTTAATCCTTCCAAAAAATGATGA<br>ACCACCGTTCCATTCAGTAGTTTGACAAGCTGT<br>TATAATGTGTATTTTTCCTCAATTATTCTTGAA<br>ATATTTAGAGCCTCTCCTGCTTCTAACATGAAG<br>GCCTTTAGATGCCAGTCTGCCAGAAATCTGGAA<br>ACAGAGGAACCGGTGAAGTGAAGATGTAATGG<br>AGATTTAGCTAATGATGTACTTCACAATCCACC<br>TTGGATCTCCTGCATGTCCAAATCTCAGTAGTT<br>AATCAAGTGTCTGCTGCCATTAACAGAACAGAA<br>GTAATGGATAACAGAATGGAAATAAGAGATGC<br>CAGAACTACTTCCATAACTAACTCACCAAATCA<br>AATCATCAGTCCTCATATTCTTGTTTTATTTAAT<br>ACAAGGAGAAGAGGCCATGCACTTTTCCAAAAG<br>GTCAAAGCCACATAGAATAGGAAGGCAATCTC<br>TAGTTTAAAGCTTTCTCTTGGAGTGTTTTCTCCC<br>CCTGTCTTCAAAGGGTCTACTTGAGAGATAGTG<br>GTGTTTACTGCTGCAGCATGTATCACAAGATAA<br>GAAATGAAAAATCAATCTTTCTTACCACCCTGT<br>TCTCTTTCCCTTTTTTATCTTTTCCCTTTTGTCAA<br>TTATAGAATTATAGGGACATTTTTCTCTGATAG<br>CTGGAAGTTGAACCTCAACCAGGTATAAAAGA<br>TGCATAACAACCTTTTAGCAGTAAGTGTCAAGT<br>GAGTGAGCACTATGATTATCAAGGTGACTTTGG<br>AAACCTTTTAAAAATGCATTTTTGCAAAACAAG<br>ATAACATATATTGATAAAAAGTGACTCTCAGAT<br>TGGTAATGCCAGAAAAAATTTTAAGAGGACTC<br>ACCAAAAGTACTAGATCTATGTAAGTTGTAGAA<br>TAGAGTGAAGTTTTTTTATATATTTGTGGTAGCC<br>TCCATCTTTTAAACTTTTTGAACTCAGTAGAAA<br>AACAGACTGAAATTTTAAAGACATGCAGTATTT | |

TABLE 1-continued

Gene sequences used in the methods of the present invention

| Gene | GenBank Accession No. | Sequence | SEQ ID NO. |
|---|---|---|---|
|  |  | GTATCATTTTAAATTCTGTAACACTGGGAATTA AATATACTCAACTTTAGAGGAAAAAAAAAAAA AAAAAA |  |
| SMAP1 | NM_001044305.2 | GACCCAGTCCCCCTCCCCCTCCCCTCGCCGGCT AGGGTGGTGCGTGCCGGCAGGCCGGTCAAGGA GGCGGGACACGTCGGCGCTACCACCGCCACCG CCGCCGCCGCCCCTCCTCCCGTTCCAGCTGCCG CTGCCGCTTCCTGGGCTGAGTCCGCCCGCGGTC CCGGCGGCGCCAGGTGCGTTCACTCTGCCCGGC TCCAGCCAGCGTCCGCCGCCGCCGTAGCTGCCC CAGGCTCCCCGCCCCGCTGCCGAGATGGCGACG CGCTCCTGTCGGGAGAAGGCTCAGAAGCTGAA CGAGCAGCACCAGCTCATCCTATCCAAGCTTCT GAGGGAGGAGGACAACAAGTACTGCGCCGACT GCGAGGCCAAAGGTCCTCGATGGGCTTCCTGGA ATATTGGTGTGTTTATTTGCATCAGATGTGCTG GAATTCATAGAAATCTTGGGGTTCATATATCCA GGGTCAAATCAGTCAACCTAGACCAATGGACA GCAGAACAGATACAGTGCATGCAAGATATGGG AAATACTAAAGCAAGACTACTCTATGAAGCCA ATCTTCCAGAGAACTTTCGAAGACCACAGACAG ATCAAGCAGTGGAATTTTTCATCAGAGATAAAT ATGAAAAGAAGAAATACTACGATAAAAATGCC ATAGCTATTACAAATATTTCCTCCTCTGATGCTC CTCTTCAGCCTTTGGTATCCTCTCCTTCTCTGCA AGCTGCTGTTGACAAAAATAAATTGGAGAAAG AAAAGGAAAAAAAAAAGGAAGAGAAAAAGAG AGAAAAGGAGCCAGAAAAGCCGGCAAAACCAC TTACAGCTGAAAAGCTGCAGAAGAAAGATCAG CAACTGGAGCCTAAAAAAAGTACCAGCCCTAA AAAAGCTGCGGAGCCCACTGTGGATCTTTTAGG ACTTGATGGCCCTGCTGTGGCACCAGTGACCAA CGGGAACACAACGGTGCCACCCCTGAACGATG ATCTGGACATCTTTGGACCGATGATTTCTAATC CCTTACCTGCAACTGTCATGCCCCCAGCTCAGG GGACACCCTCTGCACCAGCAGCTGCAACCCTGT CTACAGTAACATCTGGGGATCTAGATTTATTCA CTGAGCAAACTACAAAATCAGAAGAAGTGGCA AAGAAACAACTTTCCAAAGACTCCATCTTATCT CTGTATGGCACAGGAACCATTCAACAGCAAAG TACTCCTGGTGTATTTATGGGACCCACAAATAT ACCATTTACCTCACAAGCACCAGCTGCATTTCA GGGCTTTCCATCGATGGGCGTGCCTGTGCCTGC AGCTCCTGGCCTTATAGGAAATGTGATGGGACA GAGTCCAAGCATGATGGTGGGCATGCCCATGCC CAATGGGTTTATGGGAAATGCACAAACTGGTGT GATGCCACTTCCTCAGAACGTTGTTGGCCCCCA AGGAGGAATGGTGGGACAAATGGGTGCACCCC AGAGTAAGTTTGGCCTGCCGCAAGCTCAGCAGC CCCAGTGGAGCCTCTCACAGATGAATCAGCAG ATGGCTGGCATGAGTATCAGTAGTGCAACCCCT ACTGCAGGTTTTGGCCAGCCCTCCAGCACAACA GCAGGATGGTCTGGAAGCTCATCAGGTCAGACT CTCAGCACACAACTGTGGAAATGAAAACTGCA ATACAAGTTTCATCCAGAACTACCACCTGACAT TCCTTGCTGAAACGCATCTAGTTCCCCTGTTTAT TCATATGCATATTTTTTTCTTTTTACCCATTTGT TCATATTAAGAATGATCTGATTGACCGTGTTGG TCTGTACTGATTCAATTTGATGTGGTGAAAAGC AGGTTGATAAATCATTTTATGTCAAGGGCAGCT TTGCTCATATTTCCCATGATTTCATGTACTGCAT TATTTGAGAAGCTGCTCAACTTGCAAAATCAGT TTTCCTCTCAATAAAATTATAGCTCTAATGTTTG CATATAAGGGAAGTAGTTATCATGTTAGTAATA CCTCTAATAGTATAAACCCCACCCCAAAATTAG CCAGTAATCCTGTAGGAAGGTACTGTATGATCA AATGTTTAATCATATAAATAGAATGTAAATGTC TCACTGAGCACTGTTTTCTAGTGTATCAAAATG CTCTTATTTCATCATTCACTTCACTGTGCTGTTG TTATGATGTGCTTAACAGGGAACGTGATTAGTG AAAGGAAGATAAACGTGGATGTTACTCCAAAA CTTCGTTTAATGAATGCTTAAAGAATTCAAATT TTATCTGCCTCTCTTGTAATTTGGATCTCTTCTT AATGTACATAGTGCTAACATGAAGACCTTTTTC | 7 |

TABLE 1-continued

Gene sequences used in the methods of the present invention

| Gene | GenBank Accession No. | Sequence | SEQ ID NO. |
|---|---|---|---|
| | | TGCACTATATGCAAACAGGGTAACTAACTAAA<br>ACAAAGCCACTTTCAATCTTCAATCCTTGAAGG<br>TATATCTAGGTTTATGACAGTAATTGTGTTTAC<br>ATTTTATGGTGCCTAGTATTGACAAAATGTTAT<br>TTCCCTACATTAAACATGACTCCATAGACCTTTT<br>CATTTGTGGGTTTTTATTTCCTATGATGTATACT<br>GCCACTAACCTTCCAAAAATTACTTAGTATTGC<br>AAAGTCAGGAATCATCAGGAACGTTTAGCTGA<br>CAAAATACTTGTCTGTTTTAAAAACCTGTTCAA<br>GTCTACCAACCTGTTCAAGTCTACCAATTATAA<br>GGGCAAATTGGAGAAAAGAAAAAATATATAC<br>TCAAGAGTGGTATCTTGCAGTATCGGCACTGTA<br>CAAAAAAATCTTCCAATTTAGTTGTTGTAGAGA<br>AAACATGCAGAACAAATGAAGACAAAACATAC<br>ATTTTGTACCAACCATCCAATTAGCTTATGTTA<br>ACTGACAAGCTCCATTTAAACAGATGTCCATCA<br>GATGACAAGAAAGGCTGCTGTACTGAAGTAAA<br>ACAAACAATACCTGAATGCTCTGTAGCCTAAAC<br>TCCAAACATCCTCTTCCATATGGATCCACTGGC<br>TGGACAAACTGCACCAGTTGCTGCTTCAATTTA<br>TACCTCAATTTTCACTGTGTCCAGGTGGTACTTT<br>GGCTCGTTGGCTAGATTAACCTTCTCTGTCCGA<br>GTGTGCCACACGAGAACCTGAAGGGGAAGGAA<br>ATAGCTTGGGTAGCGCACTCTTCATGGTGACAC<br>TCGAGGTCGGGCAGCACAAGTGTAATGAATAC<br>CTTAGTGCAGTTATTTGCTTTCGGTTCCAGTTCT<br>TCGACTGTTGTTATCTGTTTGAGAAAGTCAGAT<br>TCTTGCATCCCTGGCTGGGATCCACGACGCTTA<br>AATACAGCTTTTGGATTGGACAAAATGACTTGA<br>AGACTTACAGCAAATCCTTTGTGAAAAATAAAA<br>AAAAAAAAGAGACTTTAAAAAAAAAAAAAAA | |
| RNLS | NM_001031709.2 | AAAGCTCAGGGCCCAGGTCGGCCCAGGGAGCA<br>CGGAACCAAAGAGCGCTAGCGCCGGTTCGGCC<br>GCCTTTCCAGAAAGCCCGGGCCGAACGGCCCC<br>GCCGCAGAGACTCAGCGCGGATCGCTGCTCCCT<br>CTCGCCATGGCGCAGGTGCTGATCGTGGGCGCC<br>GGGATGACAGGAAGCTTGTGCGCTGCGCTGCTG<br>AGGAGGCAGACGTCCGGTCCCTTGTACCTTGCT<br>GTGTGGGACAAGGCTGAGGACTCAGGGGGAAG<br>AATGACTACAGCCTGCAGTCCTCATAATCCTCA<br>GTGCACAGCTGACTTGGGTGCTCAGTACATCAC<br>CTGCACTCCTCATTATGCCAAAAAACACCAACG<br>TTTTTATGATGAACTGTTAGCCTATGGCGTTTTG<br>AGGCCTCTAAGCTCGCCTATTGAAGGAATGGTG<br>ATGAAAGAAGGAGACTGTAACTTTGTGGCACCT<br>CAAGGAATTTCTTCAATTATTAAGCATTACTTG<br>AAAGAATCAGGTGCAGAAGTCTACTTCAGACA<br>TCGTGTGACACAGATCAACCTAAGAGATGACA<br>AATGGGAAGTATCCAAACAAACAGGCTCCCCT<br>GAGCAGTTTGATCTTATTGTTCTCACAATGCCA<br>GTTCCTGAGATTCTGCAGCTTCAAGGTGACATC<br>ACCACCTTAATTAGTGAATGCCAAAGGCAGCA<br>ACTGGAGGCTGTGAGCTACTCCTCTCGATATGC<br>TCTGGGCCTCTTTTATGAAGCTGGTACGAAGAT<br>TGATGTCCCTTGGGCTGGGCAGTACATCACCAG<br>TAATCCCTGCATACGCTTCGTCTCCATTGATAAT<br>AAGAAGCGCAATATAGAGTCATCAGAAATTGG<br>GCCTTCCCTCGTGATTCACACCACTGTCCCATTT<br>GGAGTTACATACTTGGAACACAGCATTGAGGAT<br>GTGCAAGAGTTAGTCTTCCAGCAGCTGGAAAAC<br>ATTTTGCCGGGTTTGCCTCAGCCAATTGCTACC<br>AAATGCCAAAAATGGAGACATTCACAGGTTAC<br>AAATGCTGCTGCCAACTGTCCTGGCCAAATGAC<br>TCTGCATCACAAACCTTTCCTTGCATGTGGAGG<br>GGATGGATTTACTCAGTCCAACTTTGATGGCTG<br>CATCACTTCTGCCCTATGTGTTCTGGAAGCTTTA<br>AAGAATTATATTTAGTGCCTATATCCTTATTCTC<br>TACATGTGTATTGGGTTTTTATTTTCACAATTTT<br>CTGTTATTGATTATTTTGTTTTCTATTTTGCTAA<br>GAAAAATTACTGGAAAATTGTTCTTCACTTATT<br>ATCATTTTTCATGTGGAGTATAAAATCAATTTT<br>GTAATTTTGATAGTTACAACCCATGCTAGAATG<br>GAAATTCCTCACACCTTGCACCTTCCCTACTTTT<br>CTGAATTGCTATGACTACTCCTTGTTGGAGGAA | 8 |

TABLE 1-continued

Gene sequences used in the methods of the present invention

| Gene | GenBank Accession No. | Sequence | SEQ ID NO. |
|---|---|---|---|
| | | AAGTGGTACTTAAAAAATAACAAACGACTCTCT<br>CAAAAAAATTACATTAAATCACAATAACAGTTT<br>GTGTGCCAAAAACTTGATTATCCTTATGAAAAT<br>TTCAATTCTGAATAAAGAATAATCACATTATCA<br>AAGCCCCATCTTAAGTCTTCGGATGTGTCCTTG<br>AATCAATATTTTTGCAAATTATACAAAACAAGA<br>TTTTTCCAAAATGTAGGTAACAGAGTGTAATTC<br>TTATTTCTCATTTATCCCCCAAGTTATTAAGTGA<br>TCCTGAATTGTAGGTCATATATGTCATCATCTTA<br>GTGTGGAGGGCAACTTGACTGATAAAGAGACC<br>TTCCTTCAGATTTTCAGAAAGTATAAGATTCCA<br>CATGATTTTCCCAGCCACACAGTACTTTTTAACT<br>TTCAAACAAATTCCAGTCCTAATATGAAAGATA<br>AAAATTAAATAGAAACAGAGAGAAAGTATATC<br>GATCCTTACCTTTTGCTATATTTTATAGCTGTTG<br>CTGTTACTTTATGGGTTCTCCAGTATGTGCTGTG<br>GCATTTAGACTGTGTCGAGTTTAATGAATTTAA<br>CACAACAAAAAATTTACTGAACCAGAAAATAG<br>ATGCACTTAAAATAGTTCAATATTTGCCAAGTT<br>GGTGGTTCAGCATATCACCCACATGCTTCAGTG<br>ACCTGACCCCACGACTTGCTAGCTGGAGAGAA<br>ATCAATCTCCAGCCTTCCAAACCAGCTACCTGT<br>TGCTAATTTGAAAAGCAAAATGATGAGTTCTAT<br>TCAGCATTTTGAAAGGAGAAAAATCATTGCAG<br>CCTCTCAAACTAACAAAAGTTCAACAAAAGACT<br>TCTTACTGTAATAGTGTTTAAAGTTTCACACTTA<br>CATGTCCACTGTCATACATACACATACACAGGC<br>ACAGGCAGAACTTGCTTCTATAGCTGCAAAGTG<br>GGTTTTATGACCCTATAGCATATTATTATATGTT<br>TCCTCTTAGCAATAAATTGGTGAAAAACTTAAA<br>TGCCAAAAAA | |
| WNT11 | XM_011545241.2 | CCGGGCCTTTGCCGACATGCGCTGGAACTGCTC<br>CTCCATTGAGCTCGCCCCCAACTATTTGCTTGA<br>CCTGGAGAGAGGACACCAGCCACTGGCCTAGG<br>GCCCACCCTGATCCGGTATGACCTCGTCTCAGC<br>CCCATTACATCTGCAAAGACCCCACTTCGTCAT<br>AAGATTATGCTCACAGGGACCCGGGAGTCGGC<br>CTTCGTGTATGCGCTGTCGGCCGCCGCCATCAG<br>CCACGCCATCGCCCGGGCCTGCACCTCCGGCGA<br>CCTGCCCGGCTGCTCCTGCGGCCCCGTCCCAGG<br>TGAGCCACCCGGGCCCGGGAACCGCTGGGGAG<br>GATGTGCGGACAACCTCAGCTACGGGCTCCTCA<br>TGGGGGCCAAGTTTTCCGATGCTCCTATGAAGG<br>TGAAAAAAACAGGATCCCAAGCCAATAAACTG<br>ATGCGTCTACACAACAGTGAAGTGGGGAGACA<br>GGCTCTGCGCGCCTCTCTGGAAATGAAGTGTAA<br>GTGCCATGGGGTGTCTGGCTCCTGCTCCATCCG<br>CACCTGCTGGAAGGGGCTGCAGGAGCTGCAGG<br>ATGTGGCTGCTGACCTCAAGACCCGATACCTGT<br>CGGCCACCAAGGTAGTGCACCGACCCATGGGC<br>ACCCGCAAGCACCTGGTGCCCAAGGACCTGGA<br>TATCCGGCCTGTGAAGGACTCGGAACTCGTCTA<br>TCTGCAGAGCTCACCTGACTTCTGCATGAAGAA<br>TGAGAAGGTGGGCTCCCACGGGACACAAGACA<br>GGCAGTGCAACAAGACATCCAACGGAAGCGAC<br>AGCTGCGACCTTATGTGCTGCGGGCGTGGCTAC<br>AACCCCTACACAGACCGCGTGGTCGAGCGGTG<br>CCACTGTAAGTACCACTGGTGCTGCTACGTCAC<br>CTGCCGCAGGTGTGAGCGTACCGTGGAGCGCTA<br>TGTCTGCAAGTGAGGCCCTGCCCTCCGCCCCAC<br>GCAGGAGCGAGGACTCTGCTCAAGGACCCTCA<br>GCAACTGGGGCCAGGGGCCTGGAGACACTCCA<br>TGGAGCTCTGCTTGTGAATTCCAGATGCCAGGC<br>ATGGGAGGCGGCTTGTGCTTTGCCTTCACTTGG<br>AAGCCACCAGGAACAGAAGGTCTGGCCACCCT<br>GGAAGGAGGGCAGGACATCAAAGGAAACCGAC<br>AAGATTAAAAATAACTTGGCAGCCTGAGGCTCT<br>GGAGTGCCCACAGGCTGGTGTAAGGAGCGGGG<br>CTTGGGATCGGTGAGACTGATACAGACTTGACC<br>TTTCAGGGCCACAGAGACCAGCCTCCGGGAAG<br>GGGTCTGCCCGCCTTCTTCAGAATGTTCTGCGG<br>GACCCCCTGGCCCACCCTGGGGTCTGAGCCTGC<br>TGGGCCCACCACATGGAATCACTAGCTTGGGTT<br>GTAAATGTTTTCTTTTGTTTTTTGCTTTTTCTTCC | 9 |

TABLE 1-continued

Gene sequences used in the methods of the present invention

| Gene | GenBank Accession No. | Sequence | SEQ ID NO. |
|---|---|---|---|
| | | TTTGGGATGTGGAAGCTACAGAAATATTTATAA<br>AACATAGCTTTTTCTTTGGGGTGGCACTTCTCA<br>ATTCCTCTTTATATATTTTATATATATAAATATA<br>TATGTATATATATAATGATCTCTATTTTAAAACT<br>AGCTTTTTAAGCAGCTGTATGAAATAAATGCTG<br>AGTGAGCCCCAGCCCGCCCCTGCA | |
| SFXN1 | NM_001322977.1 | CGGACGCGCGCTCACAGGCGCGCGCGAGGACG<br>CGCTCCGGGGACGCGCGAGGACGCCGTGGCGG<br>GAGAAGCGTTTCCGGTGGCGGCGGAGGCTGCA<br>CTGAGCGGGACCTGCGAGCAGCGCGGGCGGCA<br>GCCCGGGGGAAGCGGTGAGTCGCGGGCGGCAG<br>GCCCAGCCAGTCCGGGACCATGTCTGGAGAACT<br>ACCACCAAACATTAACATCAAGGAACCTCGAT<br>GGGATCAAAGCACTTTCATTGGACGAGCCAATC<br>ATTTCTTCACTGTAACTGACCCCAGGAACATTC<br>TGTTAACCAACGAACAACTCGAGAGTGCGAGA<br>AAAATAGTACATGATTACAGGCAAGGAATTGTT<br>CCTCCTGGTCTTACAGAAAATGAATTGTGGAGA<br>GCAAAGTACATCTATGATTCAGCTTTTCATCCT<br>GACACTGGTGAGAAGATGATTTTGATAGGAAG<br>AATGTCAGCCCAGGTTCCCATGAACATGACCAT<br>CACAGGTTGTATGATGACGTTTTACAGGACTAC<br>GCCGGCTGTGCTGTTCTGGCAGTGGATTAACCA<br>GTCCTTCAATGCCGTCGTCAATTACACCAACAG<br>AAGTGGAGACGCACCCCTCACTGTCAATGAGTT<br>GGGAACAGCTTACGTTTCTGCAACAACTGGTGC<br>CGTAGCAACAGCTCTAGGACTCAATGCATTGAC<br>CAAGCATGTCTCACCACTGATAGGACGTTTTGT<br>TCCCTTTGCTGCCGTAGCTGCTGCTAATTGCATT<br>AATATTCCATTAATGAGGCAAAGGGAACTCAA<br>AGTTGGCATTCCCGTCACGGATGAGAATGGGA<br>ACCGCTTGGGGGAGTCGGCGAACGCTGCGAAA<br>CAAGCCATCACGCAAGTTGTCGTGTCCAGGATT<br>CTCATGGCAGCCCCTGGCATGGCCATCCCTCCA<br>TTCATTATGAACACTTTGGAAAAGAAAGCCTTT<br>TTGAAGAGGTTCCCATGGATGAGTGCACCCATT<br>CAAGTTGGGTTAGTTGGCTTCTGTTTGGTGTTTG<br>CTACACCCCTGTGTTGTGCCCTGTTTCCTCAGAA<br>AAGTTCCATGTCTGTGACAAGCTTGGAGGCCGA<br>GTTGCAAGCTAAGATCCAAGAGAGCCATCCTG<br>AATTGCGACGCGTGTACTTCAATAAGGGATTGT<br>AAAGCAGGGAGGAAACCTCTGCAGCTCATTCT<br>GCCACTGCAAAGCTGGTGTAGCCATGCTGGTGA<br>GAAAAATCCTGTTCAACCTGGGTTCTCCCAGTT<br>ACGGAAACCTTTTAAAGATCCACATTAGCCTTT<br>TAGAATAAAGCTGCTACTTTAACAGAGCACCTG<br>GCGTGGGCCAAGTGCCTGATACTCCCTTACACT<br>GAATCATGTTATGATTTATAGAAATACCTTTCC<br>TGTAGCTTTTATAGTCATTGTTTTTCAAAGACGA<br>TATACCAGCCCTCACCCAGGTTTTAAAAAAGCA<br>CTGGTAGGCATAGAATAGGTGCTCAGTATATGG<br>TCAGTAAATGTTCTATTGATTATCAATCAGTGA<br>AAAAAGAAATCTGTTTAAAATACTGAATTTTCA<br>TCTCACTCCCATTGCAAATCAAGGAGATCTCAG<br>CAGTGAACTGGGAAAATACAAAAGCTCTGGGC<br>TAATCTATAAAAACTTACCCTGAAATATTAAGG<br>GCAGTTTGCTTCTAGTTTGGGGATTGCGCTAGC<br>CCAATGAAGGTGATGAAGCTTTTGGATTTGGAG<br>GGTAAAAGCTCCTTCACACCCCTTCCAAAAGTC<br>AGTCACAGACCACTGCAACATGCCTTCCCTGCT<br>GGATCATTATATACATTCAGATTGTGAGTGGAT<br>TGCCTTGGTTGACTTTTAATTTATTGTTTTTTGTT<br>CTTATAAAGATGATAATCTTACCTTGCAGTTAT<br>TGACTTTATATTCAATTATTTACATCAAATAATG<br>AAATAACTGAAATGTACAAATGTCAAATTTTGG<br>AAGTATATTCAATACCAATGCTGTATGAGTGGG<br>CTGAATCCAGTTCATTGTTTTTTTTTGGTAAGA<br>AGTGAGACTACAGTTCCAGCTACCTACATGTCT<br>TTTCTTGTCATCCTTATAGATCTCTTTGGCTTTC<br>AGAAAGATACAGTGATAATGTGTGTATGAATC<br>AGTCACAATGAATTTTACTTGAATATTGTATGT<br>TGCATTCCACTTCATTTGAAAATAATGAAACCA<br>TGTACCACTGTTTACATCATCTGTAGTGATTTCA<br>TAGATAATATATTTAATATGACAGATTATGTTT | 10 |

TABLE 1-continued

Gene sequences used in the methods of the present invention

| Gene | GenBank Accession No. | Sequence | SEQ ID NO. |
|---|---|---|---|
| | | CAACTCTGTAGATGTTTAACGTCATAGACAGTT<br>GGCCCTCTGTATCCGTGAGCTCTATATCTGTGA<br>ATTCAACCAAGTTTGGATGGAAAATTTTTTTTT<br>TTTTTTTTTTTTGAGACGGAGTCTCGCTCTGTCA<br>CCCAGGCTGGAGTGCAGTGGCGTAGTCTCGGCT<br>CACTGCAAGCTCCGCCTCCCGGGTTCACGCCGT<br>TCTCCTGCCTCAGCCTCTCTGAGAAGCTGGGAC<br>TACAGGCGCCCGCCACCACGCCCGGCTAATTTT<br>TTTGTATTTTTAGTAGAGACGGGGTTTCACTGT<br>GGTCTCGATCTCCTGACCTCGTGATCCGCCCGC<br>CTTGGCCTCCCAAGGTGCTGGGATTACAAGCGT<br>GAGCCACCGCACCCGGCCTGAAAATATTTTCTA<br>AAAAGATAAAAAATATACATAACGATGAAAAA<br>TAATACAAATTTAAAAACCAATACAGTATAACA<br>ACTATTTACATAGTGCTTACATTGTATTAGGTGT<br>TATAAGCAATCTAGAGATGATTTAGCAAGTATA<br>CAGGAGGATGTGCCTAGGTTATATGCAAATACT<br>GTGCCATTTTATATCAGGAACTTGAGCATCTGC<br>AGATATTGGTATCGGAGGGCGGTCCTGGAACC<br>AAGCATCCACGGATACTGAGGGGTGACATTTCA<br>TGAAGTGTAGATCATTGTATTCAGAGATTGTAA<br>ATGAAAAAAATATAGAAACTATTTAGTTTTGGT<br>AGATTTTTTTTCTGACAATGTGACCAGACTGAA<br>TTTCCTCATAAAGAAAAAATGGCGTGCCTTGTG<br>TCTGTGTTTCTCTTTTCTCTGAAAGGATTAATAG<br>ATCTGAAGCTTTGGGCCACTCAGAGCCTTCCTT<br>GATGCTGCCAGAGTCTTCTTATTTAGATTTTCTG<br>TCTTAAACCATTGGAAGCAAAACGGTTTTCCCA<br>TGACATTCTGGCCTTGGACAGATTCTGTTGTCCT<br>CGACGCGTCTCTTTATAAAGTGGTAAAAGCCTG<br>AAATTCAGGGCAGCTCTCCATGAGGTGCTGAAG<br>GGCTCTTTTCATAAGAAGCTAAGGCACTGCTGC<br>CTGCCCCAGGTGTCCCGCTCCTCTCAGAGTCCT<br>CCCCCTACCAGGTAGTGTGTAGCTCCATTTCAG<br>AATGTTAACCTCCAGTGAAGAGCTAATGACTGG<br>TTAGAAGATTGACAAACTAACCAAAATTTTACA<br>CACTCCGGTTATGTGTGTGAAAGGTTATAAAG<br>GAATGGCCGGGTGCGGTGGCTCACCCCTGTAAT<br>CCCAGCACTTTGGGAGGCCGAGGCGGGTGGAT<br>CACCTGAGGTCAGGAGTTTGAGACCAGCCTGGC<br>CAACATGGAGAAACCCCGCCTCTACTAAAAAT<br>ACAAAAAATTAGCCAGGCATGGAGGCACATGC<br>CTATAATCCCAGCTACTCGGGAGGCTGAGGTAG<br>GAGAATCGCTTGAATCCGGGAGCTGGAGGTTG<br>CAGTGAGCCAAGATCGCACCATTGCACTCCAGC<br>CTGGGCAACAAGAGCGAAACTCCATCTCAAAA<br>AAAAAAAAAAGAGATTATAAAGGGATGATGA<br>ACATGGAGCTGCATCTTTTTAAACGTTGTTTTTT<br>GATGCTTCAGACTCTTAATGCTTTTATATAAAG<br>CTATCAACTGTATGTTGATCACAGTTTATAAGA<br>AAGAACAAATCAAGATTGGCAATCCTTGCCGAT<br>CTTTTAGAAATACCTTTTCTGGAGAAAAAAAAA<br>TCCACATGAAGTGCAATAAGCTTATAAAGCTAA<br>GTAGTTATTAATATTTCTATTAACATGATACAA<br>AGGATGATGATTGTAAGTGTTTACTGACTGGCA<br>GCTTTTATTTCAGTATTAGCACAGCGTCTTGCCA<br>GTGTTGGAGGCCATGTATTATTTCAGTTCAACT<br>GGATGAAATGTTAAATAAACTCAGAATGAAAA<br>TAAA | |
| SREBF1 | NM_001005291.1 | AGCAGAGCTGCGGCCGGGGGAACCCAGTTTCC<br>GAGGAACTTTTCGCCGGCGCCGGGCCGCCTCTG<br>AGGCCAGGGCAGGACACGAACGCGCGGAGCGG<br>CGGCGGCGACTGAGAGCCGGGGCCGCGGCGGC<br>GCTCCCTAGGAAGGGCCGTACGAGGCGGCGGG<br>CCCGGCGGGCCTCCCGGAGGAGGCGGCTGCGC<br>CATGGACGAGCCACCCTTCAGCGAGGCGGCTTT<br>GGAGCAGGCGCTGGGCGAGCCGTGCGATCTGG<br>ACGCGGCGCTGCTGACCGACATCGAAGGTGAA<br>GTCGGCGCGGGGAGGGGTAGGGCCAACGGCCT<br>GGACGCCCCAAGGGCGGGCGCAGATCGCGGAG<br>CCATGGATTGCACTTTCGAAGACATGCTTCAGC<br>TTATCAACAACCAAGACAGTGACTTCCCTGGCC<br>TATTTGACCCACCCTATGCTGGGAGTGGGGCAG<br>GGGGCACAGACCCTGCCAGCCCCGATACCAGC | 11 |

TABLE 1-continued

Gene sequences used in the methods of the present invention

| Gene | GenBank Accession No. | Sequence | SEQ ID NO. |
|------|----------------------|----------|------------|
| | | TCCCCAGGCAGCTTGTCTCCACCTCCTGCCACA | |
| | | TTGAGCTCCTCTCTTGAAGCCTTCCTGAGCGGG | |
| | | CCGCAGGCAGCGCCCTCACCCCTGTCCCCTCCC | |
| | | CAGCCTGCACCCACTCCATTGAAGATGTACCCG | |
| | | TCCATGCCCGCTTTCTCCCCTGGGCCTGGTATCA | |
| | | AGGAAGAGTCAGTGCCACTGAGCATCCTGCAG | |
| | | ACCCCCACCCCACAGCCCCTGCCAGGGGCCCTC | |
| | | CTGCCACAGAGCTTCCCAGCCCCAGCCCCACCG | |
| | | CAGTTCAGCTCCACCCCTGTGTTAGGCTACCCC | |
| | | AGCCCTCCGGGAGGCTTCTCTACAGGAAGCCCT | |
| | | CCCGGGAACACCCAGCAGCCGCTGCCTGGCCTG | |
| | | CCACTGGCTTCCCCGCCAGGGGTCCCGCCCGTC | |
| | | TCCTTGCACACCCAGGTCCAGAGTGTGGTCCCC | |
| | | CAGCAGCTACTGACAGTCACAGCTGCCCCCACG | |
| | | GCAGCCCCTGTAACGACCACTGTGACCTCGCAG | |
| | | ATCCAGCAGGTCCCGGTCCTGCTGCAGCCCCAC | |
| | | TTCATCAAGGCAGACTCGCTGCTTCTGACAGCC | |
| | | ATGAAGACAGACGGAGCCACTGTGAAGGCGGC | |
| | | AGGTCTCAGTCCCCTGGTCTCTGGCACCACTGT | |
| | | GCAGACAGGGCCTTTGCCGACCCTGGTGAGTGG | |
| | | CGGAACCATCTTGGCAACAGTCCCACTGGTCGT | |
| | | AGATGCGGAGAAGCTGCCTATCAACCGGCTCG | |
| | | CAGCTGGCAGCAAGGCCCCGGCCTCTGCCCAG | |
| | | AGCCGTGGAGAGAAGCGCACAGCCCACAACGC | |
| | | CATTGAGAAGCGCTACCGCTCCTCCATCAATGA | |
| | | CAAAATCATTGAGCTCAAGGATCTGGTGGTGGG | |
| | | CACTGAGGCAAAGCTGAATAAATCTGCTGTCTT | |
| | | GCGCAAGGCCATCGACTACATTCGCTTTCTGCA | |
| | | ACACAGCAACCAGAAACTCAAGCAGGAGAACC | |
| | | TAAGTCTGCGCACTGCTGTCCACAAAAGCAAAT | |
| | | CTCTGAAGGATCTGGTGTCGGCCTGTGGCAGTG | |
| | | GAGGGAACACAGACGTGCTCATGGAGGGCGTG | |
| | | AAGACTGAGGTGGAGGACACACTGACCCCACC | |
| | | CCCCTCGGATGCTGGCTCACCTTTCCAGAGCAG | |
| | | CCCCTTGTCCCTTGGCAGCAGGGGCAGTGGCAG | |
| | | CGGTGGCAGTGGCAGTGACTCGGAGCCTGACA | |
| | | GCCCAGTCTTTGAGGACAGCAAGGCAAAGCCA | |
| | | GAGCAGCGGCCGTCTCTGCACAGCCGGGGCAT | |
| | | GCTGGACCGCTCCCGCCTGGCCCTGTGCACGCT | |
| | | CGTCTTCCTCTGCCTGTCCTGCAACCCCTTGGCC | |
| | | TCCTTGCTGGGGGCCCGGGGGCTTCCCAGCCCC | |
| | | TCAGATACCACCAGCGTCTACCATAGCCCTGGG | |
| | | CGCAACGTGCTGGGCACCGAGAGCAGAGATGG | |
| | | CCCTGGCTGGGCCCAGTGGCTGCTGCCCCCAGT | |
| | | GGTCTGGCTGCTCAATGGGCTGTTGGTGCTCGT | |
| | | CTCCTTGGTGCTTCTCTTTGTCTACGGTGAGCCA | |
| | | GTCACACGGCCCCACTCAGGCCCCGCCGTGTAC | |
| | | TTCTGGAGGCATCGCAAGCAGGCTGACCTGGAC | |
| | | CTGGCCCGGGGAGACTTTGCCCAGGCTGCCAG | |
| | | CAGCTGTGGCTGGCCCTGCGGGCACTGGGCCGG | |
| | | CCCCTGCCCACCTCCCACCTGGACCTGGCTTGT | |
| | | AGCCTCCTCTGGAACCTCATCCGTCACCTGCTG | |
| | | CAGCGTCTCTGGGTGGGCCGCTGGCTGGCAGGC | |
| | | CGGGCAGGGGCCTGCAGCAGGACTGTGCTCT | |
| | | GCGAGTGGATGCTAGCGCCAGCGCCCGAGACG | |
| | | CAGCCCTGGTCTACCATAAGCTGCACCAGCTGC | |
| | | ACACCATGGGGAAGCACACAGGCGGGCACCTC | |
| | | ACTGCCACCAACCTGGCGCTGAGTGCCCTGAAC | |
| | | CTGGCAGAGTGTGCAGGGGATGCCGTGTCTGTG | |
| | | GCGACGCTGGCCGAGATCTATGTGGCGGCTGCA | |
| | | TTGAGAGTGAAGACCAGTCTCCCACGGGCCTTG | |
| | | CATTTTCTGACACGCTTCTTCCTGAGCAGTGCCC | |
| | | GCCAGGCCTGCCTGGCACAGAGTGGCTCAGTGC | |
| | | CTCCTGCCATGCAGTGGCTCTGCCACCCCGTGG | |
| | | GCCACCGTTTCTTCGTGGATGGGGACTGGTCCG | |
| | | TGCTCAGTACCCCATGGGAGAGCCTGTACAGCT | |
| | | TGGCCGGGAACCCAGTGGACCCCCTGGCCCAG | |
| | | GTGACTCAGCTATTCCGGGAACATCTCTTAGAG | |
| | | CGAGCACTGAACTGTGTGACCCAGCCCAACCCC | |
| | | AGCCCTGGGTCAGCTGATGGGGACAAGGAATT | |
| | | CTCGGATGCCCTCGGGTACCTGCAGCTGCTGAA | |
| | | CAGCTGTTCTGATGCTGCGGGGGCTCCTGCCTA | |
| | | CAGCTTCTCCATCAGTTCCAGCATGGCCACCAC | |
| | | CACCGGCGTAGACCCGGTGGCCAAGTGGTGGG | |
| | | CCTCTCTGACAGCTGTGGTGATCCACTGGCTGC | |

TABLE 1-continued

Gene sequences used in the methods of the present invention

| Gene | GenBank Accession No. | Sequence | SEQ ID NO. |
|---|---|---|---|
| | | GGCGGGATGAGGAGGCGGCTGAGCGGCTGTGC<br>CCGCTGGTGGAGCACCTGCCCCGGGTGCTGCAG<br>GAGTCTGAGAGACCCCTGCCCAGGGCAGCTCTG<br>CACTCCTTCAAGGCTGCCCGGGCCCTGCTGGGC<br>TGTGCCAAGGCAGAGTCTGGTCCAGCCAGCCTG<br>ACCATCTGTGAGAAGGCCAGTGGGTACCTGCA<br>GGACAGCCTGGCTACCACACCAGCCAGCAGCT<br>CCATTGACAAGGCCGTGCAGCTGTTCCTGTGTG<br>ACCTGCTTCTTGTGGTGCGCACCAGCCTGTGGC<br>GGCAGCAGCAGCCCCCGGCCCCGGCCCCAGCA<br>GCCCAGGGCACCAGCAGCAGGCCCCAGGCTTC<br>CGCCCTTGAGCTGCGTGGCTTCCAACGGGACCT<br>GAGCAGCCTGAGGCGGCTGGCACAGAGCTTCC<br>GGCCCGCCATGCGGAGGGTGTTCCTACATGAGG<br>CCACGGCCCGGCTGATGGCGGGGCCAGCCCC<br>ACACGGACACACCAGCTCCTCGACCGCAGTCTG<br>AGGCGGCGGGCAGGCCCCGGTGGCAAAGGAGG<br>CGCGGTGGCGGAGCTGGAGCGCGGCCCACGC<br>GGCGGGAGCACGCGGAGGCCTTGCTGCTGGCC<br>TCCTGCTACCTGCCCCCCGGCTTCCTGTCGGCG<br>CCCGGGCAGCGCGTGGGCATGCTGGCTGAGGC<br>GGCGCGCACACTCGAGAAGCTTGGCGATCGCC<br>GGCTGCTGCACGACTGTCAGCAGATGCTCATGC<br>GCCTGGGCGGTGGGACCACTGTCACTTCCAGCT<br>AGACCCCGTGTCCCCGGCCTCAGCACCCCTGTC<br>TCTAGCCACTTTGGTCCCGTGCAGCTTCTGTCCT<br>GCGTCGAAGCTTTGAAGGCCGAAGGCAGTGCA<br>AGAGACTCTGGCCTCCACAGTTCGACCTGCGGC<br>TGCTGTGTGCCTTCGCGGTGGAAGGCCCGAGGG<br>GCGCGATCTTGACCCTAAGACCGGCGGCCATGA<br>TGGTGCTGACCTCTGGTGGCCGATCGGGGCACT<br>GCAGGGGCCGAGCCATTTTGGGGGGCCCCCCTC<br>CTTGCTCTGCAGGCACCTTAGTGGCTTTTTTCCT<br>CCTGTGTACAGGGAAGAGAGGGGTACATTTCCC<br>TGTGCTGACGGAAGCCAACTTGGCTTTCCCGGA<br>CTGCAAGCAGGGCTCTGCCCCAGAGGCCTCTCT<br>CTCCGTCGTGGGAGAGAGACGTGTACATAGTGT<br>AGGTCAGCGTGCTTAGCCTCCTGACCTGAGGCT<br>CCTGTGCTACTTTGCCTTTTGCAAACTTTATTTT<br>CATAGATTGAGAAGTTTTGTACAGAGAATTAAA<br>AATGAAATTATTTATAATCTGGAAAAAA | |
| TYMS | NM_001071.1 | GGGGGGGGGGGGACCACTTGGCCTGCCTCCGT<br>CCCGCCGCGCCACTTGGCCTGCCTCCGTCCCGC<br>CGCGCCACTTCGCCTGCCTCCGTCCCCGCCCG<br>CCGCGCCATGCCTGTGGCCGGCTCGGAGCTGCC<br>GCGCCGGCCCTTGCCCCCCGCCGCACAGGAGCG<br>GGACGCCGAGCCGCGTCCGCCGCACGGGGAGC<br>TGCAGTACCTGGGGCAGATCCAACACATCCTCC<br>GCTGCGGCGTCAGGAAGGACGACCGCACGGGC<br>ACCGGCACCCTGTCGGTATTCGGCATGCAGGCG<br>CGCTACAGCCTGAGAGATGAATTCCCTCTGCTG<br>ACAACCAAACGTGTGTTCTGGAAGGGTGTTTTG<br>GAGGAGTTGCTGTGGTTTATCAAGGGATCCACA<br>AATGCTAAAGAGCTGTCTTCCAAGGGAGTGAA<br>AATCTGGGATGCCAATGGATCCCGAGACTTTTT<br>GGACAGCCTGGGATTCTCCACCAGAGAAGAAG<br>GGGACTTGGGCCCAGTTTATGGCTTCCAGTGGA<br>GGCATTTTGGGGCAGAATACAGAGATATGGAA<br>TCAGATTATTCAGGACAGGGAGTTGACCAACTG<br>CAAAGAGTGATTGACACCATCAAAACCAACCC<br>TGACGACAGAAGAATCATCATGTGCGCTTGGA<br>ATCCAAGAGATCTTCCTCTGATGGCGCTGCCTC<br>CATGCCATGCCCTCTGCCAGTTCTATGTGGTGA<br>ACAGTGAGCTGTCCTGCCAGCTGTACCAGAGAT<br>CGGGAGACATGGGCCTCGGTGTGCCTTTCAACA<br>TCGCCAGCTACGCCCTGCTCACGTACATGATTG<br>CGCACATCACGGGCCTGAAGCCAGGTGACTTTA<br>TACACACTTTGGGAGATGCACATATTTACCTGA<br>ATCACATCGAGCCACTGAAAATTCAGCTTCAGC<br>GAGAACCCAGACCTTTCCCAAAGCTCAGGATTC<br>TTCGAAAAGTTGAGAAATTGATGACTTCAAAG<br>CTGAAGACTTTCAGATTGAAGGGTACAATCCGC<br>ATCCAACTATTAAAATGGAAATGGCTGTTTAGG<br>GTGCTTTCAAAGGAGCTTGAAGGATATTGTCAG | 12 |

TABLE 1-continued

Gene sequences used in the methods of the present invention

| Gene | GenBank Accession No. | Sequence | SEQ ID NO. |
|---|---|---|---|
| | | TCTTTAGGGGTTGGGCTGGATGCCGAGGTAAAA<br>GTTCTTTTTGCTCTAAAAGAAAAAGGAACTAGG<br>TCAAAAATCTGTCCGTGACCTATCAGTTATTAA<br>TTTTTAAGGATGTTGCCACTGGCAAATGTAACT<br>GTGCCAGTTCTTTCCATAATAAAAGGCTTTGAG<br>TTAACTCACTGAGGGTATCTGACAATGCTGAGG<br>TTATGAACAAAGTGAGGAGAATGAAATGTATG<br>TGCTCTTAGCAAAAACATGTATGTGCATTTCAA<br>TCCCACGTACTTATAAAGAAGGTTGGTGAATTT<br>CACAAGCTATTTTTGGAATATTTTTAGAATATTT<br>TAAGAATTTCACAAGCTATTCCCTCAAATCTGA<br>GGGAGCTGAGTAACACCATCGATCATGATGTA<br>GAGTGTGGTTATGAACTTTATAGTTGTTTTATAT<br>GTTGCTATAATAAAGAAGTGTTCTGC | |
| EIF5AL1 | NM_001099692.1 | GGGGTCGAGTCAGTGCCGTTTGCGCCAGTTGGA<br>ATCGAAGCCTCTTAAAATGGCAGATGATTTGGA<br>CTTCGAGACAGGAGATGCAGGGGCCTCAGCCA<br>CCTTCCCAATGCAGTGCTCAGCATTACGTAAGA<br>ATGGCTTTGTGGTGCTCAAAGGCTGGCCATGTA<br>AGATCGTGGAGATGTCTGCTTCGAAGACTGGCA<br>AGCACGGCCACGCCAAGGTCCATCTGGTTGGTA<br>TTGACATCTTTACTGGGAAGAAATATGAAGATA<br>TCTGCCCGTCAACTCATAATATGGATGTCCCCA<br>ACATCAAAAGGAATGACTTCCAGCTGATTGGCA<br>TCCAGGATGGGTACCTATCACTGCTCCAGGACA<br>GCGGGGAGGTACCAGAGGACCTTCGTCTCCCTG<br>AGGGAGACCTTGGCAAGGAGATTGAGCAGAAG<br>TACGACTGTGGAGAAGAGATCCTGATCACGGT<br>GCTGTCTGCCATGACAGAGGAGGCAGCTGTTGC<br>AATCAAGGCCATGGCAAAATAACTGGCTCCCA<br>AGGTGGCAGTGGTGGCAGCAGTGATCCTCCGA<br>ACCTGCAGAGGCCCCCTCCCCCAGCCTGGCCTG<br>GCTCTGGCCTGGTCCTAGGTTGGACTCCTCCTA<br>CACAATTTATTTGACGTTTTATTTTGGTTTTCCC<br>CACCCCCTCAATCTGTCAGGGAGCCCCTGCCCT<br>TCACCTAGCTCCCTTGGCCAGGAGCGAGCGAAG<br>CCATGGCCTTGGTGAAGCTGCCCTCCTCTTCTCC<br>CCTCACACTACAGCCCTGGTGGGGAGAAGGG<br>GGTGGGTGCTGCTTGTGGTTTAGTCTTTTTTTTT<br>TTTTTAAATTCAATCTGGAATCAGAAAGCGGTG<br>GATTCTGGCAAATGGTCCTTGTGCCCTCCCCAC<br>TCATCCTTGGTCTGGTCCCCTGTTGCCCATAGCC<br>CTTTACCCTGAGCACCACCCAACAGACTGGGGA<br>CCAGCCCCCTCGCCTGCCTGTGTCTCTCCCCAA<br>ACCCCTTTAGATGGGGAGGGAAGAAGAGGAGA<br>GGGGAGGGGACCTGCCCCCTCCTCAGGCATCTG<br>GGAAGGGCCTGCCCCCATGGGCTTTACCCTTCC<br>CTGCGGGCTCTCTCCCCGACACATTTGTTAAAA<br>TCAAACCTGAATAAAACTACAAGTTTAATATGA<br>AAAAAAAAAAAAAGAAAGAAAGACGTGTAA<br>AATGCCAAGAACTCTAGGAAACAGGGACAAAA<br>ACACTTCAAAGAGAAAGTTCATGCACTTGTTTC<br>TGACCACCCAGGGCACCCTTCAGCACACGCTGT<br>CTGGAGTGGCCTGAAGCAAGGAGTGTCTTGTGA<br>GGTGCAGAGGATGCAATGGGAGCAGGGTCCTG<br>TCCCCACCCTAAAGGAGTTCACAGTTTAACGCA<br>AATGAGAAGCCAGTGAGGACATCACTACTCCT<br>GCTGTGAACTTGGGAACTAGAAACACAAAACC<br>TGAGTCTGGAGGGAAGCTAAGGAAGCATTCTG<br>CTCTGGAGTAGACATGAGTGCGTGTGAAGCTTC<br>TGATCTCCCATGAGAGCAATGGGGACATGGGG<br>CAGAATCTAAAACCCATGACTGAAAGCACCAA<br>ATTGCTAAAATGGCAATAAAGAGACATGAGGC<br>CAAGATGGAGAAGAAGGAACCCAGGACGAGG<br>GTCAGCCTCACATTTGGGGCTCATTTCCCTCAG<br>TTTCCTCACTGAATTTCAGAAGGGACTAACTGA<br>GATGCAAAGAAGCAGAGCAGCTTTTGCACCAT<br>GTGGAGGACTAGATGGAAAACAAGTAGACTGA<br>GGGTCTGCTAGTGAAGGTGACCCCTACTGAAGT<br>CCACTGGCTTTGGTTGGGACCCAGAAGAGTCAC<br>ACGCCAGGAATAGAGGTGGACAGGAAACACCC<br>TGACTTTTGTAGGGACTGAACCTCACTGATAAC<br>CTCAATTGCGGATGGTATGGAGGGTGTCTAGGT<br>GTGCTAGGACCCCTGCCCATTCCCCAGAAATAG | 13 |

TABLE 1-continued

Gene sequences used in the methods of the present invention

| Gene | GenBank Accession No. | Sequence | SEQ ID NO. |
|---|---|---|---|
| | | ACTCCCATCTTTTCTACAGCAAGATAACGTGCT AGTAGGCCTCAATTCATTGCTAAATATTTTAA CGAGTGTCTTACATTTAGCCAAAAAGACTAGTC ATGTGGCAGGAAAAATACAATGTCATATGACC AAAAGCTAAAAGACTGTGAAAATGAATCCAGA GGTGACCCAAGCATTGAATTTAACAATGCCAGT ACCTGGACCTCCGCTTGCCCCTAAAACATTACA ATCAAGAATGTAGGAAGGGAAAGGAAACACGA AGATTAATCAAGCAGGAAGGACAAGCTCAGTT TTGCACCCACTGAATTTGCCACAAATATTGTGG AAAATATTCTCGGGGACATTGCAGTTGTCTACT TTGGTTGGCACATGGTTCATACAACAGTGTTTG TGTCAGTGAACATCTTACTCTTCCTCGGCAGTCT TTCTTTGCCCAGAGATTTCGCAATGACTGTTGA CCTTCATCATCACCTTTTGGACTTTGGCTTGCAC TTTAGCTTCTGTAGATCTCCATGATGTAAAGAA GTATTTTAGGTCCATTTTAATTCCTGCAAAGGA TAAAATCCTTCTATTTGTGTGCATATAAGTGGA CCTGAGCCCTTGGTTAGGGTGTAGAGAGGAGA AGGGGAGAAACCTGAGGGCCAGAAGCTGTTCT TTCCCTTAAAAGGGCAAACTCATTTCCACACTA TGGGGACTCTGACAGATAGCATACCTTCCTGTC TATGGCTATTGGACCTGCAGGCTTTCCCCTGTA AATCCGTGTTCTGTCATTGACATTTTGTGACTGT AAGACAGACTTGAGATAAGACATCTAGAAAAC AATAATTGAACAATGATGTGAATATATTTCACA CAACTGAACTGTACATTTCAACAAGGTTAAGAT GGTAATTATCACGTTATACATTTTTTACCGCAG GTTAAAATGTTTCACAGGTTGAAAGGAAAGCA ACTACCTTCAGTTCTCTGAGTTCAAGAATTTGT AACATTTCACCCCCTGCTCCTTCCTGATCTTCTG TGGAGCATCTTTTTTCCATCCATGCTCTACTCAG AGCCCACTTTCCCTTCCCTGACACCAGCTTCACT GAGGCTGGTTGGAACCTAACACAAAACATTCTC AGTAATGACTGAATTCCCACAAAGAATTCCATA TAGACTGCATATGAGTTGAATCTTCTAAGACAT GAAATATTTGTTCTCTTCTTGGCTAATATGCAAT GCAAATCCTGTTGCAGATGTACGTCATATACCT CTGAAATTCCTGATGTATTCAATGAAATAACAT CTTTAAAGTTCTGTGTAGAATGTTTTTTTTCTGA TTTCTTCACATACGATAGAAAAAAAAACCCAAA AAAACATGTACTAGGATTTCAATAGAAGCAAT GGGTGATCTAAAAAGATGAAAGAGCAACCGCA TGCGCCCTACAGCTACCGCTAGATTTTATGGGG AAAGCAGCTGGCCCAGTTTGCAGCTAGGAGAA ATGTCAAACACATGAAGAAATGAGAAGCAAAG AAAAACCATGAGGCATGAACATTTCATGGCAA TCACGATGTCCTGGTTTGTGAGATAATGGGATA GAGGAGTAGAAAACAAGGAGAAAGATGAGAA GGTACAAAGTGGTTCAAGTCAAACAGCTCAACT GAACTTTTCTTAATGGAATATTTAAAAAGTGGT ACATTAAAAAACTTCCCCCAGTTCACATCAAAA ATTCTCTCTTCAGGACTAAGTTGGGTAGAGACT GTTCAATGTGCCTAGATATCTTCAGAACTTATA TATTTTCTGTTTTCTACGTATGTTGAAGGGCAGT GCCAAATGATGTGTAATTATCTAGGTTGTAAAA ATAAAACATACTCCCCCTTCCCTTGAGGATAAA AAAAAAAAAAA | |
| WDR76 | NM_024908.3 | CTGCTCTGGCGCTGCGGCCGCTGGGGATCTGAG TGGGCTCCGCCCCGCCTCGGACCCGCCCCTCCC GGCCTCCCGCCGCAATCTTGGCGGGAAGGCGCC GGCCGCTAAGAAGCCGAAAGATGTCCAGGTCG GGCGCGGCGGCTGAGAAGGCGGACTCCAGACA GCGACCCCAGATGAAGGTAAATGAATATAAAG AAAATCAAAACATCGCTTATGTGTCTCTGAGAC CAGCACAGACTACAGTTTTAATAAAAACAGCTA AGGTCTATCTTGCCCCCTTTTCACTCAGTAATTA CCAGCTAGACCAGCTTATGTGCCCCAAATCCCT ATCAGAAAAGAATTCTAACAATGAAGTGGCGT GTAAGAAGACTAAAATAAAGAAAACTTGCAGA AGGATTATACCTCCAAAGATGAAAAACACATCT TCCAAGGCAGAATCCACGCTGCAAAATTCATCC TCAGCTGTTCATACTGAAAGTAACAAGCTACAA CCCAAGAGAACGGCAGATGCGATGAATCTCAG | 14 |

TABLE 1-continued

Gene sequences used in the methods of the present invention

| Gene | GenBank Accession No. | Sequence | SEQ ID NO. |
|---|---|---|---|
| | | TGTTGATGTGGAAAGTAGTCAGGATGGAGACA GTGATGAAGATACCACACCATCCCTGGATTTTT CGGGATTGTCACCCTACGAAAGGAAGAGACTG AAGAACATATCAGAAAACGCAGACTTTTTTGCT TCTCTTCAGTTGTCTGAGTCTGCTGCAAGACTCC GTGAAATGATAGAGAAGAGACAGCCTCCTAAA TCCAAAAGAAAGAAGCCTAAGAGAGAAAATGG GATTGGATGTAGAAGGTCAATGCGATTACTAAA AGTTGATCCTTCGGGAGTTTCATTACCAGCAGC TCCAACACCGCCGACATTAGTAGCAGATGAAA CTCCTTTGTTACCTCCTGGGCCTTTAGAAATGAC TTCTGAAAATCAAGAAGACAACAATGAACGAT TTAAAGGATTTCTGCACACATGGGCAGGAATGA GCAAGCCAAGTAGTAAGAACACTGAGAAGGGA TTATCTAGCATTAAAAGCTACAAAGCCAATTTA AATGGCATGGTCATTAGTGAAGATACCGTTTAC AAAGTTACCACAGGCCCAATATTCTCTATGGCT CTCCATCCATCAGAAACTAGAACTTTGGTAGCA GTTGGGGCCAAATTTGGGCAAGTTGGACTTTGT GATTTGACCCAGCAACCTAAAGAAGATGGAGT TTATGTTTTTCATCCCCATAGTCAGCCAGTTAGC TGTCTTTACTTCTCACCCGCCAATCCGGCCCAC ATACTGTCACTGAGCTATGATGGCACGTTACGC TGTGGGGATTTTTCCAGGGCTATTTTTGAAGAG GTGTATAGAAATGAAAGAAGTAGCTTTTCCTCC TTCGACTTCTTGGCAGAAGATGCCTCCACTTTA ATAGTAGGACACTGGGATGGAAATATGTCACT GGTGGATAGACGGACACCTGGAACTTCTTATGA GAAACTTACCAGTTCTTCTATGGGAAAAATAAG AACTGTTCATGTCCACCCAGTGCATAGACAGTA TTTTATCACTGCCGGATTGAGGGATACTCATAT TTATGATGCAAGGCGATTGAATTCCAGGAGAA GTCAGCCTTTGATTTCTTTGACTGAACATACAA AGAGCATTGCTTCCGCCTATTTTTCACCTCTTAC TGGTAACAGAGTGGTGACCACATGTGCTGATTG TAATCTGAGAATTTTTGACAGCAGCTGTATATC TTCTAAGATTCCGCTCCTCACCACCATCAGGCA CAACACTTTCACTGGGCGATGGCTGACCAGGTT CCAAGCCATGTGGGATCCTAAACAAGAAGACT GTGTCATAGTTGGCAGCATGGCCCATCCACGAC GGGTAGAAATCTTCCATGAGACAGGAAAGAGG GTGCATTCGTTTGGTGGAGAATACCTTGTCTCT GTGTGTTCCATCAATGCCATGCACCCAACTCGG TATATTTTGGCTGGAGGTAATTCCAGCGGGAAG ATACATGTTTTTATGAATGAAAAAAGCTGCTGA GTTTTTGGTTTAGGAACATCAATTTGTTCAAATT GACCACTGTCTAAGGAGCCTAGTAATCGGCGTG CCTTAGTGTGTTTATGTGGTAATGTGTTACATTT AGCAATTATAACATTGTTTTATTAATAAGACTA TAAGAAGAGTGTACTTTTAGTAAGGGAGAAGT CTTGGAGGGTTGCTTCTGCAGGACGGGGAGGG AATTTGAGGGGAGGCTGAGGTGCCGTCAGGAC TTTTTTTTTTTTTTTTTTTGAGATGGAGTTTTG CTCTTGTTGCCCAGGCTGGAGTGCAATAGCGCG ATCTTGGCTCACCGCAACCTCCGCCTCCCAGGT TCAAGCGATTCTCCTGCCTCAGACTCCTAAGTA GCTGGGATTACAGGCACCTGCCACCACGCCTGG CTATTTTTTTGTATTTTTAGTAGAGATGGGGTTT CATCATGTTGGCCAGGCTGGTCTCGAGCTCCTG ACCTCAGGTGATCTGCCCGCCTCGGCCTCCAAA AGTGCTGGAATTACAGGCGTGAGCCACCATGCC TGGCCATCAGAACTTGTAATCAAGACAGTATGT TGAGAAATTCTAACATTATAAATTACAAAGCTT TGACTATTAAAGTTTTTGTGATCTAATGATACA GTTTTGATTCTATAGTAATTTGTGGCTTATTTTA TAGTTTATAATGAATACTTATTTCTAGACTCATA CACTGAAGGGGACCCGGAAAGGTAATGTAAC TCAGTGATTTTAAAACTTGATTTTTTAACTGAG AACTTTTTTTGCCCCCTGCCTGTAGGTTAAGTCT TACGTGAAATGCCAAGATAATTGCTGAGCAGCT TTGGTTACCCAGGGCGGGGTCTGGGTCTGTCTG TACTTTGCCTTTACTCTAGATGGCTCCTGAGAC ACAGGCAGGACTCCCAAGCACCGGGTTGGGAT CTGCCCTGGTCCCGGCATTCCAGTATAAGATTG CCTCAGACCTGTGTTTTTCAGACTGGGTTTTGC | |

TABLE 1-continued

Gene sequences used in the methods of the present invention

| Gene | GenBank Accession No. | Sequence | SEQ ID NO. |
|------|----------------------|----------|------------|
| | | TCTTCACATGAAATCAAGTTAGATGACAATGAC<br>TGGTGTTGAAAAAAATGAAAAGGAAAGAATTT<br>GTAAAGAACAGAAAATATATTTGAGTAAGTATT<br>GTTTGGTAAAACTTAGTTACATATGCATATATA<br>TTTGTTAGGTATATATGTTTATGTGTATTCTGAT<br>GTAAAATATATATATATATATATTTTATTACTAT<br>AGTACCATGGGTAATGGATAAAGAAGTTAAAG<br>CTACTGCTTAGAATGAAGAAGGCCCCAGGCTTA<br>CCTGTCCCGATCTTTAAACTGTCCGAAGGAAAT<br>TCAATAGCCTGTTAAGTGAATACCTTCATTCTT<br>ACTTGTATTTGGGGGAATATTATGAAATACTCA<br>CCACTTTTGGTATTTTATGAAAATGTTTTCTTTT<br>CAGAAGTTATGGTAATTTCAATGTGTTTGTTGTT<br>GGGAGGGGAGCTGCCAAATCAGTTACTAATATT<br>ACTGTGTGACATCTATCCAACTTTTTTCATTATT<br>CTTCATTGCCAAATACTGAAAGACTTGTAAATG<br>GCTTTGGCAATATGTTTGAATTCTAAGAGGAAA<br>TATTTTCCCATAATTGTATATCAGAGAAATATA<br>GTGATATACAATTTCCTTGAAAACCAATTTCTA<br>AATAATTTTCTTCTCTGTAATCTAAGTGTAAAA<br>AGGTTTAGTTTTTTAATAGGTTTAGGTGTTTATA<br>AGCAATAGTTCTCTATTTTCTAGTTGATATAAGT<br>AGAAGAATTGACAAGTGAGATGGAAATGTTAA<br>TTTATAAAGGGAAAGAAAAGCTAGGTGAGGTT<br>GAGTTATAATTAAACTGTTCAGGAAACATCGTA<br>AAGGCTTTAGGCTCCCTTTTTCATTTCTATACCA<br>ATTAATCTCATGGGTTCTAGAGTGGTTAGTTCT<br>ACGGGAATTGTTTTTGTTTTTGTTTTTAAAGATG<br>CTGAAAACTACTCTCAATCAAATTAGTACCATC<br>ATTTAAGCTTTGAATACTTGGCAGTAATTGCCT<br>GGGCTCGTCAATAAATGTTAGCAAATTCTTGAT<br>GTTCAAAAAAAAAA | |

In one aspect, the present disclosure provides a method of identifying mismatch repair deficiency in a subject comprising: a) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; b) determining a score HPS, wherein HPS=$(y-\mu_2)/\sigma_2$, wherein $y=\Sigma_{i=1}^{10} y_i w_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and $\sigma_2$ is the standard deviation of the linear combination of the log-transformed normalized expression of the at least one gene in non-hypermutated samples; c) comparing the HPS score with a predetermined cutoff value, wherein the cutoff value identifies mismatch repair deficiency in a subject with at least 95% specificity; and d) producing a report identifying the presence of mismatch repair deficiency in the subject when the HPS score is equal to or greater than the predetermined cutoff value or producing a report identifying the absence of mismatch repair deficiency in the subject when the HPS score is less than the predetermined cutoff value.

In one aspect, the present disclosure provides a method of identifying mismatch repair deficiency in a subject comprising: a) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; b) determining a score HPS, wherein HPS=$(y-\mu_2)/\sigma_2$, wherein $y=\Sigma_{i=1}^{10} y_i w_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and $\sigma_2$ is the standard deviation of the linear combination of the log-transformed normalized expression of the at least one gene in non-hypermutated samples; c) comparing the HPS score with a predetermined cutoff value, wherein the cutoff value identifies mismatch repair deficiency in a subject with at least 95% specificity; and d) identifying the presence of mismatch repair deficiency in the subject when the HPS score is equal to or greater than the predetermined cutoff value or identifying the absence of mismatch repair deficiency in the subject when the HPS score is less than the predetermined cutoff value.

In some aspects, the preceding methods can further comprise administering at least one treatment to a subject identified as having mismatch repair deficiency. A treatment can comprise anti-cancer therapy. A treatment can comprise administering to the subject immunotherapy. The at least one treatment can comprise administering to the subject at least one checkpoint inhibitor. A treatment can comprise administering to the subject pembrolizumab, nivolumab, atezolizumab, avelumab, durvalumab, pidilizumab, REGN2810, AMP-224, MEDI0680, PDR001, CT-001 or a combination thereof. A treatment can comprise administering to the subject a CTLA4 antibody. A CTLA4 antibody can comprise ipilimumab, tremelimumab or a combination thereof.

In one aspect, the present disclosure provides a method of identifying mismatch repair deficiency in a subject comprising: a) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; b) determining a score HPS, wherein HPS=$(y-\mu_2)/\sigma_2$, wherein $y=\Sigma_{i=1}^{10} y_i w_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and $\sigma_2$ is the standard deviation of the linear combination of the log-transformed normalized expression of the at least one gene in non-hypermutated samples; c) comparing the HPS score with a predetermined cutoff value, wherein the cutoff value identifies mismatch repair deficiency in a subject with at least 95% specificity; and d) administering at least one treatment to the subject when the HPS score is equal to or greater than the predetermined cutoff value. A treatment can comprise anti-cancer therapy. A treatment can comprise administering to the subject immunotherapy. The at least one treatment can comprise administering to the subject at least one checkpoint inhibitor. A treatment can comprise administering to the subject pembrolizumab, nivolumab, atezolizumab, avelumab, durvalumab, pidilizumab, REGN2810, AMP-224, MEDI0680, PDR001, CT-001 or a combination thereof. A treatment can comprise administering to the subject a CTLA4 antibody. A CTLA4 antibody can comprise ipilimumab, tremelimumab or a combination thereof.

In some aspects of the preceding methods, determining $\mu_2$ in step (b), wherein $\mu_2$ is the mean of the linear combination of the log-transformed normalized expression of the at least one gene in non-hypermutated samples, comprises: 1) measuring the gene expression level of the at least one gene in a plurality of analogous, non-hypermutated tumor samples from at least one subject, wherein at least one sample in the plurality of analogous, non-hypermutated samples originates from the same tissue as the tumor sample in step (a) of the preceding methods; 2) determining z, wherein $z=\sum_{i=1}^{10} z_i w_i$, wherein $z_i$ is the log-transformed normalized expression of the at least one gene i from step (1) and $w_i$ is the prespecified weight for gene i; and 3) determining for each of the at least one gene the mean of z from step (2).

In some aspects of the preceding methods, determining $\sigma_2$ in step (b), wherein $\sigma 2$ is the standard deviation of the linear combination of the log-transformed normalized expression of the at least one gene in non-hypermutated samples, comprises: 1) measuring the gene expression level of the at least one gene in a plurality of analogous, non-hypermutated tumor samples from at least one subject, wherein at least one sample in the plurality of analogous, non-hypermutated samples originates from the same tissue as the tumor sample in step (a) of the preceding methods; 2) determining z, wherein $z=\sum_{i=1}^{10} z_i w_i$, wherein $z_i$ is the log-transformed normalized expression of the at least one gene i from step (1) and $w_i$ is the prespecified weight for gene i; and 3) determining for each of the at least one gene the standard deviation of z from step (2).

In some aspects of the preceding methods, measuring the gene expression of the at least one gene in a tumor sample from the subject and measuring the gene expression of the at least one gene in a plurality of analogous non-hypermutated tumor samples is performed using the same method. In some aspects of the preceding methods, measuring the gene expression of the at least one gene in a tumor sample from the subject and measuring the gene expression of the at least one gene in a plurality of analogous non-hypermutated tumor samples is performed using the same apparatus. In preferred aspects of the preceding methods, measuring the gene expression of the at least one gene in a tumor sample from the subject and measuring the gene expression of the at least one gene in a plurality of analogous non-hypermutated tumor samples is performed using the same method and apparatus.

In some aspects, the prespecified weight for gene i, $w_i$, in step (b) of the preceding methods can be:

| Gene | Weight |
| --- | --- |
| EPM2AIP1 | −0.31218 |
| TTC30A | −0.19894 |
| SMAP1 | −0.1835 |
| RNLS | −0.19023 |
| WNT11 | −0.11515 |
| SFXN1 | 0.214676 |
| SREBF1 | 0.194835 |
| TYMS | 0.206972 |
| EIF5AL1 | 0.194935 |
| WDR76 | 0.188582 |

In some aspects, the predetermined cutoff value in the preceding methods that identifies mismatch repair deficiency in a subject can have a specificity of 99%. In some aspects, the predetermined cutoff value in the preceding methods that identifies mismatch repair deficiency in a subject can have a specificity of at least 99%. In preferred aspects, the cutoff value that identifies mismatch repair deficiency in a subject can have a specificity of 99.5%. In preferred aspects, the cutoff value that identifies mismatch repair deficiency in a subject can have a specificity of at least 99.5%.

In some aspects, the predetermined cutoff value in the preceding methods that identifies mismatch repair deficiency in a subject can have a specificity of at least 70%, or at least 75%, or at least 80%, or at least 85%, or at least 90%, or at least 91%, or at least 92%, or at least 93%, or at least 94%, or at least 95%, or at least 96%, or at least 97% or at least 98%.

In some aspects, the predetermined cutoff value of the preceding methods that identifies mismatch repair deficiency in a subject can be 1.645. Alternatively, the predetermined cutoff value can be 2.326. Alternatively still, the predetermined cutoff value can be 2.576.

The at least one gene in step (a) of the preceding methods can comprise each of EPM2AIP1, TTC30A, SMAP1, RNLS, WNT11, SFXN1, SREBF1, TYMS, EIF5AL1, and WDR76.

In some aspects, step (a) of the preceding methods can comprise measuring the gene expression level of at least two genes, or at least three genes, or at least four genes, or at least five genes, or at least six genes, or at least seven genes, or at least eight genes, or at least nine genes or at least 10 genes comprising EPM2AIP1, TTC30A, SMAP1, RNLS, WNT11, SFXN1, SREBF1, TYMS, EIF5AL1, and WDR76.

In some aspects, when the tumor sample is a colon adenocarcinoma (COAD), esophageal carcinoma (ESCA), stomach adenocarcinoma (STAD) or uterine corpus endometrial carcinoma (UCEC) tumor sample, $\sigma_2$, the standard deviation of the linear combination of the log transformed gene expression of the at least one gene in non-hypermutated samples, in step (b) of the preceding methods can be:

| Tumor Type | $\sigma_2$ |
|---|---|
| COAD | 0.6604 |
| ESCA | 0.7617 |
| STAD | 0.8153 |
| UCEC | 0.7027 |

Table 1 shows the sequences of the at least one gene from step (a) of the preceding methods.

In one aspect, the present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three genes are used, or $c_1$ is 1.03 and $c_2$ is 0.70 when four genes are used; d) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; e) determining a score HPS, wherein $HPS=(y-\mu_2)/\sigma_2$, wherein $y=\Sigma_{i=1}^{10}y_iw_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and $\sigma_2$ is the standard deviation of the linear combination of the log-transformed normalized expression of the at least one gene in non-hypermutated samples; f) determining a score MPS wherein $MPS=(\max(HPS,0)^2+\min(MLS,0)^2)^{1/2}$; g) comparing the MPS score with a predetermined cutoff value, wherein the cutoff value identifies mismatch repair deficiency in a subject with at least 95% specificity; and h) producing a report identifying the presence of mismatch repair deficiency in the subject when the MPS score is equal to or greater than the predetermined cutoff value or producing a report identifying the absence of mismatch repair deficiency in the subject when the MPS score is less than the predetermined cutoff value.

In one aspect, the present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_2$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three genes are used, or $c_1$ is 1.03 and $c_2$ is 0.70 when four genes are used; d) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; e) determining a score HPS, wherein $HPS=(y-\mu_2)/\sigma_2$, wherein $y=\Sigma_{i=1}^{10}y_iw_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and 02 is the standard deviation of the linear combination of the log-transformed normalized expression of the at least one gene in non-hypermutated samples; f) determining a score MPS wherein $MPS=(\max(HPS,0)^2+\min(MLS,0)^2)^{1/2}$; g) comparing the MPS score with a predetermined cutoff value, wherein the cutoff value identifies mismatch repair deficiency in a subject with at least 95% specificity; and h) identifying the presence of mismatch repair deficiency in the subject when the MPS score is equal to or greater than the predetermined cutoff value or identifying the absence of mismatch repair deficiency in the subject when the MPS score is less than the predetermined cutoff value.

In some aspects, the preceding methods can further comprise administering at least one treatment to a subject identified as having mismatch repair deficiency. A treatment can comprise anti-cancer therapy. A treatment can comprise administering to the subject immunotherapy. The at least one treatment can comprise administering to the subject at least one checkpoint inhibitor. A treatment can comprise administering to the subject pembrolizumab, nivolumab, atezolizumab, avelumab, durvalumab, pidilizumab, REGN2810, AMP-224, MEDI0680, PDR001, CT-001 or a combination thereof. A treatment can comprise administering to the subject a CTLA4 antibody. A CTLA4 antibody can comprise ipilimumab, tremelimumab or a combination thereof.

In one aspect, the present disclosure provides a method of identifying mismatch repair deficiency in a subject comprising: a) measuring the gene expression level of at least one gene comprising MLH1, MSH2, MSH6 or PMS2 in a tumor sample from the subject; b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples; c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used, $c_1$ is 0.56 and $c_2$ is 0.83 when two genes are used, $c_1$ is 0.85 and $c_2$ is 0.75 when three genes are used, or $c_1$ is 1.03 and $c_2$ is 0.70 when four genes are used; d) measuring the gene expression level of at least one gene comprising EPM2AIP1, TTC30A, SMAP1, RNLS, WNT11, SFXN1, SREBF1, TYMS, EIF5AL1, or WDR76 in a tumor sample from the subject; e) determining a score HPS, wherein $HPS=(y-\mu_2)/\sigma_2$, wherein $y=\Sigma_{i=1}^{10}y_iw_i$, wherein $y_i$ is the log-transformed normalized expression of the at least one gene i in the tumor sample and $w_i$ is the prespecified weight for gene i, $\mu_2$ is the mean of the linear combination of the log-transformed normalized expression of the at least one gene in non-hypermutated samples, and 02 is the standard deviation of the linear combination of the log-transformed normalized expression of the at least one gene in non-hypermutated samples; f) determining a score MPS wherein MPS=$(\max(HPS,0)^2+\min(MLS,0)^2)^{1/2}$; g) comparing the MPS score with a predetermined cutoff value, wherein the cutoff value identifies mismatch repair deficiency in a subject with at least 95% specificity; and h) administering at least one treatment to the subject when the MPS score is equal to or greater than the predetermined cutoff value. A treatment can comprise anti-cancer therapy. A treatment can comprise administering to the subject immunotherapy. The at least one treatment can comprise administering to the subject at least one checkpoint inhibitor. A treatment can comprise administering to the subject pembrolizumab, nivolumab, atezolizumab, avelumab, durvalumab, pidilizumab, REGN2810, AMP-224, MEDI0680, PDR001, CT-001 or a combination thereof. A treatment can comprise administering to the subject a CTLA4 antibody. A CTLA4 antibody can comprise ipilimumab, tremelimumab or a combination thereof.

In some aspects of the preceding methods, determining $\mu_1$ in step (b), wherein $\mu_1$ is the mean of the log-transformed normalized expression of the at least one gene in non-hypermutated samples, comprises: 1) measuring the gene expression level of the at least one gene in a plurality of analogous, non-hypermutated tumor samples from at least one subject, wherein at least one sample in the plurality of analogous, non-hypermutated samples originates from the same tissue as the tumor sample in step (a) of the preceding methods; 2) determining for each of the at least one gene the log-transformed normalized expression; and 3) determining for each of the at least one gene the mean of the log 2-transformed expression from step (2).

In some aspects of the preceding methods, determining $\sigma_1$ in step (b), wherein $\sigma_1$ is the standard deviation of the log-transformed normalized expression of the at least one gene in non-hypermutated samples, comprises: 1) measuring the gene expression level of the at least one gene in a plurality of analogous, non-hypermutated tumor samples from at least one subject, wherein at least one sample in the plurality of analogous, non-hypermutated samples originates from the same tissue as the tumor sample in step (a) of the preceding methods; 2) determining for each of the at least one gene the log-transformed normalized expression; and 3) determining for each of the at least one gene the standard deviation of the log 2-transformed expression from step (2).

In some aspects of the preceding methods, determining $\mu_2$ in step (e), wherein $\mu_2$ is the mean of the linear combination of the log-transformed normalized expression of the at least one gene in non-hypermutated samples, comprises: 1) measuring the gene expression level of the at least one gene in a plurality of analogous, non-hypermutated tumor samples from at least one subject, wherein at least one sample in the plurality of analogous, non-hypermutated samples originates from the same tissue as the tumor sample in step (a) of the preceding methods; 2) determining z, wherein $z=\Sigma_{i=1}^{10} z_i w_i$, wherein $z_i$ is the log-transformed normalized expression of the at least one gene i from step (1) and $w_i$ is the prespecified weight for gene i; and 3) determining for each of the at least one gene the mean of z from step (2).

In some aspects of the preceding methods, determining $\sigma_2$ in step (e), wherein $\sigma_2$ is the standard deviation of the linear combination of the log-transformed normalized expression of the at least one gene in non-hypermutated samples, comprises: 1) measuring the gene expression level of the at least one gene in a plurality of analogous, non-hypermutated tumor samples from at least one subject, wherein at least one sample in the plurality of analogous, non-hypermutated samples originates from the same tissue as the tumor sample in step (a) of the preceding methods; 2) determining z, wherein $z=\Sigma_{i=1}^{10} z_i w_i$, wherein $z_i$ is the log-transformed normalized expression of the at least one gene i from step (1) and $w_i$ is the prespecified weight for gene i; and 3) determining for each of the at least one gene the standard deviation of z from step (2).

In some aspects of the preceding methods, measuring the gene expression of the at least one gene in a tumor sample from the subject and measuring the gene expression of the at least one gene in a plurality of analogous non-hypermutated tumor samples is performed using the same method. In some aspects of the preceding methods, measuring the gene expression of the at least one gene in a tumor sample from the subject and measuring the gene expression of the at least one gene in a plurality of analogous non-hypermutated tumor samples is performed using the same apparatus. In preferred aspects of the preceding methods, measuring the gene expression of the at least one gene in a tumor sample from the subject and measuring the gene expression of the at least one gene in a plurality of analogous non-hypermutated tumor samples is performed using the same method and apparatus.

In some aspects, the prespecified weight for gene i, $w_i$, in step (e) of the preceding methods can be:

| Gene | Weight |
| --- | --- |
| EPM2AIP1 | −0.31218 |
| TTC30A | −0.19894 |
| SMAP1 | −0.1835 |
| RNLS | −0.19023 |
| WNT11 | −0.11515 |
| SFXN1 | 0.214676 |
| SREBF1 | 0.194835 |
| TYMS | 0.206972 |
| EIF5AL1 | 0.194935 |
| WDR76 | 0.188582 |

In some aspects, the predetermined cutoff value in the preceding methods that identifies mismatch repair deficiency in a subject can have a specificity of 99%. In some aspects, the predetermined cutoff value in the preceding methods that identifies mismatch repair deficiency in a subject can have a specificity of at least 99%. In preferred aspects, the cutoff value that identifies mismatch repair deficiency in a subject can have a specificity of 99.5%. In preferred aspects, the cutoff value that identifies mismatch repair deficiency in a subject can have a specificity of at least 99.5%.

In some aspects, the predetermined cutoff value in the preceding methods that identifies mismatch repair deficiency in a subject can have a specificity of at least 70%, or at least 75%, or at least 80%, or at least 85%, or at least 90%, or at least 91%, or at least 92%, or at least 93%, or at least 94%, or at least 95%, or at least 96%, or at least 97% or at least 98%.

In some aspects, the predetermined cutoff value of the preceding methods that identifies mismatch repair deficiency in a subject can be 2.058. Alternatively, the predetermined cutoff value can be 2.699. Alternatively still, the predetermined cutoff value can be 2.939.

The at least one gene in step (a) of the preceding methods can comprise MLH1. Alternatively, the at least one gene in step (a) can comprise each of MLH1, MSH2, MSH6 and PMS2.

The at least one gene in step (d) of the preceding can comprise each of EPM2AIP1, TTC30A, SMAP1, RNLS, WNT11, SFXN1, SREBF1, TYMS, EIF5AL1 and WDR76.

The at least one gene in step (a) of the preceding can comprise MLH1 and the at least one gene in step (d) of the preceding can comprise each of EPM2AIP1, TTC30A, SMAP1, RNLS, WNT11, SFXN1, SREBF1, TYMS, EIF5AL1 and WDR76. Alternatively, the at least one gene in step (a) of the preceding can comprise each of MLH1, MSH2, MSH6 and PMS2 and the at least one gene in step (d) of the preceding can comprise each of EPM2AIP1, TTC30A, SMAP1, RNLS, WNT11, SFXN1, SREBF1, TYMS, EIF5AL1 and WDR76.

In some aspects, step (a) of the preceding methods can comprise measuring the gene expression level of at least two genes, or at least three genes or at least four genes comprising MLH1, MSH2, MSH6 or PMS2 in a tumor sample from the subject.

In some aspects, step (d) of the preceding methods can comprise measuring the gene expression level of at least two genes, or at least three genes, or at least four genes, or at least five genes, or at least six genes, or at least seven genes, or at least eight genes, or at least nine genes or at least 10 genes comprising EPM2AIP1, TTC30A, SMAP1, RNLS, WNT11, SFXN1, SREBF1, TYMS, EIF5AL1, and WDR76.

In some aspects, when the tumor sample is a colon adenocarcinoma (COAD), esophageal carcinoma (ESCA), stomach adenocarcinoma (STAD) or uterine corpus endometrial carcinoma (UCEC) tumor sample, $\sigma_1$, the standard deviation of the expression of the at least one gene in non-hypermutated samples, in step (b) of the preceding methods can be

|  | MLH1 | MSH2 | MSH6 | PMS2 |
| --- | --- | --- | --- | --- |
| COAD | 0.3241 | 0.4108 | 0.4198 | 0.3259 |
| ESCA | 0.5221 | 0.6602 | 0.7347 | 0.4927 |
| STAD | 0.4245 | 0.6020 | 0.4814 | 0.4314 |
| UCEC | 0.4543 | 0.7312 | 0.6158 | 0.4217 |

In some aspects, when the tumor sample is a colon adenocarcinoma (COAD), esophageal carcinoma (ESCA), stomach adenocarcinoma (STAD) or uterine corpus endometrial carcinoma (UCEC) tumor sample, $\sigma_2$, the standard deviation of the linear combination of the log transformed gene expression of the at least one gene in non-hypermutated samples, in step (e) of the preceding methods can be

| Tumor Type | $\sigma_2$ |
| --- | --- |
| COAD | 0.6604 |
| ESCA | 0.7617 |
| STAD | 0.8153 |
| UCEC | 0.7027 |

Table 1 shows the sequences of the at least one gene from step (a) and the at least one gene from step (d) of the preceding methods.

In some aspects, a subject can be diagnosed with cancer.

In some aspects, a report of the preceding methods identifying mismatch repair deficiency can further identify the subject as having cancer. In some aspects of the methods of the present disclosure, identifying mismatch repair deficiency in a subject can further identify the subject as having cancer.

In some aspects, a report of the preceding method that identifies the presence of mismatch repair deficiency in a subject can further identify the subject for treatment with an anti cancer therapy. In some aspects of the methods of the present disclosure, identifying the presence of mismatch repair deficiency in a subject can further identify the subject for treatment with anti-cancer therapy.

In some aspects, a treatment with an anti-cancer therapy can comprise administering a treatment to a subject identified as having mismatch repair deficiency. A treatment can comprise administering to the subject immunotherapy. A treatment can also comprise administering to the subject checkpoint inhibitors. A treatment can comprise administering to the subject pembrolizumab, nivolumab, atezolizumab, avelumab, durvalumab, pidilizumab, REGN2810, AMP-224, MEDI0680, PDR001, CT-001 or a combination thereof. A treatment can comprise administering to the subject a CTLA4 antibody. The CTLA4 antibody can comprise ipilimumab, tremelimumab or a combination thereof.

In aspects of the methods of the present disclosure, gene expression is measured using methods known in the art. In preferred aspects, the methods are enzyme free methods e.g. US2003/0013091, US2007/0166708, US2010/0015607, US2010/0261026, US2010/0262374, US2010/0112710, US2010/0047924, and US2014/0371088, each of which is incorporated herein by reference in its entirety. Preferably, nCounter® probes, systems, and methods from NanoString Technologies®, as described in US2003/0013091, US2007/0166708, US2010/0015607, US2010/0261026, US2010/0262374, US2010/0112710, US2010/0047924, US2014/0371088, US2014/0017688, and US2011/0086774) are a preferred means for measuring gene expression. nCounter® probes, systems, and methods from NanoString Technologies® allow simultaneous multiplexed identification a plurality (800 or more) distinct target proteins and/or target nucleic acids. Each of the above-mentioned patent publications is incorporated herein by reference in its entirety. The above-mentioned nCounter® probes, systems, and methods from NanoString Technologies® can be combined with any aspect or embodiment described herein.

In one aspect, the present disclosure provides a method of determining a tumor inflammation signature score in a subject comprising: a) measuring the raw RNA level of at least one gene comprising CCL5, CD27, CD274, CD276, CD8A, CMKRLR1, CXCL9, CXCR6, HLA-DQA1, HLA-DRB1, HLA-E, IDO1, LAG3, NKG7, PDCD1LG2, PSMB10, STAT1 and TIGIT; b) measuring the raw RNA level of at least one gene comprising ABCF1, C14ORF102, G6PD, OAZ1, POLR2A, SDHA, STK11IP, TBC1D10B, TBP, UBB and ZBTB34; c) normalizing the measured raw RNA level of the at least one gene from step (a) using the measured raw RNA levels of the at least one gene from step (b); and d) generating a tumor inflammation signature score (TIS) wherein $TIS=\Sigma_{i=1}^{18} q_i w_i$, wherein $q_i$ is the normalized raw RNA level of the at least one gene i from step (c), and $w_i$ is a prespecified weight for gene i.

A more detailed description for determining a tumor inflammation signature score in a subject is disclosed in PCT/US2015/064445 (WO2016/094377), which is incorporated by reference in its entirety. See also Ayers M et al. The Journal of clinical investigation. 2017 Aug. 1; 127(8):2930-40.

In some aspects, the prespecified weight for gene i, $w_i$ in step (d) of the preceding methods can be

| Gene | Weight |
| --- | --- |
| CCL5 | 0.008346 |
| CD27 | 0.072293 |
| CD274 | 0.042853 |
| CD276 | −0.0239 |
| CD8A | 0.031021 |
| CMKRLR1 | 0.151253 |
| CXCL9 | 0.074135 |
| CXCR6 | 0.004313 |
| HLA-DQA1 | 0.020091 |
| HLA-DRB1 | 0.058806 |
| HLA-E | 0.07175 |
| IDO1 | 0.060679 |
| LAG3 | 0.123895 |
| NKG7 | 0.075524 |
| PDCDILG2 | 0.003734 |
| PSMB10 | 0.032999 |
| STAT1 | 0.250229 |
| TIGIT | 0.084767 |

In alternative aspects of the preceding method, step (a) comprises measuring the raw RNA level of at least two genes, or at least three genes, or at least four genes, or at least five genes, or at least six genes, or at least seven genes, or at least eight genes, or at least nine genes, or at least 10 genes, or at least 11 genes, or at least 12 genes, or at least 13 genes, or at least 14 genes, or at least 15 genes, or at least 16 genes, at least 17 genes comprising CCL5, CD27, CD274, CD276, CD8A, CMKRLR1, CXCL9, CXCR6, HLA-DQA1, HLA-DRB1, HLA-E, 1D01, LAG3, NKG7, PDCD1LG2, PSMB10, STAT1 and TIGIT. In a preferred aspect, step (a) comprises measuring the raw RNA level of at least 18 genes comprising each of CCL5, CD27, CD274, CD276, CD8A, CMKRLR1, CXCL9, CXCR6, HLA-DQA1, HLA-DRB1, HLA-E, IDO1, LAG3, NKG7, PDCD1LG2, PSMB10, STAT1 and TIGIT.

In alternative aspects of the preceding method, step (b) comprises measuring the raw RNA level of at least two genes, or at least three genes, or at least four genes, or at least five genes, or at least six genes, or at least seven genes, or at least eight genes, or at least nine genes, or at least 10 genes or at least 11 genes comprising ABCF1, C14ORF102, G6PD, OAZ1, POLR2A, SDHA, STK11IP, TBC1D10B, TBP, UBB and ZBTB34. In a preferred aspect, step (b) comprises measuring the raw RNA level of at least 11 genes comprising each of ABCF1, C14ORF102, G6PD, OAZ1, POLR2A, SDHA, STK11IP, TBC1D10B, TBP, UBB and ZBTB34.

Table 2 shows the sequences of the at least one gene from step (a) and the at least one gene from step (b) of the preceding method.

TABLE 2

Sequences of genes measured for determining tumor inflammation signature score

| Gene | Gen Bank Accession No. | Sequence | SEQ ID No. |
| --- | --- | --- | --- |
| CCL5 | NM_002985.2 | GCTGCAGAGGATTCCTGCAGAGGATCAAGACAG CACGTGGACCTCGCACAGCCTCTCCCACAGGTA CCATGAAGGTCTCCGCGGCAGCCCTCGCTGTCAT CCTCATTGCTACTGCCCTCTGCGCTCCTGCATCT GCCTCCCCATATTCCTCGGACACCACACCCTGCT GCTTTGCCTACATTGCCCGCCCACTGCCCCGTGC CCACATCAAGGAGTATTTCTACACCAGTGGCAA GTGCTCCAACCCAGCAGTCGTCTTTGTCACCCGA AAGAACCGCCAAGTGTGTGCCAACCCAGAGAAG AAATGGGTTCGGGAGTACATCAACTCTTTGGAG ATGAGCTAGGATGGAGAGTCCTTGAACCTGAAC TTACACAAATTTGCCTGTTTCTGCTTGCTCTTGTC CTAGCTTGGGAGGCTTCCCCTCACTATCCTACCC CACCCGCTCCTTGAAGGGCCCAGATTCTACCACA CAGCAGCAGTTACAAAAACCTTCCCCAGGCTGG ACGTGGTGGCTCACGCCTGTAATCCCAGCACTTT GGGAGGCCAAGGTGGGTGGATCACTTGAGGTCA GGAGTTCGAGACCAGCCTGGCCAACATGATGAA ACCCCATCTCTACTAAAAATACAAAAAATTAGC CGGGCGTGGTAGCGGGCGCCTGTAGTCCCAGCT ACTCGGGAGGCTGAGGCAGGAGAATGGCGTGAA CCCGGGAGGCGGAGCTTGCAGTGAGCCGAGATC GCGCCACTGCACTCCAGCCTGGGCGACAGAGCG AGACTCCGTCTCAAAAAAAAAAAAAAAAAAAA AAATACAAAAATTAGCCGGGCGTGGTGGCCCAC GCCTGTAATCCCAGCTACTCGGGAGGCTAAGGC AGGAAAATTGTTTGAACCCAGGAGGTGGAGGCT GCAGTGAGCTGAGATTGTGCCACTTCACTCCAGC CTGGGTGACAAAGTGAGACTCCGTCACAACAAC AACAACAAAAAGCTTCCCCAACTAAAGCCTAGA AGAGCTTCTGAGGCGCTGCTTTGTCAAAAGGAA GTCTCTAGGTTCTGAGCTCTGGCTTTGCCTTGGC TTTGCCAGGGCTCTGTGACCAGGAAGGAAGTCA GCATGCCTCTAGAGGCAAGGAGGGGAGGAACAC TGCACTCTTAAGCTTCCGCCGTCTCAACCCCTCA CAGGAGCTTACTGGCAAACATGAAAAATCGGCT TACCATTAAAGTTCTCAATGCAACCATAAAAAA AAAA | 15 |
| CD27 | NM_001242.4 | CGGAAGGGGAAGGGGTGGAGGTTGCTGCTATG AGAGAGAAAAAAAAAACAGCCACAATAGAGAT TCTGCCTTCAAAGGTTGGCTTGCCACCTGAAGCA | 16 |

TABLE 2-continued

Sequences of genes measured for determining tumor inflammation signature score

| Gene | Gen Bank Accession No. | Sequence | SEQ ID No. |
|---|---|---|---|
| | | GCCACTGCCCAGGGGGTGCAAAGAAGAGACAGC<br>AGCGCCCAGCTTGGAGGTGCTAACTCCAGAGGC<br>CAGCATCAGCAACTGGGCACAGAAAGGAGCCGC<br>CTGGGCAGGGACCATGGCACGGCCACATCCCTG<br>GTGGCTGTGCGTTCTGGGGACCCTGGTGGGCTC<br>TCAGCTACTCCAGCCCCCAAGAGCTGCCCAGAG<br>AGGCACTACTGGGCTCAGGGAAAGCTGTGCTGC<br>CAGATGTGTGAGCCAGGAACATTCCTCGTGAAG<br>GACTGTGACCAGCATAGAAAGGCTGCTCAGTGT<br>GATCCTTGCATACCGGGGGTCTCCTTCTCTCCTG<br>ACCACCACACCCGGCCCCACTGTGAGAGCTGTC<br>GGCACTGTAACTCTGGTCTTCTCGTTCGCAACTG<br>CACCATCACTGCCAATGCTGAGTGTGCCTGTCGC<br>AATGGCTGGCAGTGCAGGGACAAGGAGTGCACC<br>GAGTGTGATCCTCTTCCAAACCCTTCGCTGACCG<br>CTCGGTCGTCTCAGGCCCTGAGCCCACACCCTCA<br>GCCCACCCACTTACCTTATGTCAGTGAGATGCTG<br>GAGGCCAGGACAGCTGGGCACATGCAGACTCTG<br>GCTGACTTCAGGCAGCTGCCTGCCCGGACTCTCT<br>CTACCCACTGGCCACCCCAAAGATCCCTGTGCA<br>GCTCCGATTTTATTCGCATCCTTGTGATCTTCTCT<br>GGAATGTTCCTTGTTTTCACCCTGGCCGGGGCCC<br>TGTTCCTCCATCAACGAAGGAAATATAGATCAA<br>ACAAAGGAGAAAGTCCTGTGGAGCCTGCAGAGC<br>CTTGTCGTTACAGCTGCCCCAGGGAGGAGGAGG<br>GCAGCACCATCCCCATCCAGGAGGATTACCGAA<br>AACCGGAGCCTGCCTGCTCCCCCTGAGCCAGCA<br>CCTGCGGGAGCTGCACTACAGCCCTGGCCTCCA<br>CCCCCACCCCGCCGACCATCCAAGGGAGAGTGA<br>GACCTGGCAGCCACAACTGCAGTCCCATCCTCTT<br>GTCAGGGCCCTTTCCTGTGTACACGTGACAGAGT<br>GCCTTTTCGAGACTGGCAGGGACGAGGACAAAT<br>ATGGATGAGGTGGAGAGTGGGAAGCAGGAGCC<br>CAGCCAGCTGCGCCTGCGCTGCAGGAGGGCGGG<br>GGCTCTGGTTGTAAAACACACTTCCTGCTGCGAA<br>AGACCCACATGCTACAAGACGGGCAAAATAAAG<br>TGACAGATGACCACCCTGCA | |
| CD274 | NM_014143.3 | GGCGCAACGCTGAGCAGCTGGCGCGTCCCGCGC<br>GGCCCCAGTTCTGCGCAGCTTCCCGAGGCTCCGC<br>ACCAGCCGCGCTTCTGTCCGCCTGCAGGGCATTC<br>CAGAAAGATGAGGATATTTGCTGTCTTTATATTC<br>ATGACCTACTGGCATTTGCTGAACGCATTTACTG<br>TCACGGTTCCCAAGGACCTATATGTGGTAGAGT<br>ATGGTAGCAATATGACAATTGAATGCAAATTCC<br>CAGTAGAAAAACAATTAGACCTGGCTGCACTAA<br>TTGTCTATTGGGAAATGGAGGATAAGAACATTA<br>TTCAATTTGTGCATGGAGAGGAAGACCTGAAGG<br>TTCAGCATAGTAGCTACAGACAGAGGGCCCGGC<br>TGTTGAAGGACCAGCTCTCCCTGGGAAATGCTG<br>CACTTCAGATCACAGATGTGAAATTGCAGGATG<br>CAGGGGTGTACCGCTGCATGATCAGCTATGGTG<br>GTGCCGACTACAAGCGAATTACTGTGAAAGTCA<br>ATGCCCCATACAACAAAATCAACCAAAGAATTT<br>TGGTTGTGGATCCAGTCACCTCTGAACATGAACT<br>GACATGTCAGGCTGAGGGCTACCCCAAGGCCGA<br>AGTCATCTGGACAAGCAGTGACCATCAAGTCCT<br>GAGTGGTAAGACCACCACCACCAATTCCAAGAG<br>AGAGGAGAAGCTTTTCAATGTGACCAGCACACT<br>GAGAATCAACACAACAACTAATGAGATTTTCTA<br>CTGCACTTTTAGGAGATTAGATCCTGAGGAAAA<br>CCATACAGCTGAATTGGTCATCCCAGAACTACCT<br>CTGGCACATCCTCCAAATGAAAGGACTCACTTG<br>GTAATTCTGGGAGCCATCTTATTATGCCTTGGTG<br>TAGCACTGACATTCATCTTCCGTTTAAGAAAGG<br>GAGAATGATGGATGTGAAAAAATGTGGCATCCA<br>AGATACAAACTCAAAGAAGCAAAGTGATACACA<br>TTTGGAGGAGACGTAATCCAGCATTGGAACTTCT<br>GATCTTCAAGCAGGGATTCTCAACCTGTGGTTTA<br>GGGGTTCATCGGGGCTGAGCGTGACAAGAGGAA<br>GGAATGGGCCCGTGGGATGCAGGCAATGTGGGA<br>CTTAAAAGGCCCAAGCACTGAAAATGGAACCTG<br>GCGAAAGCAGAGGAGGAGAATGAAGAAAGATG<br>GAGTCAAACAGGGAGCCTGGAGGGAGACCTTGA | 17 |

TABLE 2-continued

Sequences of genes measured for determining tumor inflammation signature score

| Gene | Gen Bank Accession No. | Sequence | SEQ ID No. |
|------|------------------------|----------|------------|
|      |                        | TACTTTCAAATGCCTGAGGGGCTCATCGACGCCT GTGACAGGGAGAAAGGATACTTCTGAACAAGGA GCCTCCAAGCAAATCATCCATTGCTCATCCTAGG AAGACGGGTTGAGAATCCCTAATTTGAGGGTCA GTTCCTGCAGAAGTGCCCTTTGCCTCCACTCAAT GCCTCAATTTGTTTTCTGCATGACTGAGAGTCTC AGTGTTGGAACGGGACAGTATTTATGTATGAGTT TTTCCTATTTATTTTGAGTCTGTGAGGTCTTCTTG TCATGTGAGTGTGGTTGTGAATGATTTCTTTTGA AGATATATTGTAGTAGATGTTACAATTTTGTCGC CAAACTAAACTTGCTGCTTAATGATTTGCTCACA TCTAGTAAAACATGGAGTATTTGTAAGGTGCTTG GTCTCCTCTATAACTACAAGTATACATTGGAAGC ATAAAGATCAAACCGTTGGTTGCATAGGATGTC ACCTTTATTTAACCCATTAATACTCTGGTTGACC TAATCTTATTCTCAGACCTCAAGTGTCTGTGCAG TATCTGTTCCATTTAAATATCAGCTTTACAATTA TGTGGTAGCCTACACACATAATCTCATTTCATCG CTGTAACCACCCTGTTGTGATAACCACTATTATT TTACCCATCGTACAGCTGAGGAAGCAAACAGAT TAAGTAACTTGCCCAAACCAGTAAATAGCAGAC CTCAGACTGCCACCCACTGTCCTTTTATAATACA ATTTACAGCTATATTTTACTTTAAGCAATTCTTTT ATTCAAAAACCATTTATTAAGTGCCCTTGCAATA TCAATCGCTGTGCCAGGCATTGAATCTACAGATG TGAGCAAGACAAAGTACCTGTCCTCAAGGAGCT CATAGTATAATGAGGAGATTAACAAGAAAATGT ATTATTACAATTTAGTCCAGTGTCATAGCATAAG GATGATGCGAGGGGAAAACCCGAGCAGTGTTGC CAAGAGGAGGAAATAGGCCAATGTGGTCTGGGA CGGTTGGATATACTTAAACATCTTAATAATCAGA GTAATTTTCATTTACAAAGAGAGGTCGGTACTTA AAATAACCCTGAAAAATAACACTGGAATTCCTT TTCTAGCATTATATTTATTCCTGATTTGCCTTTGC CATATAATCTAATGCTTGTTTATATAGTGTCTGG TATTGTTTAACAGTTCTGTCTTTTCTATTTAAATG CCACTAAATTTTAAATTCATACCTTTCCATGATT CAAAATTCAAAAGATCCCATGGGAGATGGTTGG AAAATCTCCACTTCATCCTCCAAGCCATTCAAGT TTCCTTTCCAGAAGCAACTGCTACTGCCTTTCAT TCATATGTTCTTCTAAAGATAGTCTACATTTGGA AATGTATGTTAAAAGCACGTATTTTTAAAATTTT TTTCCTAAATAGTAACACATTGTATGTCTGCTGT GTACTTTGCTATTTTTATTTATTTTAGTGTTTCTT ATATAGCAGATGGAATGAATTTGAAGTTCCCAG GGCTGAGGATCCATGCCTTCTTTGTTTCTAAGTT ATCTTTCCCATAGCTTTTCATTATCTTTCATATGA TCCAGTATATGTTAAATATGTCCTACATATACAT TTAGACAACCACCATTTGTTAAGTATTTGCTCTA GGACAGAGTTTGGATTTGTTTATGTTTGCTCAAA AGGAGACCCATGGGCTCTCCAGGGTGCACTGAG TCAATCTAGTCCTAAAAAGCAATCTTATTATTAA CTCTGTATGACAGAATCATGTCTGGAACTTTTGT TTTCTGCTTTCTGTCAAGTATAAACTTCACTTTGA TGCTGTACTTGCAAAATCACATTTTCTTTCTGGA AATTCCGGCAGTGTACCTTGACTGCTAGCTACCC TGTGCCAGAAAAGCCTCATTCGTTGTGCTTGAAC CCTTGAATGCCACCAGCTGTCATCACTACACAGC CCTCCTAAGAGGCTTCCTGGAGGTTTCGAGATTC AGATGCCCTGGGAGATCCCAGAGTTTCCTTTCCC TCTTGGCCATATTCTGGTGTCAATGACAAGGAGT ACCTTGGCTTTGCCACATGTCAAGGCTGAAGAA ACAGTGTCTCCAACAGAGCTCCTTGTGTTATCTG TTTGTACATGTGCATTTGTACAGTAATTGGTGTG ACAGTGTTCTTTGTGTGAATTACAGGCAAGAATT GTGGCTGAGCAAGGCACATAGTCTACTCAGTCT ATTCCTAAGTCCTAACTCCTCCTTGTGGTGTTGG ATTTGTAAGGCACTTTATCCCTTTTGTCTCATGTT TCATCGTAAATGGCATAGGCAGAGATGATACCT AATTCTGCATTTGATTGTCACTTTTTGTACCTGCA TTAATTTAATAAAATATTCTTATTTATTTTGTTAC TTGGTACACCAGCATGTCCATTTTCTTGTTTATTT TGTGTTTAATAAAATGTTCAGTTTAACATCCCAG TGGAGAAAGTTAAAAAA |            |

TABLE 2-continued

Sequences of genes measured for determining tumor inflammation signature score

| Gene | Gen Bank Accession No. | Sequence | SEQ ID No. |
|---|---|---|---|
| CD276 | NM_001024736.1 | CCGGCCTCAGGGACGCACCGGAGCCGCCTTTCC<br>GGGCCTCAGGCGGATTCTCCGGCGCGGCCCGCC<br>CCGCCCCTCGGACTCCCCGGGCCGCCCCCGGCCC<br>CCATTCGGGCCGGGCCTCGCTGCGGCGGCGACT<br>GAGCCAGGCTGGGCCGCGTCCTGAGTCCCAGA<br>GTCGGCGCGGCGCGGCAGGGGCAGCCTTCCACC<br>ACGGGGAGCCCAGCTGTCAGCCGCCTCACAGGA<br>AGATGCTGCGTCGGCGGGGCAGCCCTGGCATGG<br>GTGTGCATGTGGGTGCAGCCCTGGGAGCACTGT<br>GGTTCTGCCTCACAGGAGCCCTGGAGGTCCAGG<br>TCCCTGAAGACCCAGTGGTGGCACTGGTGGGCA<br>CCGATGCCACCCTGTGCTGCTCCTTCTCCCCTGA<br>GCCTGGCTTCAGCCTGGCACAGCTCAACCTCATC<br>TGGCAGCTGACAGATACCAAACAGCTGGTGCAC<br>AGCTTTGCTGAGGGCCAGGACCAGGGCAGCGCC<br>TATGCCAACCGCACGGCCCTCTTCCCGGACCTGC<br>TGGCACAGGGCAACGCATCCCTGAGGCTGCAGC<br>GCGTGCGTGTGGCGGACGAGGGCAGCTTCACCT<br>GCTTCGTGAGCATCCGGGATTTCGGCAGCGCTGC<br>CGTCAGCCTGCAGGTGGCCGCTCCCTACTCGAA<br>GCCCAGCATGACCCTGGAGCCCAACAAGGACCT<br>GCGGCCAGGGGACACGGTGACCATCACGTGCTC<br>CAGCTACCAGGGCTACCCTGAGGCTGAGGTGTT<br>CTGGCAGGATGGGCAGGGTGTGCCCCTGACTGG<br>CAACGTGACCACGTCGCAGATGGCCAACGAGCA<br>GGGCTTGTTTGATGTGCACAGCATCCTGCGGGTG<br>GTGCTGGGTGCAAATGGCACCTACAGCTGCCTG<br>GTGCGCAACCCCGTGCTGCAGCAGGATGCGCAC<br>AGCTCTGTCACCATCACACCCCAGAGAAGCCCC<br>ACAGGAGCCGTGGAGGTCCAGGTCCCTGAGGAC<br>CCGGTGGTGGCCCTAGTGGGCACCGATGCCACC<br>CTGCGCTGCTCCTTCTCCCCCGAGCCTGGCTTCA<br>GCCTGGCACAGCTCAACCTCATCTGGCAGCTGA<br>CAGACACCAAACAGCTGGTGCACAGTTTCACCG<br>AAGGCCGGGACCAGGGCAGCGCCTATGCCAACC<br>GCACGGCCCTCTTCCCGGACCTGCTGGCACAAG<br>GCAATGCATCCCTGAGGCTGCAGCGCGTGCGTG<br>TGGCGGACGAGGGCAGCTTCACCTGCTTCGTGA<br>GCATCCGGGATTTCGGCAGCGCTGCCGTCAGCCT<br>GCAGGTGGCCGCTCCCTACTCGAAGCCCAGCAT<br>GACCCTGGAGCCCAACAAGGACCTGCGGCCAGG<br>GGACACGGTGACCATCACGTGCTCCAGCTACCG<br>GGGCTACCCTGAGGCTGAGGTGTTCTGGCAGGA<br>TGGGCAGGGTGTGCCCCTGACTGGCAACGTGAC<br>CACGTCGCAGATGGCCAACGAGCAGGGCTTGTT<br>TGATGTGCACAGCGTCCTGCGGGTGGTGCTGGG<br>TGCGAATGGCACCTACAGCTGCCTGGTGCGCAA<br>CCCCGTGCTGCAGCAGGATGCGCACGGCTCTGT<br>CACCATCACAGGGCAGCCTATGACATTCCCCCC<br>AGAGGCCCTGTGGGTGACCGTGGGGCTGTCTGT<br>CTGTCTCATTGCACTGCTGGTGGCCCTGGCTTTC<br>GTGTGCTGGAGAAAGATCAAACAGAGCTGTGAG<br>GAGGAGAATGCAGGAGCTGAGGACCAGGATGG<br>GGAGGGAGAAGGCTCCAAGACAGCCCTGCAGCC<br>TCTGAAACACTCTGACAGCAAAGAAGATGATGG<br>ACAAGAAATAGCCTGACCATGAGGACCAGGGAG<br>CTGCTACCCCTCCCTACAGCTCCTACCCTCTGGC<br>TGCAATGGGGCTGCACTGTGAGCCCTGCCCCCA<br>ACAGATGCATCCTGCTCTGACAGGTGGGCTCCTT<br>CTCCAAAGGATGCGATACACAGACCACTGTGCA<br>GCCTTATTTCTCCAATGGACATGATTCCCAAGTC<br>ATCCTGCTGCCTTTTTCTTATAGACACAATGAA<br>CAGACCACCCACAACCTTAGTTCTCTAAGTCATC<br>CTGCCTGCTGCCTTATTTCACAGTACATACATTT<br>CTTAGGGACACAGTACACTGACCACATCACCAC<br>CCTCTTCTTCCAGTGCTGCGTGGACCATCTGCT<br>GCCTTTTTTCTCCAAAAGATGCAATATTCAGACT<br>GACTGACCCCCTGCCTTATTTCACCAAAGACACG<br>ATGCATAGTCACCCCGGCCTTGTTTCTCCAATGG<br>CCGTGATACACTAGTGATCATGTTCAGCCCTGCT<br>TCCACCTGCATAGAATCTTTTCTTCTCAGACAGG<br>GACAGTGCGGCCTCAACATCTCCTGGAGTCTAG<br>AAGCTGTTTCCTTTCCCCTCCTTCCTCCTCTTGCT | 18 |

TABLE 2-continued

Sequences of genes measured for determining tumor inflammation signature score

| Gene | Gen Bank Accession No. | Sequence | SEQ ID No. |
|---|---|---|---|
| | | CTAGCCTTAATACTGGCCTTTTCCCTCCCTGCCC<br>CAAGTGAAGACAGGGCACTCTGCGCCCACCACA<br>TGCACAGCTGTGCATGGAGACCTGCAGGTGCAC<br>GTGCTGGAACACGTGTGGTTCCCCCCTGGCCCAG<br>CCTCCTCTGCAGTGCCCCTCTCCCCTGCCCATCC<br>TCCCCACGGAAGCATGTGCTGGTCACACTGGTTC<br>TCCAGGGGTCTGTGATGGGGCCCCTGGGGGTCA<br>GCTTCTGTCCCTCTGCCTTCTCACCTCTTTGTTCC<br>TTTCTTTTCATGTATCCATTCAGTTGATGTTTATT<br>GAGCAACTACAGATGTCAGCACTGTGTTAGGTG<br>CTGGGGCCCTGCGTGGGAAGATAAAGTTCCTC<br>CCTCAAGGACTCCCCATCCAGCTGGGAGACAGA<br>CAACTAACTACACTGCACCCTGCGGTTTGCAGG<br>GGGCTCCTGCCTGGCTCCCTGCTCCACACCTCCT<br>CTGTGGCTCAAGGCTTCCTGGATACCTCACCCCC<br>ATCCCACCCATAATTCTTACCCAGAGCATGGGGT<br>TGGGGCGGAAACCTGGAGAGAGGGACATAGCCC<br>CTCGCCACGGCTAGAGAATCGGTGGTGTCCAA<br>AATGTCTGTCCAGGTGTGGGCAGGTGGGCAGGC<br>ACCAAGGCCCTCTGGACCTTTCATAGCAGCAGA<br>AAAGGCAGAGCCTGGGCAGGGCAGGGCCAGG<br>AATGCTTTGGGGACACCGAGGGGACTGCCCCCC<br>ACCCCCACCATGGTGCTATTCTGGGGCTGGGGC<br>AGTCTTTTCCTGGCTTGCCTCTGGCCAGCTCCTG<br>GCCTCTGGTAGAGTGAGACTTCAGACGTTCTGAT<br>GCCTTCCGGATGTCATCTCCCTGCCCCAGGAA<br>TGGAAGATGTGAGGACTTCTAATTTAAATGTGG<br>GACTCGGAGGGATTTTGTAAACTGGGGGTATAT<br>TTTGGGGAAAATAAATGTCTTTGTAAAAAGCTTA<br>AAAAAAAAAAAAAAAA | |
| CD8A | NM_001768.5 | CGAAAAGGAGGGTGACTCTCCTCGGCGGGGGCT<br>TCGGGTGACATCACATCCTCCAAATGCGAAATC<br>AGGCTCCGGGCCGGCCGAAGGGCGCAACTTTCC<br>CCCCTCGGCGCCCCACCGGCTCCCGCGCGCCTCC<br>CCTCGCGCCCGAGCTTCGAGCCAAGCAGCGTCC<br>TGGGGAGCGCGTCATGGCCTTACCAGTGACCGC<br>CTTGCTCCTGCCGCTGGCCTTGCTGCTCCACGCC<br>GCCAGGCCGAGCCAGTTCCGGGTGTCGCCGCTG<br>GATCGGACCTGGAACCTGGGCGAGACAGTGGAG<br>CTGAAGTGCCAGGTGCTGCTGTCCAACCCGACG<br>TCGGGCTGCTCGTGGCTCTTCCAGCCGCGCGGCG<br>CCGCCGCCAGTCCCACCTTCCTCCTATACCTCTC<br>CCAAAACAAGCCCAAGGCGGCCGAGGGGCTGG<br>ACACCCAGCGGTTCTCGGGCAAGAGGTTGGGGG<br>ACACCTTCGTCCTCACCCTGAGCGACTTCCGCCG<br>AGAGAACGAGGGCTACTATTTCTGCTCGGCCCT<br>GAGCAACTCCATCATGTACTTCAGCCACTTCGTG<br>CCGGTCTTCCTGCCAGCGAAGCCCACCACGACG<br>CCAGCGCCGCGACCACCAACACCGGCGCCCACC<br>ATCGCGTCGCAGCCCCTGTCCCTGCGCCCAGAG<br>GCGTGCCGGCCAGCGGCGGGGGGCGCAGTGCAC<br>ACGAGGGGGCTGGACTTCGCCTGTGATATCTAC<br>ATCTGGGCGCCCTTGGCCGGGACTTGTGGGGTCC<br>TTCTCCTGTCACTGGTTATCACCCTTTACTGCAA<br>CCACAGGAACCGAAGACGTGTTTGCAAATGTCC<br>CCGGCCTGTGGTCAAATCGGGAGACAAGCCCAG<br>CCTTTCGGCGAGATACGTCTAACCCTGTGCAACA<br>GCCACTACATTACTTCAAACTGAGATCCTTCCTT<br>TTGAGGGAGCAAGTCCTTCCCTTTCATTTTTTCC<br>AGTCTTCCTCCCTGTGTATTCATTCTCATGATTAT<br>TATTTTAGTGGGGCGGGTGGGAAAGATTACT<br>TTTTCTTTATGTGTTTGACGGGAAACAAAACTAG<br>GTAAAATCTACAGTACACCACAAGGGTCACAAT<br>ACTGTTGTGCGCACATCGCGGTAGGGCGTGGAA<br>AGGGGCAGGCCAGAGCTACCCGCAGAGTTCTCA<br>GAATCATGCTGAGAGAGCTGGAGGCACCCATGC<br>CATCTCAACCTCTTCCCCGCCCGTTTTACAAAGG<br>GGGAGGCTAAAGCCCAGAGACAGCTTGATCAAA<br>GGCACACAGCAAGTCAGGGTTGGAGCAGTAGCT<br>GGAGGGACCTTGTCTCCCAGCTCAGGGCTCTTTC<br>CTCCACACCATTCAGGTCTTTCTTTCCGAGGCCC<br>CTGTCTCAGGGTGAGGTGCTTGAGTCTCCAACGG<br>CAAGGGAACAAGTACTTCTTGATACCTGGGATA | 19 |

TABLE 2-continued

Sequences of genes measured for determining tumor inflammation signature score

| Gene | Gen Bank Accession No. | Sequence | SEQ ID No. |
|------|------------------------|----------|------------|
|  |  | CTGTGCCCAGAGCCTCGAGGAGGTAATGAATTA<br>AAGAAGAGAACTGCCTTTGGCAGAGTTCTATAA<br>TGTAAACAATATCAGACTTTTTTTTTTTATAATC<br>AAGCCTAAAATTGTATAGACCTAAAATAAAATG<br>AAGTGGTGAGCTTAACCCTGGAAAATGAATCCC<br>TCTATCTCTAAAGAAAATCTCTGTGAAACCCCTA<br>TGTGGAGGCGGAATTGCTCTCCCAGCCCTTGCAT<br>TGCAGAGGGGCCCATGAAAGAGGACAGGCTACC<br>CCTTTACAAATAGAATTTGAGCATCAGTGAGGTT<br>AAACTAAGGCCCTCTTGAATCTCTGAATTTGAGA<br>TACAAACATGTTCCTGGGATCACTGATGACTTTT<br>TATACTTTGTAAAGACAATTGTTGGAGAGCCCCT<br>CACACAGCCCTGGCCTCTGCTCAACTAGCAGAT<br>ACAGGGATGAGGCAGACCTGACTCTCTTAAGGA<br>GGCTGAGAGCCCAAACTGCTGTCCCAAACATGC<br>ACTTCCTTGCTTAAGGTATGGTACAAGCAATGCC<br>TGCCCATTGGAGAGAAAAAACTTAAGTAGATAA<br>GGAAATAAGAACCACTCATAATTCTTCACCTTAG<br>GAATAATCTCCTGTTAATATGGTGTACATTCTTC<br>CTGATTATTTTCTACACATACATGTAAAATATGT<br>CTTTCTTTTTAAATAGGGTTGTACTATGCTGTTA<br>TGAGTGGCTTTAATGAATAAACATTTGTAGCATC<br>CTCTTTAATGGGTAAACAGCATCCGAAAAAAAA<br>AAAAAAAAAAAAAAAAAAAAAAAAAAAAAAA<br>AAAAAAAAAAAAAAAAAAAAAAAAAAAAAAA<br>AAAAAAAAAAAAAAAAAAAAAAAAAAAAAAA<br>AAAAAAAAAAAAAAAAAAAA |  |
| CMKRLR1 | NM_004072.1 | GAATTCGGCACGAGTCAGGGAAGCAGCCCCGGC<br>GGCCAGCAGGGAGCTCAGGACAGAGCAGGCTCC<br>CTGGGAAGCCTCCGGGTGATAGGGGTGTTCCAG<br>CTGCGGCGCTCTGGGGGTTCAGAGGGGGATCTT<br>GAATGAACAAATGAATGAACTGCTTTCTGGGCA<br>AACAGCCACAGCCAGAGGAGCCTGTGATTGGCA<br>GAAAGAAGCCAGGGTGTGCAAGTCTCCCCAACA<br>GCCTCGAGTGGCCTGCAGTCACAGGGAACCCTC<br>AGGAAGACCTTCCGGGCAGAGACCAGAGGGAA<br>GCCCATCTCTCCAGCAGAACTGCTTGGATTTTTC<br>TACCAGGAGGCTCAGGGCTCTGCAACAATGATA<br>GCAGAAGCTGATGGCATCTAGAGATCTAGGCTG<br>GGACTAGCACAGCATCACTTCTACCACTTTCTGT<br>TGGTCACAGCAACTCACCATGCCAGTGCAGATT<br>CAAGGGGAGGAGAAATAGAGTCCACTTCTTGAT<br>GGGAGGCGTGACATAGAATGGAGGATGAAGATT<br>ACAACACTTCCATCAGTTACGGTGATGAATACCC<br>TGATTATTTAGACTCCATTGTGGTTTTGGAGGAC<br>TTATCCCCCTTGGAAGCCAGGGTGACCAGGATCT<br>TCCTGGTGGTGGTCTACAGCATCGTCTGCTTCCT<br>CGGGATTCTGGGCAATGGTCTGGTGATCATCATT<br>GCCACCTTCAAGATGAAGAAGACAGTGAACATG<br>GTCTGGTTCCTCAACCTGGCAGTGGCAGATTTCC<br>TGTTCAACGTCTTCCTCCCAATCCATATCACCTA<br>TGCCGCCATGGACTACCACTGGGTTTTCGGGACA<br>GCCATGTGCAAGATCAGCAACTTCCTTCTCATCC<br>ACAACATGTTCACCAGCGTCTTCCTGCTGACCAT<br>CATCAGCTCTGACCGCTGCATCTCTGTGCTCCTC<br>CCTGTCTGGTCCCAGAACCACCGCAGCGTTCGCC<br>TGGCTTACATGGCCTGCATGGTCATCTGGGTCCT<br>GGCTTTCTTCTTGAGTTCCCCATCTCTCGTCTTCC<br>GGGACACAGCCAACCTGCATGGGAAAATATCCT<br>GCTTCAACAACTTCAGCCTGTCCACACCTGGGTC<br>TTCCTCGTGGCCCACTCACTCCCAAATGGACCCT<br>GTGGGGTATAGCCGGCACATGGTGGTGACTGTC<br>ACCCGCTTCCTCTGTGGCTTCCTGGTCCCAGTCC<br>TCATCATCACAGCTTGCTACCTCACCATCGTGTG<br>CAAACTGCAGCGCAACCGCCTGGCCAAGACCAA<br>GAAGCCCTTCAAGATTATTGTGACCATCATCATT<br>ACCTTCTTCCTCTGCTGGTGCCCCTACCACACAC<br>TCAACCTCCTAGAGCTCCACCACACTGCCATGCC<br>TGGCTCTGTCTTCAGCCTGGGTTTGCCCCTGGCC<br>ACTGCCCTTGCCATTGCCAACAGCTGCATGAACC<br>CCATTCTGTATGTTTTCATGGGTCAGGACTTCAA<br>GAAGTTCAAGGTGGCCCTCTTCTCTCGCCTGGTC<br>AATGCTCTAAGTGAAGATACAGGCCACTCTTCCT | 20 |

TABLE 2-continued

Sequences of genes measured for determining tumor inflammation signature score

| Gene | Gen Bank Accession No. | Sequence | SEQ ID No. |
|---|---|---|---|
|  |  | ACCCCAGCCATAGAAGCTTTACCAAGATGTCAT CAATGAATGAGAGGACTTCTATGAATGAGAGGG AGACCGGCATGCTTTGATCCTCACTGTGGAACCC CTCAATGGACTCTCTCAACCCAGGGACACCCAA GGATATGTCTTCTGAAGATCAAGGCAAGAACCT CTTTAGCATCCACCAATTTTCACTGCATTTTGCA TGGGATGAACAGTGTTTTATGCTGGGAATCTAG GGCCTGGAACCCCTTTCTTCTAGTGGACAGAACA TGCTGTGTTCCATACAGCCTTGGACTAGCAATTT ATGCTTCTTGGGAGGCCAGCCTTGACTGACTCAA AGCAAAAAAGGAAGAATTC |  |
| CXCL9 | NM_002416.1 | ATCCAATACAGGAGTGACTTGGAACTCCATTCTA TCACTATGAAGAAAAGTGGTGTTCTTTTCCTCTT GGGCATCATCTTGCTGGTTCTGATTGGAGTGCAA GGAACCCCAGTAGTGAGAAAGGGTCGCTGTTCC TGCATCAGCACCAACCAAGGGACTATCCACCTA CAATCCTTGAAAGACCTTAAACAATTTGCCCCAA GCCCTTCCTGCGAGAAAATTGAAATCATTGCTAC ACTGAAGAATGGAGTTCAAACATGTCTAAACCC AGATTCAGCAGATGTGAAGGAACTGATTAAAAA GTGGGAGAAACAGGTCAGCCAAAAGAAAAAGC AAAAGAATGGGAAAAAACATCAAAAAAAGAAA GTTCTGAAAGTTCGAAAATCTCAACGTTCTCGTC AAAAGAAGACTACATAAGAGACCACTTCACCAA TAAGTATTCTGTGTTAAAAATGTTCTATTTTAAT TATACCGCTATCATTCCAAAGGAGGATGGCATA TAATACAAAGGCTTATTAATTTGACTAGAAAATT TAAAACATTACTCTGAATTGTAACTAAAGTTAG AAAGTTGATTTTAAGAATCCAAACGTTAAGAAT TGTTAAAGGCTATGATTGTCTTTGTTCTTCTACC ACCCACCAGTTGAATTTCATCATGCTTAAGGCCA TGATTTTAGCAATACCCATGTCTACACAGATGTT CACCCAACCACATCCCACTCACAACAGCTGCCT GGAAGAGCAGCCCTAGGCTTCCACGTACTGCAG CCTCCAGAGAGTATCTGAGGCACATGTCAGCAA GTCCTAAGCCTGTTAGCATGCTGGTGAGCCAAG CAGTTTGAAATTGAGCTGGACCTCACCAAGCTG CTGTGGCCATCAACCTCTGTATTTGAATCAGCCT ACAGGCCTCACACACAATGTGTCTGAGAGATTC ATGCTGATTGTTATTGGGTATCACCACTGGAGAT CACCAGTGTGTGGCTTTCAGAGCCTCCTTTCTGG CTTTGGAAGCCATGTGATTCCATCTTGCCCGCTC AGGCTGACCACTTTATTTCTTTTTGTTCCCCTTTG CTTCATTCAAGTCAGCTCTTCTCCATCCTACCAC AATGCAGTGCCTTTCTTCTCTCCAGTGCACCTGT CATATGCTCTGATTTATCTGAGTCAACTCCTTTCT CATCTTGTCCCCAACACCCCACAGAAGTGCTTTC TTCTCCCAATTCATCCTCACTCAGTCCAGCTTAG TTCAAGTCCTGCCTCTTAAATAAACCTTTTTGGA CACACAAATTATCTTAAAACTCCTGTTTCACTTG GTTCAGTACCACATGGGTGAACACTCAATGGTT AACTAATTCTTGGGTGTTTATCCTATCTCTCCAA CCAGATTGTCAGCTCCTTGAGGGCAAGAGCCAC AGTATATTTCCCTGTTTCTTCCACAGTGCCTAAT AATACTGTGGAACTAGGTTTTAATAATTTTTTAA TTGATGTTGTTATGGGCAGGATGGCAACCAGAC CATTGTCTCAGAGCAGGTGCTGGCTCTTTCCTGG CTACTCCATGTTGGCTAGCCTCTGGTAACCTCTT ACTTATTATCTTCAGGACACTCACTACAGGGACC AGGGATGATGCAACATCCTTGTCTTTTTATGACA GGATGTTTGCTCAGCTTCTCCAACAATAAGAAGC ACGTGGTAAAACACTTGCGGATATTCTGGACTGT TTTTAAAAAATATACAGTTTACCGAAAATCATAT AATCTTACAATGAAAAGGACTTTATAGATCAGC CAGTGACCAACCTTTTCCCAACCATACAAAAATT CCTTTTCCCGAAGGAAAAGGGCTTTCTCAATAAG CCTCAGCTTTCTAAGATCTAACAAGATAGCCACC GAGATCCTTATCGAAACTCATTTTAGGCAAATAT GAGTTTTATTGTCCGTTTACTTGTTTCAGAGTTTG TATTGTGATTATCAATTACCACACCATCTCCCAT GAAGAAAGGGAACGGTGAAGTACTAAGCGCTA GAGGAAGCAGCCAAGTCGGTTAGTGGAAGCATG ATTGGTGCCCAGTTAGCCTCTGCAGGATGTGGA | 21 |

TABLE 2-continued

Sequences of genes measured for determining tumor inflammation signature score

| Gene | Gen Bank Accession No. | Sequence | SEQ ID No. |
|---|---|---|---|
| | | AACCTCCTTCCAGGGGAGGTTCAGTGAATTGTGT AGGAGAGGTTGTCTGTGGCCAGAATTTAAACCT ATACTCACTTTCCCAAATTGAATCACTGCTCACA CTGCTGATGATTTAGAGTGCTGTCCGGTGGAGAT CCCACCCGAACGTCTTATCTAATCATGAAACTCC CTAGTTCCTTCATGTAACTTCCCTGAAAAATCTA AGTGTTTCATAAATTTGAGAGTCTGTGACCCACT TACCTTGCATCTCACAGGTAGACAGTATATAACT AACAACCAAAGACTACATATTGTCACTGACACA CACGTTATAATCATTTATCATATATATACATACA TGCATACACTCTCAAAGCAAATAATTTTTCACTT CAAAACAGTATTGACTTGTATACCTTGTAATTTG AAATATTTTCTTTGTTAAAATAGAATGGTATCAA TAAATAGACCATTAATCAG | |
| CXCR6 | NM_006564.1 | GCAGACCTTGCTTCATGAGCAAGCTCATCTCTGG AACAAACTGGCAAAGCATCTCTGCTGGTGTTCAT CAGAACAGACACCATGGCAGAGCATGATTACCA TGAAGACTATGGGTTCAGCAGTTTCAATGACAG CAGCCAGGAGGAGCATCAAGACTTCCTGCAGTT CAGCAAGGTCTTTCTGCCCTGCATGTACCTGGTG GTGTTTGTCTGTGGTCTGGTGGGGAACTCTCTGG TGCTGGTCATATCCATCTTCTACCATAAGTTGCA GAGCCTGACGGATGTGTTCCTGGTGAACCTACCC CTGGCTGACCTGGTGTTTGTCTGCACTCTGCCCT TCTGGGCCTATGCAGGCATCCATGAATGGGTGTT TGGCCAGGTCATGTGCAAGAGCCTACTGGGCAT CTACACTATTAACTTCTACACGTCCATGCTCATC CTCACCTGCATCACTGTGGATCGTTTCATTGTAG TGGTTAAGGCCACCAAGGCCTACAACCAGCAAG CCAAGAGGATGACCTGGGGCAAGGTCACCAGCT TGCTCATCTGGGTGATATCCCTGCTGGTTTCCTT GCCCCAAATTATCTATGGCAATGTCTTTAATCTC GACAAGCTCATATGTGGTTACCATGACGAGGCA ATTTCCACTGTGGTTCTTGCCACCCAGATGACAC TGGGGTTCTTCTTGCCACTGCTCACCATGATTGT CTGCTATTCAGTCATAATCAAAACACTGCTTCAT GCTGGAGGCTTCCAGAAGCACAGATCTCTAAAG ATCATCTTCCTGGTGATGGCTGTGTTCCTGCTGA CCCAGATGCCCTTCAACCTCATGAAGTTCATCCG CAGCACACACTGGGAATACTATGCCATGACCAG CTTTCACTACACCATCATGGTGACAGAGGCCATC GCATACCTGAGGGCCTGCCTTAACCCTGTGCTCT ATGCCTTTGTCAGCCTGAAGTTTCGAAAGAACTT CTGGAAACTTGTGAAGGACATTGGTTGCCTCCCT TACCTTGGGGTCTCACATCAATGGAAATCTTCTG AGGACAATTCCAAGACTTTTTCTGCCTCCCACAA TGTGGAGGCCACCAGCATGTTCCAGTTATAGGC CTTGCCAGGGTTTCGAGAAGCTGCTCTGGAATTT GCAAGTCATGGCTGTGCCCTCTTGATGTGGTGAG GCAGGCTTTGTTTATAGCTTGCGCATTCTCATGG AGAAGTTATCAGACACTCTGGCTGGTTTGGAAT GCTTCTTCTCAGGCATGAACATGTACTGTTCTCT TCTTGAACACTCATGCTGAAAGCCCAAGTAGGG GGTCTAAAATTTTTAAGGACTTTCCTTCCTCCAT CTCCAAGAATGCTGAAACCAAGGGGGATGACAT GTGACTCCTATGATCTCAGGTTCTCCTTGATTGG GACTGGGGCTGAAGGTTGAAGAGGTGAGCACGG CCAACAAAGCTGTTGATGGTAGGTGGCACACTG GGTGCCCAAGCTCAGAAGGCTCTTCTGACTACTG GGCAAAGAGTGTAGATCAGAGCAGCAGTGAAA ACAAGTGCTGGCACCACCAGGCACCTCACAGAA ATGAGATCAGGCTCTGCCTCACCTTGGGGCTTGA CTTTTGTATAGGTAGATGTTCAGATTGCTTTGAT TAATCCAGAATAACTAGCACCAGGGACTATGAA TGGGCAAAACTGAATTATAAGAGGCTGATAATT CCAGTGGTCCATGGAATGCTTGAAAAATGTGCA AAACAGCGTTTAAGACTGTAATGAATCTAAGCA GCATTTCTGAAGTGGACTCTTTGGTGGCTTTGCA TTTTAAAAATGAAATTTTCCAATGTCTGCCACAC AAACGTATGTAAATGTATATACCCACACACATA CACACATATGTCATATATTACTAGCATATGAGTT TCATAGCTAAGAAATAAAACTGTTAAAGTCTCC AAACT | 22 |

TABLE 2-continued

Sequences of genes measured for determining tumor inflammation signature score

| Gene | Gen Bank Accession No. | Sequence | SEQ ID No. |
|---|---|---|---|
| HLA-DQA1 | NM_002122.3 | ACAATTACTCTACAGCTCAGAACACCAACTGCT GAGGCTGCCTTGGGAAGAGGATGATCCTAAACA AAGCTCTGCTGCTGGGGGCCCTCGCTCTGACCAC CGTGATGAGCCCCTGTGGAGGTGAAGACATTGT GGCTGACCACGTTGCCTCTTGTGGTGTAAACTTG TACCAGTTTTACGGTCCCTCTGGCCAGTACACCC ATGAATTTGATGGAGATGAGCAGTTCTACGTGG ACCTGGAGAGGAAGGAGACTGCCTGGCGGTGGC CTGAGTTCAGCAAATTTGGAGGTTTTGACCCGCA GGGTGCACTGAGAAACATGGCTGTGGCAAAACA CAACTTGAACATCATGATTAAACGCTACAACTCT ACCGCTGCTACCAATGAGGTTCCTGAGGTCACA GTGTTTTCCAAGTCTCCCGTGACACTGGGTCAGC CCAACACCCTCATTTGTCTTGTGGACAACATCTT TCCTCCTGTGGTCAACATCACATGGCTGAGCAAT GGGCAGTCAGTCACAGAAGGTGTTTCTGAGACC AGCTTCCTCTCCAAGAGTGATCATTCCTTCTTCA AGATCAGTTACCTCACCTTCCTCCCTTCTGCTGA TGAGATTTATGACTGCAAGGTGGAGCACTGGGG CCTGGACCAGCCTCTTCTGAAACACTGGGAGCCT GAGATTCCAGCCCCTATGTCAGAGCTCACAGAG ACTGTGGTCTGTGCCCTGGGGTTGTCTGTGGGCC TCATGGGCATTGTGGTGGGCACTGTCTTCATCAT CCAAGGCCTGCGTTCAGTTGGTGCTTCCAGACAC CAAGGGCCATTGTGAATCCCATCCTGGAAGGGA AGGTGCATCGCCATCTACAGGAGCAGAAGAATG GACTTGCTAAATGACCTAGCACTATTCTCTGGCC CGATTTATCATATCCCTTTTCTCCTCCAAATATTT CTCCTCTCACCTTTTCTCTGGGACTTAAGCTGCT ATATCCCCTCAGAGCTCACAAATGCCTTTACATT CTTTCCCTGACCTCCTGATTTTTTTTTTCTTTTCTC AAATGTTACCTACAAAGACATGCCTGGGGTAAG CCACCCGGCTACCTAATTCCTCAGTAACCTCCAT CTAAAATCTCCAAGGAAGCAATAAATTCCTTTTA TGAGATCTATGTCAAATTTTTCCATCTTTCATCC AGGGCTGACTGAAACTATGGCTAATAATTGGGG TACTCTTATGTTTCAATCCAATTTAACCTCATTTC CCAGATCATTTTTCATGTCCAGTAACACAGAAGC CACCAAGTACAGTATAGCCTGATAATATGTTGAT TTCTTAGCTGACATTAATATTTCTTGCTTCCTTGT GTTCCCACCCTTGGCACTGCCACCCACCCCTCAA TTCAGGCAACAATGAAATTAATGGATACCGTCT GCCCTTGGCCCAGAATTGTTATAGCAAAAATTTT AGAACCAAAAAATAAGTCTGTACTAATTTCAAT GTGGCTTTTAAAAGTATGACAGAGAAATAAGTT AGGATAAAGGAAATTTGAATCTCA | 23 |
| HLA-DRB1 | NM_002124.1 | TAGTTCTCCCTGAGTGAGACTTGCCTGCTTCTCT GGCCCCTGGTCCTGTCCTGTTCTCCAGCATGGTG TGTCTGAAGCTCCCTGGAGGCTCCTGCATGACAG CGCTGACAGTGACACTGATGGTGCTGAGCTCCC CACTGGCTTTGGCTGGGACACCCGACCACGTTT CTTGTGGCAGCTTAAGTTTGAATGTCATTCTTC AATGGGACGGAGCGGGTGCGGTTGCTGGAAAGA TGCATCTATAACCAAGAGGAGTCCGTGCGCTTC GACAGCGACGTGGGGGAGTACCGGGCGGTGACG GAGCTGGGGCGGCCTGATGCCGAGTACTGGAAC AGCCAGAAGGACCTCCTGGAGCAGAGGCGGGCC GCGGTGGACACCTACTGCAGACACAACTACGGG GTTGGTGAGAGCTTCACAGTGCAGCGGCGAGTT GAGCCTAAGGTGACTGTGTATCCTTCAAAGACC CAGCCCCTGCAGCACCACAACCTCCTGGTCTGCT CTGTGAGTGGTTTCTATCCAGGCAGCATTGAAGT CAGGTGGTTCCGGAACGGCCAGGAAGAGAAGGC TGGGGTGGTGTCCACAGGCCTGATCCAGAATGG AGATTGGACCTTCCAGACCCTGGTGATGCTGGA AACAGTTCCTCGGAGTGGAGAGGTTTACACCTG CCAAGTGGAGCACCCAAGTGTGACGAGCCCTCT CACAGTGGAATGGAGAGCACGGTCTGAATCTGC ACAGAGCAAGATGCTGAGTGGAGTCGGGGGCTT CGTGCTGGGCCTGCTCTTCCTTGGGGCCGGGCTG TTCATCTACTTCAGGAATCAGAAAGGACACTCTG GACTTCAGCCAACAGGATTCCTGAGCTGAAATG | 24 |

TABLE 2-continued

Sequences of genes measured for determining tumor inflammation signature score

| Gene | Gen Bank Accession No. | Sequence | SEQ ID No. |
|---|---|---|---|
| | | CAGATGACCACATTCAAGGAAGAACCTTCTGTC CCAGCTTTGCAGAATGAAAAGCTTTCCTGCTTGG CAGTTATTCTTCCACAAGAGAGGGCTTTCTCAGG ACCTGGTTGCTACTGGTTCGGCAACTGCAGAAA ATGTCCTCCCTTGTGGCTTCCTCAGCTCCTGCCCT TGGCCTGAAGTCCCAGCATTGATGACAGCGCCT CATCTTCAACTTTTGTGCTCCCCTTTGCCTAAACC GTATGGCCTCCCGTGCATCTGTACTCACCCTGTA CGACAAACACATTACATTATTAAATGTTTCTCAA AGATGGAGTT | |
| HLA-E | NM_005516.4 | CGGACTCAAGAAGTTCTCAGGACTCAGAGGCTG GGATCATGGTAGATGGAACCCTCCTTTTACTCCT CTCGGAGGCCCTGGCCCTTACCCAGACCTGGGC GGGCTCCCACTCCTTGAAGTATTTCCACACTTCC GTGTCCCGGCCCGGCCGCGGGGAGCCCCGCTTC ATCTCTGTGGGCTACGTGGACGACACCCAGTTCG TGCGCTTCGACAACGACGCCGCGAGTCCGAGGA TGGTGCCGCGGGCGCCGTGGATGGAGCAGGAGG GGTCAGAGTATTGGGACCGGGAGACACGGAGCG CCAGGGACACCGCACAGATTTTCCGAGTGAACC TGCGGACGCTGCGCGGCTACTACAATCAGAGCG AGGCCGGGTCTCACACCCTGCAGTGGATGCATG GCTGCGAGCTGGGGCCCGACGGGCGCTTCCTCC GCGGGTATGAACAGTTCGCCTACGACGGCAAGG ATTATCTCACCCTGAATGAGGACCTGCGCTCCTG GACCGCGGTGGACACGGCGGCTCAGATCTCCGA GCAAAAGTCAAATGATGCCTCTGAGGCGGAGCA CCAGAGAGCCTACCTGGAAGACACATGCGTGGA GTGGCTCCACAAATACCTGGAGAAGGGGAAGGA GACGCTGCTTCACCTGGAGCCCCCAAAGACACA CGTGACTCACCACCCCATCTCTGACCATGAGGCC ACCCTGAGGTGCTGGGCCCTGGGCTTCTACCCTG CGGAGATCACACTGACCTGGCAGCAGGATGGGG AGGGCCATACCCAGGACACGGAGCTCGTGGAGA CCAGGCCTGCAGGGGATGGAACCTTCCAGAAGT GGGCAGCTGTGGTGGTGCCTTCTGGAGAGGAGC AGAGATACACGTGCCATGTGCAGCATGAGGGGC TACCCGAGCCCGTCACCCTGAGATGGAAGCCGG CTTCCCAGCCCACCATCCCCATCGTGGGCATCAT TGCTGGCCTGGTTCTCCTTGGATCTGTGGTCTCT GGAGCTGTGGTTGCTGCTGTGATATGGAGGAAG AAGAGCTCAGGTGGAAAAGGAGGGAGCTACTCT AAGGCTGAGTGGAGCGACAGTGCCCAGGGGTCT GAGTCTCACAGCTTGTAAAGCCTGAGACAGCTG CCTTGTGTGCGACTGAGATGCACAGCTGCCTTGT GTGCGACTGAGATGCAGGATTTCCTCACGCCTCC CCTATGTGTCTTAGGGGACTCTGGCTTCTCTTTTT GCAAGGGCCTCTGAATCTGTCTGTGTCCCTGTTA GCACAATGTGAGGAGGTAGAGAAACAGTCCACC TCTGTGTCTACCATGACCCCCTTCCTCACACTGA CCTGTGTTCCTTCCCTGTTCTCTTTTCTATTAAA ATAAGAACCTGGGCAGAGTGCGGCAGCTCATGC CTGTAATCCCAGCACTTAGGGAGGCCGAGGAGG GCAGATCACGAGGTCAGGAGATCGAAACCATCC TGGCTAACACGGTGAAACCCCGTCTCTACTAAA AAATACAAAAAATTAGCTGGGCGCAGAGGCACG GGCCTGTAGTCCCAGCTACTCAGGAGGCGGAGG CAGGAGAATGGCGTCAACCCGGGAGGCGGAGGT TGCAGTGAGCCAGGATTGTGCGACTGCACTCCA GCCTGGGTGACAGGGTGAAACGCCATCTCAAAA AATAAAAATTGAAAAATAAAAAAAAAAAAAAA AAA | 25 |
| IDO1 | NM_002164.3 | AATTTCTCACTGCCCCTGTGATAAACTGTGGTCA CTGGCTGTGGCAGCAACTATTATAAGATGCTCTG AAAACTCTTCAGACACTGAGGGGCACCAGAGGA GCAGACTACAAGAATGGCACACGCTATGGAAAA CTCCTGGACAATCAGTAAAGAGTACCATATTGA TGAAGAAGTGGGCTTTGCTCTGCCAAATCCACA GGAAAATCTACCTGATTTTTATAATGACTGGATG TTCATTGCTAAACATCTGCCTGATCTCATAGAGT CTGGCCAGCTTCGAGAAAGAGTTGAGAAGTTAA ACATGCTCAGCATTGATCATCTCACAGACCACA | 26 |

TABLE 2-continued

Sequences of genes measured for determining tumor inflammation signature score

| Gene | Gen Bank Accession No. | Sequence | SEQ ID No. |
|---|---|---|---|
| | | AGTCACAGCGCCTTGCACGTCTAGTTCTGGGATG<br>CATCACCATGGCATATGTGTGGGGCAAAGGTCA<br>TGGAGATGTCCGTAAGGTCTTGCCAAGAAATAT<br>TGCTGTTCCTTACTGCCAACTCTCCAAGAAACTG<br>GAACTGCCTCCTATTTTGGTTTATGCAGACTGTG<br>TCTTGGCAAACTGGAAGAAAAAGGATCCTAATA<br>AGCCCCTGACTTATGAGAACATGGACGTTTTGTT<br>CTCATTTCGTGATGGAGACTGCAGTAAAGGATTC<br>TTCCTGGTCTCTCTATTGGTGGAAATAGCAGCTG<br>CTTCTGCAATCAAAGTAATTCCTACTGTATTCAA<br>GGCAATGCAAATGCAAGAACGGGACACTTTGCT<br>AAAGGCGCTGTTGGAAATAGCTTCTTGCTTGGA<br>GAAAGCCCTTCAAGTGTTTCACCAAATCCACGAT<br>CATGTGAACCCAAAAGCATTTTTCAGTGTTCTTC<br>GCATATATTTGTCTGGCTGGAAAGGCAACCCCC<br>AGCTATCAGACGGTCTGGTGTATGAAGGGTTCT<br>GGGAAGACCCAAAGGAGTTTGCAGGGGGCAGTG<br>CAGGCCAAAGCAGCGTCTTTCAGTGCTTTGACGT<br>CCTGCTGGGCATCCAGCAGACTGCTGGTGGAGG<br>ACATGCTGCTCAGTTCCTCCAGGACATGAGAAG<br>ATATATGCCACCAGCTCACAGGAACTTCCTGTGC<br>TCATTAGAGTCAAATCCCTCAGTCCGTGAGTTTG<br>TCCTTTCAAAAGGTGATGCTGGCCTGCGGGAAG<br>CTTATGACGCCTGTGTGAAAGCTCTGGTCTCCCT<br>GAGGAGCTACCATCTGCAAATCGTGACTAAGTA<br>CATCCTGATTCCTGCAAGCCAGCAGCCAAAGGA<br>GAATAAGACCTCTGAAGACCCTTCAAAACTGGA<br>AGCCAAAGGAACTGGAGGCACTGATTTAATGAA<br>TTTCCTGAAGACTGTAAGAAGTACAACTGAGAA<br>ATCCCTTTTGAAGGAAGGTTAATGTAACCCAAC<br>AAGAGCACATTTTATCATAGCAGAGACATCTGT<br>ATGCATTCCTGTCATTACCCATTGTAACAGAGCC<br>ACAAACTAATACTATGCAATGTTTTACCAATAAT<br>GCAATACAAAAGACCTCAAAATACCTGTGCATT<br>TCTTGTAGGAAAACAACAAAAGGTAATTATGTG<br>TAATTATACTAGAAGTTTTGTAATCTGTATCTTA<br>TCATTGGAATAAAATGACATTCAATAAATAAAA<br>AAAAAAAAAAAAAAAAAAAAAAAAAAAAA<br>AAAAAAAAAAAAAAAAAAAAAAAAAAAAA<br>AAAAAAAAAAAAAAAAAAA | |
| LAG3 | NM_002286.5 | ACAGGGGTGAAGGCCCAGAGACCAGCAGAACG<br>GCATCCCAGCCACGACGGCCACTTTGCTCTGTCT<br>GCTCTCCGCCACGGCCCTGCTCTGTTCCCTGGGA<br>CACCCCCGCCCCCACCTCCTCAGGCTGCCTGATC<br>TGCCCAGCTTTCCAGCTTTCCTCTGGATTCCGGC<br>CTCTGGTCATCCCTCCCCACCCTCTCTCCAAGGC<br>CCTCTCCTGGTCTCCCTTCTTCTAGAACCCCTTCC<br>TCCACCTCCCTCTCTGCAGAACTTCTCCTTTACCC<br>CCCACCCCCCACCACTGCCCCCTTTCCTTTTCTG<br>ACCTCCTTTTGGAGGGCTCAGCGCTGCCCAGACC<br>ATAGGAGAGATGTGGGAGGCTCAGTTCCTGGGC<br>TTGCTGTTTCTGCAGCCGCTTTGGGTGGCTCCAG<br>TGAAGCCTCTCCAGCCAGGGGCTGAGGTCCCGG<br>TGGTGTGGGCCCAGGAGGGGGCTCCTGCCCAGC<br>TCCCCTGCAGCCCCACAATCCCCCTCCAGGATCT<br>CAGCCTTCTGCGAAGAGCAGGGGTCACTTGGCA<br>GCATCAGCCAGACAGTGGCCCGCCCGCTGCCGC<br>CCCCGGCCATCCCCTGGCCCCCGGCCCTCACCCG<br>GCGGCGCCCTCCTCCTGGGGGCCCAGGCCCCGC<br>CGCTACACGGTGCTGAGCGTGGGTCCCGGAGGC<br>CTGCGCAGCGGGAGGCTGCCCCTGCAGCCCCGC<br>GTCCAGCTGGATGAGCGCGGCCGGCAGCGCGGG<br>GACTTCTCGCTATGGCTGCGCCCAGCCCGGCGCG<br>CGGACGCCGGCGAGTACCGCGCCGCGGTGCACC<br>TCAGGGACCGCGCCCTCTCCTGCCGCCTCCGTCT<br>GCGCCTGGGCCAGGCCTCGATGACTGCCAGCCC<br>CCCAGGATCTCTCAGAGCCTCCGACTGGGTCATT<br>TTGAACTGCTCCTTCAGCCGCCCTGACCGCCCAG<br>CCTCTGTGCATTGGTTCCGGAACCGGGGCCAGG<br>GCCGAGTCCCTGTCCGGGAGTCCCCCCATCACCA<br>CTTAGCGGAAAGCTTCCTCTTCCTGCCCCAAGTC<br>AGCCCCATGGACTCTGGGCCCTGGGGCTGCATC<br>CTCACCTACAGAGATGGCTTCAACGTCTCCATCA | 27 |

TABLE 2-continued

Sequences of genes measured for determining tumor inflammation signature score

| Gene | Gen Bank Accession No. | Sequence | SEQ ID No. |
|---|---|---|---|
| | | TGTATAACCTCACTGTTCTGGGTCTGGAGCCCCC<br>AACTCCCTTGACAGTGTACGCTGGAGCAGGTTCC<br>AGGGTGGGGCTGCCCTGCCGCCTGCCTGCTGGT<br>GTGGGGACCCGGTCTTTCCTCACTGCCAAGTGGA<br>CTCCTCCTGGGGGAGGCCCTGACCTCCTGGTGAC<br>TGGAGACAATGGCGACTTTACCCTTCGACTAGA<br>GGATGTGAGCCAGGCCCAGGCTGGGACCTACAC<br>CTGCCATATCCATCTGCAGGAACAGCAGCTCAA<br>TGCCACTGTCACATTGGCAATCATCACAGTGACT<br>CCCAAATCCTTTGGGTCACCTGGATCCCTGGGGA<br>AGCTGCTTTGTGAGGTGACTCCAGTATCTGGACA<br>AGAACGCTTTGTGTGGAGCTCTCTGGACACCCCA<br>TCCCAGAGGAGTTTCTCAGGACCTTGGCTGGAG<br>GCACAGGAGGCCCAGCTCCTTTCCCAGCCTTGGC<br>AATGCCAGCTGTACCAGGGGGAGAGGCTTCTTG<br>GAGCAGCAGTGTACTTCACAGAGCTGTCTAGCC<br>CAGGTGCCCAACGCTCTGGGAGAGCCCCAGGTG<br>CCCTCCCAGCAGGCCACCTCCTGCTGTTTCTCAT<br>CCTTGGTGTCCTTTCTCTGCTCCTTTTGGTGACTG<br>GAGCCTTTGGCTTTCACCTTTGGAGAAGACAGTG<br>GCGACCAAGACGATTTTCTGCCTTAGAGCAAGG<br>GATTCACCCTCCGCAGGCTCAGAGCAAGATAGA<br>GGAGCTGGAGCAAGAACCGGAGCCGGAGCCGG<br>AGCCGGAACCGGAGCCCGAGCCCGAGCCCGAGC<br>CGGAGCAGCTCTGACCTGGAGCTGAGGCAGCCA<br>GCAGATCTCAGCAGCCCAGTCCAAATAAACTCC<br>CTGTCAGCAGCAAAAA | |
| NKG7 | NM_005601.3 | TCATGTGACAAAGCGCAGGACCCCTCACTGCCC<br>CAACTGCTTGCTGTTCTCTCTTTCTTGGGCTCTAA<br>GGACCCAGGAGTCTGGGTGCACAGCCTCCTTCTC<br>TCTGAGATTCAAGAGTCTGATCAGCAGCCTCTTC<br>CTCCTCCAGGACCCAGAAGCCCTGAGCTTATCCC<br>CATGGAGCTCTGCCGGTCCCTGGCCCTGCTGGGG<br>GGCTCCCTGGGCCTGATGTTCTGCCTGATTGCTT<br>TGAGCACCGATTTCTGGTTTGAGGCTGTGGGTCC<br>CACCCACTCAGCTCACTCGGGCCTCTGGCCAACA<br>GGGCATGGGGACATCATATCAGGCTACATCCAC<br>GTGACGCAGACCTTCAGCATTATGGCTGTTCTGT<br>GGGCCCTGGTGTCCGTGAGCTTCCTGGTCCTGTC<br>CTGCTTCCCCTCACTGTTCCCCCCAGGCCACGGC<br>CCGCTTGTCTCAACCACCGCAGCCTTTGCTGCAG<br>CCATCTCCATGGTGGTGGCCATGGCGGTGTACAC<br>CAGCGAGCGGTGGGACCAGCCTCCACACCCCCA<br>GATCCAGACCTTCTTCTCCTGGTCCTTCTACCTG<br>GGCTGGGTCTCAGCTATCCTCTTGCTCTGTACAG<br>GTGCCCTGAGCCTGGGTGCTCACTGTGGCGGTCC<br>CCGTCCTGGCTATGAAACCTTGTGAGCAGAAGG<br>CAAGAGCGGCAAGATGAGTTTTGAGCGTTGTAT<br>TCCAAAGGCCTCATCTGGAGCCTCGGGAAAGTC<br>TGGTCCCACATCTGCCCGCCCTTCCAGCCCTTCC<br>CCAGCCCCTCCTCTTGTTTCTTCATTCATTCAACA<br>AAATTTGGCTGGAA | 28 |
| PDCDILG2 | NM_025239.3 | GCAAACCTTAAGCTGAATGAACAACTTTTCTTCT<br>CTTGAATATATCTTAACGCCAAATTTTGAGTGCT<br>TTTTTGTTACCCATCCTCATATGTCCCAGCTAGA<br>AAGAATCCTGGGTTGGAGCTACTGCATGTTGATT<br>GTTTTGTTTTTCCTTTTGGCTGTTCATTTTGGTGG<br>CTACTATAAGGAAATCTAACACAAACAGCAACT<br>GTTTTTTGTTGTTTACTTTTGCATCTTTACTTGTG<br>GAGCTGTGGCAAGTCCTCATATCAAATACAGAA<br>CATGATCTTCCTCCTGCTAATGTTGAGCCTGGAA<br>TTGCAGCTTCACCAGATAGCAGCTTTATTCACAG<br>TGACAGTCCCTAAGGAACTGTACATAATAGAGC<br>ATGGCAGCAATGTGACCCTGGAATGCAACTTTG<br>ACACTGGAAGTCATGTGAACCTTGGAGCAATAA<br>CAGCCAGTTTGCAAAAGGTGGAAAATGATACAT<br>CCCCACACCGTGAAAGAGCCACTTTGCTGGAGG<br>AGCAGCTGCCCCTAGGGAAGGCCTCGTTCCACA<br>TACCTCAAGTCCAAGTGAGGGACGAAGGACAGT<br>ACCAATGCATAATCATCTATGGGGTCGCCTGGG<br>ACTACAAGTACCTGACTCTGAAAGTCAAAGCTT<br>CCTACAGGAAAATAAACACTCACATCCTAAAGG | 29 |

TABLE 2-continued

Sequences of genes measured for determining tumor inflammation signature score

| Gene | Gen Bank Accession No. | Sequence | SEQ ID No. |
|---|---|---|---|
| | | TTCCAGAAACAGATGAGGTAGAGCTCACCTGCC AGGCTACAGGTTATCCTCTGGCAGAAGTATCCTG GCCAAACGTCAGCGTTCCTGCCAACACCAGCCA CTCCAGGACCCCTGAAGGCCTCTACCAGGTCAC CAGTGTTCTGCGCCTAAAGCCACCCCCTGGCAG AAACTTCAGCTGTGTGTTCTGGAATACTCACGTG AGGGAACTTACTTTGGCCAGCATTGACCTTCAAA GTCAGATGGAACCCAGGACCCATCCAACTTGGC TGCTTCACATTTTCATCCCCTTCTGCATCATTGCT TTCATTTTCATAGCCACAGTGATAGCCCTAAGAA AACAACTCTGTCAAAAGCTGTATTCTTCAAAAG ACACAACAAAAAGACCTGTCACCACAACAAAGA GGGAAGTGAACAGTGCTATCTGAACCTGTGGTC TTGGGAGCCAGGGTGACCTGATATGACATCTAA AGAAGCTTCTGGACTCTGAACAAGAATTCGGTG GCCTGCAGAGCTTGCCATTTGCACTTTTCAAATG CCTTTGGATGACCCAGCACTTTAATCTGAAACCT GCAACAAGACTAGCCAACACCTGGCCATGAAAC TTGCCCCTTCACTGATCTGGACTCACCTCTGGAG CCTATGGCTTTAAGCAAGCACTACTGCACTTTAC AGAATTACCCCACTGGATCCTGGACCCACAGAA TTCCTTCAGGATCCTTCTTGCTGCCAGACTGAAA GCAAAAGGAATTATTTCCCCTCAAGTTTTCTAAG TGATTTCCAAAAGCAGAGGTGTGTGGAAATTTC CAGTAACAGAAACAGATGGGTTGCCAATAGAGT TATTTTTTATCTATAGCTTCCTCTGGGTACTAGA AGAGGCTATTGAGACTATGAGCTCACAGACAGG GCTTCGCACAAACTCAAATCATAATTGACATGTT TTATGGATTACTGGAATCTTGATAGCATAATGAA GTTGTTCTAATTAACAGAGAGCATTTAAATATAC ACTAAGTGCACAAATTGTGGAGTAAAGTCATCA AGCTCTGTTTTTGAGGTCTAAGTCACAAAGCATT TGTTTTAACCTGTAATGGCACCATGTTTAATGGT GGTTTTTTTTTGAACTACATCTTTCCTTTAAAAA TTATTGGTTTCTTTTTATTTGTTTTTACCTTAGAA ATCAATTATATACAGTCAAAAATATTTGATATGC TCATACGTTGTATCTGCAGCAATTTCAGATAAGT AGCTAAAATGGCCAAAGCCCCAAACTAAGCCTC CTTTTCTGGCCCTCAATATGACTTTAAATTTGAC TTTTCAGTGCCTCAGTTTGCACATCTGTAATACA GCAATGCTAAGTAGTCAAGGCCTTTGATAATTG GCACTATGGAAATCCTGCAAGATCCCACTACAT ATGTGTGGAGCAGAAGGGTAACTCGGCTACAGT AACAGCTTAATTTTGTTAAATTTGTTCTTTATACT GGAGCCATGAAGCTCAGAGCATTAGCTGACCCT TGAACTATTCAAATGGGCACATTAGCTAGTATA ACAGACTTACATAGGTGGGCCTAAAGCAAGCTC CTTAACTGAGCAAAATTTGGGGCTTATGAGAAT GAAAGGGTGTGAAATTGACTAACAGACAAATCA TACATCTCAGTTTCTCAATTCTCATGTAAATCAG AGAATGCCTTTAAAGAATAAAACTCAATTGTTAT TCTTCAACGTTCTTTATATATTCTACTTTTGGGTA | |
| PSMB10 | NM_002801.2 | AGACGTGAAGCCTAGCAGAGGACTTTTTAGCTG CTCACTGGCCCCGCTTGTCTGGCCGACTCATCCG CCCGCGACCCCTAATCCCCTCTGCCTGCCCCAAG ATGCTGAAGCCAGCCCTGGAGCCCCGAGGGGGC TTCTCCTTCGAGAACTGCCAAAGAAATGCATCAT TGGAACGCGTCCTCCCGGGGCTCAAGGTCCCTC ACGCACGCAAGACCGGGACCACCATCGCGGGCC TGGTGTTCCAAGACGGGGTCATTCTGGGCGCCG ATACGCGAGCCACTAACGATTCGGTCGTGGCGG ACAAGAGCTGCGAGAAGATCCACTTCATCGCCC CCAAAATCTACTGCTGTGGGGCTGGAGTAGCCG CGGACGCCGAGATGACCACACGGATGGTGGCGT CCAAGATGGAGCTACACGCGTTATCTACGGGCC GCGAGCCCCGCGTGGCCACGGTCACTCGCATCC TGCGCCAGACGCTCTTCAGGTACCAGGGCCACG TGGGTGCATCGCTGATCGTGGGCGGCGTAGACC TGACTGGACCGCAGCTCTACGGCGTGCATCCCC ATGGCTCCTACAGCCGTCTGCCCTTCACAGCCCT GGGCTCTGGTCAGGACGCGGCCCTGGCGGTGCT AGAAGACCGGTTCCAGCCGAACATGACGCTGGA GGCTGCTCAGGGGCTGCTGGTGGAAGCCGTCAC | 30 |

TABLE 2-continued

Sequences of genes measured for determining tumor inflammation signature score

| Gene | Gen Bank Accession No. | Sequence | SEQ ID No. |
|---|---|---|---|
| | | CGCCGGGATCTTGGGTGACCTGGGCTCCGGGGG CAATGTGGACGCATGTGTGATCACAAAGACTGG CGCCAAGCTGCTGCGGACACTGAGCTCACCCAC AGAGCCCGTGAAGAGGTCTGGCCGCTACCACTT TGTGCCTGGAACCACAGCTGTCCTGACCCAGAC AGTGAAGCCACTAACCCTGGAGCTAGTGGAGGA AACTGTGCAGGCTATGGAGGTGGAGTAAGCTGA GGCTTAGAGCTTGGAACAAGGGGGAATAAACCC AGAAAATACAGTTAAACAAAAAAAAAAAAAAA AAAAAAAAAAAAAAAA | |
| STAT1 | NM_007315.2 | AGCGGGGCGGGGCGCCAGCGCTGCCTTTTCTCCT GCCGGGTAGTTTCGCTTTCCTGCGCAGAGTCTGC GGAGGGGCTCGGCTGCACCGGGGGATCGCGCC TGGCAGACCCCAGACCGAGCAGAGGCGACCCAG CGCGCTCGGGAGAGGCTGCACCGCCGCGCCCCC GCCTAGCCCTTCCGGATCCTGCGCGCAGAAAAG TTTCATTTGCTGTATGCCATCCTCGAGAGCTGTC TAGGTTAACGTTCGCACTCTGTGTATATAACCTC GACAGTCTTGGCACCTAACGTGCTGTGCGTAGCT GCTCCTTTGGTTGAATCCCCAGGCCCTTGTTGGG GCACAAGGTGGCAGGATGTCTCAGTGGTACGAA CTTCAGCAGCTTGACTCAAAATTCCTGGAGCAG GTTCACCAGCTTTATGATGACAGTTTTCCCATGG AAATCAGACAGTACCTGGCACAGTGGTTAGAAA AGCAAGACTGGGAGCACGCTGCCAATGATGTTT CATTTGCCACCATCCGTTTTCATGACCTCCTGTC ACAGCTGGATGATCAATATAGTCGCTTTTCTTTG GAGAATAACTTCTTGCTACAGCATAACATAAGG AAAAGCAAGCGTAATCTTCAGGATAATTTTCAG GAAGACCCAATCCAGATGTCTATGATCATTTACA GCTGTCTGAAGGAAGAAAGGAAAATTCTGGAAA ACGCCCAGAGATTTAATCAGGCTCAGTCGGGGA ATATTCAGAGCACAGTGATGTTAGACAAACAGA AAGAGCTTGACAGTAAAGTCAGAAATGTGAAGG ACAAGGTTATGTGTATAGAGCATGAAATCAAGA GCCTGGAAGATTTACAAGATGAATATGACTTCA AATGCAAAACCTTGCAGAACAGAGAACACGAGA CCAATGGTGTGGCAAAGAGTGATCAGAAACAAG AACAGCTGTTACTCAAGAAGATGTATTTAATGCT TGACAATAAGAGAAAGGAAGTAGTTCACAAAAT AATAGAGTTGCTGAATGTCACTGAACTTACCCA GAATGCCCTGATTAATGATGAACTAGTGGAGTG GAAGCGGAGACAGCAGAGCGCCTGTATTGGGGG GCCGCCCAATGCTTGCTTGGATCAGCTGCAGAA CTGGTTCACTATAGTTGCGGAGAGTCTGCAGCA AGTTCGGCAGCAGCTTAAAAAGTTGGAGGAATT GGAACAGAAATACACCTACGAACATGACCCTAT CACAAAAAACAAACAAGTGTTATGGGACCGCAC CTTCAGTCTTTTCCAGCAGCTCATTCAGAGCTCG TTTGTGGTGGAAAGACAGCCCTGCATGCCAACG CACCCTCAGAGGCCGCTGGTCTTGAAGACAGGG GTCCAGTTCACTGTGAAGTTGAGACTGTTGGTGA AATTGCAAGAGCTGAATTATAATTTGAAAGTCA AAGTCTTATTTGATAAAGATGTGAATGAGAGAA ATACAGTAAAAGGATTTAGGAAGTTCAACATTT TGGGCACGCACACAAAAGTGATGAACATGGAGG AGTCCACCAATGGCAGTCTGGCGGCTGAATTTC GGCACCTGCAATTGAAAGAACAGAAAAATGCTG GCACCAGAACGAATGAGGGTCCTCTCATCGTTA CTGAAGAGCTTCACTCCCTTAGTTTTGAAACCCA ATTGTGCCAGCCTGGTTTGGTAATTGACCTCGAG ACGACCTCTCTGCCCGTTGTGGTGATCTCCAACG TCAGCCAGCTCCCGAGCGGTTGGGCCTCCATCCT TTGGTACAACATGCTGGTGGCGGAACCCAGGAA TCTGTCCTTCTTCCTGACTCCACCATGTGCACGA TGGGCTCAGCTTTCAGAAGTGCTGAGTTGGCAGT TTTCTTCTGTCACCAAAAGAGGTCTCAATGTGGA CCAGCTGAACATGTTGGGAGAGAAGCTTCTTGG TCCTAACGCCAGCCCCGATGGTCTCATTCCGTGG ACGAGGTTTTGTAAGGAAAATATAAATGATAAA AATTTTCCCTTCTGGCTTTGGATTGAAAGCATCC TAGAACTCATTAAAAAACACCTGCTCCCTCTCTG GAATGATGGGTGCATCATGGGCTTCATCAGCAA | 31 |

TABLE 2-continued

Sequences of genes measured for determining tumor inflammation signature score

| Gene | Gen Bank Accession No. | Sequence | SEQ ID No. |
|---|---|---|---|
| | | GGAGCGAGAGCGTGCCCTGTTGAAGGACCAGCA GCCGGGGACCTTCCTGCTGCGGTTCAGTGAGAG CTCCCGGGAAGGGGCCATCACATTCACATGGGT GGAGCGGTCCCAGAACGGAGGCGAACCTGACTT CCATGCGGTTGAACCCTACACGAAGAAAGAACT TTCTGCTGTTACTTTCCCTGACATCATTCGCAATT ACAAAGTCATGGCTGCTGAGAATATTCCTGAGA ATCCCCTGAAGTATCTGTATCCAAATATTGACAA AGACCATGCCTTTGGAAAGTATTACTCCAGGCC AAAGGAAGCACCAGAGCCAATGGAACTTGATGG CCCTAAAGGAACTGGATATATCAAGACTGAGTT GATTTCTGTGTCTGAAGTTCACCCTTCTAGACTT CAGACCACAGACAACCTGCTCCCCATGTCTCCTG AGGAGTTTGACGAGGTGTCTCGGATAGTGGGCT CTGTAGAATTCGACAGTATGATGAACACAGTAT AGAGCATGAATTTTTTTCATCTTCTCTGGCGACA GTTTTCCTTCTCATCTGTGATTCCCTCCTGCTACT CTGTTCCTTCACATCCTGTGTTTCTAGGGAAATG AAAGAAAGGCCAGCAAATTCGCTGCAACCTGTT GATAGCAAGTGAATTTTTCTCTAACTCAGAAACA TCAGTTACTCTGAAGGGCATCATGCATCTTACTG AAGGTAAAATTGAAAGGCATTCTCTGAAGAGTG GGTTTCACAAGTGAAAAACATCCAGATACACCC AAAGTATCAGGACGAGAATGAGGGTCCTTTGGG AAAGGAGAAGTTAAGCAACATCTAGCAAATGTT ATGCATAAAGTCAGTGCCCAACTGTTATAGGTTG TTGGATAAATCAGTGGTTATTAGGGAACTGCTT GACGTAGGAACGGTAAATTTCTGTGGGAGAATT CTTACATGTTTCTTTGCTTTAAGTGTAACTGGC AGTTTTCCATTGGTTTACCTGTGAAATAGTTCAA AGCCAAGTTTATATACAATTATATCAGTCCTCTT TCAAAGGTAGCCATCATGGATCTGGTAGGGGGA AAATGTGTATTTTATTACATCTTTCACATTGGCT ATTTAAAGACAAAGACAAATTCTGTTTCTTGAGA AGAGAATATTAGCTTTACTGTTTGTTATGGCTTA ATGACACTAGCTAATATCAATAGAAGGATGTAC ATTTCCAAATTCACAAGTTGTGTTTGATATCCAA AGCTGAATACATTCTGCTTTCATCTTGGTCACAT ACAATTATTTTTACAGTTCTCCCAAGGGAGTTAG GCTATTCACAACCACTCATTCAAAAGTTGAAATT AACCATAGATGTAGATAAACTCAGAAATTTAAT TCATGTTTCTTAAATGGGCTACTTTGTCCTTTTTG TTATTAGGGTGGTATTTAGTCTATTAGCCACAAA ATTGGGAAAGGAGTAGAAAAAGCAGTAACTGAC AACTTGAATAATACACCAGAGATAATATGAGAA TCAGATCATTTCAAAACTCATTTCCTATGTAACT GCATTGAGAACTGCATATGTTTCGCTGATATATG TGTTTTTCACATTTGCGAATGGTTCCATTCTCT CCTGTACTTTTTCCAGACACTTTTTTGAGTGGAT GATGTTTCGTGAAGTATACTGTATTTTTACCTTTT TCCTTCCTTATCACTGACACAAAAAGTAGATTAA GAGATGGGTTTGACAAGGTTCTTCCCTTTTACAT ACTGCTGTCTATGTGGCTGTATCTTGTTTTTCCAC TACTGCTACCACAACTATATTATCATGCAAATGC TGTATTCTTCTTTGGTGGAGATAAAGATTTCTTG AGTTTTGTTTTAAAATTAAAGCTAAAGTATCTGT ATTGCATTAAATATAATATGCACACAGTGCTTTC CGTGGCACTGCATACAATCTGAGGCCTCCTCTCT CAGTTTTTATATAGATGGCGAGAACCTAAGTTTC AGTTGATTTTACAATTGAAATGACTAAAAAACA AAGAAGACAACATTAAAACAATATTGTTTCTA | |
| TIGIT | NM_173799.2 | ACATCTGCTTCCTGTAGGCCCTCTGGGCAGAAGC ATGCGCTGGTGTCTCCTCCTGATCTGGGCCCAGG GGCTGAGGCAGGCTCCCCTCGCCTCAGGAATGA TGACAGGCACAATAGAAACAACGGGGAACATTT CTGCAGAGAAAGGTGGCTCTATCATCTTACAAT GTCACCTCTCCTCCACCACGGCACAAGTGACCCA GGTCAACTGGGAGCAGCAGGACCAGCTTCTGGC CATTTGTAATGCTGACTTGGGGTGGCACATCTCC CCATCCTTCAAGGATCGAGTGGCCCCAGGTCCC GGCCTGGGCCTTACCCTCCAGTCGCTGACCGTGA ACGATACAGGGGAGTACTTCTGCATCTATCACA CCTACCCTGATGGGACGTACACTGGGAGAATCT | 32 |

TABLE 2-continued

Sequences of genes measured for determining tumor inflammation signature score

| Gene | Gen Bank Accession No. | Sequence | SEQ ID No. |
|---|---|---|---|
| | | TCCTGGAGGTCCTAGAAAGCTCAGTGGCTGAGC<br>ACGGTGCCAGGTTCCAGATTCCATTGCTTGGAGC<br>CATGGCCGCGACGCTGGTGGTCATCTGCACAGC<br>AGTCATCGTGGTGGTCGCGTTGACTAGAAAGAA<br>GAAAGCCCTCAGAATCCATTCTGTGGAAGGTGA<br>CCTCAGGAGAAAATCAGCTGGACAGGAGGAATG<br>GAGCCCCAGTGCTCCCTCACCCCCAGGAAGCTG<br>TGTCCAGGCAGAAGCTGCACCTGCTGGGCTCTGT<br>GGAGAGCAGCGGGGAGAGGACTGTGCCGAGCT<br>GCATGACTACTTCAATGTCCTGAGTTACAGAAGC<br>CTGGGTAACTGCAGCTTCTTCACAGAGACTGGTT<br>AGCAACCAGAGGCATCTTCTGGAAGATACACTT<br>TTGTCTTTGCTATTATAGATGAATATATAAGCAG<br>CTGCACTCTCCATCAGTGCTGCGTGTGTGTGTGT<br>GTGTGTATGTGTGTGTGTTCAGTTGAGTGAAT<br>AAATGTCATCCTCTTCTCCATCTTCATTTCCTTGG<br>CCTTTTCGTTCTATTCCATTTGCATTATGGCAGG<br>CCTAGGGTGAGTAACGTGGATCTTGATCATAAA<br>TGCAAAATTAAAAAATATCTTGACCTGGTTTTAA<br>ATCTGGCAGTTTGAGCAGATCCTATGTCTCTGAG<br>AGACACATTCCTCATAATGGCCAGCATTTTGGGC<br>TACAAGGTTTTGTGGTTGATGATGAGGATGGCAT<br>GACTGCAGAGCCATCCTCATCTCATTTTTTCACG<br>TCATTTTCAGTAACTTTCACTCATTCAAAGGCAG<br>GTTATAAGTAAGTCCTGGTAGCAGCCTCTATGGG<br>GAGATTTGAGAGTGACTAAATCTTGGTATCTGCC<br>CTCAAGAACTTACAGTTAAATGGGGAGACAATG<br>TTGTCATGAAAAGGTATTATAGTAAGGAGAGAA<br>GGAGACATACACAGGCCTTCAGGAAGAGACGAC<br>AGTTTGGGGTGAGGTAGTTGGCATAGGCTTATCT<br>GTGATGAAGTGGCCTGGGAGCACCAAGGGGATG<br>TTGAGGCTAGTCTGGGAGGAGCAGGAGTTTTGT<br>CTAGGGAACTTGTAGGAAATTCTTGGAGCTGAA<br>AGTCCCACAAAGAAGGCCCTGGCACCAAGGGAG<br>TCAGCAAACTTCAGATTTTATTCTCTGGGCAGGC<br>ATTTCAAGTTTCCTTTTGCTGTGACATACTCATCC<br>ATTAGACAGCCTGATACAGGCCTGTAGCCTCTTC<br>CGGCCGTGTGTGCTGGGGAAGCCCCAGGAAACG<br>CACATGCCCACACAGGGAGCCAAGTCGTAGCAT<br>TTGGGCCTTGATCTACCTTTTCTGCATCAATACA<br>CTCTTGAGCCTTTGAAAAAAGAACGTTTCCCACT<br>AAAAAGAAAATGTGGATTTTTAAAATAGGGACT<br>CTTCCTAGGGGAAAAAGGGGGGCTGGGAGTGAT<br>AGAGGGTTTAAAAAATAAACACCTTCAAACTAA<br>CTTCTTCGAACCCTTTTATTCACTCCCTGACGACT<br>TTGTGCTGGGGTTGGGGTAACTGAACTGCTTATT<br>TCTGTTTAATTGCATTCAGGCTGGATCTTAGAAG<br>ACTTTTATCCTTCCACCATCTCTCTCAGAGGAAT<br>GAGCGGGGAGGTTGGATTTACTGGTGACTGATT<br>TTCTTTCATGGGCCAAGGAACTGAAAGAGAATG<br>TGAAGCAAGGTTGTGTCTTGCGCATGGTTAAAA<br>ATAAAGCATTGTCCTGCTTCCTAAG | |
| ABCF1 | NM_001090.2 | GCGCCAGCTTGGAGAGCCAGCCCCATCGGGGTT<br>CCCCGCCGCCGGAAGCGGAAATAGCACCGGGCG<br>CCGCCACAGTAGCTGTAACTGCCACCGCGATGC<br>CGAAGGCGCCCAAGCAGCAGCCGCCGGAGCCCG<br>AGTGGATCGGGGACGGAGAGAGCACGAGCCCAT<br>CAGACAAAGTGGTGAAGAAAGGGAAGAAGGAC<br>AAGAAGATCAAAAAAACGTTCTTTGAAGAGCTG<br>GCAGTAGAAGATAAACAGGCTGGGAAGAAGA<br>GAAAGTGCTCAAGGAGAAGGAGCAGCAGCAGC<br>AGCAACAGCAACAGCAGCAAAAAAAAAAGCGA<br>GATACCCGAAAAGGCAGGCGGAAGAAGGATGT<br>GGATGATGATGGAGAAGAGAAAGAGCTCATGG<br>AGCGTCTTAAGAAGCTCTCAGTGCCAACCAGTG<br>ATGAGGAGGATGAAGTACCCGCCCCAAAACCCC<br>GCGGAGGGAAGAAAACCAAGGGTGGTAATGTTT<br>TTGCAGCCCTGATTCAGGATCAGAGTGAGGAAG<br>AGGAGGAGGAAGAAAAACATCCTCCTAAGCCTG<br>CCAAGCCGGAGAAGAATCGGATCAATAAGGCCG<br>TATCTGAGGAACAGCAGCCTGCACTCAAGGGCA<br>AAAAGGGAAAGGAAGAGAAGTCAAAAGGGAAG<br>GCTAAGCCTCAAAATAAATTCGCTGCTCTGGAC | 33 |

TABLE 2-continued

Sequences of genes measured for determining tumor inflammation signature score

| Gene | Gen Bank Accession No. | Sequence | SEQ ID No. |
|---|---|---|---|
| | | AATGAAGAGGAGGATAAAGAAGAAGAAATTAT | |
| | | AAAGGAAAAGGAGCCTCCCAAACAAGGGAAGG | |
| | | AGAAGGCCAAGAAGGCAGAGCAGATGGAGTAT | |
| | | GAGCGCCAAGTGGCTTCATTAAAAGCAGCCAAT | |
| | | GCAGCTGAAAATGACTTCTCCGTGTCCCAGGCG | |
| | | GAGATGTCCTCCCGCCAAGCCATGTTAGAAAAT | |
| | | GCATCTGACATCAAGCTGGAGAAGTTCAGCATC | |
| | | TCCGCTCATGGCAAGGAGCTGTTCGTCAATGCA | |
| | | GACCTGTACATTGTAGCCGGCCGCCGCTACGGG | |
| | | CTGGTAGGACCCAATGGCAAGGGCAAGACCACA | |
| | | CTCCTCAAGCACATTGCCAACCGAGCCCTGAGC | |
| | | ATCCCTCCCAACATTGATGTGTTGCTGTGTGAGC | |
| | | AGGAGGTGGTAGCAGATGAGACACCAGCAGTCC | |
| | | AGGCTGTTCTTCGAGCTGACACCAAGCGATTGA | |
| | | AGCTGCTGGAAGAGGAGCGGCGGCTTCAGGGAC | |
| | | AGCTGGAACAAGGGGATGACACAGCTGCTGAGA | |
| | | GGCTAGAGAAGGTGTATGAGGAATTGCGGGCCA | |
| | | CTGGGGCGGCAGCTGCAGAGGCCAAAGCACGGC | |
| | | GGATCCTGGCTGGCCTGGGCTTTGACCCTGAAAT | |
| | | GCAGAATCGACCCACACAGAAGTTCTCAGGGGG | |
| | | CTGGCGCATGCGTGTCTCCCTGGCCAGGGCACTG | |
| | | TTCATGGAGCCCACACTGCTGATGCTGGATGAG | |
| | | CCCACCAACCACCTGGACCTCAACGCTGTCATCT | |
| | | GGCTTAATAACTACCTCCAGGGCTGGCGGAAGA | |
| | | CCTTGCTGATCGTCTCCCATGACCAGGGCTTCTT | |
| | | GGATGATGTCTGCACTGATATCATCCACCTCGAT | |
| | | GCCCAGCGGCTCCACTACTATAGGGGCAATTAC | |
| | | ATGACCTTCAAAAAGATGTACCAGCAGAAGCAG | |
| | | AAAGAACTGCTGAAACAGTATGAGAAGCAAGA | |
| | | GAAAAAGCTGAAGGAGCTGAAGGCAGGCGGGA | |
| | | AGTCCACCAAGCAGGCGGAAAAACAAACGAAG | |
| | | GAAGCCCTGACTCGGAAGCAGCAGAAATGCCGA | |
| | | CGGAAAAACCAAGATGAGGAATCCCAGGAGGC | |
| | | CCCTGAGCTCCTGAAGCGCCCTAAGGAGTACAC | |
| | | TGTGCGCTTCACTTTTCCAGACCCCCCACCACTC | |
| | | AGCCCTCCAGTGCTGGGTCTGCATGGTGTGACAT | |
| | | TCGGCTACCAGGGACAGAAACCACTCTTTAAGA | |
| | | ACTTGGATTTTGGCATCGACATGGATTCAAGGAT | |
| | | TTGCATTGTGGGCCCTAATGGTGTGGGGAAGAG | |
| | | TACGCTACTCCTGCTGCTGACTGGCAAGCTGACA | |
| | | CCGACCCATGGGGAAATGAGAAAGAACCACCGG | |
| | | CTGAAAATTGGCTTCTTCAACCAGCAGTATGCAG | |
| | | AGCAGCTGCGCATGGAGGAGACGCCCACTGAGT | |
| | | ACCTGCAGCGGGGCTTCAACCTGCCCTACCAGG | |
| | | ATGCCCGCAAGTGCCTGGGCCGCTTCGGCCTGG | |
| | | AGAGTCACGCCCACACCATCCAGATCTGCAAAC | |
| | | TCTCTGGTGGTCAGAAGGCGCGAGTTGTGTTTGC | |
| | | TGAGCTGGCCTGTCGGGAACCTGATGTCCTCATC | |
| | | TTGGACGAGCCAACCAATAACCTGGACATAGAG | |
| | | TCTATTGATGCTCTAGGGGAGGCCATCAATGAAT | |
| | | ACAAGGGTGCTGTGATCGTTGTCAGCCATGATG | |
| | | CCCGACTCATCACAGAAACCAATTGCCAGCTGT | |
| | | GGGTGGTGGAGGAGCAGAGTGTTAGCCAAATCG | |
| | | ATGGTGACTTTGAAGACTACAAGCGGGAGGTGT | |
| | | TGGAGGCCCTGGGTGAAGTCATGGTCAGCCGGC | |
| | | CCCGAGAGTGAGCTTTCCTTCCCAGAAGTCTCCC | |
| | | GAGAGACATATTTGTGTGGCCTAGAAGTCCTCTG | |
| | | TGGTCTCCCCTCCTCTGAAGACTGCCTCTGGCCT | |
| | | GCAGCTGACCTGGCAACCATTCAGGCACATGAA | |
| | | GGTGGAGTGTGACCTTGATGTGACCGGGATCCC | |
| | | ACTCTGATTGCATCCATTTCTCTGAAAGACTTGT | |
| | | TTGTTCTGCTTCTCTTCATATAACTGAGCTGGCCT | |
| | | TATCCTTGGCATCCCCCTAAACAAACAAGAGGT | |
| | | GACCACCTTATTGTGAGGTTCCATCCAGCCAAGT | |
| | | TTATGTGGCCTATTGTCTCAGGACTCTCATCACT | |
| | | CAGAAGCCTGCCTCTGATTTACCCTACAGCTTCA | |
| | | GGCCCAGCTGCCCCCAGTCTTTGGGTGGTGCTG | |
| | | TTCTTTTCTGGTGGATTTAATGCTGACTCACTGG | |
| | | TACAAACAGCTGTTGAAGCTCAGAGCTGGAGGT | |
| | | GAGCTTCTGAGGCCTTTGCCATTATCCAGCCCAA | |
| | | GATTTGGTGCCTGCAGCCTCTTGTCTGGTTGAGG | |
| | | ACTTGGGGCAGGAAAGGAATGCTGCTGAACTTG | |
| | | AATTTCCCTTTACAAGGGGAAGAAATAAAGGAA | |
| | | AGGAGTTGCTGCCGACCTGTCACTGTTTGGAGAT | |

TABLE 2-continued

Sequences of genes measured for determining tumor inflammation signature score

| Gene | Gen Bank Accession No. | Sequence | SEQ ID No. |
|---|---|---|---|
| | | TGATGGGAGTTGGAACTGTTCTCAGTCTTGATTT GCTTTATTCAGTTTTCTAGCAGCTTTTAATAGTCC CCTCTTCCCCACTAAATGGATCTTGTTTGCAGTC TTGCTGACAGTGTTTGCTGTTTAAGGATCATAGG ATTCCTTTCCCCCAACCCTTCACGCAAGGAAAAA GCAAAGTGATTCATACCTTCTATCTTGGAAAAAA AAAAAA | |
| C14ORF102 | NM_017970.3 | CCCCTTGGCCCCGCCCCACCCTGCTTTGCCCTGC CTCTCCCTGCCCCGCCGCGCCCCAGTCCCTTGAC GACCCTCCTCTCTGGGCCCCGCCCCTCCCGCTTC GGGGTCAAGCCCCAGAGAGCGCCGCGAAAACCA CATTTCCCAGAGTGCACCGCGACGGCAGGGGTC CTCAGACCGGCGCTCGCTCGCCGGCGCCATCCCT ATAGAGAAGAACGGAGGTACGGCCTGTGGTCAT GGCGCTGTTCCCAGCCTTTGCGGGGCTTAGTGAG GCTCCCGATGGCGGGAGCTCCAGGAAAGAGTTA GACTGGCTGAGCAACCCAAGCTTTTGTGTTGGAT CCATAACGTCCCTGAGCCAACAAACTGAAGCAG CTCCAGCCCATGTTTCTGAAGGGTTACCGCTGAC AAGGAGTCATCTGAAATCAGAGTCTTCAGATGA AAGTGACACTAACAAAAAGCTCAAACAAACAAG TAGAAAAAAGAAGAAAGAGAAAAAGAAAAAAA GGAAGCATCAGCATCATAAGAAAACAAAGAGG AAGCATGGGCCGTCGAGTAGCAGCAGGTCTGAG ACAGACACCGATTCTGAAAAGGACAAACCTTCC AGAGGCGTTGGAGGCAGTAAAAAGGAATCTGAG GAACCGAATCAAGGAAATAATGCTGCAGCTGAT ACTGGACATCGCTTTGTTTGGCTTGAGGACATTC AGGCTGTGACGGGAGAAACCTTCAGAACAGATA AGAAACCAGATCCTGCGAACTGGGAGTACAAGT CTCTCTACCGAGGGGATATAGCAAGATACAAGA GGAAAGGAGACTCCTGCCTTGGCATTAACCCTA AGAAGCAGTGCATATCTTGGGAAGGGACTTCCA CAGAGAAGAAGCATTCACGCAAGCAGGTTGAAC GCTATTTTACTAAGAAGAGTGTGGGATTAATGA ACATCGATGGAGTTGCCATTAGCAGTAAAACTG AACCTCCCTCATCTGAGCCCATCTCCTTTATACC AGTGAAGGACTTGGAAGATGCGGCTCCTGTTAC AACCTGGTTGAATCCTCTGGGGATTTATGATCAG TCAACCACACATTGGCTACAAGGACAGGGTCCT CCAGAGCAGGAATCAAAGCAGCCAGACGCACA GCCAGACAGCGAGAGTGCGGCTCTCAAGGCCAA GGTGGAGGAGTTTAACAGGAGGGTGCGGGAGA ATCCTCGGGATACGCAGCTGTGGATGGCATTTGT TGCTTTTCAGGACGAGGTCATGAAAAGTCCTGG CCTGTATGCCATCGAGGAAGGAGAGCAGGAAAA GCGAAAGAGGTCCCTGAAGCTCATTCTGGAGAA GAAGCTGGCCATTCTGGAGCGGGCCATTGAGAG CAACCAGAGCAGTGTGGATCTGAAACTGGCCAA GCTGAAGCTCTGCACAGAGTTCTGGGAGCCCTC CACTCTGGTCAAAGAGTGGCAGAAACTGATATT TTTGCATCCCAATAATACAGCCCTTTGGCAGAAA TACCTTTTATTTTGCCAGAGCCAGTTTAGTACCT TTTCGATATCAAAAATTCACAGTCTTTATGGAAA ATGCTTGAGCACTTTGTCTGCTGTTAAGGACGGC AGCATCTTATCTCACCCTGCGTTGCCTGGCACGG AAGAGGCCATGTTTGCACTCTTTCTTCAGCAGTG CCACTTTCTGCGGCAGGCTGGCCACTCTGAGAA GGCCATCTCATTGTTCCAGGCCATGGTGGACTTC ACCTTCTTCAAACCCGACAGCGTGAAAGATCTG CCTACCAAAGGACAGGTGGAATTCTTTGAACCC TTTTGGGACAGTGGAGAGCCCGGGCTGGGGAG AAGGGAGCCCGAGGCTGGAAGGCGTGGATGCAC CAGCAGGAACGAGGTGGCTGGGTGGTCATCAAC CCAGATGAGGATGACGATGAACCAGAAGAGGAT GACCAGGAAATAAAAGATAAGACTCTGCCCAGG TGGCAGATCTGGCTTGCTGCTGAGCGTTCCCGTG ACCAGAGGCACTGGCGGCCCTGGCGCCCTGATA AGACCAAGAAGCAAACCGAGGAAGACTGTGAG GATCCCGAGAGACAGGTGTTGTTTGATGATATTG GGCAATCTTTGATCAGACTTTCCAGCCATGATCT TCAGTTCCAGCTGGTGGAGGCCTTCCTGCAGTTC TTGGGTGTGCCTTCTGGCTTTACTCCTCCAGCCT | 34 |

TABLE 2-continued

Sequences of genes measured for determining tumor inflammation signature score

| Gene | Gen Bank Accession No. | Sequence | SEQ ID No. |
|---|---|---|---|
| | | CCTGTCTTTATCTGGCCATGGATGAGAACAGCAT<br>CTTTGATAATGGACTTTATGATGAAAAGCCCTTG<br>ACTTTTTTCAACCCTTTGTTTTCTGGGGCTAGCTG<br>TGTTGGCCGCATGGATAGGTTGGGCTATCCTCGC<br>TGGACCAGGGGTCAGAACCGAGAGGGCGAGGA<br>GTTCATCCGCAATGTCTTCCACCTTGTCATGCCT<br>TTATTTTCAGGCAAAGAGAAGTCCCAGCTCTGCT<br>TCTCCTGGTTACAGTATGAGATTGCAAAGGTCAT<br>TTGGTGCCTGCACACTAAAAACAAGAAGAGATT<br>AAAGTCTCAAGGGAAGAACTGCAAAAAACTAGC<br>CAAGAATCTCCTTAAGGAGCCAGAAAACTGCAA<br>CAACTTTTGCCTGTGGAAGCAGTATGCACATCTG<br>GAGTGGTTGCTTGGCAACACGGAGGATGCCAGA<br>AAAGTTTTTGACACAGCACTTGGCATGGCAGGA<br>AGCAGAGAACTGAAAGACTCTGACCTCTGTGAG<br>CTCAGTCTGCTCTATGCTGAGCTGGAGGTGGAGC<br>TGTCGCCAGAAGTGAGAAGGGCTGCCACAGCTC<br>GAGCTGTTCACATATTAACCAAGCTGACTGAGA<br>GCAGCCCTATGGGCCTACACTGGACAGGTGT<br>TGGCTGTTCACATTTTGAAAGCGCGAAAGGCTTA<br>TGAGCACGCACTGCAGGACTGTTTGGGTGACAG<br>CTGTGTCTCCAATCCAGCTCCCACCGATTCCTGT<br>AGCCGCCTAATTAGCCTGGCTAAATGCTTCATGC<br>TCTTCCAGTATTTGACCATAGGGATTGATGCTGC<br>TGTGCAGATATACGAACAGGTGTTTGCAAAACT<br>GAACAGTTCTGTTTTCCCAGAAGGCTCTGGCGAG<br>GGGGACAGTGCCAGCTCCCAGAGTTGGACCAGT<br>GTTCTCGAAGCCATCACACTGATGCACACGAGC<br>CTGCTGAGATTCCACATGAAAGTGAGTGTTTACC<br>CGCTGGCCCCTCTGCGAGAGGCACTCTCACAGG<br>CTTTAAAGTTGTATCCAGGCAACCAGGTTCTTTG<br>GAGGTCCTATGTACAGATTCAGAATAAGTCCCA<br>CAGTGCCAGCAAAACCAGGAGATTTTTTGACAC<br>AATCACCAGGTCTGCCAAACCCTTGGAGCCTTG<br>GTTGTTTGCAATTGAAGCTGAGAAACTGAGGAA<br>GAGACTGGTGGAAACTGTCCAGAGGTTAGACGG<br>TAGAGAGATCCACGCCACAATTCCTGAGACCGG<br>CTTAATGCATCGGATCCAAGCCCTGTTTGAAAAT<br>GCCATGCGCAGCGACAGTGGCAGCCAGTGCCCC<br>TTGCTGTGGAGGATGTATTTGAACTTTCTGGTTT<br>CCTTAGGAAATAAAGAAAGAAGCAAAGGTGTAT<br>TCTACAAAGCACTTCAGAATTGCCCTTGGGCAA<br>AGGTGTTGTACCTGGACGCCGTGGAGTATTTCCC<br>CGATGAGATGCAGGAGATCCTGGACCTGATGAC<br>TGAGAAGGAGCTCCGGGTGCGCCTGCCGCTGGA<br>GGAGCTGGAGCTGCTGGAGGATTAGAGAGC<br>AGCGGGAAAACGGGCTGTGCCTGCGAGGCCAAG<br>TTGCCCACCCTGCGGAGCTAGGAGGCGCGAGCA<br>GAGAACGTGTGTTAGGAGAACTCGGCTTTTG<br>AAATGTTCTTTCTCGATAGTAATAATGTGGGCTG<br>CCAGCCTCTCACATCTTGCACACTTTTTGGGTGT<br>GTAAATGACACAAAAGTTATTTACATATTTATA<br>TGTGAATATGTGTATATATGTACATAGCCAGAG<br>AGTCATGCCACGTGGTCATTAAACCGATGATGA<br>TTGAGGCGTGAAAAAAAAAAAAAAAA | |
| G6PD | NM_000402.2 | AGGGACAGCCCAGAGGAGGCGTGGCCACGCTGC<br>CGGCGGAAGTGGAGCCCTCCGCGAGCGCGCGAG<br>GCCGCCGGGGCAGGCGGGGAAACCGGACAGTA<br>GGGGCGGGGCCGGGCCGGCGATGGGGATGCGG<br>GAGCACTACGCGGAGCTGCACCCGTGCCCGCCG<br>GAATTGGGGATGCAGAGCAGCGGCAGCGGGTAT<br>GGCAGGCAGCCGGCGGGCCGGCCTCCAGCGCAG<br>GTGCCCGAGAGGCAGGGGCTGGCCTGGGATGCG<br>CGCGCACCTGCCCTCGCCCCGCCCCGCCCGCACG<br>AGGGGTGGTGGCCGAGGCCCCGCCCCGCACGCC<br>TCGCCTGAGGCGGGTCCGCTCAGCCCAGGCGCC<br>CGCCCCCGCCCCGCCGATTAAATGGGCCGGCG<br>GGGCTCAGCCCCCGGAAACGGTCGTAACTTCGG<br>GGCTGCGAGCGCGGAGGGCGACGACGACGAAG<br>CGCAGACAGCGTCATGGCAGAGCAGGTGGCCCT<br>GAGCCGGACCCAGGTGTGCGGGATCCTGCGGGA<br>AGAGCTTTTCCAGGGCGATGCCTTCCATCAGTCG<br>GATACACACATATTCATCATCATGGGTGCATCGG | 35 |

TABLE 2-continued

Sequences of genes measured for determining tumor inflammation signature score

| Gene | Gen Bank Accession No. | Sequence | SEQ ID No. |
|---|---|---|---|
| | | GTGACCTGGCCAAGAAGAAGATCTACCCCACCA<br>TCTGGTGGCTGTTCCGGGATGGCCTTCTGCCCGA<br>AAACACCTTCATCGTGGGCTATGCCCGTTCCCGC<br>CTCACAGTGGCTGACATCCGCAAACAGAGTGAG<br>CCCTTCTTCAAGGCCACCCCAGAGGAGAAGCTC<br>AAGCTGGAGGACTTCTTTGCCCGCAACTCCTATG<br>TGGCTGGCCAGTACGATGATGCAGCCTCCTACC<br>AGCGCCTCAACAGCCACATGGATGCCCTCCACC<br>TGGGGTCACAGGCCAACCGCCTCTTCTACCTGGC<br>CTTGCCCCCGACCGTCTACGAGGCCGTCACCAA<br>GAACATTCACGAGTCCTGCATGAGCCAGATAGG<br>CTGGAACCGCATCATCGTGGAGAAGCCCTTCGG<br>GAGGGACCTGCAGAGCTCTGACCGGCTGTCCAA<br>CCACATCTCCTCCCTGTTCCGTGAGGACCAGATC<br>TACCGCATCGACCACTACCTGGGCAAGGAGATG<br>GTGCAGAACCTCATGGTGCTGAGATTTGCCAAC<br>AGGATCTTCGGCCCCATCTGGAACCGGGACAAC<br>ATCGCCTGCGTTATCCTCACCTTCAAGGAGCCCT<br>TTGGCACTGAGGGTCGCGGGGGCTATTTCGATG<br>AATTTGGGATCATCCGGGACGTGATGCAGAACC<br>ACCTACTGCAGATGCTGTGTCTGGTGGCCATGGA<br>GAAGCCCGCCTCCACCAACTCAGATGACGTCCG<br>TGATGAGAAGGTCAAGGTGTTGAAATGCATCTC<br>AGAGGTGCAGGCCAACAATGTGGTCCTGGGCCA<br>GTACGTGGGGAACCCCGATGGAGAGGGCGAGGC<br>CACCAAAGGGTACCTGGACGACCCCACGGTGCC<br>CCGCGGGTCCACCACCGCCACTTTTGCAGCCGTC<br>GTCCTCTATGTGGAGAATGAGAGGTGGGATGGG<br>GTGCCCTTCATCCTGCGCTGCGGCAAGGCCCTGA<br>ACGAGCGCAAGGCCGAGGTGAGGCTGCAGTTCC<br>ATGATGTGGCCGGCGACATCTTCCACCAGCAGT<br>GCAAGCGCAACGAGCTGGTGATCCGCGTGCAGC<br>CCAACGAGGCCGTGTACACCAAGATGATGACCA<br>AGAAGCCGGGCATGTTCTTCAACCCCGAGGAGT<br>CGGAGCTGGACCTGACCTACGGCAACAGATACA<br>AGAACGTGAAGCTCCCTGACGCCTACGAGCGCC<br>TCATCCTGGACGTCTTCTGCGGGAGCCAGATGCA<br>CTTCGTGCGCAGCGACGAGCTCCGTGAGGCCTG<br>GCGTATTTTCACCCCACTGCTGCACCAGATTGAG<br>CTGGAGAAGCCCAAGCCCATCCCCTATATTTATG<br>GCAGCCGAGGCCCCACGGAGGCAGACGAGCTGA<br>TGAAGAGAGTGGGTTTCCAGTATGAGGGCACCT<br>ACAAGTGGGTGAACCCCCACAAGCTCTGAGCCC<br>TGGGCACCCACCTCCACCCCCGCCACGGCCACC<br>CTCCTTCCCGCCGCCCGACCCCGAGTCGGGAGG<br>ACTCCGGGACCATTGACCTCAGCTGCACATTCCT<br>GGCCCCGGGCTCTGGCCACCCTGGCCCGCCCCTC<br>GCTGCTGCTACTACCCGAGCCCAGCTACATTCCT<br>CAGCTGCCAAGCACTCGAGACCATCCTGGCCCC<br>TCCAGACCCTGCCTGAGCCCAGGAGCTGAGTCA<br>CCTCCTCCACTCACTCCAGCCCAACAGAAGGAA<br>GGAGGAGGGCGCCCATTCGTCTGTCCCAGAGCT<br>TATTGGCCACTGGGTCTCACTCCTGAGTGGGGCC<br>AGGGTGGGAGGGAGGGACAAGGGGGAGGAAAG<br>GGGCGAGCACCCACGTGAGAGAATCTGCCTGTG<br>GCCTTGCCCGCCAGCCTCAGTGCCACTTGACATT<br>CCTTGTCACCAGCAACATCTCGAGCCCCCTGGAT<br>GTCCCCTGTCCCACCAACTCTGCACTCCATGGCC<br>ACCCCGTGCCACCCGTAGGCAGCCTCTCTGCTAT<br>AAGAAAAGCAGACGCAGCAGCTGGGACCCCTCC<br>CAACCTCAATGCCCTGCCATTAAATCCGCAAAC<br>AGCCAAAAAAAAAAAAAAAAAAA | |
| OAZ1 | NM_004152.2 | TTTTGCAACGGCGAGCAGCGGCGGCGGCGCGG<br>AGAGACGCAGCGGAGGTTTTCCTGGTTTCGGAC<br>CCCAGCGGCCGGATGGTGAAATCCTCCCTGCAG<br>CGGATCCTCAATAGCCACTGCTTCGCCAGAGAG<br>AAGGAAGGGGATAAACCCAGCGCCACCATCCAC<br>GCCAGCCGCACCATGCCGCTCCTAAGCCTGCAC<br>AGCCGCGGCGGCAGCAGCAGTGAGAGTTCCAGG<br>GTCTCCCTCCACTGCTGTAGTAACCCGGGTCCGG<br>GGCCTCGGTGGTGCTCCTGATGCCCCTCACCCAC<br>CCCTGAAGATCCCAGGTGGGCAGGGAATAGTC<br>AGAGGGATCACAATCTTTCAGCTAACTTATTCTA | 36 |

TABLE 2-continued

Sequences of genes measured for determining tumor inflammation signature score

| Gene | Gen Bank Accession No. | Sequence | SEQ ID No. |
|---|---|---|---|
| | | CTCCGATGATCGGCTGAATGTAACAGAGGAACT<br>AACGTCCAACGACAAGACGAGGATTCTCAACGT<br>CCAGTCCAGGCTCACAGACGCCAAACGCATTAA<br>CTGGCGAACAGTGCTGAGTGGCGGCAGCCTCTA<br>CATCGAGATCCCGGGCGGCGCGCTGCCCGAGGG<br>GAGCAAGGACAGCTTTGCAGTTCTCCTGGAGTTC<br>GCTGAGGAGCAGCTGCGAGCCGACCATGTCTTC<br>ATTTGCTTCCACAAGAACCGCGAGGACAGAGCC<br>GCCTTGCTCCGAACCTTCAGCTTTTTGGGCTTTG<br>AGATTGTGAGACCGGGGCATCCCCTTGTCCCCA<br>AGAGACCCGACGCTTGCTTCATGGCCTACACGTT<br>CGAGAGAGAGTCTTCGGGAGAGGAGGAGGAGT<br>AGGGCCGCCTCGGGGCTGGGCATCCGGCCCCTG<br>GGGCCACCCCTTGTCAGCCGGGTGGGTAGGAAC<br>CGTAGACTCGCTCATCTCGCCTGGGTTTGTCCGC<br>ATGTTGTAATCGTGCAAATAAACGCTCACTCCGA<br>ATTAGCGGTGTATTTCTTGAAGTTTAATATTGTG<br>TTTGTGATACTGAAGTATTTGCTTTAATTCTAAA<br>TAAAAATTTATATTTTACTTTTTTATTGCTGGTTT<br>AAGATGATTCAGATTATCCTTGTACTTTGAGGAG<br>AAGTTTCTTATTTGGAGTCTTTTGGAAACAGTCT<br>TAGTCTTTTAACTTGGAAAGATGAGGTATTAATC<br>CCCTCCATTGCTCTCCAAAAGCCAATAAAGTGAT<br>TACACCCGA | |
| POLR2A | NM_000937.2 | GAGAGCGCGGCCGGGACGGTTGGAGAAGAAGG<br>CGGCTCCCCGGAAGGGGGAGAGACAAACTGCCG<br>TAACCTCTGCCGTTCAGGAACCCGGTTACTTATT<br>TATTCGTTACCCTTTTTCTTCTTCCTCCCCCAAAA<br>ACCTTTTCCTTTTCCCTTCTTTTTTTTCCTTTTTG<br>GGAGCTGAAAAATTTCCGGTAAGGGAAAGAAGG<br>GCTCCTTTCGCTCCTTATTTCGCCGCCTCCTTCCC<br>TCCGCCACCTTCCCCTCCTCCGGCTTTTTCCTCCC<br>AACTCGGGGAGGTCCTTCCCGGTGGCCGCCCTG<br>ACGAGGTCTGAGCACCTAGGCGGAGGCGGCGCA<br>GGCTTTTTGTAGTGAGGTTTGCGCCTGCGCAGGC<br>GCCTGCCTCCGCCATGCACGGGGGTGGCCCCCC<br>CTCGGGGGACAGCGCATGCCCGCTGCGCACCAT<br>CAAGAGAGTCCAGTTCGGAGTCCTGAGTCCGGA<br>TGAACTGAAGCGAATGTCTGTGACGGAGGGTGG<br>CATCAAATACCCAGAGACGACTGAGGGAGGCCG<br>CCCCAAGCTTGGGGGGCTGATGGACCCGAGGCA<br>GGGGGTGATTGAGCGGACTGGCCGCTGCCAAAC<br>ATGTGCAGGAAACATGACAGAGTGTCCTGGCCA<br>CTTTGGCCACATTGAACTGGCCAAGCCTGTGTTT<br>CACGTGGGCTTCCTGGTGAAGACAATGAAAGTT<br>TTGCGCTGTGTCTGCTTCTTCTGCTCCAAACTGCT<br>TGTGGACTCTAACAACCCAAAGATCAAGGATAT<br>CCTGGCTAAGTCCAAGGGACAGCCCAAGAAGCG<br>GCTCACACATGTCTACGACCTTTGCAAGGGCAA<br>AAACATATGCGAGGGTGGGGAGGAGATGGACA<br>ACAAGTTCGGTGTGGAACAACCTGAGGGTGACG<br>AGGATCTGACCAAAGAAAAGGGCCATGGTGGCT<br>GTGGGCGGTACCAGCCCAGGATCCGGCGTTCTG<br>GCCTAGAGCTGTATGCGGAATGGAAGCACGTTA<br>ATGAGGACTCTCAGGAGAAGAAGATCCTGCTGA<br>GTCCAGAGCGAGTGCATGAGATCTTCAAACGCA<br>TCTCAGATGAGGAGTGTTTTGTGCTGGGCATGGA<br>GCCCCGCTATGCACGGCCAGAGTGGATGATTGT<br>CACAGTGCTGCCTGTGCCCCCGCTCTCCGTGCGG<br>CCTGCTGTTGTGATGCAGGGCTCTGCCCGTAACC<br>AGGATGACCTGACTCACAAACTGGCTGACATCG<br>TGAAGATCAACAATCAGCTGCGGCGCAATGAGC<br>AGAACGGCGCAGCGGCCCATGTCATTGCAGAGG<br>ATGTGAAGCTCCTCCAGTTCCATGTGGCCACCAT<br>GGTGGACAATGAGCTGCCTGGCTTGCCCCGTGC<br>CATGCAGAAGTCTGGGCGTCCCCTCAAGTCCCTG<br>AAGCAGCGGTTGAAGGGCAAGGAAGGCCGGGT<br>GCGAGGGAACCTGATGGGCAAAAGAGTGGACTT<br>CTCGGCCCGTACTGTCATCACCCCGACCCCAAC<br>CTCTCCATTGACCAGGTTGGCGTGCCCCGCTCCA<br>TTGCTGCCAACATGACCTTTGCGGAGATTGTCAC<br>CCCCTTCAACATTGACAGACTTCAAGAACTAGTG<br>CGCAGGGGGAACAGTCAGTACCCAGGCGCCAAG | 37 |

TABLE 2-continued

Sequences of genes measured for determining tumor inflammation signature score

| Gene | Gen Bank Accession No. | Sequence | SEQ ID No. |
|---|---|---|---|
| | | TACATCATCCGAGACAATGGTGATCGCATTGACT<br>TGCGTTTCCACCCCAAGCCCAGTGACCTTCACCT<br>GCAGACCGGCTATAAGGTGGAACGGCACATGTG<br>TGATGGGGACATTGTTATCTTCAACCGGCAGCCA<br>ACTCTGCACAAAATGTCCATGATGGGGCATCGG<br>GTCCGCATTCTCCCATGGTCTACCTTTCGCTTGA<br>ATCTTAGCGTGACAACTCCGTACAATGCAGACTT<br>TGACGGGGATGAGATGAACTTGCACCTGCCACA<br>GTCTCTGGAGACGCGAGCAGAGATCCAGGAGCT<br>GGCCATGGTTCCTCGCATGATTGTCACCCCCCAG<br>AGCAATCGGCCTGTCATGGGTATTGTGCAGGAC<br>ACACTCACAGCAGTGCGCAAATTCACCAAGAGA<br>GACGTCTTCCTGGAGCGGGGTGAAGTGATGAAC<br>CTCCTGATGTTCCTGTCGACGTGGGATGGGAAG<br>GTCCCACAGCCGGCCATCCTAAAGCCCCGGCCC<br>CTGTGGACAGGCAAGCAAATCTTCTCCCTCATCA<br>TACCTGGTCACATCAATTGTATCCGTACCCACAG<br>CACCCATCCCGATGATGAAGACAGTGGCCCTTA<br>CAAGCACATCTCTCCTGGGGACACCAAGGTGGT<br>GGTGGAGAATGGGGAGCTGATCATGGGCATCCT<br>GTGTAAGAAGTCTCTGGGCACGTCAGCTGGCTC<br>CCTGGTCCACATCTCCTACCTAGAGATGGGTCAT<br>GACATCACTCGCCTCTTCTACTCCAACATTCAGA<br>CTGTCATTAACAACTGGCTCCTCATCGAGGGTCA<br>TACTATTGGCATTGGGGACTCCATTGCTGATTCT<br>AAGACTTACCAGGACATTCAGAACACTATTAAG<br>AAGGCCAAGCAGGACGTAATAGAGGTCATCGAG<br>AAGGCACACAACAATGAGCTGGAGCCCACCCCA<br>GGGAACACTCTGCGGCAGACGTTTGAGAATCAG<br>GTGAACCGCATTCTTAACGATGCCCGAGACAAG<br>ACTGGCTCCTCTGCTCAGAAATCCCTGTCTGAAT<br>ACAACAACTTCAAGTCTATGGTCGTGTCCGGAG<br>CTAAAGGTTCCAAGATTAACATCTCCCAGGTCAT<br>TGCTGTCGTTGGACAGCAGAACGTCGAGGGCAA<br>GCGGATTCCATTTGGCTTCAAGCACCGGACTCTG<br>CCTCACTTCATCAAGGATGACTACGGGCCTGAG<br>AGCCGTGGCTTTGTGGAGAACTCCTACCTAGCCG<br>GCCTCACACCCACTGAGTTCTTTTTCCACGCCAT<br>GGGGGGTCGTGAGGGGCTCATTGACACGGCTGT<br>CAAGACTGCTGAGACTGGATACATCCAGCGGCG<br>GCTGATCAAGTCCATGGAGTCAGTGATGGTGAA<br>GTACGACGCGACTGTGCGGAACTCCATCAACCA<br>GGTGGTGCAGCTGCGCTACGGCGAAGACGGCCT<br>GGCAGGCGAGAGCGTTGAGTTCCAGAACCTGGC<br>TACGCTTAAGCCTTCCAACAAGGCTTTTGAGAAG<br>AAGTTCCGCTTTGATTATACCAATGAGAGGGCCC<br>TGCGGCGCACTCTGCAGGAGGACCTGGTGAAGG<br>ACGTGCTGAGCAACGCACACATCCAGAACGAGT<br>TGGAGCGGGAATTTGAGCGGATGCGGGAGGATC<br>GGGAGGTGCTCAGGGTCATCTTCCCAACTGGAG<br>ACAGCAAGGTCGTCCTCCCCTGTAACCTGCTGCG<br>GATGATCTGGAATGCTCAGAAAATCTTCCACATC<br>AACCCACGCCTTCCCTCCGACCTGCACCCCATCA<br>AAGTGGTGGAGGGAGTCAAGGAATTGAGCAAG<br>AAGCTGGTGATTGTGAATGGGGATGACCCACTA<br>AGTCGACAGGCCCAGGAAAATGCCACGCTGCTC<br>TTCAACATCCACCTGCGGTCCACGTTGTGTTCCC<br>GCCGCATGGCAGAGGAGTTTCGGCTCAGTGGGG<br>AGGCCTTCGACTGGCTGCTTGGGGAGATTGAGT<br>CCAAGTTCAACCAAGCCATTGCGCATCCCGGGG<br>AAATGGTGGGGCTCTGGCTGCGCAGTCCCTTG<br>GAGAACCTGCCACCCAGATGACCTTGAATACCT<br>TCCACTATGCTGGTGTGTCTGCCAAGAATGTGAC<br>GCTGGGTGTGCCCCGACTTAAGGAGCTCATCAA<br>CATTTCCAAGAAGCCAAAGACTCCTTCGCTTACT<br>GTCTTCCTGTTGGGCCAGTCCGCTCGAGATGCTG<br>AGAGAGCCAAGGATATTCTGTGCCGTCTGGAGC<br>ATACAACGTTGAGGAAGGTGACTGCCAACACAG<br>CCATCTACTATGACCCCAACCCCCAGAGCACGG<br>TGGTGGCAGAGGATCAGGAATGGGTGAATGTCT<br>ACTATGAAATGCCTGACTTTGATGTGGCCCGAAT<br>CTCCCCCTGGCTGTTGCGGGTGGAGCTGGATCGG<br>AAGCACATGACTGACCGGAAGCTCACCATGGAG<br>CAGATTGCTGAAAAGATCAATGCTGGTTTTGGTG | |

TABLE 2-continued

Sequences of genes measured for determining tumor inflammation signature score

| Gene | Gen Bank Accession No. | Sequence | SEQ ID No. |
|------|------------------------|----------|------------|
| | | ACGACTTGAACTGCATCTTTAATGATGACAATGC<br>AGAGAAGCTGGTGCTCCGTATTCGCATCATGAA<br>CAGCGATGAGAACAAGATGCAAGAGGAGGAAG<br>AGGTGGTGGACAAGATGGATGATGATGTCTTCC<br>TGCGCTGCATCGAGTCCAACATGCTGACAGATA<br>TGACCCTGCAGGGCATCGAGCAGATCAGCAAGG<br>TGTACATGCACTTGCCACAGACAGACAACAAGA<br>AGAAGATCATCATCACGGAGGATGGGGAATTCA<br>AGGCCCTGCAGGAGTGGATCCTGGAGACGGACG<br>GCGTGAGCTTGATGCGGGTGCTGAGTGAGAAGG<br>ACGTGGACCCCGTACGCACCACGTCCAATGACA<br>TTGTGGAGATCTTCACGGTGCTGGGCATTGAAGC<br>CGTGCGGAAGGCCCTGGAGCGGGAGCTGTACCA<br>CGTCATCTCCTTTGATGGCTCCTATGTCAATTAC<br>CGACACTTGGCTCTCTTGTGTGATACCATGACCT<br>GTCGTGGCCACTTGATGGCCATCACCCGACACG<br>GAGTCAACCGCCAGGACACAGGACCACTCATGA<br>AGTGTTCCTTTGAGGAAACGGTGGACGTGCTTAT<br>GGAAGCAGCCGCACACGGTGAGAGTGACCCCAT<br>GAAGGGGGTCTCTGAGAATATCATGCTGGGCCA<br>GCTGGCTCCGGCCGGCACTGGCTGCTTTGACCTC<br>CTGCTTGATGCAGAGAAGTGCAAGTATGGCATG<br>GAGATCCCCACCAATATCCCCGGCCTGGGGGCT<br>GCTGGACCCACCGGCATGTTCTTTGGTTCAGCAC<br>CCAGTCCCATGGGTGGAATCTCTCCTGCCATGAC<br>ACCTTGGAACCAGGGTGCAACCCCTGCCTATGG<br>CGCCTGGTCCCCCAGTGTTGGGAGTGGAATGAC<br>CCCAGGGGCAGCCGGCTTCTCTCCCAGTGCTGCG<br>TCAGATGCCAGCGGCTTCAGCCCAGGTTACTCCC<br>CTGCCTGGTCTCCCACACCGGGCTCCCCGGGGTC<br>CCCAGGTCCCTCAAGCCCCTACATCCCTTCACCA<br>GGTGGTGCCATGTCTCCCAGCTACTCGCCAACGT<br>CACCTGCCTACGAGCCCCGCTCTCCTGGGGGCTA<br>CACACCCCAGAGTCCCTCTTATTCCCCCACTTCA<br>CCCTCCTACTCCCCTACCTCTCCATCCTATTCTCC<br>AACCAGTCCCAACTATAGTCCCACATCACCCAG<br>CTATTCGCCAACGTCACCCAGCTACTCACCGACC<br>TCTCCCAGCTACTCACCCACCTCTCCCAGCTACT<br>CGCCCACCTCTCCCAGCTATTCGCCCACCTCTCC<br>CAGCTACTCACCCACTTCCCCTAGCTATTCGCCC<br>ACTTCCCCTAGCTACTCGCCAACGTCTCCCAGCT<br>ACTCGCCGACATCTCCCAGCTACTCGCCAACTTC<br>ACCCAGCTATTCTCCCACTTCTCCCAGCTACTCA<br>CCTACCTCTCCAAGCTATTCACCCACCTCCCCCA<br>GCTACTCACCCACTTCCCCAAGTTACTCACCCAC<br>CAGCCCGAACTATTCTCCAACCAGTCCCAATTAC<br>ACCCCAACATCACCCAGCTACAGCCCGACATCA<br>CCCAGCTATTCCCCTACTAGTCCCAACTACACAC<br>CTACCAGCCCTAACTACAGCCCAACCTCTCCAAG<br>CTACTCTCCAACATCACCCAGCTATTCCCCGACC<br>TCACCAAGTTACTCCCCTTCCAGCCCACGATACA<br>CACCACAGTCTCCAACCTATACCCCAAGCTCACC<br>CAGCTACAGCCCCAGTTCGCCCAGCTACAGCCC<br>AACCTCACCCAAGTACACCCCAACCAGTCCTTCT<br>TATAGTCCCAGCTCCCCAGAGTATACCCCAACCT<br>CTCCCAAGTACTCACCTACCAGTCCCAAATATTC<br>ACCCACCTCTCCCAAGTACTCGCCTACCAGTCCC<br>ACCTATTCACCCACCACCCCAAAATACTCCCCAA<br>CATCTCCTACTTATTCCCCAACCTCTCCAGTCTA<br>CACCCCAACCTCTCCCAAGTACTCACCTACTAGC<br>CCCACTTACTCGCCCACTTCCCCCAAGTACTCGC<br>CCACCAGCCCCACCTACTCGCCCACCTCCCCCAA<br>AGGCTCAACCTACTCTCCCACTTCCCCTGGTTAC<br>TCGCCCACCAGCCCCACCTACAGTCTCACAAGCC<br>CGGCTATCAGCCCGGATGACAGTGACGAGGAGA<br>ACTGAGGGCACGTGGGGTGCGGCAGCGGGCTAG<br>GGCCCAGGGCAGCTTGCCCGTGCTGCCGTGCAG<br>TTCTTGCCTCCCTCACGGGGCGTCACCCCCAGCC<br>CAGCTCCGTTGTACATAAATACCTTGTGACAGAG<br>CTCCCGGTGAACTTCTGGATCCCGTTTCTGATGC<br>AGATTCTTGTCTTGTTCTCCACTTGTGCTGTTAGA<br>ACTCACTGGCCCAGTGGTGTTCTACCTCCTACCC<br>CACCCACCCCCTGCCTGTCCCCAAATTGAAGATC<br>CTTCCTTGCCTGTGGCTTGATGCGGGGGGGGTAA | |

TABLE 2-continued

Sequences of genes measured for determining tumor inflammation signature score

| Gene | Gen Bank Accession No. | Sequence | SEQ ID No. |
|---|---|---|---|
| | | AGGGTATTTTAACTTAGGGGTAGTTCCTGCTGTG AGTGGTTACAGCTGATCCTCGGGAAGAACAAAG CTAAAGCTGCCTTTTGTCTGTTATTTTATTTTTTT GAAGTTTAAATAAAGTTTACTAATTTTGACC | |
| SDHA | NM_004168.1 | GACTGCGCGGCGGCAACAGCAGACATGTCGGGG GTCCGGGGCCTGTCGCGGCTGCTGAGCGCTCGG CGCCTGGCGCTGGCCAAGGCGTGGCCAACAGTG TTGCAAACAGGAACCCGAGGTTTTCACTTCACTG TTGATGGGAACAAGAGGGCATCTGCTAAAGTTT CAGATTCCATTTCTGCTCAGTATCCAGTAGTGGA TCATGAATTTGATGCAGTGGTGGTAGGCGCTGG AGGGGCAGGCTTGCGAGCTGCATTTGGCCTTTCT GAGGCAGGGTTTAATACAGCATGTGTTACCAAG CTGTTTCCTACCAGGTCACACACTGTTGCAGCGC AGGGAGGAATCAATGCTGCTCTGGGGAACATGG AGGAGGACAACTGGAGGTGGCATTTCTACGACA CCGTGAAGGGCTCCGACTGGCTGGGGACCAGG ATGCCATCCACTACATGACGGAGCAGGCCCCCG CCGCCGTGGTCGAGCTAGAAAATTATGGCATGC CGTTTAGCAGAACTGAAGATGGGAAGATTTATC AGCGTGCATTTGGTGGACAGAGCCTCAAGTTTG GAAAGGGCGGGCAGGCCCATCGGTGCTGCTGTG TGGCTGATCGGACTGGCCACTCGCTATTGCACAC CTTATATGGACGGTCTCTGCGATATGATACCAGC TATTTTGTGGAGTATTTTGCCTTGGATCTCCTGAT GGAGAACGGGGAGTGCCGTGGTGTCATCGCACT GTGCATAGAGGACGGGTCCATCCATCGCATAAG AGCAAAGAACACTGTTGTTGCCACAGGAGGCTA CGGGCGCACCTACTTCAGCTGCACGTCTGCCCAC ACCAGCACTGGCGACGGCACGGCCATGATCACC AGGGCAGGCCTTCCTTGCCAGGACCTAGAGTTT GTTCAGTTCCACCCCACAGGCATATATGGTGCTG GTTGTCTCATTACGGAAGGATGTCGTGGAGAGG GAGGCATTCTCATTAACAGTCAAGGCGAAAGGT TTATGGAGCGATACGCCCCTGTCGCGAAGGACC TGGCGTCTAGAGATGTGGTGTCTCGGTCGATGAC TCTGGAGATCCGAGAAGGAAGAGGCTGTGGCCC TGAGAAAGATCACGTCTACCTGCAGCTGCACCA CCTACCTCCAGAGCAGCTGGCCACGCGCCTGCCT GGCATTTCAGAGACAGCCATGATCTTCGCTGGC GTGGACGTCACGAAGGAGCCGATCCCTGTCCTC CCCACCGTGCATTATAACATGGGCGGCATTCCCA CCAACTACAAGGGGCAGGTCCTGAGGCACGTGA ATGGCCAGGATCAGATTGTGCCCGGCCTGTACG CCTGTGGGGAGGCCGCCTGTGCCTCGGTACATG GTGCCAACCGCCTCGGGGCAAACTCGCTCTTGG ACCTGGTTGTCTTTGGTCGGGCATGTGCCCTGAG CATCGAAGAGTCATGCAGGCCTGGAGATAAAGT CCCTCCAATTAAACCAAACGCTGGGGAAGAATC TGTCATGAATCTTGACAAATTGAGATTTGCTGAT GGAAGCATAAGAACATCGGAACTGCGACTCAGC ATGCAGAAGTCAATGCAAAATCATGCTGCCGTG TTCCGTGTGGGAAGCGTGTTGCAAGAAGGTTGT GGGAAAATCAGCAAGCTCTATGGAGACCTAAAG CACCTGAAGACGTTCGACCGGGGAATGGTCTGG AACACAGACCTGGTGGAGACCCTGGAGCTGCAG AACCTGATGCTGTGTGCGCTGCAGACCATCTACG GAGCAGAGGCGCGGAAGGAGTCACGGGCGCG CATGCCAGGGAAGACTACAAGGTGCGGATTGAT GAGTACGATTACTCCAAGCCCATCCAGGGGCAA CAGAAGAAGCCCTTTGAGGAGCACTGGAGGAAG CACACCCTGTCCTTTGTGGACGTTGGCACTGGGA AGGTCACTCTGGAATATAGACCCGTAATCGACA AAACTTTGAACGAGGCTGACTGTGCCACCATCC CGCCAGCCATTCGCTCCTACTGATGAGACAAGA TGTGGTGATGACAGAATCAGCTTTTGTAATTATG TATAATAGCTCATGCATGTGTCCATGTCATAACT GTCTTCATACGCTTCTGCACTCTGGGGAAGAAGG AGTACATTGAAGGGAGATTGGCACCTAGTGGCT GGGAGCTTGCCAGGAACCCAGTGGCCAGGGAGC GTGGCACTTACCTTTGTCCCTTGCTTCATTCTTGT GAGATGATAAAACTGGGCACAGCTCTTAAATAA AATATAAATGAG | 38 |

TABLE 2-continued

Sequences of genes measured for determining tumor inflammation signature score

| Gene | Gen Bank Accession No. | Sequence | SEQ ID No. |
|------|------------------------|----------|------------|
| STK11IP | NM_052902.2 | GATAGGCGCCGGGCAGCTGAGCTGGTAGGAGGA<br>CCAGACGGGGATGTTCGGCTCCGCCCCCAGCG<br>TCCCGTGGCCATGACGACCGCTCAGAGGGACTC<br>CCTGTTGTGGAAGCTCGCGGGGTTGCTGCGGGA<br>GTCCGGGGATGTGGTCCTGTCTGGCTGTAGCACC<br>CTGAGCCTGCTGACTCCCACACTGCAACAGCTG<br>AACCACGTATTTGAGCTGCACCTGGGGCCATGG<br>GGCCCTGGCCAGACAGGCTTTGTGGCTCTGCCCT<br>CCCATCCTGCCGACTCCCCTGTTATTCTTCAGCTT<br>CAGTTTCTCTTCGATGTGCTGCAGAAAACACTTT<br>CACTCAAGCTGGTCCATGTTGCTGGTCCTGGCCC<br>CACAGGGCCCATCAAGATTTTCCCCTTCAAATCC<br>CTTCGGCACCTGGAGCTCCGAGGTGTTCCCCTCC<br>ACTGTCTGCATGGCCTCCGAGGCATCTACTCCCA<br>GCTGGAGACCCTGATTTGCAGCAGGAGCCTCCA<br>GGCATTAGAGGAGCTCCTCTCAGCCTGCGGCGG<br>CGACTTCTGCTCTGCCCTCCCTTGGCTGGCTCTG<br>CTTTCTGCCAACTTCAGCTACAATGCACTGACCG<br>CCTTAGACAGCTCCCTGCGCCTCTTGTCAGCTCT<br>GCGTTTCTTGAACCTAAGCCACAATCAAGTCAG<br>GACTGTCAGGGATTCCTGATGGATTTGTGTGAGC<br>TCCACCATCTGGACATCTCCTATAATCGCCTGCA<br>TTTGGTGCCAAGAATGGGACCCTCAGGGGCTGC<br>TCTGGGGGTCCTGATACTGCGAGGCAATGAGCT<br>TCGGAGCCTGCATGGCCTAGAGCAGCTGAGGAA<br>TCTGCGGCACCTGGATTTGGCATACAACCTGCTG<br>GAAGGACACCGGGAGCTGTCACCACTGTGGCTG<br>CTGGCTGAGCTCCGCAAGCTCTACCTGGAGGGG<br>AACCCTCTTTGGTTCCACCCTGAGCACCGAGCAG<br>CCACTGCCCAGTACTTGTCACCCCGGGCCAGGG<br>ATGCTGCTACTGGCTTCCTTCTCGATGGCAAGGT<br>CTTGTCACTGACAGATTTTCAGACTCACACATCC<br>TTGGGGCTCAGCCCCATGGGCCCACCTTTGCCCT<br>GGCCAGTGGGGAGTACTCCTGAAACCTCAGGTG<br>GCCCTGACCTGAGTGACAGCCTCTCCTCAGGGG<br>GTGTTGTGACCCAGCCCCTGCTTCATAAGGTTAA<br>GAGCCGAGTCCGTGTGAGGCGGGCAAGCATCTC<br>TGAACCCAGTGATACGGACCCGGAGCCCCGAAC<br>TCTGAACCCCTCTCCGGCTGGATGGTTCGTGCAG<br>CAGCACCCGGAGCTGGAGCTCATGAGCAGCTTC<br>CGGGAACGGTTCGGCCGCAACTGGCTGCAGTAC<br>AGGAGTCACCTGGAGCCCTCCGGAAACCCTCTG<br>CCGGCCACCCCCACTACTTCTGCACCCAGTGCAC<br>CTCCAGCCAGCTCCCAGGGCCCCGACACTGCAC<br>CCAGACCTTCACCCCCGCAGGAGGAAGCCAGAG<br>GCCCCCAGGAGTCACCACAGAAAATGTCAGAGG<br>AGGTCAGGGCGGAGCCACAGGAGGAGGAAGAG<br>GAGAAGGAGGGGAAGGAGGAGAAGGAGGAGGG<br>GGAGATGGTGGAACAGGGAGAAGAGGAGGCAG<br>GAGAGGAGGAAGAAGAGGAGCAGGACCAGAAG<br>GAAGTGGAAGCGGAACTCTGTCGCCCCTTGTTG<br>GTGTGTCCCCTGGAGGGGCCTGAGGGCGTACGG<br>GGCAGGGAATGCTTTCTCAGGGTCACTTCTGCCC<br>ACCTGTTTGAGGTGGAACTCCAAGCAGCTCGCA<br>CCTTGGAGCGACTGGAGCTCCAGAGTCTGGAGG<br>CAGCTGAGATAGAGCCGGAGGCCCAGGCCCAGA<br>GGTCGCCCAGGCCCACGGGCTCAGATCTGCTCC<br>CTGGAGCCCCATCCTCAGTCTGCGCTTCTCCTA<br>CATCTGCCCTGACCGGCAGTTGCGTCGCTATTTG<br>GTGCTGGAGCCTGATGCCCACGCAGCTGTCCAG<br>GAGCTGCTTGCCGTGTTGACCCCAGTCACCAATG<br>TGGCTCGGGAACAGCTTGGGGAGGCCAGGGACC<br>TCCTGCTGGGTAGATTCCAGTGTCTACGCTGTGG<br>CCATGAGTTCAAGCCAGAGGAGCCCAGGATGGG<br>ATTAGACAGTGAGGAAGGCTGGAGGCCTCTGTT<br>CCAAAAGACAGAATCTCCTGCTGTGTGTCCTAAC<br>TGTGGTAGTGACCACGTGGTTCTCCTCGCTGTGT<br>CTCGGGGAACCCCAACAGGGAGCGGAAACAG<br>GGAGAGCAGTCTCTGGCTCCTTCTCCGTCTGCCA<br>GCCCTGTCTGCCACCCTCCTGGCCATGGTGACCA<br>CCTTGACAGGGCCAAGAACAGCCCACCTCAGGC<br>ACCGAGCACCCGTGACCATGGTAGTTGGAGCCT<br>CAGTCCCCCCCTGAGCGCTGTGGCCTCCGCTCT | 39 |

TABLE 2-continued

Sequences of genes measured for determining tumor inflammation signature score

| Gene | Gen Bank Accession No. | Sequence | SEQ ID No. |
|---|---|---|---|
| | | GTGGACCACCGACTCCGGCTCTTCCTGGATGTTG<br>AGGTGTTCAGCGATGCCCAGGAGGAGTTCCAGT<br>GCTGCCTCAAGGTGCCAGTGGCATTGGCAGGCC<br>ACACTGGGGAGTTCATGTGCCTTGTGGTTGTGTC<br>TGACCGCAGGCTGTACCTGTTGAAGGTGACTGG<br>GGAGATGCGTGAGCCTCCAGCTAGCTGGCTGCA<br>GCTGACCCTGGCTGTTCCCCTGCAGGATCTGAGT<br>GGCATAGAGCTGGGCCTGGCAGGCCAGAGCCTG<br>CGGCTAGAGTGGGCAGCTGGGGGGGCCGCTGT<br>GTGCTGCTGCCCCGAGATGCCAGGCATTGCCGG<br>GCCTTCCTAGAGGAGCTCCTTGATGTCTTGCAGT<br>CTCTGCCCCCTGCCTGGAGGAACTGTGTCAGTGC<br>CACAGAGGAGGAGGTCACCCCCCAGCACCGGCT<br>CTGGCCATTGCTGGAAAAAGACTCATCCTTGGA<br>GGCTCGCCAGTTCTTCTACCTTCGGGCGTTCCTG<br>GTTGAAGGCCCTTCCACCTGCCTCGTATCCCTGT<br>TGCTGACTCCGTCCACCCTGTTCCTGTTAGATGA<br>GGATGCTGCAGGGTCCCCGGCAGAGCCCTCTCC<br>TCCAGCAGCATCTGGCGAAGCCTCTGAGAAGGT<br>GCCTCCCTCGGGGCCGGGCCCTGCTGTGCGTGTC<br>AGGGAGCAGCAGCCACTCAGCAGCCTGAGCTCC<br>GTGCTGCTCTACCGCTCAGCCCTGAGGACTTGC<br>GGCTGCTCTTCTACGATGAGGTGTCCCGGCTGGA<br>GAGCTTTTGGGCACTCCGTGTGGTGTGTCAGGAG<br>CAGCTGACAGCCCTGCTTGCCTGGATCCGGGAA<br>CCATGGGAGGAGCTGTTTTCCATCGGACTCCGG<br>ACAGTGATCCAAGAGGCGCTGGCCCTTGACCGA<br>TGAGGGTCCCACGCTGACCTTGGCCCTGACCTCA<br>GGAGCCACGCTGTAGACATTCCCTCTCCTGGTCT<br>CTGGGTCTGGCTTCCAGGCTCTGGCTGTGGATGT<br>CTTCAGCCTCTGGGTGCTGGCCAGTGAGGTCCCA<br>AATGACCCAGGGCTTAAGGGAGAGGCGAGAGA<br>ATGATCTGGCCTCAGGGGACAGGCCACCTGGTC<br>AGGAGGAATATTTTTCCTGCACTTTTTCTCAGGT<br>ATCAATAAAGTTGTTTCCAACTCATAA | |
| TBC1D10B | NM_015527.3 | GAGGGGCGGCCCGCGGCCATGGAGACGGGCAC<br>GGCGCCCCTGGTGGCCCCGCCGCGCCGTCATGG<br>CGCCCCCGCGGCCCCCTCGCCGCCGCCCCGGGG<br>TTCCCGGGCCGGGCCCGTCGTGGTGGTGGCTCCG<br>GGACCTCCAGTGACTACGGCCACTTCGGCCCCC<br>GTCACCCTGGTGGCCCCCGGGGAGGCGCGGCCC<br>GCCTGGGTCCCGGGGTCGGCCGAGACCTCTGCT<br>CCGGCCCCGGCCCCAGCCCCGGCCCCAGCCCCG<br>GCTGTCACGGGCAGCACGGTGGTGGTGCTGACC<br>CTGGAGGCCTCGCCCGAAGCCCCAAAGCCGCAG<br>CTCCCCTCCGGCCCGGAATCCCCAGAGCCCGCG<br>GCAGTGGCTGGAGTTGAGACATCGAGGGCTCTG<br>GCCGCAGGGGCAGACTCGCCGAAGACAGAGGA<br>GGCTCGACCCTCACCCGCCCCAGGACCAGGGAC<br>CCCCACCGGGACCCCTACCAGGACCCCTTCCAG<br>AACGGCTCCTGGTGCCCTGACCGCCAAACCCCC<br>GCTTGCCCCCAAGCCGGGAACCACAGTGGCCTC<br>AGGAGTGACTGCACGGAGTGCATCAGGACAAGT<br>GACAGGTGGGCATGGAGCTGCCGCAGCAACATC<br>AGCATCAGCAGGACAGGCTCCTGAGGACCCCTC<br>AGGCCCTGGCACAGGCCCCTCTGGGACTTGTGA<br>GGCTCCGGTAGCTGTCGTGACCGTGACCCCAGCT<br>CCGGAGCCTGCTGAAAACTCTCAAGACCTGGGC<br>TCCACGTCCAGCCTGGGACCTGGCATCTCTGGGC<br>CTCGAGGGCAGGCCCCGGACACGCTGAGTTACT<br>TGGACTCCGTGAGCCTCATGTCTGGGACCTTGGA<br>GTCCTTGGCGGATGATGTGAGCTCCATGGGCTCA<br>GATTCAGAGATAAACGGGCTGGCCCTGCGCAAG<br>ACGGACAAGTATGGCTTCCTTGGGGGCAGCCAG<br>TACTCGGGCAGCCTAGAGAGCTCCATTCCCGTG<br>GACGTGGCTCGGCAGCGGGAGCTCAAATGGCTG<br>GACATGTTCAGTAACTGGGATAAGTGGCTGTCA<br>CGGCGATTCCAGAAGGTGAAGCTGCGCTGCCGG<br>AAGGGGATCCCCTCCTCTCTCAGAGCCAAAGCC<br>TGGCAGTACCTGTCTAATAGCAAGGAACTTCTG<br>GAGCAGAACCCAGGAAAGTTTGAGGAGCTGGAA<br>CGGGCTCCTGGGGACCCCAAGTGGCTGGATGTG<br>ATTGAGAAGGACCCTGCACCGCCAGTTCCCTTTCC | 40 |

TABLE 2-continued

Sequences of genes measured for determining tumor inflammation signature score

| Gene | Gen Bank Accession No. | Sequence | SEQ ID No. |
|------|------------------------|----------|------------|
| | | ACGAGATGTTTGCTGCTCGAGGGGGGCATGGGC<br>AACAGGACCTGTACCGAATCCTGAAGGCCTACA<br>CCATCTACCGGCCTGACGAGGGTTACTGCCAGG<br>CCCAGGCCCCCGTGGCTGCGGTCCTGCTCATGCA<br>CATGCCTGCGGAGCAAGCCTTTTGGTGCCTGGTG<br>CAGATCTGCGACAAGTACCTCCCAGGTTACTAC<br>AGTGCAGGGCTGGAGGCCATTCAGCTGGACGGG<br>GAGATCTTTTTTGCACTCCTGCGCCGGGCCTCCC<br>CGCTGGCGCATCGCCACCTGCGGCGGCAGCGCA<br>TTGACCCTGTGCTCTACATGACGGAGTGGTTCAT<br>GTGCATCTTCGCCCGCACCCTGCCCTGGGCGTCG<br>GTGCTGCGTGTCTGGGACATGTTTTTCTGTGAAG<br>GCGTTAAGATCATCTTCCGGGTGGCCCTGGTCCT<br>GCTGCGCCACACGCTGGGCTCAGTGGAGAAGCT<br>GCGCTCCTGCCAAGGCATGTATGAGACCATGGA<br>GCAGCTGCGTAACCTGCCCCAGCAGTGCATGCA<br>GGAAGACTTCCTGGTGCATGAGGTGACCAATCT<br>GCCGGTGACAGAAGCACTGATTGAGCGGGAGAA<br>TGCAGCCCAGCTCAAGAAGTGGCGGGAAACGCG<br>GGGGGAGCTGCAGTATCGGCCCTCACGGCGACT<br>GCATGGGTCCCGGGCCATCCACGAGGAGCGCCG<br>GCGGCAACAGCCACCCCTGGGCCCCTCCTCCAG<br>CCTCCTCAGCCTCCCTGGCCTCAAGAGCCGAGGC<br>TCCCGGGCAGCTGGAGGGGCCCCGTCCCCGCCG<br>CCCCCCGTCCGCAGAGCCAGTGCTGGGCCTGCC<br>CCAGGGCCTGTGGTCACTGCTGAGGGACTGCAT<br>CCATCCCTTCCCTCACCCACTGGCAATAGCACCC<br>CCTTGGGTTCCAGCAAGGAGACCCGGAAGCAGG<br>AGAAGGAGCGGCAGAAACAGGAGAAGGAGCGG<br>CAGAAACAGGAGAAGGAGCGGGAGAAGGAGCG<br>GCAGAAGCAGGAGAAAGAGCGAGAGAAGCAGG<br>AAAAGGAGCGAGAGAAGCAGGAGAAGGAGCGG<br>CAGAAGCAGGAGAAGAAGGCTCAAGGCCGGAA<br>GCTTTCGCTGCGTCGAAAGGCAGATGGGCCCCC<br>AGGCCCCCATGATGGTGGGGACAGGCCCTCAGC<br>CGAGGCCCGGCAGGACGCTTACTTCTGACCTCTG<br>CCCTGGGGCTGGACTGCATGGCCCCCCTCTTTCC<br>CTCAGCCAAGAACAGGCCTGGCCCAAGGTGCCA<br>CCCCCTAGCACCTTGTCAGGCTGTCCCTTGCTGG<br>GGAAAGTGGCTTGGTTCCCCATCTCCTCGCCAGC<br>TGCTGATCCCTACACGGGCAGGACAGATGGGCA<br>GCTGCAAATGAGTCTGGAGCCTCTCATCTCCCAT<br>GAGGCTCAGCTGGGGTCTCTGTCGCTCCTGCCCC<br>AGTTCCCTCTGGGTCCCCTCCTAGGTGCTGTCCT<br>GAATGGCCCGTTGTCATCCCAGGGGTGACTCCTG<br>GTGATGGGAGTCAGCAGTTTCAGATTCTTACACT<br>CCATAGCTCCCCTTACCATGAGGTGGAGCTGGCT<br>TCCTTTTCCCTGTCTTCAGCCCTCCCTGTCTCCCC<br>CACTTCCTGGCCAGGGCTCTCATTCTGGACCTGT<br>GTTGTAATTGTGTACAGAGGATGGCGTTGGCCTG<br>GGGTGGGGGTGCTCGCTTTGTCTTCTGTCCTTTG<br>GTTCTCCTTCCATAATGCTCCTGTACCCAGTTTAT<br>TTAAGGGGACATGCACTGGAATAGGAAATGTCC<br>CCCATCTCCCTTCCTGCACCCTGCTGTGCTCCCTC<br>CAAACCCACCTTGCTCTGTGTTCTCAGGCCCCCC<br>TGCTTTTGTCTCACCAGGACCCATACCTTTCACC<br>TTGTTCCCTTCCACCCCTCCAGTTAGTCCCTATCT<br>GGGTAAGGGTCTTCCCTTGAGCTCCAGGGGGTG<br>GAACCCAATGTTTACATTCTCTTCTGTCTCTGCC<br>CCCACCCCATGCAGCGCTTTGAGGAATTGGAAA<br>AGAACCTGCTGTTGTACCTGGGAAAAAAAAAAA<br>AAAAAAAAAAAAAAAAAAAAAAAAAA | |
| TBP | NM_001172085.1 | GGCGGAAGTGACATTATCAACGCGCGCCAGGGG<br>TTCAGTGAGGTCGGGCAGGTTCGCTGTGGCGGG<br>CGCCTGGGCCGCCGGCTGTTTAACTTCGCTTCCG<br>CTGGCCCATAGTGATCTTTGCAGTGACCCAGGGT<br>GCCATGACTCCCGGAATCCCTATCTTTAGTCCAA<br>TGATGCCTTATGGCACTGGACTGACCCCACAGCC<br>TATTCAGAACACCAATAGTCTGTCTATTTTGGAA<br>GAGCAACAAAGGCAGCAGCAGCAACAACAACA<br>GCAGCAGCAGCAGCAGCAGCAACAGCAAC<br>AGCAGCAGCAGCAGCAGCAGCAGCAGCAGCAG<br>CAGCAGCAGCAGCAGCAGCAGCAGCAACAGGC | 41 |

TABLE 2-continued

Sequences of genes measured for determining tumor inflammation signature score

| Gene | Gen Bank Accession No. | Sequence | SEQ ID No. |
|------|------------------------|----------|------------|
| | | AGTGGCAGCTGCAGCCGTTCAGCAGTCAACGTC CCAGCAGGCAACACAGGGAACCTCAGGCCAGGC ACCACAGCTCTTCCACTCACAGACTCTCACAACT GCACCCTTGCCGGGCACCACTCCACTGTATCCCT CCCCCATGACTCCCATGACCCCCATCACTCCTGC CACGCCAGCTTCGGAGAGTTCTGGGATTGTACC GCAGCTGCAAAATATTGTATCCACAGTGAATCTT GGTTGTAAACTTGACCTAAAGACCATTGCACTTC GTGCCCGAAACGCCGAATATAATCCCAAGCGGT TTGCTGCGGTAATCATGAGGATAAGAGAGCCAC GAACCACGGCACTGATTTTCAGTTCTGGGAAAA TGGTGTGCACAGGAGCCAAGAGTGAAGAACAGT CCAGACTGGCAGCAAGAAAATATGCTAGAGTTG TACAGAAGTTGGGTTTTCCAGCTAAGTTCTTGGA CTTCAAGATTCAGAATATGGTGGGGAGCTGTGA TGTGAAGTTTCCTATAAGGTTAGAAGGCCTTGTG CTCACCCACCAACAATTTAGTAGTTATGAGCCAG AGTTATTTCCTGGTTTAATCTACAGAATGATCAA ACCCAGAATTGTTCTCCTTATTTTTGTTTCTGGAA AAGTTGTATTAACAGGTGCTAAAGTCAGAGCAG AAATTTATGAAGCATTTGAAAACATCTACCCTAT TCTAAAGGGATTCAGGAAGACGACGTAATGGCT CTCATGTACCCTTGCCTCCCCCACCCCCTTCTTTT TTTTTTTTTAAACAAATCAGTTTGTTTTGGTACCT TTAAATGGTGGTGTTGTGAGAAGATGGATGTTG AGTTGCAGGGTGTGGCACCAGGTGATGCCCTTCT GTAAGTGCCCACCGCGGGATGCCGGGAAGGGGC ATTATTTGTGCACTGAGAACACCGCGCAGCGTG ACTGTGAGTTGCTCATACCGTGCTGCTATCTGGG CAGCGCTGCCCATTTATTTATATGTAGATTTTAA ACACTGCTGTTGACAAGTTGGTTTGAGGGAGAA AACTTTAAGTGTTAAAGCCACCTCTATAATTGAT TGGACTTTTTAATTTTAATGTTTTTCCCCATGAAC CACAGTTTTATATTTCTACCAGAAAAGTAAAAA TCTTTTTTAAAAGTGTTGTTTTCTAATTTATAAC TCCTAGGGGTTATTTCTGTGCCAGACACATTCCA CCTCTCCAGTATTGCAGGACAGAATATATGTGTT AATGAAAATGAATGGCTGTACATATTTTTTTCTT TCTTCAGAGTACTCTGTACAATAAATGCAGTTTA TAAAAGTGTTAGATTGTTGTTAAAAAAAAAAAA AAAAAA | |
| UBB | NM_018955.2 | CACTCGTTGCATAAATTTGCGCTCCGCCAGCCCG GAGCATTTAGGGGCGGTTGGCTTTGTTGGGTGA GCTTGTTTGTGTCCCTGTGGGTGGACGTGGTTGG TGATTGGCAGGATCCTGGTATCCGCTAACAGGTC AAAATGCAGATCTTCGTGAAAACCCTTACCGGC AAGACCATCACCCTTGAGGTGGAGCCCAGTGAC ACCATCGAAAATGTGAAGGCCAAGATCCAGGAT AAGGAAGGCATTCCCCCCGACCAGCAGAGGCTC ATCTTTGCAGGCAAGCAGCTGGAAGATGGCCGT ACTCTTTCTGACTACAACATCCAGAAGGAGTCG ACCCTGCACCTGGTCCTGCGTCTGAGAGGTGGTA TGCAGATCTTCGTGAAGACCCTGACCGGCAAGA CCATCACCCTGGAAGTGGAGCCCAGTGACACCA TCGAAAATGTGAAGGCCAAGATCCAGGATAAAG AAGGCATCCCTCCCGACCAGCAGAGGCTCATCT TTGCAGGCAAGCAGCTGGAAGATGGCCGCACTC TTTCTGACTACAACATCCAGAAGGAGTCGACCCT GCACCTGGTCCTGCGTCTGAGAGGTGGTATGCA GATCTTCGTGAAGACCCTGACCGGCAAGACCAT CACTCTGGAGGTGGAGCCCAGTGACACCATCGA AAATGTGAAGGCCAAGATCCAAGATAAAGAAG GCATCCCCCCCGACCAGCAGAGGCTCATCTTTGC AGGCAAGCAGCTGGAAGATGGCCGCACTCTTTC TGACTACAACATCCAGAAAGAGTCGACCCTGCA CCTGGTCCTGCGCCTGAGGGGTGGCTGTTAATTC TTCAGTCATGGCATTCGCAGTGCCCAGTGATGGC ATTACTCTGCACTATAGCCATTTGCCCCAACTTA AGTTTAGAAATTACAAGTTTCAGTAATAGCTGA ACCTGTTCAAAATGTTAATAAAGGTTTCGTTGCA TGGTA | 42 |

TABLE 2-continued

Sequences of genes measured for determining tumor inflammation signature score

| Gene | Gen Bank Accession No. | Sequence | SEQ ID No. |
|---|---|---|---|
| ZBTB34 | NM_001099270.1 | CGGGGACTGGCCTGGCGCCGGCGGCGGCGGAGG GGGCGCCGCGGGCGGGCGATGTGAGCGCGGCGC TCTGGACAGAGTACGCTTCATGTCAGTAGAAAT GGACAGCAGCAGTTTTATTCAGTTTGATGTGCCC GAGTACAGCAGCACCGTTCTGAGCCAGCTAAAC GAACTCCGCCTGCAGGGGAAACTATGTGACATC ATTGTACACATTCAGGGTCAGCCATTCCGAGCCC ACAAAGCAGTCCTTGCTGCCAGCTCCCCATATTT CCGGGACCATTCAGCGTTAAGTACCATGAGTGG CTTGTCAATATCAGTGATTAAAAATCCCAATGTG TTTGAGCAGTTGCTTTCTTTTTGTTACACTGGAA GAATGTCCTTGCAGCTGAAGGATGTTGTCAGTTT TCTGACTGCAGCCAGCTTTCTTCAGATGCAGTGT GTCATTGACAAGTGCACGCAGATCCTAGAGAGC ATCCATTCCAAAATCAGCGTTGGAGATGTTGACT CTGTTACCGTCGGTGCTGAAGAGAATCCCGAGA GTCGAAACGGAGTGAAAGACAGCAGCTTCTTTG CCAACCCAGTGGAGATCTCTCCTCCATATTGCTC TCAGGGACGGCAGCCCACCGCAAGCAGTGACCT CCGGATGGAGACGACCCCCAGCAAAGCTTTGCG CAGCCGCTTACAGGAGGAGGGGCACTCAGACCG CGGGAGCAGTGGGAGCGTTTCTGAATATGAGAT TCAGATAGAGGGAGACCATGAGCAAGGAGACCT ATTGGTGAGGGAGAGCCAGATCACCGAGGTGAA AGTGAAGATGGAGAAGTCCGACCGGCCCAGCTG TTCCGACAGCTCCTCCCTGGGTGACGATGGGTAC CACACCGAGATGGTTGATGGGGAACAAGTTGTG GCAGTGAATGTGGGCTCCTATGGTTCTGTGCTCC AGCACGCATACTCCTATTCCCAAGCAGCCTCACA GCCAACCAATGTATCAGAAGCTTTTGGAAGTTTG AGTAATTCCAGCCCATCCAGGTCCATGCTGAGCT GTTTCCGAGGAGGGCGTGCCCGCCAGAAGCGGG CTTTGTCTGTCCACCTGCACAGTGACCTGCAGGG CCTGGTGCAGGGCTCTGACAGTGAAGCCATGAT GAACAACCCCGGGTATGAGAGCAGTCCCCGGGA GAGGAGTGCGAGAGGGCATTGGTACCCGTACAA TGAGAGGTTGATCTGTATTTACTGTGGAAAGTCC TTCAACCAGAAAGGAAGCCTTGATAGGCACATG CGACTCCATATGGGAATCACCCCCTTTGTGTGCA AGTTCTGTGGGAAGAAGTACACACACGGAAGGACC AACTGGAGTACCACATCCGGGGCCATACAGATG ATAAACCATTCCGCTGTGAGATCTGCGGGAAGT GCTTTCCATTCCAAGGTACCCTCAACCAGCACTT GCGGAAAAACCACCCAGGCGTTGCTGAAGTCAG GAGTCGCATTGAGTCCCCCGAGAGAACAGATGT GTACGTGGAACAGAAACTAGAAAATGACGCATC GGCCTCAGAGATGGGCCTAGATTCCCGGATGGA AATTCACACAGTGTCTGATGCTCCCGATTAAGAT GGTAAAGAAGTGCACCCAAACAAAGCACATTAA TCAATGCATATTTGTGATTTGCTTTGTTGTAATCT TTGGTTTTCCCAACCATCTGGAAATCTCTTGGTC TCTTGGCAGTTTTTCTAAAGTTTCTGGATGGAAC ACTTCGTTGTGTTTATCCTTTCCCCTGCCCTCCCT CCCCGAAGGAGCTCAAAGCATGAAGGGCAACGC ATCCAGGGAAAACACAGGCTGACAGTATTCCTC TTTGGCTGAACTCTTAATCCAAAATCTGCCAGTG ATTTAGCTATGCCAACTGGTTGACCCTCCATTCT CTGCCAAGAGGCATACTCTTTCTCATTGTGTGCG CTGGCAGCAGTGCACTTCCACGGAGGGAGATTA GGATGCCGTCAGCTGATACAAATGGGTAACCTT TTCTAATTTAAAATTCCTTTTAGGGGGTAGTTAG ACAATTTATATATATATATAATAAAACTATTATT ATATATATAGTATATATACATTTTCAAATTTGAT TTTATTCTGGTTGAGGTGAATGTAAGAGGAATAT ATAATTTAATACAATGTGAACAGGGCTTCTGAGT CTATCTCATCCCTACCTAATATGTTAGGGTTTTG CCCCTTCATTTCCCTTACAAAAGAATGTTAGTAG GTTTATATTAATCATTGTGTCCAAAAGCAAGCAA AGCAAATCACAGTGTTCACAGCTCTGCTTCATAA CAAATACATAAACCAAATGCCATAAAATTTCTTC AACTCTAGTTGGAAACCGTTTGGAATTTTTGTTA GTTGTCCAGCAGGTAAGCTGGATGACCTGTGGT GCTGACCTTTTTACATAGTGTAGTGTTATATTAG CCAACCCCAAAGGAGCAGTGGTTTTCAAGGTTTT | 43 |

TABLE 2-continued

Sequences of genes measured for determining tumor inflammation signature score

| Gene | Gen Bank Accession No. | Sequence | SEQ ID No. |
|------|------------------------|----------|------------|
| | | TACTGGCCTACAAATCTACCTTCATTCCGTACTG | |
| | | TAGAAACATACATACCAGGTAACTAAATCGAAT | |
| | | CACTCTCTATCATGAGTTAGTACTCACTCGCACT | |
| | | TAAGGAAAGGGATTTGTAGTTCTGTCTACAAAA | |
| | | TTCTCCAAGCAGTGTTGTGGTTTTTTTGTTTTTG | |
| | | TTTTTTTTCTTTCTCTTTTCAAACAGCCAGTTCAG | |
| | | GTGCACAGCAACTTTTTCTACATGCAGTTCCCAG | |
| | | GGAAACTGCAGAACTTAGAATTTGTACTTTTTGT | |
| | | AAAGCTATACTCTATGGGAATTGCAAGCAATAT | |
| | | ATCTATCTTAGTATTGTGTGTGCTAATGAGAGCC | |
| | | TCAGTGGCTCCCCCACTCTCTCAGTGTTTCCTGC | |
| | | TTAAAGAACCAACAGTTTAAAAGCCCTCTAAGA | |
| | | TACTCTGTGTGTCACCAAATCTGTGTGTCACCAT | |
| | | TTTTTGGTCATGTGGTGCTATTTTGTTAAGTGTC | |
| | | TTTTTAGGTCAGTATAGTTGTAGAAAATGTGAAA | |
| | | TCTGATGGTAATAATGAATTATAATTGTTTTCCT | |
| | | CTCTTGAGTTCATAGCTTGAAAAGAGACCTCAA | |
| | | AAGCATGTGCTGGCAAACACGTTACTGTATGAA | |
| | | AACATACCTGAGTCCATTTGAATAATGTTTTATT | |
| | | AGTACTTTCGGAAATGTCTTCAGTTCTGTATTGT | |
| | | GTTCACATACACAAACAGGCTTTACAAGATTGCT | |
| | | TCGGTACTGTAAACTCTGGCAGAGAGTAATTTTG | |
| | | TAGGCAGTTTGGTGGTGAGTTTGTGCTGCAGGCT | |
| | | GCCTGTGGGATGTCAGCGTTCTGGTATCTGCCTG | |
| | | AGAACCTGGGCTCTGAGACGCACAACCAGTGCA | |
| | | CCTCCATAGGAGAACAGTGCAGCCACCTAAAAG | |
| | | AAAAACGAACGAAGGACCAGCCTCAGAGGCTA | |
| | | GAAGTTAAAGGAATACAGAATTAGATGTTTGCT | |
| | | GGTTTTCTGTGCTTTTTTGGCTCCTAAAATACCA | |
| | | ATGGTGGATTTGTTTTTGTTTTTGTTTTTTGTTTT | |
| | | GAGAAATAAAAAGTCATTCAAGCCCTTTGTGTG | |
| | | TAATAGCCCCCAGGGGTGGCAGCTGTGCAGTCG | |
| | | CATCTCTTTGGCACACAGGATCTGTTCACGTGTG | |
| | | AACTGCTGCGCTACACATCAGTGTTAACTCCCTA | |
| | | CAGATTACACTCTAATCCCGCTGCTCCCGAGGAG | |
| | | CGGCTTTGCTAAATCGGGTATATAGTATATGCCT | |
| | | TTTTCCTCGTCAAACTGCCTAAGTAGGGGTTCGT | |
| | | TCTCTCCCTGAAGCACTTGTTCAACTCCTGTTAA | |
| | | AGCCGCGTGCCTCAAGGGGAGGCTGGACCCCAA | |
| | | GTGTTTACCCACTTAAATATGTTCTGGGGTTTCA | |
| | | GGTAAATGTTTGTGGGTTTTTTTTCCTTACATGA | |
| | | ATAAGTTTGGTTTGATTTTTTTTAATTGAATGC | |
| | | AAAAAATTTGTGTTGTGATACAAATTAAGTTTGT | |
| | | GACAAGAAATGCCCAAATCCAAGGACATAAGAG | |
| | | GTCAAGCTCAGGGAAGGAACCTCCTTTTCACTCA | |
| | | GGCTTGGGGCCTCCAGCGAGGTTTCCAGAGCAT | |
| | | TCCATGGTATGAGAGACAGTGAGGAGGGAGGGC | |
| | | ACCTGGCGCGGGCACTTCCAGCGTCCTGGCTCTT | |
| | | GGCATTGTCCGTCTTAACCTTATTTACATGGAGT | |
| | | TCTTTGTATTTGTGAATCTGTTTAACTGGTTTGAG | |
| | | TTTACCAAAGAGTGACTTATCCAAAATTGTCTTT | |
| | | GACAAAAATATCCATTGCTTTGATTGTACAGTTC | |
| | | AGGTTCAAACATTGTAATGGGACTGTTAAGGGG | |
| | | CAGAAAATTGATTGAGTTTCTCTCTAAGAATCAT | |
| | | GATTCCACATTTTGCAAGTTCCACTTGCTCCCAT | |
| | | TCGTGTTGCTAACACTTTACCCTTTCCACTGCTC | |
| | | GCAGTGTTAAGAATGAATTCTCAAGCCATAACA | |
| | | CAGTACTGTAAAGTTCCGCAGGGCTTCGAGGGA | |
| | | GGCAGCGCCTAGGCCAGCACGGAGCTGTGTAGC | |
| | | CTCTCTGAGCGTTCGCACTGTCATGCTTCCCAGG | |
| | | GGTGTGACTGGTGAGAGATTAACTCCATTCAGA | |
| | | TCGGGCAGCAGCAATTAATTGTGCCTTGCCGCAT | |
| | | GAGGATGTGTCAGGAGGATTAACATGACCACAG | |
| | | AACCGAAACATTCTCTCCCTGAAGTTCACTTCAC | |
| | | GTCTCCGCAGACGAAGTACGCTGTGTAACTCCTT | |
| | | AGAGCAACTCTTTTTGGAAAGCAAAGTCCCTATT | |
| | | TCTGTACAGTTTTAGGTTAGGTGTTTCATTTATA | |
| | | ACAGATGCAGAAATCAATTAAGATAAAGTGATA | |
| | | TGTGAAGAAATCTTTTACAGTAAAATATATCCTG | |
| | | AATTCATATAGGCTTGTTCATAATTGAGTCTCTT | |
| | | CTTGAGCTACCTTTTCAATATTAGACAATGTGAA | |
| | | GACAGTGACAGCGTCCTTTTCTAGAGATATTTAG | |
| | | CCTGTTATTACAAACTGTGAAGACAAAGAATTTT | |
| | | ATACTTTTACTAATGTTTGTGGTTTTAAACAGTT | |

TABLE 2-continued

Sequences of genes measured for determining tumor inflammation signature score

| Gene | Gen Bank Accession No. | Sequence | SEQ ID No. |
|---|---|---|---|
| | | ATTTTCATTCTAATCAGTTCTCTACCCTCTAATTT<br>CTACTAAAGCTGTAAATACATTTAGAAATTATAT<br>TTGTAAATACAGTATATGGAGACAAGTTAATTTT<br>TTGGTCAGTGGAAAAAGCCTCCCAACCAATTGG<br>CCCTGCCTTGGCAGTTGTGTTTTTGTTGTTGTTG<br>TTGTTGTTTAGTTTAGTTTTTTTTTTAAACAGC<br>AGAAAGGATACTGTCGGTTCACTGTTGAGCAGA<br>ATATACTGTAGAACGAAAATGATAATTTTTAAAT<br>CTTCCAGAGCATGAGTAAATGTCTTTTCTAATGA<br>TAGCAAATATAACCAACTCTTTGTTTTTCCCTTA<br>GCCCAGACCATATAGACCTGCGTATTTTGTGTGT<br>GGTTTTGTTTTTATTTTTGTTCTTACAGCCTAGAC<br>CCTAGGAAAAATTTGCAGGAACACGAAACAAGG<br>GCTGGGGGGAAAATCATCTATGTGAATGAGCTT<br>TACTTTAAAGAGATCAATGTATTTTATTTTATCA<br>ACTTTTTCTCTTAGTTACTGTGATTTTTGTTGTTG<br>TTGTCCTCGTTATTGTTAAATTCTGTAATGGTTTC<br>CTGTGAAGCCTCCACTGAAAGGGACTCAAATAT<br>GCAACACCTAAACTATTTTCCAAGGGCACATGC<br>CCCTTGAATGGTGCTTCTAGACTGGTCAGGGTTA<br>TTTATTAAATTTTATATATGAAAGTATTGGGGAA<br>TTATGTAAATTCTTTATATGAAACTATCTAGTTC<br>ATAAATCATAGATTTCATATTACTCAGTGCAACT<br>GAACTAAAAGTTCAGAAAAGTCATTCACATTGT<br>TCCAAATTTGTAATGGTTGTCACATGTCACATGC<br>GTCTTTTTCAGTAAGTGCCAGAGTGTTCCCACTG<br>TTTCTGCCCAGTGCTTGACTTCTCGGCCCGGAAG<br>AGAACCTGCTTTCTCTGGTTTCCTTCCTGAGTCT<br>GGCACAGACGGGCTATTGTAGTTCTTGATCAA<br>GTCCTGGAGTCAGCCTTGCCTGGCTCTCCTTGTA<br>GCAGATTCAGTCCACAGACCTCTTGCTGCCCCTC<br>AGTGACAAGTATGCTGTGAATTCAACCTTTGGAC<br>TTGCTGCCCAAGCCTTTGGTTGCTGCCCTGACTA<br>TTGTAAGAGGTAAACTTACCTGGTTTGTTTGAGA<br>ATGACCATTTTCCTAATGTGAAAACCATCTCTCT<br>CACCACTTTTATTAGTAGGGCTAACATTTTTTTC<br>CGTTATAAATGGTTGAGCAATTTGAATGACTTAA<br>CACAGTGTCATTATCTTGCAATATAAACTGGTAA<br>CCTCACAACTCCACACTTCATCACCATATGAAGT<br>AAATGAAGCTAGCTAAGCGGATGCTGTATCAAC<br>TAGTAACTTGCCATTAAGGATTATTTTATAGCAT<br>GAATTTAAGACTATTTATTCAAATGATATTTTAC<br>TCTTGTATTCACTTTGTTTTAGATTTGTGACATGA<br>ATATTTCAGTGCTGCTTAATTTTGTTCTGAATTCT<br>TGTTTCTTGCTTGTAAATGGCTTTTTTATGGTATA<br>AATAAAGTCAATGGACATTGCTGTTTGTAAATA<br>AAAATGCTGCTAGAGCAAAAAAAAAAAAAAA | |

In aspects of the methods of the present disclosure, gene expression is measured using methods known in the art that utilize probes targeting the genes of interest. The genes and exemplary target regions of those genes useful for determining gene expression in the methods of identifying mismatch repair deficiency in a subject disclosed herein are shown in Table 3.

TABLE 3

Exemplary Gene Targets for Determining Gene Expression

| Gene | GenBank Accession No. | Exemplary Target Region | Target Sequence | SEQ. ID NO. |
|---|---|---|---|---|
| MLH1 | NM_000249.2 | 1606-1705 | CAGGGACATGAGGTTCTCCGGGAGATGTT GCATAACCACTCCTTCGTGGGCTGTGTGA ATCCTCAGTGGGCCTTGGCACAGCATCAA ACCAAGTTATACC | 44 |

TABLE 3-continued

Exemplary Gene Targets for Determining Gene Expression

| Gene | GenBank Accession No. | Exemplary Target Region | Target Sequence | SEQ. ID NO. |
|---|---|---|---|---|
| MSH2 | NM_000251.1 | 2515-2614 | AGGTGAAGAAAGGTGTCTGTGATCAAAGT TTTGGGATTCATGTTGCAGAGCTTGCTAAT TTCCCTAAGCATGTAATAGAGTGTGCTAA ACAGAAAGCCCT | 45 |
| MSH6 | NM_000179.2 | 1016-1115 | AGGCCTGAACAGCCCTGTCAAAGTTGCTC GAAAGCGGAAGAGAATGGTGACTGGAAA TGGCTCTCTTAAAAGGAAAAGCTCTAGGA AGGAAACGCCCTCA | 46 |
| PMS2 | NM_000535.6 | 895-994 | TCAGGTTTCATTTCACAATGCACGCATGGA GTTGGAAGGAGTTCAACAGACAGACAGTT TTTCTTTATCAACCGGCGGCCTTGTGACCC AGCAAAGGTCT | 47 |
| EPM2AIP1 | NM_014805.3 | 1323-1422 | GGGGCAACAACAGTCCACTTCTCAGACAA ACAATGGCTTTGTGACTTTGGCTTCTTGGT GGACATTATGGAACACCTTCGAGAACTCA GTGAAGAATTAC | 48 |
| TTC30A | NM_152275.3 | 2493-2592 | TGCCCTCAAGCAACAATTGCTAGAGTAAC ATCTTTGTATAAGCAAGTAACCCCAGATA GAGTTGACGTTTCAGCTTTGGGCTGTCAAA AGGGTATGTCAT | 49 |
| SMAP1 | NM_001044305.2 | 824-923 | GAAAAGCTGCAGAAGAAAGATCAGCAAC TGGAGCCTAAAAAAAGTACCAGCCCTAAA AAAGCTGCGGAGCCCACTGTGGATCTTTT AGGACTTGATGGCC | 50 |
| RNLS | NM_001031709.2 | 727-826 | CTCTTTTATGAAGCTGGTACGAAGATTGAT GTCCCTTGGGCTGGGCAGTACATCACCAG TAATCCCTGCATACGCTTCGTCTCCATTGA TAATAAGAAGC | 51 |
| WNT11 | XM_011545241.2 | 1016-1115 | CTCTGCTTGTGAATTCCAGATGCCAGGCAT GGGAGGCGGCTTGTGCTTTGCCTTCACTTG GAAGCCACCAGGAACAGAAGGTCTGGCCA CCCTGGAAGGA | 52 |
| SFXN1 | NM_001322977.1 | 192-291 | CTACCACCAAACATTAACATCAAGGAACC TCGATGGGATCAAAGCACTTTCATTGGAC GAGCCAATCATTTCTTCACTGTAACTGACC CCAGGAACATTC | 53 |
| SREBF1 | NM_001005291.1 | 1393-1492 | TTCGCTTTCTGCAACACAGCAACCAGAAA CTCAAGCAGGAGAACCTAAGTCTGCGCAC TGCTGTCCACAAAAGCAAATCTCTGAAGG ATCTGGTGTCGGC | 54 |
| TYMS | NM_001071.1 | 396-495 | TGCTAAAGAGCTGTCTTCCAAGGGAGTGA AAATCTGGGATGCCAATGATCCCGAGACT TTTTGGACAGCCTGGGATTCTCCACCAGA GAAGAAGGGGAC | 55 |
| EIF5AL1 | NM_001099692.1 | 2211-2310 | AAAGGAAACACGAAGATTAATCAAGCAG GAAGGACAAGCTCAGTTTTGCACCCACTG AATTTGCCACAAATATTGTGGAAAATATT CTCGGGGACATTGC | 56 |
| WDR76 | NM_024908.3 | 1876-1975 | CGTTTGGTGGAGAATACCCTTGTCTCTGTGT GTTCCATCAATGCCATGCACCCAACTCGGT ATATTTTGGCTGGAGGTAATTCCAGCGGG AAGATACATGT | 57 |

Definitions

The terms "non-hypermutated" and "non-hypermutated samples" refer to tumor samples that have a mutation rate of less than 7 mutations in every $10^6$ bases, or have a mutation rate of less than 8 mutations in every $10^6$ bases, or have a mutation rate of less than 9 mutations in every $10^6$ bases, or have a mutation rate of less than 10 mutations in every $10^6$ bases, or have a mutation rate of less than 11 mutations in every $10^6$ bases, or have a mutation rate of less than 12 mutations in every $10^6$ bases.

The terms "hypermutated" and "hypermutated samples" refer to tumor samples that have a mutation rate of more than 12 mutations in every $10^6$ bases, or have a mutation rate of more than 13 mutations in every $10^6$ bases, or have a mutation rate of more than 14 mutations in every $10^6$ bases, or have a mutation rate of more than 15 mutations in every $10^6$ bases.

The term "mismatch repair deficiency" (MMRd), refers to the loss of function of at least one gene involved in DNA mismatch repair due to biallelic inactivation of the at least one gene. The biallelic inactivation can be caused by a variety of factors, including, but not limited to, somatic or germline mutations within the coding region of the at least one gene, methylation of the promoter of the at least one gene, leading to silencing of that promoter through a mechanism referred to as the CpG island methylator phenotype (CpG), and/or microRNA-induced downregulation of the expression of the at least one gene. The current state of the art for determining whether a sample displays mismatch repair deficiency is through the use of immunohistochemistry to visualize the expression of genes involved in DNA mismatch repair. The at least one gene involved in DNA mismatch repair can comprise MLH1, MSH2, MSH6 and PMS2. Mismatch repair deficiency causes hypermutation and microsatellite instability. Thus, determining that a tumor is mismatch repair deficient also indicates that the tumor is hypermutated and that the tumor is microsatellite instable.

The term "microsatellite instability" refers to length variations at short, repetitive DNA sequences, known as microsatellites (MS), within the genome. Tumors that are said to be microsatellite instable are tumors that display higher variations in the length of these short, repetitive DNA sequences as compared to normal, non-cancerous cells. Microsatellite instability can be caused by mismatch repair deficiency. In clinical settings, detection of MSI is customarily profiling the Bethesda markers, which often include two mononucleotide (BAT25 and BAT26) and three dinucleotide (D5S346, D2S123 and D17S250) MS loci. Colorectal tumors unstable at >40% of the Bethesda markers are considered high level microsatellite instable (MSI-H) and are known to have a better prognosis and to be less prone to metastasis than microsatellite stable (MSS) tumors. More recent guidelines suggest analyzing the length of four mononucleotide repeat loci comprising BAT25, BAT26, BAT40, and transforming growth factor receptor type II and three dinucleotide repeat loci comprising D2S123, D5S346 and D17S250 to determine the MSI status of a tumor sample. The length of these loci in a tumor sample is compared to the length of these loci in a non-tumor sample of the same tissue or mononuclear blood cells using multiplex-fluorescent labeled PCR and capillary electrophoresis. Tumors are classified as microsatellite stable (MSS) if none of the loci show a change in size in the tumor sample as compared to the non-tumor and blood cell sample. Tumors are classified as low level microsatellite instable (MSI-L) if one or two of the loci show a change in size in the tumor sample as compared to the non-tumor and blood cell sample. Tumors are classified as high level microsatellite instable (MSI-H) if three or more loci show a change in size in the tumor sample as compared to the non-tumor and blood cell sample.

As described in the preceding, the methods of the present disclosure can be used to identify mismatch repair deficiency in a subject using gene expression data in a tumor sample from a subject. The sample can be a biological sample. As will be appreciated by those in the art, the sample may comprise any number of things, including, but not limited to: cells (including both primary cells and cultured cell lines) and tissues (including cultured or explanted). In aspects, a tissue sample (fixed or unfixed) is embedded, serially sectioned, and immobilized onto a microscope slide. As is well known, a pair of serial sections will include at least one cell that is present in both serial sections. Structures and cell types, located on a first serial section will have a similar location on an adjacent serial section. The sample can be cultured cells or dissociated cells (fixed or unfixed) that have been immobilized onto a slide.

In aspects, a tissue sample is a biopsied tumor or a portion thereof, i.e., a clinically-relevant tissue sample. For example, the tumor may be from a breast cancer. The sample may be an excised lymph node.

The sample can be obtained from virtually any organism including multicellular organisms, e.g., of the plant, fungus, and animal kingdoms; preferably, the sample is obtained from an animal, e.g., a mammal. Human samples are particularly preferred.

In some aspects, the preceding methods are used in the diagnosis of a condition. As used herein the term diagnose or diagnosis of a condition includes predicting or diagnosing the condition, determining predisposition to the condition, monitoring treatment of the condition, diagnosing a therapeutic response of the disease, and prognosis of the condition, condition progression, and response to particular treatment of the condition. For example, a tissue sample can be assayed according to any of the methods described herein to determine the presence and/or quantity of markers of a disease or malignant cell type in the sample (relative to the non-diseased condition), thereby diagnosing or staging a disease or a cancer.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer or cervical cancer.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

Any of the above aspects and embodiments can be combined with any other aspect or embodiment as disclosed here in the Summary and/or Detailed Description sections.

The term "immunotherapy" can refer to activating immunotherapy or suppressing immunotherapy. As will be appreciated by those in the art, activating immunotherapy refers to the use of a therapeutic agent that induces, enhances, or promotes an immune response, including, e.g., a T cell response while suppressing immunotherapy refers to the use of a therapeutic agent that interferes with, suppresses, or inhibits an immune response, including, e.g., a T cell response.

As will be appreciated by those in the art, activating immunotherapy may comprise the use of checkpoint inhibitors. Checkpoint inhibitors are readily available in the art and include, but are not limited to, a PD-1 inhibitor, PD-L1 inhibitor, PD-L2 inhibitor, or a combination thereof. Checkpoint inhibitors can comprise antibodies. These antibodies can include, but are not limited to anti-PD1 antibodies, anti-PDL1 antibodies, or anti-CTLA4 antibodies. Anti-PD1 antibodies and anti-PD-L1 antibodies can include, but are not limited to, pembrolizumab, nivolumab, atezolizumab, avelumab, durvalumab, pidilizumab, REGN2810, AMP-224, MEDI0680, PDR001 and CT-001. Anti-CTLA4 antibodies can include but are not limited to ipilimumab and tremelimumab.

Additionally, the immunotherapy that is provided to a patient in need thereof according to the methods of the present invention comprises providing a cytokine agonist or cytokine antagonist, that is an agonist or antagonist of interferon, IL-2, GMCSF, IL-17E, IL-6, IL-1a, IL-12, TFGB2, IL-15, IL-3, IL-13, IL-2R, IL-21, IL-4R, IL-7, M-CSF, MIF, myostatin, Il-10, Il-24, CEA, IL-11, IL-9, IL-15, IL-2Ra, TNF or a combination thereof.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (RIA) or biacore assay. In certain embodiments, an antibody that binds to a target has a dissociation constant (Kd) of <1 µM, <100 nM, <10 nM, <1 nM, <0.1 nM, <0.01 nM, or <0.001 nM (e.g. $10^8$ M or less, e.g. from $10^8$ M to $10^{13}$ M, e.g., from $10^9$ M to $10^{13}$ M). In certain embodiments, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some embodiments, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present disclosure, the preferred materials and methods are described herein. It is to be understood that the terminology used herein is for the purpose of describing particular aspects only, and is not intended to be limiting.

EXAMPLES

Example 1—Loss of Mismatch Repair Gene Expression Predicts Microsatellite Instability and Hypermutation Because loss of protein expression for any of the mismatch repair (MMR) genes MLH1, MSH2, MSH6, or PMS2 is sufficient to identify tumors with microsatellite instability, it is plausible that loss of mRNA expression in these genes can provide a surrogate measurement of tumor microsatellite instability (MSI). FIG. 1 shows a series of graphs in which MMR gene expression is plotted against mutation burden and MSI status in colon adenocarcinoma (COAD), esophageal carcinoma (ESCA), stomach adenocarcinoma (STAD) and uterine corpus endometrial carcinoma (UCEC) tumors. FIG. 1 reveals the strong association between these three phenomena, and it shows that loss of MMR gene expression predicts MSI and hypermutation with high specificity.

In all 4 tumor types (colon, esophageal, stomach, and uterine), a cluster of hypermutated tumors is easily visible, with the subtype being relatively abundant in the colon, stomach, and uterine cancer The Cancer Genome Atlas (TCGA) data sets and rare in esophageal cancers. In all four datasets, these hypermutated tumors are strongly enriched for MSI. In colon, stomach, and uterine cancers, a small third cluster of tumors with an even higher mutation burden is apparent. These ultramutated tumors are often MSS or low-level MSI (MSI-L) in the TCGA datasets. Instead, these tumors have a mutation in one of the polymerase genes POLE or POLD1, consistent with a mechanism in which defective polymerase leads to widespread errors in DNA replication. A small fraction of each cancer type is minimally mutated. Furthermore, the average mutation burden within a given cluster is not preserved across tumor types; for example, non-hypermutated (typical) esophageal cancers have 3.8 times the mutation rate of non-hypermutated colon cancers.

MSI-H status as determined by PCR occurs in most (67%-86%) of the hypermutated tumors in these cancers types and in a smaller fraction of the ultramutated tumors. MSI-H occurs in less than 1.4% of non-hypermutated tumors in each dataset. MSI-L status occurs primarily (>92%) in non-hypermutated tumors in the colon, esophageal, and stomach datasets, while in the uterine dataset MSI-L status occurs with approximately equal frequency across non-hypermutated, hypermutated, and ultramutated tumors.

FIG. 1 also shows that loss of expression of the four MMR genes, observed as low-expression outliers, are also apparent within each cancer type. MLH1 is by far the most frequently under-expressed of these genes. In TCGA, MLH1 expression loss occurs in 16% of colon cancers, 3% of esophageal cancers, 20% of stomach cancers, and 29% of uterine cancers. MLH1 loss on its own is a surprisingly sensitive biomarker, detecting two thirds or more of the hypermutation cases in each of these cancer types. Expression loss in the other three MMR genes detects a small number of additional hypermutated/MSI samples not captured by MLH1: MSH2 loss detects 5 additional MSI-H tumors in these 4 datasets, MSH6 loss detects 2, and PMS2 loss detects none. These loss of expression events are highly specific predictors of both MSI and hypermutation, occurring almost exclusively within hypermutated and MSI-H tumors. However, a subset of less than 10% of MSI tumors display normal expression levels of these 4 genes, indicating MMR dysfunction arising from a cause other than loss of mRNA expression.

Example 2—Hypermutated Tumors Share Common Transcriptional Patterns in Colon, Stomach, and Uterine Cancers Approximately one third of hypermutation or ultramutation events as measured by next-generation sequencing cannot be detected by loss of MMR gene expression. In such cases, transcriptomic events downstream of mismatch repair deficiency (MMRd) might enable detection of hypermutation independent of the expression levels of the classic MMR genes. In cancers where hypermutation has a common origin in MMRd, and possibly in CpG island methylator phenotype (CIMP), it is plausible that hypermutated tumors will display common transcriptional patterns across tumor types. To evaluate whether broader expression patterns could predict MSI and hypermutation, univariate linear models testing the association of hypermutation status with each gene in the TCGA whole transcriptome RNA-Seq datasets were run. These models were fit separately within the colon, stomach, and uterine cancer datasets, omitting esophageal cancer because the presence of only 4 hypermutated tumors in that dataset limited statistical power.

Figure 2:
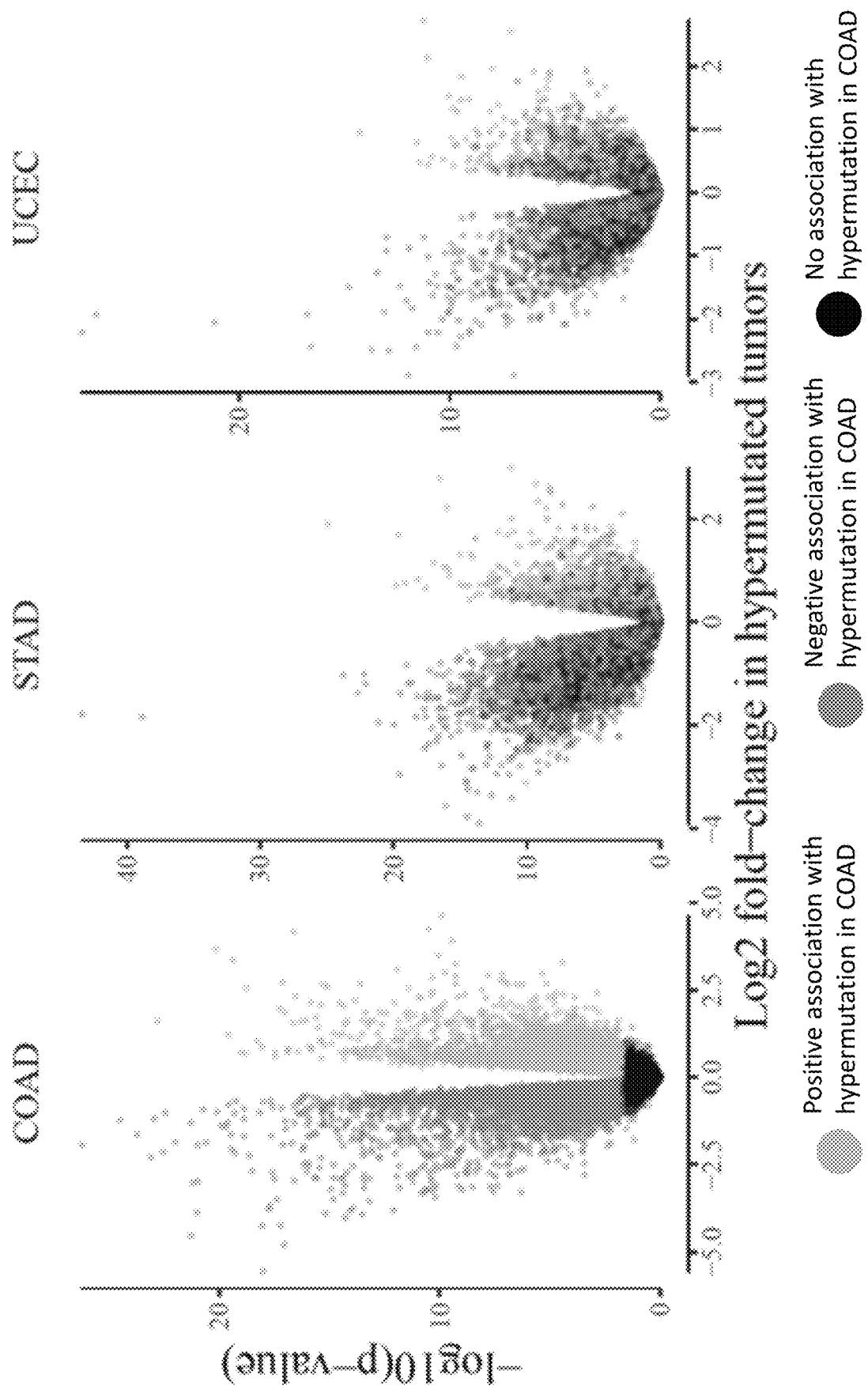
FIG. 2 is a series of volcano plots that shows that particular genes are positively and negatively associated with hypermutation in three different cancer types.

A great deal of the transcriptome had significant association with hypermutation status in these datasets: a Benjamini-Hochberg false discovery rate (FDR)<0.05 was achieved by 7800 genes in colon adenocarcinomas, 9337 genes in stomach adenocarcinomas, and 3848 genes in uterine carcinomas. FIG. 2 is a series of volcano plots that show genes' associations with hypermutation in COAD, STAD and UCEC tumors. FIG. 2 shows that a number of these genes behaved similarly across all 3 cancer types: 420 genes had a FDR<0.05 and a positive association with hypermutation in all 3 datasets, and 672 genes had a FDR<0.05 and a negative association with hypermutation in all 3 cancer types.

Some consistent biology emerges from this comparison, in that gene sets relating to DNA replication machinery and metabolism are highly enriched for genes with consistent positive associations with hypermutation. Table 4 shows the proportion of the genes in each gene set that are consistently down-regulated and consistently up-regulated with hypermutation across COAD, STAD and UCEC datasets, where "consistently up-regulated" is taken to mean "false discover rate<0.05 and a positive association with hypermutation in all 3 datasets. For Table 4, Kyoto Encyclopedia of Genes and Genomes (KEGG), Biocarta, and Reactome gene sets were downloaded from the Molecular Signatures Database (MSigDB).

TABLE 4

Genes down-regulated and up-regulated in cancer datasets

| | Proportion down in COAD, STAD, and UCEC | Proportion up in COAD, STAD, and UCEC |
|---|---|---|
| BIOCARTA_KREB_PATHWAY | 0 | 0.38 |
| REACTOME_ACTIVATION_OF_THE_PRE_REPLICATIVE_COMPLEX | 0 | 0.33 |
| REACTOME_G1_S_SPECIFIC_TRANSCRIPTION | 0 | 0.31 |

TABLE 4-continued

Genes down-regulated and up-regulated in cancer datasets

| | Proportion down in COAD, STAD, and UCEC | Proportion up in COAD, STAD, and UCEC |
|---|---|---|
| REACTOME_PROCESSIVE_SYNTHESIS_ON_THE_LAGGING_STRAND | 0 | 0.27 |
| REACTOME_UNWINDING_OF_DNA | 0 | 0.27 |
| REACTOME_E2F_MEDIATED_REGULATION_OF_DNA_REPLICATION | 0 | 0.26 |
| BIOCARTA_MCM_PATHWAY | 0 | 0.25 |
| REACTOME_ASSOCIATION_OF_LICENSING_FACTORS_WITH_THE_PRE_R | 0 | 0.25 |
| REACTOME_DNA_STRAND_ELONGATION | 0 | 0.23 |
| REACTOME_CITRIC_ACID_CYCLE_TCA_CYCLE | 0 | 0.21 |
| REACTOME_LAGGING_STRAND_SYNTHESIS | 0 | 0.21 |
| BIOCARTA_DNAFRAGMENT_PATHWAY | 0 | 0.2 |
| BIOCARTA_GLYCOLYSIS_PATHWAY | 0 | 0.2 |
| REACTOME_CDC6_ASSOCIATION_WITH_THE_ORC_ORIGIN_COMPLEX | 0 | 0.2 |
| REACTOME_REMOVAL_OF_THE_FLAP_INTERMEDIATE_FROM_THE_C_STRAND | 0 | 0.2 |
| KEGG_GLYOXYLATE_AND_DICARBOXYLATE_METABOLISM | 0 | 0.19 |
| KEGG_DNA_REPLICATION | 0 | 0.19 |
| REACTOME_HOMOLOGOUS_RECOMBINATION_REPAIR_OF_REPLS | 0.06 | 0.19 |

This study demonstrates that numerous genes display strong differential expression with hypermutation across all cancer types and suggests that a data-driven predictor of hypermutation could prove informative.

Figure 3:
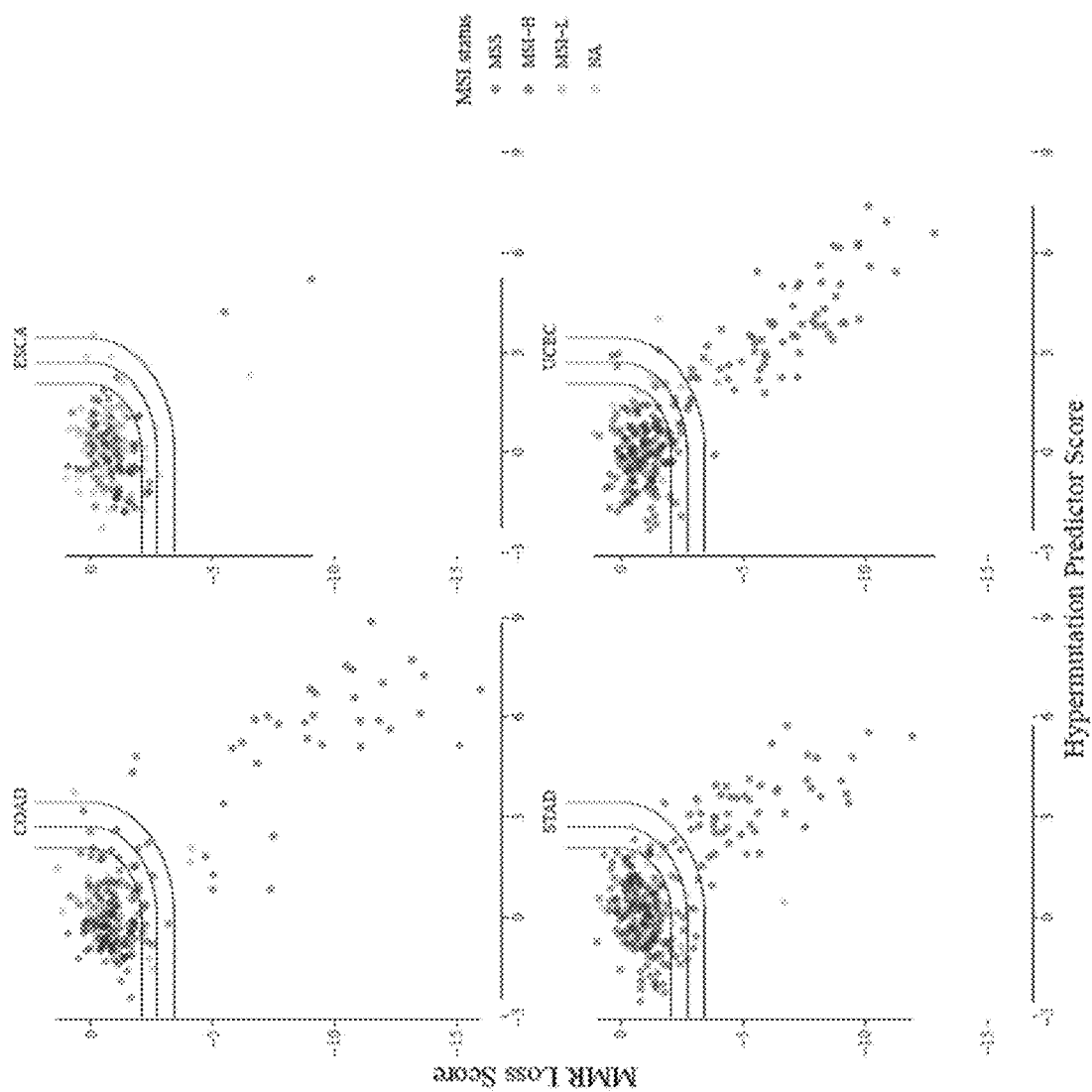
FIG. 3 is a series of graphs that shows the methods of the present disclosure can accurately predict microsatellite instability status in a tumor sample.

Example 3—Gene Expression Algorithms for Predicting MMRd, Hypermutation, and MSI Based on the results from examples 1 and 2, three gene expression algorithms for predicting MMRd, hypermutation, and MSI were trained. The "MMR Loss" algorithm uses the results from FIG. 1 to measure loss of expression of the four MMR genes (MLH1, MSH2, MSH6, and PMS2). The "Hypermutation Predictor" algorithm relies on the results from FIG. 2, using genes differentially expressed in hypermutated tumors to predict a tumor's hypermutation status. Finally, to attain the most powerful prediction with all available information, the "MSI Predictor" algorithm combines the MMR Loss and Hypermutation Predictor algorithms in a single score designed to predict MSI status. FIG. 3 is a series of graphs that show how the three algorithms relate to each other. The curved lines in FIG. 3 show the show the decision boundaries corresponding, from top-left to bottom-right, to MSI predictor score p-value cutoffs of 0.05, 0.01, and 0.00. The derivations of these algorithms are described in the materials and methods section below.
Results
The ability of the MSI Predictor algorithm and its 2 component algorithms to predict tumor MSI was evaluated. Table 5 shows that the MMR Loss (also referred to herein as MLS score) and Hypermutation Predictor (also referred to herein as HPS score) algorithms were each accurate predictors of MSI, with the MSI Predictor (also referred to herein as MPS score) algorithm showing higher accuracy as measured by True Positive Rate (TPR; the proportion of MSI-high cases detected by each algorithm) and False Positive Rate (FPR; the proportion of non-hypermutated cases falsely called hypermutated by the gene expression algorithms). A p-value threshold of 0.01 was used for all gene expression algorithms. Numbers in the parentheses in Table 5 give 95% confidence intervals calculated by the Wilson method.

TABLE 5

MMR loss and hypermutation predictor performance

| | COAD | ESCA | STAD | UCEC |
|---|---|---|---|---|
| TPR MMR loss score | 0.9 (0.76-0.96) | 1 (0.34-1) | 0.92 (0.82-0.96) | 0.94 (0.86-0.98) |
| TPR Hypermutation Predictor score | 0.74 (0.59-0.85) | 1 (0.34-1) | 0.8 (0.68-0.88) | 0.94 (0.86-0.98) |
| TPR MSI Predictor score | 0.9 (0.76-0.96) | 1 (0.34-1) | 0.9 (0.8-0.95) | 0.93 (0.84-0.97) |
| FPR MMR loss score | 0.26 (0.2-0.32) | 0.08 (0.04-0.17) | 0.3 (0.24-0.36) | 0.36 (0.3-0.43) |
| FPR Hypermutation Predictor score | 0.17 (0.12-0.23) | 0.04 (0.01-0.12) | 0.23 (0.18-0.29) | 0.37 (0.31-0.43) |
| FPR MSI Predictor score | 0.21 (0.16-0.28) | 0.03 (0.01-0.1) | 0.25 (0.19-0.31) | 0.3 (0.24-0.36) |

However, because the Hypermutation Predictor algorithm was trained from these samples it is subject to overfitting. Therefore, its performance, as well as the performance of the MSI Predictor algorithm, may be exaggerated in this data. In contrast, the MMR Loss algorithm was developed using a minimal training procedure that only required estimates of the mean and interquartile range of each gene in non-hypermutated samples; as such, this algorithm's performance is more likely to be reproduced in new datasets.

Table 6 shows that the gene expression algorithms predicted hypermutation in TCGA datasets almost as well as they predicted MSI. TCGA's PCR-based MSI assay was a slightly more powerful predictor of hypermutation, though this advantage was generally not statistically significant.

TABLE 6

Prediction of hypermutation using gene expression algorithms

| | COAD | ESCA | STAD | UCEC |
|---|---|---|---|---|
| TPR MMR loss score | 0.77 (0.62-0.87) | 0.75 (0.3-0.95) | 0.8 (0.69-0.88) | 0.73 (0.63-0.81) |
| TPR Hypermutation Predictor score | 0.65 (0.5-0.78) | 0.75 (0.3-0.95) | 0.74 (0.63-0.83) | 0.83 (0.74-0.9) |
| TPR MSI Predictor score | 0.79 (0.65-0.89) | 0.75 (0.3-0.95) | 0.79 (0.67-0.87) | 0.74 (0.65-0.82) |
| TPR MSI status | 0.86 (0.73-0.93) | 0.67 (0.21-0.94) | 0.88 (0.78-0.94) | 0.74 (0.65-0.82) |
| FPR MMR loss score | 0.1 (0.06-0.15) | 0.06 (0.03-0.11) | 0.11 (0.07-0.16) | 0.13 (0.08-0.19) |
| FPR Hypermutation Predictor score | 0.02 (0.01-0.05) | 0.03 (0.01-0.06) | 0.04 (0.02-0.08) | 0.12 (0.08-0.18) |
| FPR MSI Predictor score | 0.04 (0.02-0.08) | 0.02 (0.01-0.05) | 0.03 (0.02-0.07) | 0.03 (0.01-0.07) |
| FPR MSI status | 0.01 (0-0.04) | 0 (0-0.04) | 0 (0-0.03) | 0.01 (0-0.05) |

TABLE 7

Standard deviations of each mismatch repair gene in microsatellite stable samples in The Cancer Genome Atlas

| | MLH1 | MSH2 | MSH6 | PMS2 |
|---|---|---|---|---|
| COAD | 0.3241 | 0.4108 | 0.4198 | 0.3259 |
| ESCA | 0.5221 | 0.6602 | 0.7347 | 0.4927 |
| STAD | 0.4245 | 0.6020 | 0.4814 | 0.4314 |
| UCEC | 0.4543 | 0.7312 | 0.6158 | 0.4217 |

Upon calculation of means and standard deviations, the remainder of the algorithm was simple to execute. Each gene was Z-scored, and the minimum of the four Z-scores was taken for each sample. To place the score on a familiar scale, this minimum Z score was then rescaled by the theoretical mean and standard deviation of the minimum of four standard normal random variables, attaining a final "MMR Loss" score with a mean of 0 and standard deviation of 1 in non-hypermutated samples.

A concise description of the procedure for calculating MMR Loss score is as follows. The below algorithm is proposed for calling hypermutation events resulting from loss of expression of 1 of the 4 key MMR genes (MLH1, MSH2, MSH6, or PMS2).

1. Normalize the gene expression dataset using a sensible method.
2. For each gene, estimate μ, the gene's mean expression in non-hypermutated samples. If a low rate of hypermutation is expected in the dataset, each gene's median expression provides a good estimate. If hypermutation is expected to be common, a Gaussian mixture model with two clusters can be fit to each gene's expression data, and the mean of the higher expression cluster should be taken as μ. For single sample applications, μ must be pre-defined using a training dataset run on the same assay.
3. For each gene, look up its standard deviation (σ) in non-hypermutated tumors of the appropriate cancer type in TCGA. Examples of the 4 MMR genes' σ values are provided in Table 7.
4. For each sample, score each gene relative to its expected value in non-hypermutated samples as [Z=(x−μ)/σ], where x is the gene's normalized log 2 expression value.
5. For each sample, call Zm the minimum Z score from the 4 genes. Calculate the final MMR Loss score, [MLS=(Zm+1.03)/0.69], where 1.03 and 0.69 are the theoretical expectation and standard deviation of the minimum of 4 standard normal random variables.
6. Calculate a p-value for each sample: [p=Φ(MLS)], where Φ is the standard normal distribution function. Choose a stringent p-value threshold for calling loss events, at least as strict as 0.01. Most loss of expression events are substantial enough that they are easily detected, so p-values between 0.05 and 0.01 will often result in false positives.

Development and Validation of the Hypermutation Predictor Algorithm for Calling MSI Status from Genes Differentially Expressed in Hypermutated Tumors Given an abundance of genes with consistent and highly significant associations with hypermutation, the derivation of a data-driven predictor of hypermutation was sought. 10 genes with good performance across all 3 datasets were selected. Selection was based on multiple considerations, including effect size in the linear models described above and effect size in models fit to subsets of the data (e.g.

Materials and Methods

Development and Validation of the MMR Loss Algorithm for Calling MSI Status from Loss of MMR Genes FIG. 1 suggests that low gene expression values in MLH1, MSH2, MSH6, and PMS2 could be used to detect hypermutation and MSI. Therefore, an algorithm for predicting MSI by detecting loss of expression in these genes was developed. To do so, the uncharacteristically low expression of any one of these genes for a MSS tumor was investigated.

To quantify how atypically low a gene's expression is, knowledge of its mean expression and standard deviation in MSS samples was required. Both of these quantities will vary between cancer types, so the mean and standard deviation were estimated separately for each tumor dataset. A gene's mean expression in MSS samples will vary with platform and batch effects. Therefore, this parameter must be estimated anew when deploying this algorithm on a new platform. To ensure an unbiased procedure, this mean parameter was estimated without reference to known mutation or MSI status, either by taking each gene's median expression across a whole dataset (under the assumption that most cases are MSS) or by fitting a Gaussian mixture model with 2 clusters and taking the mean of the higher cluster. If this algorithm were to be applied in a locked assay, each gene's mean in non-hypermutated samples could be estimated directly and fixed.

The standard deviation of a gene's log-scale expression should be platform-agnostic, as platform effects are generally well-modelled as unique scaling factors applied to each gene, amounting to additive constants on the log-scale. Therefore, this parameter can be estimated in TCGA and applied it to future datasets without further calibration. In colon, stomach, and uterine cancers, each MMR gene's standard deviation in the MSS/non-hypermutated subtype was estimated using the cases where MSS status was known. In the esophageal dataset, in which many MSI calls were missing, samples with unknown MSI were included in this analysis, as MSI is rare in this indication, with only 4 cases in TCGA. These standard deviation estimates are reported Table 7.

models excluding ultramutated tumors or hypermutated tumors without MMR gene expression loss). Table 8 shows the genes selected for this process.

TABLE 8

Genes used in the hypermutation predictor score and false discovery rates (FDR) for various cancer types

| Gene | Weight | COAD FDR | STAD FDR | UCEC FDR |
|---|---|---|---|---|
| EPM2AIP1 | −0.31218 | 2.13E−19 | 1.49E−35 | 6.80E−24 |
| TTC30A | −0.19894 | 1.54E−13 | 5.22E−17 | 2.59E−07 |
| SMAP1 | −0.1835 | 7.96E−18 | 2.57E−13 | 0.001251 |
| RNLS | −0.19023 | 2.23E−14 | 0.000156 | 4.52E−18 |
| WNT11 | −0.11515 | 1.52E−08 | 0.036791 | 7.02E−06 |
| SFXN1 | 0.214676 | 1.22E−15 | 1.11E−16 | 0.000229 |
| SREBF1 | 0.194835 | 8.58E−11 | 5.48E−14 | 8.62E−06 |
| TYMS | 0.206972 | 2.08E−17 | 2.73E−14 | 0.001611 |
| EIF5AL1 | 0.194935 | 5.99E−13 | 2.86E−13 | 9.06E−05 |
| WDR76 | 0.188582 | 4.26E−12 | 3.80E−09 | 2.67E−07 |

Using the 10 selected genes, a linear predictor score was derived. Each gene was given a weight equal to its mean t-statistic across the 3 datasets and each sample's score was calculated as the sum of its weighted log 2-transformed gene expression values. As the positive and negative weights were nearly balanced, weights were rescaled such that they summed to 0, achieving a score that is invariant to any normalization scheme that adjusts each sample by a scaling constant (i.e., a sample's score was the same under any housekeeping gene normalization regimen, or even in unnormalized data. As a final step, the score was centered and scaled by its mean and standard deviation in MSS samples. Similar to the MMR Loss algorithm, the mean score was estimated in MSS samples anew on each platform. Model-based clustering was again used to estimate this parameter without reference to known MSI status. Also similar to the MMR Loss algorithm, the score's standard deviation in MSS samples in each TCGA dataset was estimated and this parameter was fixed for all future datasets. In the TCGA data from which it was trained, the Hypermutation Predictor score predicts MSI and hypermutation almost as well as the MMR Loss score.

A concise description of the algorithm for calculating Hypermutation Predictor score is as follows. The below algorithm for calling hypermutation events from genes that are differentially expressed between hypermutated/tumors with microsatellite instability (MSI) and non-hypermutated/MSS tumors is proposed.

1. For a given sample, Log 2-transform the expression data for each of the genes in Table 8, multiply each gene by its given weight, and take the sum of these weighted expression values. Call this value x.
2. If applying the assay to a new platform, calibrate the mean parameter for the dataset: fit a Gaussian mixture model with two classes to the data, and take the lower of the two mean parameters. If the mean parameter for the platform has been previously estimated, use that value instead. Call the mean parameter $\mu$.
3. Look up the score's standard deviation ($\sigma$) in non-hypermutated tumors of the appropriate cancer type in TCGA. The 4 datasets' $\sigma$ values are provided in Table 9.

TABLE 9

Standard deviations of the Hypermutation Predictor score in microsatellite stable samples in The Cancer Genome Atlas

| Tumor Type | $\sigma$ |
|---|---|
| COAD | 0.6604 |
| ESCA | 0.7617 |
| STAD | 0.8153 |
| UCEC | 0.7027 |

4. Z-transform the score to have a mean of 0 and standard deviation of 1 in non-hypermutated sample: calculate the Hypermutation Predictor score [HPS=$(x-\mu)/\sigma$].
5. For each sample: [p=$\Phi$(HPS)], where $\Phi$ is the standard normal distribution function. Choose a stringent p-value threshold for calling loss events, at least as strict as 0.01.

Development and Validation of the MSI Predictor Algorithm for Calling MSI Status from Combined Information in the MMR Loss and Hypermutation Predictor Scores Ultimately, a single procedure for calling tumors' MSI status was required. The MSI predictor algorithm described below combines the information in the MMR Loss and Hypermutation Predictor scores into a single score for predicting MSI status. First, it was observed that both the MMR Loss and Hypermutation Predictor scores were approximately Gaussian with a mean of 0 and standard deviation of 1 in MSS samples. Furthermore, they appeared uncorrelated in MSS samples. These observations suggested a test that rejects the null hypothesis of MSS/non-hypermutation in samples that fall in extreme values of the joint distribution of these two scores, which could be reasonably approximated as a bivariate normal distribution.

However, a one-sided test was desired and the rejection of the null hypothesis of MSS/non-hypermutation (e.g., when MLH1 expression was extremely high) was unwanted. Additionally, allowing a null score from one test to counteract the evidence from an impressive score from the other test was unwanted (e.g., if the Hypermutation Predictor score suggested hypermutation but all the MMR genes were unusually high, letting the MMR genes' results counteract the evidence from the Hypermutation Predictor score was unwanted). Thus, both the MMR Loss score and the Hypermutation Predictor score were truncated at 0.

This truncation and the assumption of approximate bivariate normality lead to the following test statistic: MSI predictor score=$[(\max(HPS, \text{mean}(HPS))^2 + \min(MLS, 0)^2)^{1/2}]$, where HPS is the Hypermutation Predictor score and MLS is the MMR Loss score. Selected contours of this test score, or equivalently, decision boundaries it could delineate, are shown in FIG. 3. By assuming bivariate normality a p-value for the test statistic could be calculated, equal to the mass of a bivariate normal probability distribution falling above the decision boundary implied by the test statistic's value. Using numerical integration, it was found that p-values of 0.05, 0.01, 0.005, and 0.001 correspond to test statistics of 2.058, 2.699, 2.939, and 3.429, respectively.

A concise description of the algorithm for calculating MSI status from combined information in the MMR Loss and Hypermutation Predictor scores is as follows. The below algorithm for calling hypermutation events in a given sample is proposed:

1. Calculate the MMR Loss and Hypermutation Predictor scores as described above. Call MLS the Z-score from the MMR Loss algorithm, and call HPS the Z-score from the Hypermutation Predictor algorithm.
2. Calculate the final score: MSI Predictor Score=[(max $(HPS,0)^2$+min$(MLS,0)^2)]^{1/2}$.
3. Compare the score to a pre-specified cutoff. A cutoff of 7.287 is suggested, which corresponds to a p=0.01 threshold for rejecting the null hypothesis of MSS/non-hypermutation.

Example 4—Validation of MSI Predictor Algorithm in Two Independent Sample Sets Using the NanoString nCounter System To validate the algorithms trained in TCGA, the NanoString nCounter (NanoString Technologies, Inc., Seattle, Washington, USA) was used to profile two new sample sets for which results of the MMRd IHC assay were available (MSI assays were not run, but the MMRd IHC assay is commonly accepted as a surrogate for MSI). One sample set consisted of 30 MMR-proficient and 30 MMRd colorectal carcinoma samples. The other sample set was 5 MMR-proficient and 10 MMRd endometrial and neuroendocrine tumors, with MMRd status determined by IHC. Endometrial and neuroendocrine samples were combined in a single analysis because of the limited sample sizes.

Figure 4:
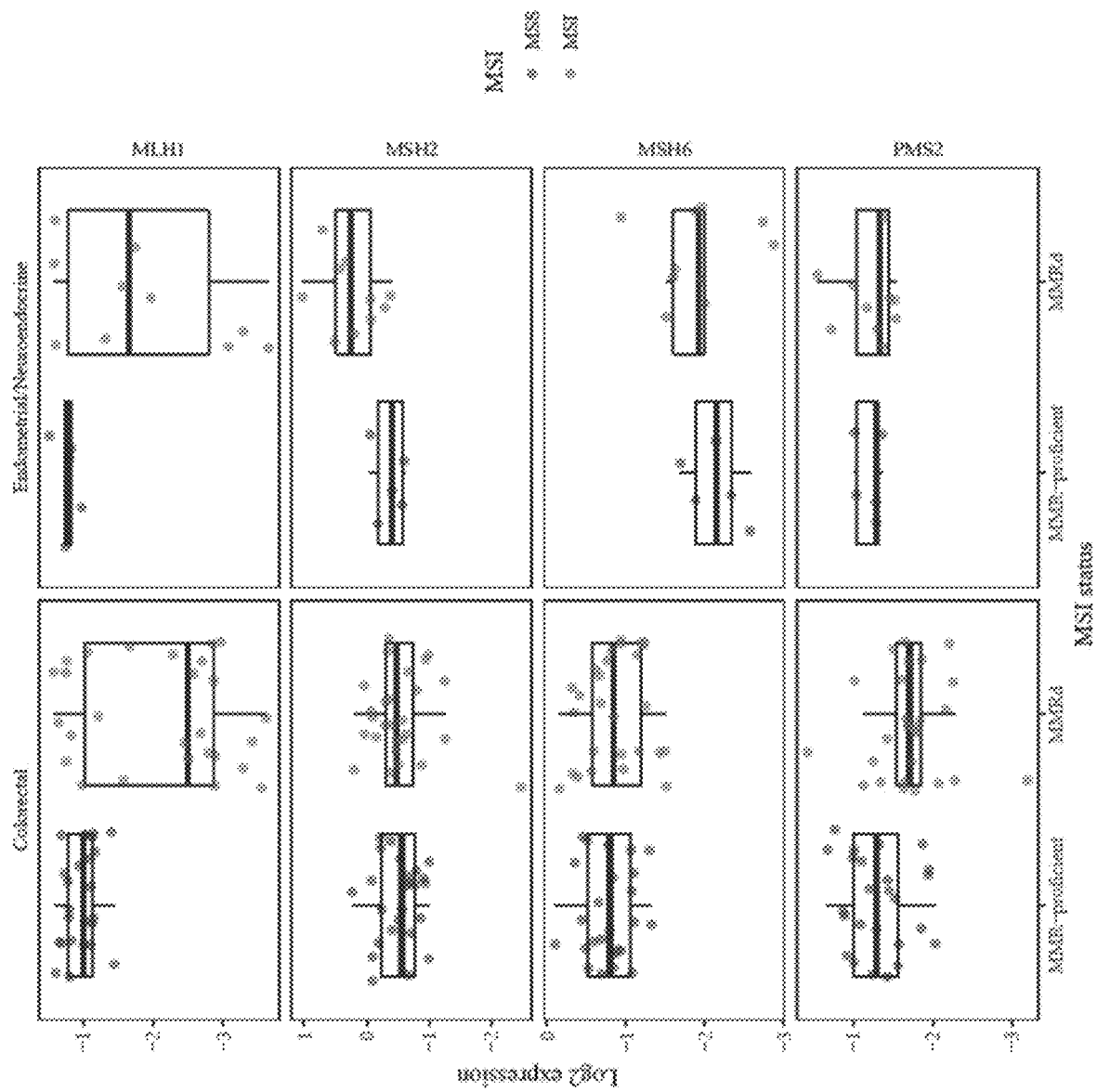
FIG. 4 is a series of box plots that shows the relationship between the expression of four mismatch repair genes and microsatellite instability in validation samples of two different cancer types.
Figure 5:
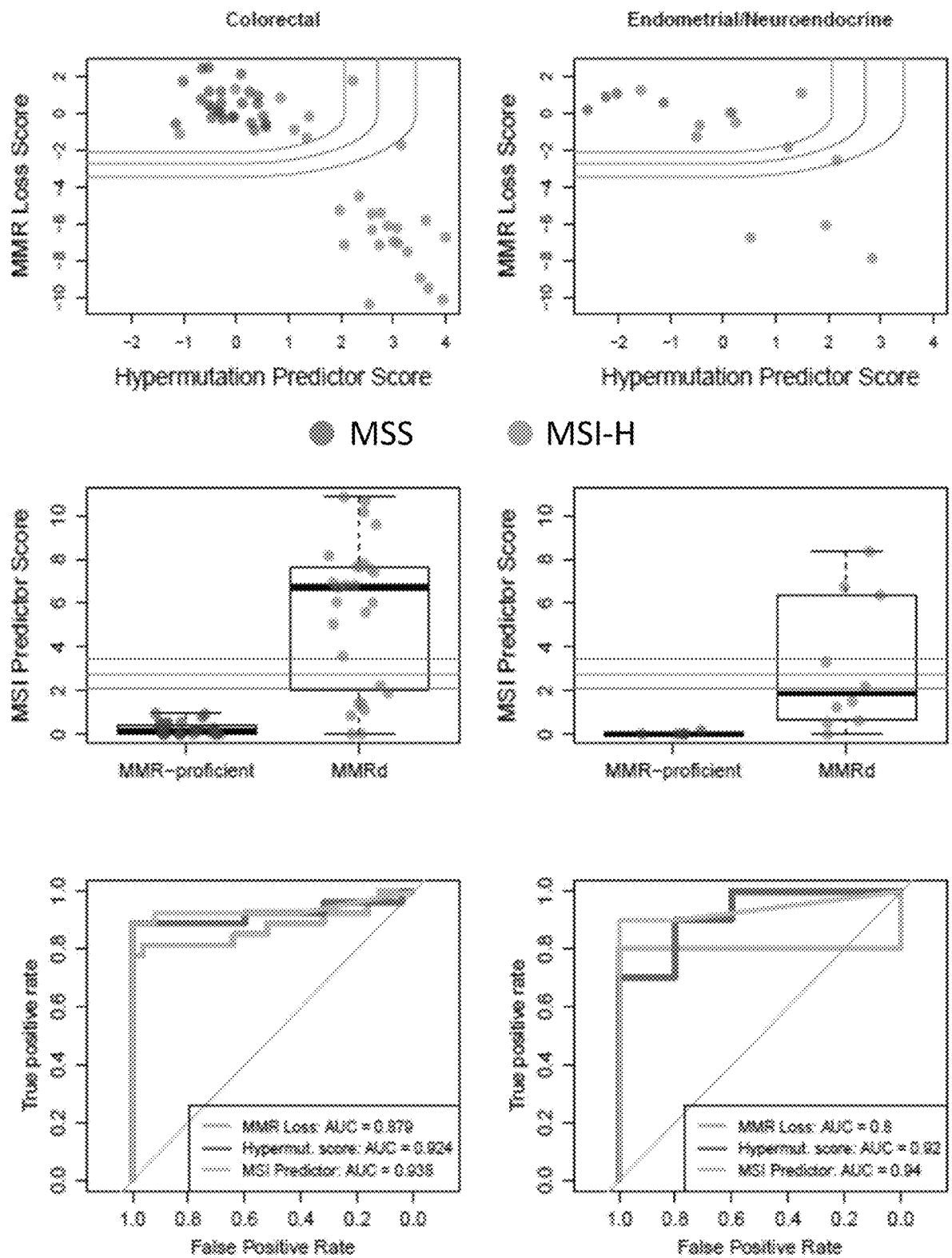
FIG. 5 is a series of graphs that shows the performance of the methods of the present disclosure in determining microsatellite instability status in validation samples of two different cancer types.

FIG. 4 is a series of box plots that show that, like the phenomenon seen in TCGA, the validation datasets revealed loss of expression events in a majority of MSI samples. In the endometrial and neuroendocrine samples, losses were only observed for MLH1. PMS2 expression was not noticeably suppressed in 2 tumors with mutations in that gene and in 2 tumors with loss of nuclear PMS2 expression seen in IHC. In the colorectal samples, frequent MLH1 loss of expression was apparent, as were a single instance each of MSH2 and PMS2 loss. Loss of expression events occurred exclusively in MMRd tumors. FIG. 5 shows that the MMR loss score, which measures the evidence for loss in any of the four MMR genes, attained an area under the ROC curve (AUC) of 0.80 in endometrial samples and 0.87 in colorectal samples.

FIG. 5 also shows that the Hypermutation Predictor score, a linear combination of 10 genes, retained strong predictive performance in these independent datasets and outperformed the MMR Loss score (area under curve [AUC]=0.902 in endometrial samples and 0.932 in colorectal samples). The MSI Predictor score added negligible predictive power to the Hypermutation Predictor score. The majority of MMRd cases are unambiguously detected by the MSI Predictor score, and the score's overall predictive power was very high (area under curve [AUC]=0.940 in endometrial samples and 0.963 in colorectal samples).

The TCGA training did not map perfectly to the validation datasets. Examining the top row of FIG. 5, it appears that moving the score contours/decision boundaries left would capture more MMRd samples while incurring no false positives. These suboptimal decision boundaries of the Hypermutation Predictor score appear to result from a lower standard deviation in the validation MSS samples than in TCGA MSS samples. If the Hypermutation Predictor score's standard deviation in MSS samples were to be estimated anew in these datasets, it would shift the score contours/decision boundaries left and thereby achieve even better prediction. By implementing the MSI Predictor score using the pre-defined standard deviation estimates from TCGA, the differential score in MSI calling is underutilized and the results are unnecessarily conservative. The reason for the narrower distribution of Hypermutation Predictor scores in MSS samples in NanoString data is unclear. It could result from more precise gene expression measurements or from some unknown difference in the studies' sample preparation methods or clinical populations.

Materials and Methods

Calculation of Gene Expression Algorithms in NanoString Validation Datasets

Before the algorithms could be applied to data from a new platform, an up-front calibration step was required: for each of the 4 MMR genes and for the Hypermutation Predictor score, the mean value in non-hypermutated samples (or the "center") had to be estimated. This calibration was performed using unsupervised techniques blind to the samples' MSI status as described in the methods sections for the respective algorithms.

MMRd Assay in Colorectal Carcinoma Samples

MSI-H and MSS/MSI-L colorectal cancer tumor samples in formalin-fixed paraffin-embedded (FFPE) blocks were purchased from iSpecimen (Lexington, Massachusetts, USA). MMR status was determined by the original clinical source using IHC for MLH1, MSH2, MSH6, and PMS2. Blocks were then sent to CellNetix (Seattle, Washington, USA) for pathology review and slide cutting.

MMRd Assay in Endometrial Samples

MMR status was determined by IHC performed at PhenoPath Laboratories, PLLC (Seattle, Washington, USA). Antibody clones used were MSH2 (mouse monoclonal FE11, catalog #M3639; Dako), MSH6 (rabbit monoclonal EP49, catalog #M3646; Dako), MLH1 (mouse monoclonal E505, catalog #M3640; Dako) and PMS2 (rabbit monoclonal EP51, catalog #M3647; Dako) (Agilent Technologies, Inc., Santa Clara, California, USA). All samples were stained with hematoxylin and eosin to allow for morphological evaluation. MMR status was reviewed by a board-certified pathologist and reported as "no loss of expression" or "loss of expression."

NanoString Assay and Normalization

Samples were run using the standard nCounter Gene Expression assay methodology (NanoString Technologies, Inc., Seattle, Washington, USA; see, e.g. Geiss G K et al. Nature biotechnology. 2008 Mar. 1; 26(3):317-25). Total RNA was extracted from each FFPE tumor sample using the Qiagen FFPE RNeasy kit (Qiagen, Inc., Hilden, Germany). A total of 100ng of RNA was hybridized with the nCounter IO 360 gene expression panel (NanoString Technologies, Inc., Seattle, Washington, USA), with downstream processing and data collection following manufacturer's instructions.

Both NanoString datasets were normalized such that the mean log 2 expression of 10 housekeeping genes was constant across all samples. All analyses used log 2-transformed data.

Calculation of MSI Algorithms in NanoString Data

Platform differences prevented us from directly applying the TCGA-trained algorithms to NanoString data. Because gene expression platforms differ in the efficiency with which they measure each target sequence, platform effects can be well-modelled by a constant shift in each gene's log-scale normalized expression. Therefore, to apply the algorithms to NanoString data, these constant factors were estimated for each MMR gene and for the Hypermutation Predictor score. To preserve the integrity of this dataset as an unbiased test set for the algorithms, all of these calibration parameters were estimated using unsupervised methods without reference to the known MSI calls. The R library Mclust was used to fit a two-component Gaussian mixture model to each MMR gene's log 2-transformed, normalized expression and to the Hypermutation Predictor score. For the MMR genes, the mean of the higher of the two clusters was taken as the estimate of the mean expression level in non-hypermutated samples; for the Hypermutation Predictor score, the mean in the lower of the two clusters was used. Apart from these mean estimates, all other parameters needed to calculate algorithm scores were calculated from TCGA data without reference to the validation dataset.

Figure 6:
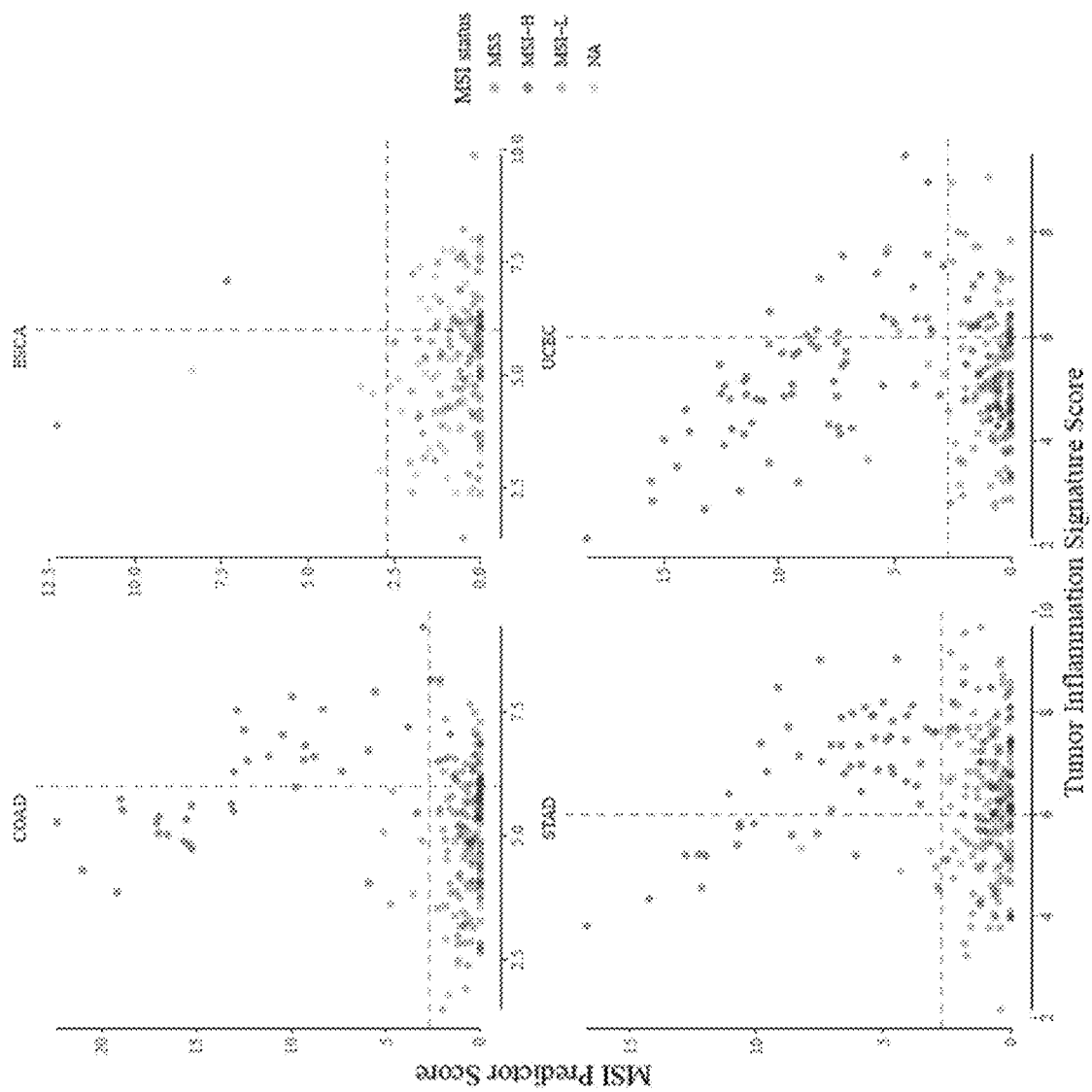
FIG. 6 is a series of graphs showing the results of the methods of the present disclosure plotted against tumor inflammation signature score and microsatellite instability status.

Example 5—Association of MSI Status with Extent of Anti-Tumor Immunity as Measured by the Tumor Inflammation Signature It is well-established that gene expression can predict immunotherapy response by measuring the inflamed microenvironment phenotype. In particular, the Tumor Inflammation Signature as disclosed in PCT/US2015/064445 (WO2016/094377), which is incorporated herein by reference in its entirety, uses 18 genes involved in adaptive anti-tumor immunity to predict response to the anti-PD-1 agent, pembrolizumab (also see e.g. Ayers M et al. The Journal of clinical investigation. 2017 Aug. 1; 127(8):2930-40). The motivation of this study was to enable gene expression to capture an additional, genotypic predictor of immunotherapy response: hypermutation. FIG. 6 compares these genotype and phenotype variables in TCGA, plotting the MSI Predictor score against the Tumor Inflammation Signature score. As a visual guide, thresholds for calling MSI or high immunity have been drawn.

Together, the Tumor Inflammation Signature and MSI scores measured in the same sample identify more potential responders than either test alone. Importantly, very few patients called MSI-H by standard techniques are missed by both the Tumor Inflammation Signature and MSI gene expression score. Interestingly, MSI scores in true MSI-H samples become attenuated in tumors with high Tumor Inflammation Signature scores. One explanation for this phenomenon is that in inflamed tumors, highly abundant immune cells contribute background expression of MLH1 and other MSI signature genes, clouding the otherwise clear signal of the tumor cells' mRNA. Importantly, nearly all MSI-H tumors missed by the MSI gene expression score have high Tumor Inflammation Signature scores, and their potential for anti-tumor immunity would be identified based on that variable alone.

SUMMARY OF EXAMPLES

In summary, the examples described herein demonstrate here that RNA expression can be used to identify MSI-H tumors with both high sensitivity and specificity. This discovery opens the possibility of using RNA expression profiling to identify multiple orthogonal biomarkers of checkpoint inhibitor efficacy in a single assay, thereby improving the ability to identify the best treatment option for every patient. Additionally, there are benefits to measuring both anti-tumor immune activity and MSI status using a single test. Rather than using multiple tissue samples and potentially sending those out to multiple laboratories for analysis, combining these two measurements into a single assay allows for conservation of biological material and simplification of personalized treatment decisions.

These findings should have broad applicability in gene expression studies of cancer types where MSI occurs. It is reasonable to posit that outlier low expression values of MHL1, MSH2, MSH6, and PMS2 will nearly always occur in tandem with MSI, regardless of tumor type.

Based on these results, MSI and immune status should together form the foundation of any analysis of immunotherapy in solid tumors. Because these variables are non-redundant, they promise to offer superior prediction together than either can alone. Responders missed by one of these variables may often be identified by the other. To more optimally guide treatment choices, drug efficacy should be evaluated separately in MSI-H/immune-high, MSI-H/immune-low, MSI-L/immune-high, and MSI-L/immune-low subsets.

What is claimed is:

1. A method of treating cancer in a subject identified as having a mismatch repair deficiency, wherein the cancer is selected from a colon cancer, an esophageal cancer, a stomach cancer, and a uterine cancer, the method including administering to the subject identified as having mismatch repair deficiency at least one treatment comprising an immunotherapy, and wherein the subject is identified as having mismatch repair deficiency by a method comprising:

a) measuring the gene expression level of at least one gene selected from MLH1, MSH2, MSH6 or PMS2 in a tumor sample from the subject, wherein measuring comprises an enzyme free method;

b) determining for each of the at least one gene a score Z, wherein $Z=(x-\mu_1)/\sigma_1$, wherein x is the log-transformed normalized expression of the at least one gene, $\mu_1$ is the mean of the log-transformed normalized expression of the at least one gene in non-hypermutated samples, and $\sigma_1$ is the standard deviation of the log-transformed normalized expression of the at least one gene in non-hypermutated samples;

c) determining a score MLS, wherein $MLS=(Z_m+c_1)/c_2$, wherein $Z_m$ is the minimum Z score of the at least one gene, and wherein $c_1$ is 0 and $c_2$ is 1 when one gene is used,
$c_1$ is 0.56 and $c_2$ is 0.83 when two genes are used,
$c_1$ is 0.85 and $c_2$ is 0.75 when three gene are used, or
$c_1$ is 1.03 and $c_2$ is 0.70 when four genes are used;

d) comparing the MLS score with a predetermined cutoff value, wherein the cutoff value identifies mismatch repair deficiency in a subject with at least 95% specificity; and e) identifying the presence of mismatch repair deficiency in the subject when the MLS score is equal to or greater than the predetermined cutoff value.

2. The method of claim 1, wherein the cutoff value identifies mismatch repair deficiency in a subject with at least 99% specificity.

3. The method of claim 1, wherein the cutoff value is 1.645.

4. The method of claim 1, wherein the cutoff value is 2.326.

5. The method of claim 1, wherein the cutoff value is 2.576.

6. The method of claim 1, wherein the at least one gene is MLH1.

7. The method of claim 1, wherein the at least one gene includes each of MLH1, MSH2, MSH6 and PMS2.

8. The method of claim 1, wherein the treatment comprises administering to the subject a checkpoint inhibitor therapy.

9. The method of claim 1, wherein the treatment comprises administering to the subject pembrolizumab, nivolumab, atezolizumab, avelumab, durvalumab or a combination thereof.

10. The method of claim 1, wherein the treatment comprises administering to the subject pidilizumab, REGN2810, AMP-224, MEDI0680, PDR001, CT-001 or a combination thereof.

11. The method of claim 1, wherein the treatment comprises administering to the subject a CTLA4 antibody.

12. The method of claim 11, wherein the CTLA4 antibody comprises ipilimumab, tremelimumab or a combination thereof.

* * * * *

SEQUENCE LISTING

```
<160> NUMBER OF SEQ ID NOS: 57

<210> SEQ ID NO 1
<211> LENGTH: 2524
<212> TYPE: DNA
<213> ORGANISM: Homo sapiens

<400> SEQUENCE: 1
attggctgaa ggcacttccg ttgagcatct agacgtttcc ttggctcttc tggcgccaaa      60
atgtcgttcg tggcaggggt tattcggcgg ctggacgaga cagtggtgaa ccgcatcgcg     120 gcggggaag ttatccagcg gccagctaat gctatcaaag agatgattga gaactgttta     180
gatgcaaaat ccacaagtat tcaagtgatt gttaaagagg gaggcctgaa gttgattcag     240
atccaagaca atggcaccgg gatcaggaaa gaagatctgg atattgtatg tgaaaggttc     300
actactagta aactgcagtc ctttgaggat ttagccagta tttctaccta tggctttcga     360
ggtgaggctt tggccagcat aagccatgtg gctcatgtta ctattacaac gaaaacagct     420
gatggaaagt gtgcatacag agcaagttac tcagatggaa aactgaaagc ccctcctaaa     480
ccatgtgctg gcaatcaagg gacccagatc acggtggagg acctttttta caacatagcc     540
acgaggagaa aagctttaaa aaatccaagt gaagaatatg ggaaaatttt ggaagttgtt     600
```

| | |
|---|---:|
| ggcaggtatt cagtacacaa tgcaggcatt agtttctcag ttaaaaaaca aggagagaca | 660 |
| gtagctgatg ttaggacact acccaatgcc tcaaccgtgg acaatattcg ctccatcttt | 720 |
| ggaaatgctg ttagtcgaga actgatagaa attggatgtg aggataaaac cctagccttc | 780 |
| aaaatgaatg gttacatatc caatgcaaac tactcagtga agaagtgcat cttcttactc | 840 |
| ttcatcaacc atcgtctggt agaatcaact tccttgagaa aagccataga aacagtgtat | 900 |
| gcagcctatt tgcccaaaaa cacacaccca ttcctgtacc tcagtttaga aatcagtccc | 960 |
| cagaatgtgg atgttaatgt gcaccccaca aagcatgaag ttcacttcct gcacgaggag | 1020 |
| agcatcctgg agcgggtgca gcagcacatc gagagcaagc tcctgggctc caattcctcc | 1080 |
| aggatgtact tcacccagac tttgctacca ggacttgctg gcccctctgg ggagatggtt | 1140 |
| aaatccacaa caagtctgac ctcgtcttct acttctggaa gtagtgataa ggtctatgcc | 1200 |
| caccagatgg ttcgtacaga ttcccgggaa cagaagcttg atgcatttct gcagcctctg | 1260 |
| agcaaacccc tgtccagtca gccccaggcc attgtcacag aggataagac agatatttct | 1320 |
| agtggcaggg ctaggcagca agatgaggag atgcttgaac tcccagcccc tgctgaagtg | 1380 |
| gctgccaaaa atcagagctt ggaggggat acaacaaagg ggacttcaga aatgtcagag | 1440 |
| aagagaggac ctacttccag caaccccaga agagacatc gggaagattc tgatgtggaa | 1500 |
| atggtggaag atgattcccg aaaggaaatg actgcagctt gtacccccg gagaaggatc | 1560 |
| attaacctca ctagtgtttt gagtctccag gaagaaatta atgagcaggg acatgaggtt | 1620 |
| ctccgggaga tgttgcataa ccactccttc gtgggctgtg tgaatcctca gtgggccttg | 1680 |
| gcacagcatc aaaccaagtt ataccttctc aacaccacca agcttagtga agaactgttc | 1740 |
| taccagatac tcatttatga ttttgccaat tttggtgttc tcaggttatc ggagccagca | 1800 |
| ccgctctttg accttgccat gcttgcctta gatagtccag agagtggctg gacagaggaa | 1860 |
| gatggtccca agaaggact tgctgaatac attgttgagt ttctgaagaa gaaggctgag | 1920 |
| atgcttgcag actatttctc tttggaaatt gatgaggaag gaacctgat tggattaccc | 1980 |
| cttctgattg acaactatgt gccccctttg gagggactgc ctatcttcat tcttcgacta | 2040 |
| gccactgagg tgaattggga cgaagaaaag gaatgttttg aaagcctcag taagaatgc | 2100 |
| gctatgttct attccatccg gaagcagtac atatctgagg agtcgaccct ctcaggccag | 2160 |
| cagagtgaag tgcctggctc cattccaaac tcctggaagt ggactgtgga acacattgtc | 2220 |
| tataaagcct tgcgctcaca cattctgcct cctaaacatt tcacagaaga tggaaatatc | 2280 |
| ctgcagcttg ctaacctgcc tgatctatac aaagtctttg agaggtgtta aatatggtta | 2340 |
| tttatgcact gtgggatgtg ttcttctttc tctgtattcc gatacaaagt gttgtatcaa | 2400 |
| agtgtgatat acaaagtgta ccaacataag tgttggtagc acttaagact tatacttgcc | 2460 |
| ttctgatagt attcctttat acacagtgga ttgattataa ataaatagat gtgtcttaac | 2520 |
| ataa | 2524 |

<210> SEQ ID NO 2
<211> LENGTH: 3145
<212> TYPE: DNA
<213> ORGANISM: Homo sapiens

<400> SEQUENCE: 2

| | |
|---|---:|
| ggcgggaaac agcttagtgg gtgtggggtc gcgcattttc ttcaaccagg aggtgaggag | 60 |
| gtttcgacat ggcggtgcag ccgaaggaga cgctgcagtt ggagagcgcg gccgaggtcg | 120 |
| gcttcgtgcg cttctttcag ggcatgccgg agaagccgac caccacagtg cgccttttcg | 180 |

```
accggggcga cttctatacg gcgcacggcg aggacgcgct gctggccgcc cgggaggtgt    240
tcaagaccca gggggtgatc aagtacatgg ggccggcagg agcaaagaat ctgcagagtg    300
ttgtgcttag taaatgaatt tttgaatctt ttgtaaaaga tcttcttctg gttcgtcagt    360
atagagttga agtttataag aatagagctg gaaataaggc atccaaggag aatgattggt    420
atttggcata taaggcttct cctggcaatc tctctcagtt tgaagacatt ctctttggta    480
acaatgatat gtcagcttcc attggtgttg tgggtgttaa aatgtccgca gttgatggcc    540
agagacaggt tggagttggg tatgtggatt ccatacagag gaaactagga ctgtgtgaat    600
tccctgataa tgatcagttc tccaatcttg aggctctcct catccagatt ggaccaaagg    660
aatgtgtttt acccggagga gagactgctg agacatggg gaaactgaga cagataattc    720
aaagaggagg aattctgatc acagaaagaa aaaagctga cttttccaca aaagacattt    780
atcaggacct caaccggttg ttgaaaggca aaagggaga gcagatgaat agtgctgtat    840
tgccagaaat ggagaatcag gttgcagttt catcactgtc tgcggtaatc aagttttag     900 aactcttatc agatgattcc aactttggac agtttgaact gactactttt gacttcagcc    960
agtatatgaa attggatatt gcagcagtca gagcccttaa ccttttttcag ggttctgttg   1020 aagataccac tggctctcag tctctggctg ccttgctgaa taagtgtaaa accccctcaag  1080 gacaaagact tgttaaccag tggattaagc agcctctcat ggataagaac agaatagagg   1140
agagattgaa tttagtggaa gcttttgtag aagatgcaga attgaggcag actttacaag   1200
aagatttact tcgtcgattc ccagatctta accgacttgc caagaagttt caaagacaag   1260
cagcaaactt acaagattgt taccgactct atcagggtat aaatcaacta cctaatgtta   1320
tacaggctct ggaaaaacat gaaggaaaac accagaaatt attgttggca gttttttgtga  1380 ctcctcttac tgatcttcgt tctgacttct ccaagtttca ggaaatgata gaaacaactt   1440
tagatatgga tcaggtggaa aaccatgaat tccttgtaaa accttcattt gatcctaatc   1500
tcagtgaatt aagagaaata atgaatgact tggaaaagaa gatgcagtca acattaataa   1560
gtgcagccag agatcttggc ttggaccctg gcaaacagat taaactggat tccagtgcac   1620
agtttggata ttactttcgt gtaacctgta aggaagaaaa agtccttcgt aacaataaaa   1680
actttagtac tgtagatatc cagaagaatg gtgttaaatt taccaacagc aaattgactt   1740
cttaaaatga gagtatacc aaaaataaaa cagaatatga agaagcccag gatgccattg    1800
ttaaagaaat tgtcaatatt tcttcaggct atgtagaacc aatgcagaca ctcaatgatg   1860
tgttagctca gctagatgct gttgtcagct ttgctcacgt gtcaaatgga gcacctgttc   1920
catatgtacg accagccatt ttggagaaag gacaaggaag aattatatta aaagcatcca   1980
ggcatgcttg tgttgaagtt caagatgaaa ttgcatttat tcctaatgac gtatactttg   2040
aaaaagataa acagatgttc cacatcatta ctggccccaa tatgggaggt aaatcaacat   2100
atattcgaca aactggggtg atagtactca tggcccaaat tgggtgtttt gtgccatgtg   2160
agtcagcaga agtgtccatt gtggactgca tcttagcccg agtaggggct ggtgacagtc   2220
aattgaaagg agtctccacg ttcatggctg aaatgttgga aactgcttct atcctcaggt   2280
ctgcaaccaa agattcatta ataatcatag atgaattggg aagaggaact tctacctacg   2340
atggatttgg gttagcatgg gctatatcag aatacattgc aacaaagatt ggtgctttt    2400 gcatgtttgc aacccatttt catgaactta ctgccttggc caatcagata ccaactgtta   2460
ataatctaca tgtcacagca ctcaccactg aagagacctt aactatgctt tatcaggtga   2520
```

| | |
|---|---|
| agaaaggtgt ctgtgatcaa agtttttggga ttcatgttgc agagcttgct aatttccta | 2580 |
| agcatgtaat agagtgtgct aaacagaaag ccctggaact tgaggagttt cagtatattg | 2640 |
| gagaatcgca aggatatgat atcatggaac cagcagcaaa gaagtgctat ctggaaagag | 2700 |
| agcaaggtga aaaaattatt caggagttcc tgtccaaggt gaaacaaatg ccctttactg | 2760 |
| aaatgtcaga gaaaacatc acaataaagt taaaacagct aaaagctgaa gtaatagcaa | 2820 |
| agaataatag ctttgtaaat gaaatcattt cacgaataaa agttactacg tgaaaaatcc | 2880 |
| cagtaatgga atgaaggtaa tattgataag ctattgtctg taatagtttt atattgtttt | 2940 |
| atattaaccc ttttccata gtgttaactg tcagtgccca tgggctatca acttaataag | 3000 |
| atatttagta atattttact ttgaggacat tttcaaagat ttttattttg aaaaatgaga | 3060 |
| gctgtaactg aggactgttt gcaattgaca taggcaataa taagtgatgt gctgaatttt | 3120 |
| ataaataaaa tcatgtagtt tgtgg | 3145 |

```
<210> SEQ ID NO 3
<211> LENGTH: 4435
<212> TYPE: DNA
<213> ORGANISM: Homo sapiens

<400> SEQUENCE: 3
```

| | |
|---|---|
| ggcgaggcgc ctgttgattg gccactgggg cccgggttcc tccggcggag cgcgcctccc | 60 |
| cccagatttc ccgccagcag gagccgcgcg gtagatgcgg tgcttttagg agctccgtcc | 120 |
| gacagaacgg ttgggccttg ccggctgtcg gtatgtcgcg acagagcacc ctgtacagct | 180 |
| tcttccccaa gtctccggcg ctgagtgatg ccaacaaggc ctcggccagg gcctcacgcg | 240 |
| aaggcggccg tgccgccgct gcccccgggg cctctccttc cccaggcggg gatgcggcct | 300 |
| ggagcgaggc tgggcctggg cccaggccct tggcgcgctc cgcgtcaccg cccaaggcga | 360 |
| agaacctcaa cggagggctg cggagatcgg tagcgcctgc tgcccccacc agttgtgact | 420 |
| tctcaccagg agatttggtt tgggccaaga tggaggtta cccctggtgg ccttgtctgg | 480 |
| tttacaacca cccctttgat ggaacattca tccgcgagaa agggaaatca gtccgtgttc | 540 |
| atgtacagtt ttttgatgac agcccaacaa ggggctgggt tagcaaaagg cttttaaagc | 600 |
| catatacagg ttcaaaatca aggaagccc agaagggagg tcattttac agtgcaaagc | 660 |
| ctgaaatact gagagcaatg caacgtgcag atgaagcctt aaataaagac aagattaaga | 720 |
| ggcttgaatt ggcagtttgt gatgagccct cagagccaga agaggaagaa gagatggagg | 780 |
| taggcacaac ttacgtaaca gataagagtg aagaagataa tgaaattgag agtgaagagg | 840 |
| aagtacagcc taagacacaa ggatctaggc gaagtagccg ccaaataaaa aaacgaaggg | 900 |
| tcatatcaga ttctgagagt gacattggtg gctctgatgt ggaatttaag ccagacacta | 960 |
| aggaggaagg aagcagtgat gaaataagca gtggagtggg ggatagtgag agtgaaggcc | 1020 |
| tgaacagccc tgtcaaagtt gctcgaaagc ggaagagaat ggtgactgga aatggctctc | 1080 |
| ttaaaaggaa aagctctagg aaggaaacgc cctcagccac caaacaagca actagcatt | 1140 |
| catcagaaac caagaatact ttgagagctt tctctgcccc tcaaaattct gaatcccaag | 1200 |
| cccacgttag tggaggtggt gatgacagta gtcgccctac tgtttggtat catgaaactt | 1260 |
| tagaatggct taaggaggaa aagagaagag atgagcacag gaggaggcct gatcaccccg | 1320 |
| attttgatgc atctcacactc tatgtgcctg aggatttcct caattcttgt actcctggga | 1380 |
| tgaggaagtg gtggcagatt aagtctcaga actttgatct tgtcatctgt tacaaggtgg | 1440 |
| ggaaattttta tgagctgtac cacatggatg ctcttattgg agtcagtgaa ctggggctgg | 1500 |

```
tattcatgaa aggcaactgg gcccattctg gctttcctga aattgcattt ggccgttatt    1560
cagattccct ggtgcagaag ggctataaag tagcacgagt ggaacagact gagactccag    1620
aaatgatgga ggcacgatgt agaaagatgg cacatatatc caagtatgat agagtggtga    1680
ggagggagat ctgtaggatc attaccaagg gtacacagac ttacagtgtg ctggaaggtg    1740
atccctctga gaactacagt aagtatcttc ttagcctcaa agaaaaagag gaagattctt    1800
ctggccatac tcgtgcatat ggtgtgtgct ttgttgatac ttcactggga aagtttttca    1860
taggtcagtt ttcagatgat cgccattgtt cgagatttag gactctagtg gcacactatc    1920
ccccagtaca agttttattt gaaaaaggaa atctctcaaa ggaaactaaa acaattctaa    1980
agagttcatt gtcctgttct cttcaggaag gtctgatacc cggctcccag ttttgggatg    2040
catccaaaac tttgagaact ctccttgagg aagaatattt tagggaaaag ctaagtgatg    2100
gcattggggt gatgttaccc caggtgctta aaggtatgac ttcagagtct gattccattg    2160
ggttgacacc aggagagaaa agtgaattgg ccctctctgc tctaggtggt tgtgtcttct    2220
acctcaaaaa atgccttatt gatcaggagc ttttatcaat ggctaatttt gaagaatata    2280
ttcccttgga ttctgacaca gtcagcacta caagatctgg tgctatcttc accaaagcct    2340
atcaacgaat ggtgctagat gcagtgacat aaacaacctt ggagattttt ctgaatggaa    2400
caaatggttc tactgaagga accctactag agagggttga tacttgccat actccttttg    2460
gtaagcggct cctaaagcaa tggctttgtg ccccactctg taaccattat gctattaatg    2520
atcgtctaga tgccatagaa gacctcatgg ttgtgcctga caaatctcc gaagttgtag    2580 agcttctaaa gaagcttcca gatcttgaga ggctactcag taaaattcat aatgttgggt    2640
ctcccctgaa gagtcagaac cacccagaca gcagggctat aatgtatgaa gaaactacat    2700
acagcaagaa gaagattatt gattttcttt ctgctctgga aggattcaaa gtaatgtgta    2760
aaattatagg gatcatggaa gaagttgctg atggttttaa gtctaaaatc cttaagcagg    2820
tcatctctct gcagacaaaa aatcctgaag gtcgttttcc tgatttgact gtagaattga    2880
accgatggga tacagccttt gaccatgaaa aggctcgaaa gactggactt attactccca    2940
aagcaggctt tgactctgat tatgaccaag ctcttgctga cataagagaa aatgaacaga    3000
gcctcctgga ataccagag aaacagcgca acagaattgg ctgtaggacc atagtctatt    3060
gggggattgg taggaaccgt taccagctgg aaattcctga gaatttcacc actcgcaatt    3120
tgccagaaga atacgagttg aaatctacca agaagggctg taaacgatac tggaccaaaa    3180
ctattgaaaa gaagttggct aatctcataa atgctgaaga acggagggat gtatcattga    3240
aggactgcat gcggcgactg ttctataact ttgataaaaa ttacaaggac tggcagtctg    3300
ctgtagagtg tatcgcagtg ttggatgttt tactgtgcct ggctaactat agtcgagggg    3360
gtgatggtcc tatgtgtcgc ccagtaattc tgttgccgga agataccccc cccttcttag    3420
agcttaaagg atcacgccat ccttgcatta cgaagacttt ttttggagat gatttttattc    3480 ctaatgacat tctaataggc tgtgaggaag aggagcagga aaatggcaaa gcctattgtg    3540
tgcttgttac tggaccaaat atggggggca agtctacgct tatgagacag gctggcttat    3600
tagctgtaat ggcccagatg ggttgttacg tccctgctga agtgtgcagg ctcacaccaa    3660
ttgatagagt gtttactaga cttggtgcct cagacagaat aatgtcaggt gaaagtacat    3720
tttttgttga attaagtgaa actgccagca tactcatgca tgcaacagca cattctctgg    3780
tgcttgtgga tgaattagga agaggtactg caacatttga tgggacggca atagcaaatg    3840
```

| | |
|---|---|
| cagttgttaa agaacttgct gagactataa aatgtcgtac attattttca actcactacc | 3900 |
| attcattagt agaagattat tctcaaaatg ttgctgtgcg cctaggacat atggcatgca | 3960 |
| tggtagaaaa tgaatgtgaa gaccccagcc aggagactat tacgttcctc tataaattca | 4020 |
| ttaagggagc ttgtcctaaa agctatggct ttaatgcagc aaggcttgct aatctcccag | 4080 |
| aggaagttat tcaaaaggga catagaaaag caagagaatt tgagaagatg aatcagtcac | 4140 |
| tacgattatt tcgggaagtt tgcctggcta gtgaaaggtc aactgtagat gctgaagctg | 4200 |
| tccataaatt gctgactttg attaaggaat tatagactga ctacattgga agctttgagt | 4260 |
| tgacttctga caaaggtggt aaattcagac aacattatga tctaataaac tttatttttt | 4320 |
| aaaaatgaaa aaaaaaaaa aaaaaaaaaa aaaaaaaaaa aaaaaaaaaa aaaaaaaaaa | 4380 |
| aaaaaaaaaa aaaaaaaaaa aaaaaaaaaa aaaaaaaaaa aaaaaaaaaa aaaaa | 4435 |

<210> SEQ ID NO 4
<211> LENGTH: 5156
<212> TYPE: DNA
<213> ORGANISM: Homo sapiens

<400> SEQUENCE: 4

| | |
|---|---|
| agccaatggg agttcaggag gcggagcgcc tgtgggagcc ctggagggaa ctttcccagt | 60 |
| ccccgaggcg gatcgggtgt tgcatccatg gagcgagctg agagctcgag tacagaacct | 120 |
| gctaaggcca tcaaacctat tgatcggaag tcagtccatc agatttgctc tgggcaggtg | 180 |
| gtactgagtc taagcactgc ggtaaaggag ttagtagaaa acagtctgga tgctggtgcc | 240 |
| actaatattg atctaaagct taaggactat ggagtggatc ttattgaagt ttcagacaat | 300 |
| ggatgtgggg tagaagaaga aaacttcgaa ggcttaactc tgaaacatca cacatctaag | 360 |
| attcaagagt ttgccgacct aactcaggtt gaaactttg gctttcgggg ggaagctctg | 420 |
| agctcacttt gtgcactgag cgatgtcacc atttctacct gccacgcatc ggcgaaggtt | 480 |
| ggaactcgac tgatgtttga tcacaatggg aaaattatcc agaaaacccc ctaccccgc | 540 |
| cccagaggga ccacagtcag cgtgcagcag ttattttcca cactacctgt gcgccataag | 600 |
| gaatttcaaa ggaatattaa gaaggagtat gccaaaatgg tccaggtctt acatgcatac | 660 |
| tgtatcattt cagcaggcat ccgtgtaagt tgcaccaatc agcttggaca aggaaaacga | 720 |
| cagcctgtgg tatgcacagg tggaagcccc agcataaagg aaaatatcgg ctctgtgttt | 780 |
| gggcagaagc agttgcaaag cctcattcct tttgttcagc tgccccctag tgactccgtg | 840 |
| tgtgaagagt acggtttgag ctgttccgat gctctgcata atcttttta catctccagg t | 900 |
| ttcatttcac aatgcacgca tggagttgga aggagttcaa cagacagaca gttttttcttt | 960 |
| atcaaccggc ggccttgtga cccagcaaag gtctgcagac tcgtgaatga ggtctaccac | 1020 |
| atgtataatc gacaccagta tccatttgtt gttcttaaca tttctgttga ttcagaatgc | 1080 |
| gttgatatca atgttactcc agataaaagg caaattttgc tacaagagga aaagcttttg | 1140 |
| ttggcagttt taaagacctc tttgatagga atgtttgata tgtgatgtcaa caagctaaat | 1200 |
| gtcagtcagc agccactgct ggatgttgaa ggtaacttaa taaaaatgca tgcagcggat | 1260 |
| ttggaaaagc ccatggtaga aaagcaggat caatccccctt cattaaggac tggagaagaa | 1320 |
| aaaaaagacg tgtccatttc cagactgcga gaggcctttt ctcttcgtca cacaacagag | 1380 |
| aacaagcctc acagcccaaa gactccagaa ccaagaagga gccctctagg acagaaaagg | 1440 |
| ggtatgctgt cttctagcac ttcaggtgcc atctctgaca aaggcgtcct gagacctcag | 1500 |
| aaagaggcag tgagttccag tcacggaccc agtgacccta cggacagagc ggaggtggag | 1560 |

```
aaggactcgg ggcacggcag cacttccgtg gattctgagg ggttcagcat cccagacacg    1620
ggcagtcact gcagcagcga gtatgcggcc agctccccag gggacagggg ctcgcaggaa    1680
catgtggact ctcaggagaa agcgcctaaa actgacgact cttttttcaga tgtggactgc   1740 cattcaaacc aggaagatac cggatgtaaa tttcgagttt tgcctcagcc aactaatctc    1800
gcaaccccaa acacaaagcg ttttaaaaaa gaagaaattc tttccagttc tgacatttgt    1860
caaaagttag taaatactca ggacatgtca gcctctcagg ttgatgtagc tgtgaaaatt    1920
aataagaaag ttgtgcccct ggactttttct atgagttctt tagctaaacg aataaagcag   1980
ttacatcatg aagcacagca aagtgaaggg gaacagaatt acaggaagtt tagggcaaag    2040
atttgtcctg gagaaaatca agcagccgaa gatgaactaa gaaaagagat aagtaaaacg    2100
atgtttgcag aaatggaaat cattggtcag tttaacctgg gatttataat aaccaaactg    2160
aatgaggata tcttcatagt ggaccagcat gccacggacg agaagtataa cttcgagatg    2220
ctgcagcagc acaccgtgct ccaggggcag aggctcatag cacctcagac tctcaactta    2280
actgctgtta atgaagctgt tctgatagaa atctggaaaa tatttagaaa gaatggcttt    2340
gattttgtta tcgatgaaaa tgctccagtc actgaaaggg ctaaactgat ttccttgcca    2400
actagtaaaa actggacctt cggaccccag gacgtcgatg aactgatctt catgctgagc    2460
gacagccctg gggtcatgtg ccggccttcc cgagtcaagc agatgtttgc ctccagagcc    2520
tgccggaagt cggtgatgat tgggactgct cttaacacaa gcgagatgaa gaaactgatc    2580
acccacatgg gggagatgga ccaccctgg aactgtcccc atggaaggcc aaccatgaga    2640
cacatcgcca acctgggtgt catttctcag aactgaccgt agtcactgta tggaataatt    2700
ggttttatcg cagattttta tgttttgaaa gacagagtct tcactaacct tttttgtttt    2760
aaaatgaacc tgctacttaa aaaaaataca catcacaccc atttaaaagt gatcttgaga    2820
accttttcaa accagatgga gcattgcttg caaattttttt ttctctatgt ttgcatgcgc    2880
tcgtgtgtgt gtgtccaggc aagaacacat tttataaaaa taagaacact tgggctgggc    2940
atggtggctc atgcctgtga tcgcagcact ttgggaggcc gaggccggcg gatcacctga    3000
gatcagaagt tcgagaccag cctgaccaac atggagaaac cctgcctcta ctaaaaatac    3060
aaaattagcc aggtgtgctg gcgcatgcct gtaatcccg ctacccagga ggctgaggca    3120
ggagaatcgc ttgaacccgg gagacggagg ttgcagtgaa ccgagattgc gccactgcgc    3180
tccagcctgg gtgagataga acaagactgt gtctcaaaaa acaaaacaaa acaaaacaaa    3240
aaaaaaaaaa ccaaaccact ttggaagtta ctcaggcctc tgctctggct ggacatagtt    3300
tagtctataa ctttcaaccc ttaatgataa ttaaattcat cttgtttaa tttcataaat     3360 ttaaaagtag ggtcctttc agttagtgat tctcagccct gattcacatt aaattttaa     3420 acacgggga ttctctgccc ggctggaaga aaatgactgg atgggacagg ggtcactatt     3480
tgaaacattc ctctgtgcgg ccaaggtcgc aaaatgctgt cctcgcaggg gaacaaaaag    3540
agtttgattt cccataattt gatgctgtga tttggtttcc tcaggatgtg aactgtagaa    3600
cattccagtt actggccttg aatggttctg ggaatataag aatccctgtc tgtcttttca    3660
aatagttttc atgaaccttt gtcctgtttg aacttggctg aaaatggaag taagatgcc     3720 ctcttggggg cccagagatg acagatgtgg ctcccctgc tgcccccacc ccttctccag    3780
actgggggcg gctcccctc ctgctttaga atccctcaga tggaggaggc agtacagtag    3840
tcactgtgcc atcgtgtctg gcactgtgct ggcgtggtct gcaggatccc acttatgaac    3900
```

-continued

| | |
|---|---|
| tctccagatt gggagctgtg gcaggataac agcccccaag acagctgtgt cctaatcccc | 3960 |
| agaacctgtg accacgctgc ctcacgtggc agaagggact cggcaggtgt gattgagtga | 4020 |
| aggatctttt ttttttttt ctttgagatg aagtttcgct cttgttgccc aggctggagt | 4080 |
| tcaatagcat gatctcagct cactgcagcc tctgcctccc aggttcaagt gattctccca | 4140 |
| cctcagcctc ccgagtagct gggattacag gtgtccagaa ccatactggc taattttgt | 4200 |
| atttttagta gagacagggt ttcaccatgt tgaccaggct ggtctcgaac tcctgacctc | 4260 |
| aggtgatccg accgcctcgg cctcccaaag tgctgggatt acaggtgtga gccatcatgc | 4320 |
| ctggctgagt taaggatctt gcaacagaga gattatcctg gattgtctgg gtgggcccag | 4380 |
| tccattgggt gagtccttca aggtggaga cctttccctg ctggccagag agaggctgtc | 4440 |
| ttgctggttt tggagatgga aggaggtacc actagtcaag gattgcaagc agtctctaga | 4500 |
| acagggattc caacactccg gacacagacc agtagtggtc catggcctat taggaagtgg | 4560 |
| ggtgcacagc aggttagggg ccggcaagcc agcgaagctt catctgtatt tatagccact | 4620 |
| ccccgtcgct ggcgttacca cccgagctcc gcctcctgtc acatcagcgg tgggcattag | 4680 |
| attctcatag cagcacgagc cctattgtga actgcacaca cgagggatgt aggttgcacg | 4740 |
| ctccttatga gaatctgatg cctgatgatc tgtcactgtc tcccgtcacc cccagatggg | 4800 |
| gctgtctagt tgcaggaaaa caagctcagg gctcccactg agtctctgtg atggtgagtt | 4860 |
| gtagaattat ttaattatat gttacaatgt aataatagta gaaataaagt gcacaataaa | 4920 |
| tgcaatgcac ttgaatcgtc ctgaaaccat ccctccccga ccccaatcca tggaaaaatt | 4980 |
| gtgttccgcg aaaccggtct ctggtgccaa aaaggttggg gaccgcttct ggaaaagctg | 5040 |
| gaaaaggcaa gaaaacgcat tctctcccct cagcctctgga aggaaccagc actgtgggac | 5100 |
| taatttacat actgtagggt aataaatttg tgttgcttcg aaccactaaa aaaaaa | 5156 |

<210> SEQ ID NO 5
<211> LENGTH: 7439
<212> TYPE: DNA
<213> ORGANISM: Homo sapiens

<400> SEQUENCE: 5

| | |
|---|---|
| gcttgcgcgt tagagatcgc tgtccgctct tcctattggt tcgttttag gagctcgggg | 60 |
| aatacgaaat atccagccaa taggagcaga gatgccggaa ccgggcttgt gtgcctctgc | 120 |
| tgaggtgatc tggcgcagag cggaggaggt gcttggcgct tctcaggctc ctcctctccc | 180 |
| cttgcggcct ttctaacgtt ggccctgctc ttgtggcctc ccgcagaatg tggatgacgc | 240 |
| ccaaaagaag caagatggaa gtcgacgagg ctctagtttt ccggcccgag tggacccagc | 300 |
| gttatttggt ggtggagcct ccggagggcg atggggccct gtgcctggtc tgtcgccgcc | 360 |
| tcatcgtagc tacccgcgaa cgcgacgtca ggcgccacta cgaggctgag cacgaatact | 420 |
| acgagcggta tgtggcggac ggcgagcgcg cggccctggt ggagcgtctg cgtcagggcg | 480 |
| acttgcccgt ggcctccttc actcctgaag agagagctgc tcgtgcaggc ctcgggctct | 540 |
| gccgcctctt ggccttgaag ggtcgcggct ggggtgaggg ggactttgta taccagtgca | 600 |
| tggaggtgtt gctgagagag gtactgcccg agcatgtaag cgtcctgcaa ggcgttgact | 660 |
| tatctccaga tatcacaagg cagaggatcc tgagcattga caggaatcta cgcaaccagc | 720 |
| tttttaaccg agcagggac tttaaagcct attctcttgc cttggacgac caggcttttg | 780 |
| tggcctatga gaactacctc ctggtctttta tccgcggtgt aggccctgag ttggaggtgc | 840 |
| aagaagatct tctgaccata atcaacctga ctcatcattt cagtgttggt gcgctcatgt | 900 |

```
cggcaatcct agagtccctg cagacagcag ggcttagctt gcagagaatg gttggactga      960
ccacgaccca tactttgagg atgattggtg agaactcagg actcgtctca tacatgagag     1020
aaaaggccgt aagccccaac tgttggaatg tcattcatta ttcaggattt cttcacttgg     1080
aactgttgag ctcctatgat gtagatgtta atcagatcat aaataccata tccgaatgga     1140
tagttttgat taagaccaga ggcgttaggc gacctgaatt tcagacttta ctaacggaat     1200
ctgaatcaga gcatggtgaa agggttaatg gacgatgtct gaacaattgg cttaggagag     1260
ggaaaacttt aaaactaata ttctctctaa gaaagaaat ggaagcgttc ttggtttcag      1320
taggggcaac aacagtccac ttctcagaca acaatggct tgtgactttt ggcttcttgg      1380
tggacattat ggaacacctt cgagaactca gtgaagaatt acgagttagt aaagtctttg     1440
ctgctgctgc ctttgaccat atttgtactt tcgaagttaa gctgaattta tttcaaagac     1500
atattgagga aaaaaatcta acagactttc ctgccctcag agaagttgtt gatgagctaa     1560
aacagcaaaa taaggaagat gaaaaaatat ttgatcctga taggtatcaa atggtgatct     1620
gtcgtctcca aaaagaattt gagagacatt ttaaggacct caggttcatt aaaaaggact     1680
tagaactttt ttcaaatcca tttaacttta aacctgaata tgcacctatt tcagtgaggg     1740
tggagctaac aaaacttcag gcaaacacta atctttggaa tgaatacaga atcaaagact     1800
tggggcagtt ttatgctgga ttgtctgctg aatcctaccc aattatcaaa ggggttgcct     1860
gtaaggtggc atccttgttt gatagtaacc aaatctgtga aaaggctttt tcatatttga     1920
ctcgaaacca acacactttg agtcagccat taacagatga gcatctccaa gccctgtttc     1980
gggttgccac aactgaaatg gagcccggtt gggatgacct tgtgagagaa agaaatgaat     2040
ctaatccata aggctttgta gtacaagatt gaaaaactca acaagaattt aattctaaaa     2100
gcaaaaattg gtttgagttt tcaagtttac taatttggat tgtgagaaag taccaagtac     2160
cagccgtcca aactgatcac aattaaaatt ctgacagttg ccttttttt catctcaaat      2220
ggcagcatgg gactgaaaca tgagaatgcc acctttttta aaacttagtt tagtgacaaa     2280
gtcattgtct tttatgatat agttaatttt aaagagattt agtattaatg tgagttgaat     2340
ttgcagtctg ttttttaggt gttctgaaga taaatgccaa aaatttcagc tcttatttta     2400
atggagtgtt aaaattctga ttcatatagt cttaaattat caactcctta aatgtgcttt     2460
tgaaccaatt tgcagaagct cacatagcaa gttcataagt ttccaaaaag gaagcccata     2520
cataacagtg gaggtgtttt gtctaaccat caaaatgttt gagacttttt tttaaacatt     2580
tctgagttcg aaggtaatac tgacagattt cttccctctt ccctcccat cacccacctc      2640
agtgataaca cattactgat agaggaagtc attagaatca ttttaagtt tcagatatag      2700
gagacttcat gcaatttgga gataagacta attattgggg gttttccttg gattttttt      2760
ttaataactg ggggctattt tatcagcttg cctattaaag gactatggta agtatagaat     2820
cttaatggtt gccagttagt aattctttt ttttttttt ttactgtaga cacaagtttg       2880
gccctatcaa aaacgatgag gaaaaaagat tgcactccag gattaggagg tgtgagatat     2940
tttagctttt ttgtcttatc tgcgtgggta ttgctgcttt attttaaaaa atcctgccta     3000
aagtaaacac tttgttttaa aatgatacag tatcagattt tgttagatgc tagaaatgga     3060
tttattctaa aatttggaac tgtcgtacac attctatatg taagatagca cacaagtaga     3120
aatatttaaa agcagtctta ttcacagatt gcagtaattc tgtatttcta ctaagataat     3180
ctgctttgtg ccaaaacagt aatttccaaa cttctgttca ccatgaaaag gcaatcttaa     3240
```

```
agttcattat gtaaaactaa ttataaacag gacccaattt atattcatag atcctctcaa    3300
gtattataca atttaaaaac tcttgttcca aagtcctgtc ttaactattg aaacacctta    3360
atctgtggtt actaatccag caaattcaag gaaccaggct atgactaaga atttaggtgg    3420
aattgatgtc tgggcaatta aaataaatgg cataagagct aaaaaccaa agttgtgcca    3480 gtggctttca actagaggca gtaacctgtc attccagagg atgctgagaa atgtgtaggg    3540
gcactttttt ggttgtcata tttactaggg gcttctgttg gcatttaagc ctaaagacac    3600
tcacccctgc agtgcatggg acagcctggc acaatgaaga attagccctc ccaaaatgta    3660
gattatttta tttcaaggga tagggcagat taccattaga agcaaaatta aaagtacaag    3720
ctgggcaaac tgacagaata ctagatagga gagactaatt ccaaccttct aaatttggct    3780
agtaaagtgc aataaaggca ttgataagtt ctgttagctc accatagcac ttgtaaatca    3840
ggaattaata attgaatcag atttaagggc tctgtcctgt tatacatatt taaggcagaa    3900
aaaaagttac atgtcgatta ggtacttatc aagaatggtc aagctgagat tttggttaat    3960
agagtaagct tacatatcta gagaaacaac atagtggaaa accgaaaaaa aaaaacagaa    4020
aaatctaccg gtaatttccc aatagctttg aatattcaca gcagagcttt attacttgag    4080
agaaagactg gaagacctga aagccacttc tgctttctaa ccccagttcc ttaaatattg    4140
aaatcttgta cattttgtga aattccagta tgttttgctt aaggtgttaa taaaattagt    4200
ttgcatcatg tagtcattga gtgaggggga gatataagcc aaggatttta aattgaccct    4260
tagctataga gaatttgcta taagctagtc ttgtttgtaa aaaaaaaaa aaaaaaagaa    4320 aaagaaaaaa gtgtattta ctgttttctg tattaagtaa ttctgtaact gcatggcagt    4380
cttttttttt ttaaataaat atagttgtta ctggtcctgt tgtagcagtg aatatagtta    4440
aaatacgtac attaaaaaaa aaattattag gtccttacca gttactgtcc tatagctcat    4500
tcctactagt tttcttgaca gatttgtatt cccagtgtcc cgtattgcca ctcaaattgc    4560
tctactatgc taagtccttg ttaatagtct taccctcctt gaaacacttg aacacttgat    4620
gactttagct ttgaggagat accatctcca ggtgtgcttt cttagtcttt gcaggcacct    4680
cttcccttca atatctgttc ttcgtatttt taaaaaaatt tgttttagac tgccttgttc    4740
tgtgtcagct cgctagctga tctcatttcc ttccatggtt tccttaccat ttatatgcaa    4800
atgactgtca gattcatatc tcctttctag atcttcccta attgatgtat ctaattgcta    4860
acaaatgctc tttgctgtct caggcactac atgtcattga tcttgccccc aatcctgctc    4920
ctcctctcat gtttcctctt tgactaaatg gcattaccac taccaaccat tcatttgtcc    4980 ttttaccaa ttctccaatg ctgccatttt aattcaggcc atcaacctac ctaaattata    5040
gcaacagcct ccttattagt ctccctgttt tttatttta ttcctttcta cactacaacc    5100
aaattgctcc aaaagactta ctgatcatgt cactgcattg ctttcaccat tgctcttagg    5160
gtacaataca aatttatctt catctttaag gtctcagtat gccacttcat ctaggaaacc    5220
ttcattgatg ccctctagat taggtgccct tactatccat tccctataca ccctgttctt    5280
tcccagacat acacttggca cactttattg ttactgctta ttgatcactg ctagactgta    5340
agctttgtaa gggcagggac catataagcc ttgttcactg ttatatctct agtgcttagc    5400
acaatgcctg gcatttcaat aaatgtttgg acaaacgaat atttgtgtag tgttttacaa    5460
tttttgaagc tctttcacag tcttatttga ccttcacagt cattctgcct tagactgtcc    5520
attgggtaac ttttatccac atattactaa ttgaaaatg aagacaagtt ctttgtaact    5580
agggacctcg ttgtattctc agaatttagt gtagtgctta gcatgtgact taaatatgta    5640
```

-continued

| | |
|---|---|
| ttatgtgact gttaaacaaa ttgtggtttt ctctgttgta tgaaaggaga gaaggataac | 5700 |
| aaattgcggt tttccctggt aaacacagta agtagtaaac tcaggattca aaaccaaata | 5760 |
| tacacaccaa atccactatg taatattaag tttgcatatc catgtataga atcttatttt | 5820 |
| tttttaccct ttgtaaacag tgtcatatat atatatatat tttttttttt tttttaaatt | 5880 |
| tccaaaggaa cctacatata gagggaaaag attagacaac tacttagtga actaaaacaa | 5940 |
| tatgttttta ctaaatgtta catttagtat tggaaaaaga taatgccgcc taagagttaa | 6000 |
| taatcatttt tccttttgta ggcatcaaca ctaggagaaa atggcatgct atttacttgc | 6060 |
| tactttcctt tacagatgat ttttggctct tctgggattt aaaagtaagt aaatttaaca | 6120 |
| aagtagaaga ctgactcagc ccttctggtc actatatatt cagttcactt gttttacac | 6180 |
| ctgcagaatg tccttatcac ccaaagggag atgacccaaa agtgacatct agttaatgta | 6240 |
| tacttctaaa gtttgctgta ttcctttgcc ttcttgttcc catgcctctc tgaacttaat | 6300 |
| ttctgggtaa ctgaggcttt tcaggcttag gtgggaaagc cacaccctta gtctgtttcc | 6360 |
| ttaagccatt ttgaccaatt tatgggatta actagtataa tcttagttgg agttttagtc | 6420 |
| tgaggcatat taagtcattc agagatctta acagtaggtg tcatagtcat ccagtgattt | 6480 |
| ggtgcttgct gcaaaactgg cttttttttt tttttttttt tttgaggcgg ggtctcactt | 6540 |
| tgtcacccag gctggagtgc agaggtacaa tctcagctca atgcaatctc tgccttcctg | 6600 |
| gctcaagcaa ttctcccact gcagcctcct aagtagctgg gaatacaggt atacacgagt | 6660 |
| acacccagct aattttttgta tttttatgtg gagacagggt cttgctgtat tccccaggct | 6720 |
| agtctcgaat tcctggactc aagcagtccg cccgcctcgg gctcccaaaa tgttggtgtt | 6780 |
| atacgtgtga gcctctgcac ccggcggcaa aactggcttt taatcaacct tttggctaaa | 6840 |
| ggatttctct ttttatttat ttgtaaaagg atttcccatt tttatctttc ttttttgatat | 6900 |
| taaaatgttg cctcatccta cccagtaagt acttgaattt gaattctctt ccttttcatt | 6960 |
| tttgcctgca aactgaccag tcttttctga gttcatctct tctgtacgtt ttgtcaagtg | 7020 |
| cagtgaacag caactacaaa atattttgtt tttctgtctt tttctttagt aaagggtaga | 7080 |
| tgatctgcct ttcaggttat ctcaaggggc agtttcacct ttccataata taaattaccc | 7140 |
| ttgtgtaagt tatttcttcc atcttctgat agcaatttcc tgaatgcctg ccagctaacc | 7200 |
| attaagccca tgttcagtat tttagcattt taaaaaacaa gggaccaatt tctgtgtcag | 7260 |
| catgggctag cttgccattg aataacaaag gcaaaatctc actgtctcac acaactttc | 7320 |
| tattgcaact tgcctaggga cttggtttta gatcataggt tggccatgat caaactatgg | 7380 |
| tccatgggca aaatctgtct agctccttat ttatctaaat aaagttttac tggaatata | 7439 |

<210> SEQ ID NO 6
<211> LENGTH: 4686
<212> TYPE: DNA
<213> ORGANISM: Homo sapiens

<400> SEQUENCE: 6

| | |
|---|---|
| gcggcgccac aggaacgatg catgccggga ccgggaagat tcagtctctg aacggcccgg | 60 |
| agtagtcgtc tttccccttc tgactgccgc cacgctgcag tccagaatat ttgaagatca | 120 |
| aaccgaactt gagagactaa cgagaacggt ccctttttat tcctaacaga ttccttccgt | 180 |
| ggcaaagtaa cccgtcgtct tccgtttccg gttgcccgt tgccctgttg ccgtggtaac | 240 |
| cgcacgcata acagccgtgg tggttatggc tggtctgagc ggcgcgcaga tccccgacgg | 300 |

```
ggagtttacc gcgctagtgt accggctcat ccgcgatgcc cgctacgccg aggcggtgca    360
gctgctgggc cgagaactgc agcggagccc caggagccgt gccggcctgt cgctgctagg    420
ctactgctac taccgcctgc aggagttcgc gctggcggcc gagtgctatg agcagctggg    480
ccagctgcac ccggaactgg agcagtaccg cctgtaccag gcccaggccc tgtacaaggc    540
ctgcctttat ccggaggcca ctcgggtcgc cttccttctc ctggataacc ccgcctacca    600
cagccgggtc ctccgcctgc aagctgccat caagtatagc gagggcgatc tgccagggtc    660
caggagcctg gtggagcagc tgctgagtgg ggaagggggga gaagaaagtg gaggcgacaa    720
tgagaccgat ggccaggtca acctgggttg tttgctctac aaggagggac agtatgaagc    780
tgcatgctcc aagttttctg ccacactgca ggcctcgggc taccagcctg accttttccta   840
caacctggct ttggcctatt acagcagccg acagtatgcc tcagcactga agcatatcgc    900
tgagattatt gagcgtggca tccgccagca tcctgagcta ggtgtgggca tgaccaccga    960
gggctttgat gttcgcagtg ttggcaacac cttagttctc catcagactg ctctggtgga   1020
agccttcaac cttaaggcag ccatagaata ccaactgaga aactatgagg tagctcaaga   1080
aaccctcacc gacatgccac caggggcaga ggaagagttg gaccctgtga ccctgcacaa   1140
ccaggcacta atgaacatgg atgccaggcc tacagaaggg tttgaaaagc tacagttttt   1200
gctccaacag aatcccttc ctccagagac ttttggcaac ctgttgctgc tctactgtaa   1260
atatgagtat tttgacctgg cagcagatgt cctggcagaa aatgcccatt tgacgtataa   1320
gttcctcaca ccctatctct atgacttctt agatgccctg atcacttgcc agacagctcc   1380
tgaagaggct ttcattaagc ttgatgggct agcaggatg ctgactgagc agcttcggag   1440
actcaccaag caagtacagg aagcaagaca aacagagat gatgaagcta tcaaaaaggc   1500
agtgaatgaa tatgatgaaa ccatggagaa atacattcct gtgttgatgg ctcaggcaaa   1560
aatctactgg aatcttgaaa attatccaat ggtggaaaag gtcttccgca aatctgtgga   1620
attctgtaac gaccatgatg tgtggaagtt gaatgtggct catgttctgt tcatgcagga   1680
aaacaaatac aaagaagcca ttggtttcta tgaacccata gtcaagaagc attatgataa   1740
catcctgaat gtcagtgcta ttgtactggc taatctctgt gtttcctata ttatgacaag   1800
tcaaaatgaa gaagcagagg agttgatgag gaagattgaa aaggaggaag agcagctctc   1860
ttatgatgac ccaaatcgga aaatgtacca tctctgcatt gtgaatttgg tgataggaac   1920
tctttattgt gccaaaggaa actatgagtt tggtatttct cgagttatca aaagcttgga   1980
gccttataat aaaaagctgg gaacagatac ctggtattat gccaaaagat gcttcctgtc   2040
cttgttagaa aacatgtcaa aacacatgat agtcattcat gacagtgtta ttcaagaatg   2100
tgtccagttt ttaggacact gtgaacttta tggcacaaac atacctgctg ttattgaaca   2160
accctcgaa gaagaaagaa tgcatgttgg gaagaataca gtcacagatg agtccagaca   2220
attgaaagct ttgatttatg agattatagg atggaataag tagttatgac tgatagtggc   2280
tttttttcaaa atggctttct tacgtaccac actttttttt atctgtattt agccttggca   2340
tctttatatt tgtcttattt tgaatcttat ccactttgta agaacaagtt tatgtttgag   2400
caactttttc atttaatcca gaagggtagg gactatgcag tgtaagctgc atcacttctg   2460
ctttcttcct actagtgaca atcatctggt cttgccctca gcaacaatt gctagagtaa    2520
catctttgta taagcaagta accccagata gagttgacgt tcagctttg ggctgtcaaa    2580
agggtatgtc atggaccaaa gcactgttag tacgggtatg tttgcatttg gtcactgata   2640
tgtaaatgac tgctagccca cggctggacc acttctcaat cagcaaataa agccatgtct   2700
```

-continued

```
attttgctat ctcagcatag actatgctgt ctgataaatc taattcttaa ctctatttct      2760
ccagtttttt agtcctttaa ctttctggat tgcaacgaag tctagtttag acctctaagc      2820
cctttttagaa gtacaagtat aatgggaatt tcttttcttg gttcttttca ggttatgagg     2880
tttggtcagt gacaaaattt tttttcataa tttggttgat tggttgcttc ttaagtttta      2940
taataaacgt ttttcttcat gttctatttt tgattttaca gaaatgattt tgcctccttg      3000
tggatactga catatattaa gtgtggaagc ttattaatat ttttggtttt ttaaaaactg      3060
aaattttttaa ttttttacttt ttaattttttt aggaaaaaat aagcactgaa ctgagaatga   3120
gaagaataaa agtatgagtt ccatacccttc taattttaggg ctgtcagaaa ttcctttatt   3180
ctttgggatt tcacaatcat ttgaactatc agaagccttt acaattactt ttagctgtaa     3240
catccgattc tgtataagcc acatagaaaa aagttgcctt tcttttttta tgacctggat     3300
atataagcaa atcagctagg aaatatataa ttgtatttta tattaatgtt ttctaggatt     3360
ttggcttaca gtaaatgtta acccctatgg taagtgattg ttattgttgg atgttatact     3420
gattattaat aagaaatttg gattttttgcc ttttttacctg gaattttttgc ttacagccgt  3480
agctatgaat atatataggg tggtccccag tctctgttat ggttgcgcat aaattaataa     3540
ttttataagt atttagaaat ggtataattc tcttaacttc ctctttcagt ttttgtacta     3600
atgtttgttt ttgttcggga agaggagatt tgcttttaat ccttccaaaa aatgatgaac     3660
caccgttcca ttcagtagtt tgacaagctg ttataatgtg tatttttttcc tcaattattc    3720
ttgaaatatt tagagcctct cctgcttcta acatgaaggc ctttagatgc cagtctgcca     3780
gaaatctgga aacagaggaa ccggtgaagt gaagatgtaa tggagattta gctaatgatg     3840
tacttcacaa tccaccttgg atctcctgca tgtccaaatc tcagtagtta atcaagtgtc     3900
tgctgccatt aacagaacag aagtaatgga taacagaatg gaaataagag atgccagaac    3960
tacttccata actaactcac caaatcaaat catcagtcct catattcttg ttttatttaa     4020
tacaaggaga agaggccatg cactttccaa aaggtcaaag ccacatagaa taggaaggca     4080
atctctagtt taaagctttc tcttggagtg ttttctcccc ctgtcttcaa agggtctact     4140
tgagagatag tggtgtttac tgctgcagca tgtatcacaa gataagaaat gaaaaatcaa     4200
tcttcttac caccctgttc tctttcccctt ttttatctttt tccctttttgt caattataga   4260
attataggga cattttttctc tgatagctgg aagttgaacc tcaaccaggt ataaaagatg    4320
cataacaacc ttttagcagt aagtgtcaag tgagtgagca ctatgattat caaggtgact     4380
ttggaaacct tttaaaaatg catttttgca aaacaagata acatatattg ataaaaagtg     4440
actctcagat tggtaatgcc agaaaaaatt ttaagaggac tcaccaaaag tactagatct     4500
atgtaagttg tagaatagag tgaagttttt ttatatattt gtggtagcct ccatcttta     4560
aactttttga actcagtaga aaaacagact gaaattttaa agacatgcag tatttgtatc     4620
attttaaatt ctgtaacact gggaattaaa tatactcaac tttagaggaa aaaaaaaaa    4680
aaaaaa                                                                4686
```

<210> SEQ ID NO 7
<211> LENGTH: 3349
<212> TYPE: DNA
<213> ORGANISM: Homo sapiens

<400> SEQUENCE: 7

```
gacccagtcc ccctccccct cccctcgccg gctagggtgg tgcgtgccgg caggccggtc        60
```

| | |
|---|---|
| aaggaggcgg gacacgtcgg cgctaccacc gccaccgccg ccgccgcccc tcctcccgtt | 120 |
| ccagctgccg ctgccgcttc ctgggctgag tccgcccgcg gtcccggcgg cgccaggtgc | 180 |
| gttcactctg cccggctcca gccagcgtcc gccgccgccg tagctgcccc aggctccccg | 240 |
| ccccgctgcc gagatggcga cgcgctcctg tcgggagaag gctcagaagc tgaacgagca | 300 |
| gcaccagctc atcctatcca agcttctgag ggaggaggac aacaagtact cgccgactg | 360 |
| cgaggccaaa ggtcctcgat gggcttcctg gaatattggt gtgtttattt gcatcagatg | 420 |
| tgctggaatt catagaaatc ttggggttca tatatccagg gtcaaatcag tcaacctaga | 480 |
| ccaatggaca gcagaacaga tacagtgcat gcaagatatg ggaaatacta aagcaagact | 540 |
| actctatgaa gccaatcttc agagaacttt cgaagacca cagacagatc aagcagtgga | 600 |
| atttttcatc agagataaat atgaaaagaa gaaatactac gataaaaatg ccatagctat | 660 |
| tacaaatatt tcctcctctg atgctcctct tcagcctttg gtatcctctc cttctctgca | 720 |
| agctgctgtt gacaaaaata aattggagaa agaaaaggaa aaaaaaagg aagagaaaaa | 780 |
| gagagaaaag gagccagaaa agccggcaaa accacttaca gctgaaaagc tgcagaagaa | 840 |
| agatcagcaa ctggagccta aaaaaagtac cagccctaaa aaagctgcgg agcccactgt | 900 |
| ggatcttta ggacttgatg gccctgctgt ggcaccagtg accaacggga acacaacggt | 960 |
| gccaccctg aacgatgatc tggacatctt tggaccgatg atttctaatc ccttacctgc | 1020 |
| aactgtcatg cccccagctc aggggacacc ctctgcacca gcagctgcaa ccctgtctac | 1080 |
| agtaacatct ggggatctag atttattcac tgagcaaact acaaaatcag aagaagtggc | 1140 |
| aaagaaacaa ctttccaaag actccatctt atctctgtat ggcacaggaa ccattcaaca | 1200 |
| gcaaagtact cctggtgtat ttatgggacc cacaaatata ccatttaccct cacaagcacc | 1260 |
| agctgcattt cagggctttc catcgatggg cgtgcctgtg cctgcagctc ctggccttat | 1320 |
| aggaaatgtg atgggacaga gtccaagcat gatggtgggc atgcccatgc caatgggtt | 1380 |
| tatgggaaat gcacaaactg gtgtgatgcc acttcctcag aacgttgttg gcccccaagg | 1440 |
| aggaatggtg ggacaaatgg gtgcacccca gagtaagttt ggcctgccgc aagctcagca | 1500 |
| gccccagtgg agcctctcac agatgaatca gcagatggct ggcatgagta tcagtagtgc | 1560 |
| aaccccctact gcaggttttg gccagccctc cagcacaaca gcaggatggt ctggaagctc | 1620 |
| atcaggtcag actctcagca cacaactgtg gaaatgaaaa ctgcaataca gtttcatcc | 1680 |
| agaactacca cctgacattc cttgctgaaa cgcatctagt tccctgtttt attcatatgc | 1740 |
| atatttttt tcttttacc catttgttca tattaagaat gatctgattg accgtgttgg | 1800 |
| tctgtactga ttcaatttga tgtggtgaaa agcaggttga taaatcattt tatgtcaagg | 1860 |
| gcagctttgc tcatatttcc catgatttca tgtactgcat tatttgagaa gctgctcaac | 1920 |
| ttgcaaaatc agttttcctc tcaataaaat tatagctcta atgtttgcat ataagggaag | 1980 |
| tagttatcat gttagtaata cctctaatag tataaaccc accccaaaat tagccagtaa | 2040 |
| tcctgtagga aggtactgta tgatcaaatg tttaatcata taaatagaat gtaaatgtct | 2100 |
| cactgagcac tgtttctag tgtatcaaaa tgctcttatt tcatcattca cttcactgtg | 2160 |
| ctgttgttat gatgtgctta acagggaacg tgattagtga aaggaagata aacgtggatg | 2220 |
| ttactccaaa acttcgttta atgaatgctt aaagaattca aattttatct gcctctcttg | 2280 |
| taatttggat ctcttcttaa tgtacatagt gctaacatga agaccttttt ctgcactata | 2340 |
| tgcaaacagg gtaactaact aaaacaaagc cactttcaat cttcaatcct tgaaggtata | 2400 |
| tctaggttta tgacagtaat tgtgtttaca ttttatggtg cctagtattg acaaaatgtt | 2460 |

-continued

```
atttccctac attaaacatg actccataga ccttttcatt tgtgggtttt tatttcctat      2520
gatgtatact gccactaacc ttccaaaaat tacttagtat tgcaaagtca ggaatcatca      2580
ggaacgttta gctgacaaaa tacttgtctg ttttaaaaac ctgttcaagt ctaccaacct      2640
gttcaagtct accaattata agggcaaatt ggagaaaaag aaaaaatata tactcaagag      2700
tggtatcttg cagtatcggc actgtacaaa aaaatcttcc aatttagttg ttgtagagaa      2760
aacatgcaga acaaatgaag acaaaacata cattttgtac caaccatcca attagcttat      2820
gttaactgac aagctccatt taaacagatg tccatcagat gacaagaaag gctgctgtac      2880
tgaagtaaaa caaacaatac ctgaatgctc tgtagcctaa actccaaaca tcctcttcca      2940
tatggatcca ctggctggac aaactgcacc agttgctgct tcaatttata cctcaatttt      3000
cactgtgtcc agtggtact ttggctcgtt ggctagatta accttctctg tccgagtgtg       3060
ccacacgaga acctgaaggg gaaggaaata gcttgggtag cgcactcttc atggtgacac      3120
tcgaggtcgg gcagcacaag tgtaatgaat accttagtgc agttatttgc tttcggttcc      3180
agttcttcga ctgttgttat ctgtttgaga aagtcagatt cttgcatccc tggctgggat      3240
ccacgacgct taaatacagc ttttggattg acaaaatga cttgaagact tacagcaaat       3300
cctttgtgaa aaataaaaaa aaaaaagaga ctttaaaaaa aaaaaaaaa                  3349
```

<210> SEQ ID NO 8
<211> LENGTH: 2420
<212> TYPE: DNA
<213> ORGANISM: Homo sapiens

<400> SEQUENCE: 8

```
aaagctcagg gcccaggtcg gcccagggag cacggaacca aagagcgcta gcgccggttc       60
ggccgccttt ccagaaagcc cgggccgaac ggccccgccg cagagactca gcgcggatcg      120
ctgctccctc tcgccatggc gcaggtgctg atcgtgggcg ccgggatgac aggaagcttg      180
tgcgctgcgc tgctgaggag gcagacgtcc ggtcccttgt accttgctgt gtgggacaag      240
gctgaggact caggggggaag aatgactaca gcctgcagtc ctcataatcc tcagtgcaca      300
gctgacttgg gtgctcagta catcacctgc actcctcatt atgccaaaaa acaccaacgt      360
ttttatgatg aactgttagc ctatggcgtt ttgaggcctc taagctcgcc tattgaagga      420
atggtgatga agaaggaga ctgtaacttt gtggcacctc aaggaatttc ttcaattatt       480
aagcattact tgaaagaatc aggtgcagaa gtctacttca gacatcgtgt gacacagatc      540
aacctaagag atgacaaatg ggaagtatcc aaacaaacag gctcccctga gcagtttgat      600
cttattgttc tcacaatgcc agttcctgag attctgcagc ttcaaggtga catcaccacc      660
ttaattagta atgccaaag gcagcaactg gaggctgtga gctactcctc tcgatatgct       720
ctgggcctct tttatgaagc tggtacgaag attgatgtcc cttgggctgg cagtacatc       780 accagtaatc cctgcatacg cttcgtctcc attgataata agaagcgcaa tatagagtca      840
tcagaaattg ggccttccct cgtgattcac accactgtcc catttggagt tacatacttg      900
gaacacagca ttgaggatgt gcaagagtta gtcttccagc agctggaaaa cattttgccg      960
ggtttgcctc agccaattgc taccaaatgc caaaaatgga acattcaca ggttacaaat     1020 gctgctgcca actgtcctgg ccaaatgact ctgcatcaca accttttcct tgcatgtgga     1080
ggggatggat ttactcagtc caactttgat ggctgcatca cttctgccct atgtgttctg     1140
gaagctttaa agaattatat ttagtgccta tatccttatt ctctacatgt gtattgggtt     1200
```

```
tttattttca caattttctg ttattgatta ttttgttttc tattttgcta agaaaaatta    1260
ctggaaaatt gttcttcact tattatcatt tttcatgtgg agtataaaat caattttgta    1320
attttgatag ttacaaccca tgctagaatg gaaattcctc acaccttgca ccttccctac    1380
ttttctgaat tgctatgact actccttgtt ggaggaaaag tggtacttaa aaataacaa     1440 acgactctct caaaaaaatt acattaaatc acaataacag tttgtgtgcc aaaaacttga    1500
ttatccttat gaaaatttca attctgaata aagaataatc acattatcaa agccccatct    1560
taagtcttcg gatgtgtcct tgaatcaata tttttgcaaa ttatacaaaa caagattttt    1620
ccaaaatgta ggtaacagag tgtaattctt atttctcatt tatcccccaa gttattaagt    1680
gatcctgaat tgtaggtcat atatgtcatc atcttagtgt ggagggcaac ttgactgata    1740
aagagacctt ccttcagatt ttcagaaagt ataagattcc acatgatttt cccagccaca    1800
cagtactttt taactttcaa acaaattcca gtcctaatat gaaagataaa aattaaatag    1860
aaacagagag aaagtatatc gatccttacc ttttgctata ttttatagct gttgctgtta    1920
ctttatgggt tctccagtat gtgctgtggc atttagactg tgtcgagttt aatgaattta    1980
acacaacaaa aaatttactg aaccagaaaa tagatgcact taaaatagtt caatatttgc    2040
caagttggtg gttcagcata tcacccacat gcttcagtga cctgacccca cgacttgcta    2100
gctggagaga aatcaatctc cagccttcca accagctac ctgttgctaa tttgaaaagc      2160
aaaatgatga gttctatttc agcatttga aggagaaaa atcattgcag cctctcaaac       2220 taacaaagt tcaacaaaag acttcttact gtaatagtgt ttaaagtttc acacttacat      2280
gtccactgtc atacatacac atacacaggc acaggcagaa cttgcttcta tagctgcaaa    2340
gtgggtttta tgaccctata gcatattatt atatgtttcc tcttagcaat aaattggtga    2400
aaaacttaaa tgccaaaaaa                                                 2420

<210> SEQ ID NO 9
<211> LENGTH: 1595
<212> TYPE: DNA
<213> ORGANISM: Homo sapiens

<400> SEQUENCE: 9
ccgggccttt gccgacatgc gctggaactg ctcctccatt gagctcgccc ccaactatt      60 gcttgacctg gagagaggac accagccact ggcctagggc ccaccctgat ccggtatgac    120
ctcgtctcag ccccattaca tctgcaaaga ccccacttcg tcataagatt atgctcacag    180
ggacccggga gtcggccttc gtgtatgcgc tgtcggccgc cgccatcagc cacgccatcg    240
cccgggcctg cacctccggc gacctgcccg gctgctcctg cggcccgtc ccaggtgagc      300 caccggggcc cgggaaccgc tggggaggat gtgcggacaa cctcagctac gggctcctca    360
tgggggccaa gttttccgat gctcctatga aggtgaaaaa acaggatcc caagccaata     420 aactgatgcg tctacacaac agtgaagtgg ggagacaggc tctgcgcgcc tctctggaaa    480
tgaagtgtaa gtgccatggg gtgtctggct cctgctccat ccgcacctgc tggaaggggc    540
tgcaggagct gcaggatgtg gctgctgacc tcaagacccg atacctgtcg gccaccaagg    600
tagtgcaccg acccatgggc acccgcaagc acctggtgcc caaggacctg atatccggc     660 ctgtgaagga ctcggaactc gtctatctgc agagctcacc tgacttctgc atgaagaatg    720
agaaggtggg ctcccacggg acacaagaca ggcagtgcaa caagacatcc aacggaagcg    780
acagctgcga ccttatgtgc tgcgggcgtg gctacaaccc ctacacagac cgcgtggtcg    840
agcggtgcca ctgtaagtac cactggtgct gctacgtcac ctgccgcagg tgtgagcgta    900
```

-continued

```
ccgtggagcg ctatgtctgc aagtgaggcc ctgccctccg ccccacgcag gagcgaggac    960
tctgctcaag gaccctcagc aactggggcc aggggcctgg agacactcca tggagctctg    1020
cttgtgaatt ccagatgcca ggcatggagg gcggcttgtg ctttgccttc acttggaagc    1080
caccaggaac agaaggtctg gccacccctgg aaggagggca ggacatcaaa ggaaaccgac    1140
aagattaaaa ataacttggc agcctgaggc tctggagtgc ccacaggctg gtgtaaggag    1200
cggggcttgg gatcggtgag actgatacag acttgacctt tcagggccac agagaccagc    1260
ctccgggaag gggtctgccc gccttcttca gaatgttctg cgggaccccc tggcccaccc    1320
tggggtctga gcctgctggg cccaccacat ggaatcacta gcttgggttg taaatgtttt    1380
cttttgtttt ttgcttttc ttcctttggg atgtggaagc tacagaaata tttataaaac    1440 atagctttt ctttggggtg gcacttctca attcctcttt atatatttta tatatataaa    1500
tatatatgta tatatataat gatctctatt ttaaaactag cttttttaagc agctgtatga    1560 aataaatgct gagtgagccc cagcccgccc ctgca                               1595
```

<210> SEQ ID NO 10
<211> LENGTH: 4156
<212> TYPE: DNA
<213> ORGANISM: Homo sapiens

<400> SEQUENCE: 10

```
cggacgcgcg ctcacaggcg cgcgcgagga cgcgctccgg ggacgcgcga ggacgccgtg    60 gcggagaag cgtttccggt ggcggcggag gctgcactga gcgggacctg cgagcagcgc    120
gggcggcagc ccgggggaag cggtgagtcg cgggcggcag gcccagccag tccgggacca    180
tgtctggaga actaccacca aacattaaca tcaaggaacc tcgatgggat caaagcactt    240
tcattggacg agccaatcat ttcttcactg taactgaccc caggaacatt ctgttaacca    300
acgaacaact cgagagtgcg agaaaaatag tacatgatta caggcaagga attgttcctc    360
ctggtcttac agaaaatgaa ttgtggagag caaagtacat ctatgattca gcttttcatc    420
ctgacactgg tgagaagatg attttgatag aagaatgtc agcccaggtt cccatgaaca    480
tgaccatcac aggttgtatg atgacgttt acaggactac gccggctgtg ctgttctggc    540
agtggattaa ccagtccttc aatgccgtcg tcaattacac caacagaagt ggagacgcac    600
ccctcactgt caatgagttg gaacagctt acgtttctgc aacaactggt gccgtagcaa    660
cagctctagg actcaatgca ttgaccaagc atgtctcacc actgatagga cgttttgttc    720
cctttgctgc cgtagctgct gctaattgca ttaatattcc attaatgagg caagggaac    780 tcaaagttgg cattcccgtc acggatgaga atgggaaccg cttgggggag tcggcgaacg    840
ctgcgaaaca agccatcacg caagttgtcg tgtccaggat tctcatggca gcccctggca    900
tggccatccc tccattcatt atgaacactt tggaaaagaa agcctttttg aagaggttcc    960
catggatgag tgcacccatt caagttgggt tagttggctt ctgtttggtg tttgctacac    1020
ccctgtgttg tgccctgttt cctcagaaaa gttccatgtc tgtgacaagc ttggaggccg    1080
agttgcaagc taagatccaa gagagccatc ctgaattgcg acgcgtgtac ttcaataagg    1140
gattgtaaag caggggaggaa acctctgcag ctcattctgc cactgcaaag ctggtgtagc    1200
catgctggtg agaaaatcc tgttcaacct gggttctccc agttacggaa acctttaaa    1260 gatccacatt agccttttag aataaagctg ctactttaac agagcacctg gcgtgggcca    1320
agtgcctgat actcccttac actgaatcat gttatgattt atagaaatac ctttcctgta    1380
```

-continued

```
gcttttatag tcattgtttt tcaaagacga tataccagcc ctcacccagg ttttaaaaaa    1440
gcactggtag gcatagaata ggtgctcagt atatggtcag taaatgttct attgattatc    1500
aatcagtgaa aaagaaatc tgtttaaaat actgaatttt catctcactc ccattgcaaa     1560
tcaaggagat ctcagcagtg aactgggaaa atacaaaagc tctgggctaa tctataaaaa    1620
cttaccctga atattaagg gcagtttgct tctagtttgg ggattgcgct agcccaatga     1680
aggtgatgaa gcttttggat ttggaggta aaagctcctt cacacccctt ccaaaagtca     1740
gtcacagacc actgcaacat gccttccctg ctggatcatt atatacattc agattgtgag    1800
tggattgcct tggttgactt ttaatttatt gttttttgtt cttataaaga tgataatctt    1860
accttgcagt tattgacttt atattcaatt atttacatca ataatgaaa taactgaaat     1920 gtacaaatgt caaattttgg aagtatattc aataccaatg ctgtatgagt gggctgaatc    1980
cagttcattg tttttttttt ggtaagaagt gagactacag ttccagctac ctacatgtct    2040
tttcttgtca tccttataga tctctttggc tttcagaaag atacagtgat aatgtgtgta    2100
tgaatcagtc acaatgaatt ttacttgaat attgtatgtt gcattccact tcatttgaaa    2160
ataatgaaac catgtaccac tgtttacatc atctgtagtg atttcataga taatatattt    2220
aatatgacag attatgtttc aactctgtag atgtttaacg tcatagacag ttggccctct    2280
gtatccgtga gctctatatc tgtgaattca accaagtttg gatggaaaat tttttttttt    2340
tttttttttt tgagacggag tctcgctctg tcacccaggc tggagtgcag tggcgtagtc    2400
tcggctcact gcaagctccg cctcccgggt tcacgccgtt ctcctgcctc agcctctctg    2460
agaagctggg actacaggcg cccgccacca cgcccggcta atttttttgt attttttagta    2520 gagacggggt ttcactgtgg tctcgatctc ctgacctcgt gatccgcccg ccttggcctc    2580
ccaaggtgct gggattacaa gcgtgagcca ccgcacccgg cctgaaaata ttttctaaaa    2640
agataaaaaa tatacataac gatgaaaaat aatacaaatt taaaaaccaa tacagtataa    2700
caactattta catagtgctt acattgtatt aggtgttata agcaatctag agatgattta    2760
gcaagtatac aggaggatgt gcctaggtta tatgcaaata ctgtgccatt ttatatcagg    2820
aacttgagca tctgcagata ttggtatcgg agggcggtcc tggaaccaag catccacgga    2880
tactgagggg tgacatttca tgaagtgtag atcattgtat tcagagattg taaatgaaaa    2940
aaatatagaa actatttagt tttggtagat ttttttttctg acaatgtgac cagactgaat    3000
ttcctcataa agaaaaaatg gcgtgccttg tgtctgtgtt tctcttttct ctgaaaggat    3060
taatagatct gaagctttgg gccactcaga gccttcctty atgctgccag agtcttctta    3120
tttagatttt ctgtcttaaa ccattggaag caaaacggtt ttcccatgac attctggcct    3180
tggacagatt ctgttgtcct cgacgcgtct ctttataaag tggtaaaagc ctgaaattca    3240
gggcagctct ccatgaggtg ctgaagggct cttttcataa gaagctaagg cactgctgcc    3300
tgccccaggt gtcccgctcc tctcagagtc ctcccctac caggtagtgt gtagctccat    3360
ttcagaatgt taacctccag tgaagagcta atgactggta gaagattga caaactaacc    3420 aaaattttac acactccggt tatgtgtgtg aaaggttata aaaggaatgg ccgggtgcgg    3480
tggctcaccc ctgtaatccc agcactttgg gaggccgagg cgggtggatc acctgaggtc    3540
aggagtttga gaccagcctg gccaacatgg agaaacccg cctctactaa aaatacaaaa     3600
aattagccag gcatggaggc acatgcctat aatcccagct actcgggagg ctgaggtagg    3660
agaatcgctt gaatccggga gctggaggtt gcagtgagcc aagatcgcac cattgcactc    3720
cagcctgggc aacaagagcg aaactccatc tcaaaaaaaa aaaaagaga ttataaaagg     3780
```

-continued

| | | |
|---|---|---|
| gatgatgaac atggagctgc atcttttttaa acgttgtttt ttgatgcttc agactcttaa | 3840 |
| tgcttttata taaagctatc aactgtatgt tgatcacagt ttataagaaa gaacaaatca | 3900 |
| agattggcaa tccttgccga tcttttagaa ataccttttc tggagaaaaa aaaatccaca | 3960 |
| tgaagtgcaa taagcttata aagctaagta gttattaata tttctattaa catgatacaa | 4020 |
| aggatgatga ttgtaagtgt ttactgactg gcagctttta tttcagtatt agcacagcgt | 4080 |
| cttgccagtg ttggaggcca tgtattattt cagttcaact ggatgaaatg ttaaataaac | 4140 |
| tcagaatgaa aataaa | 4156 |

<210> SEQ ID NO 11
<211> LENGTH: 4284
<212> TYPE: DNA
<213> ORGANISM: Homo sapiens

<400> SEQUENCE: 11

| | | |
|---|---|---|
| agcagagctg cggccggggg aacccagttt ccgaggaact tttcgccggc gccgggccgc | 60 |
| ctctgaggcc agggcaggac acgaacgcgc ggagcggcgg cggcgactga gagccggggc | 120 |
| cgcggcggcg ctccctagga agggccgtac gaggcggcgg gccggcgggg cctcccggag | 180 |
| gaggcggctg cgccatggac gagccaccct tcagcgaggc ggctttggag caggcgctgg | 240 |
| gcgagccgtg cgatctggac gcggcgctgc tgaccgacat cgaaggtgaa gtcggcgcgg | 300 |
| ggaggggtag ggccaacggc ctggacgccc aagggcggg cgcagatcgc ggagccatgg | 360 |
| attgcacttt cgaagacatg cttcagctta tcaacaacca agacagtgac ttccctggcc | 420 |
| tatttgaccc accctatgct gggagtgggg caggggcac agaccctgcc agccccgata | 480 |
| ccagctcccc aggcagcttg tctccacctc ctgccacatt gagctcctct cttgaagcct | 540 |
| tcctgagcgg gccgcaggca gcgccctcac ccctgtcccc tccccagcct gcacccactc | 600 |
| cattgaagat gtacccgtcc atgcccgctt tctcccctgg gctggtatc aaggaagagt | 660 |
| cagtgccact gagcatcctg cagaccccca cccccacagcc cctgccaggg gccctcctgc | 720 |
| cacagagctt cccagcccca gccccaccgc agttcagctc cacccctgtg ttaggctacc | 780 |
| ccagccctcc gggaggcttc tctacaggaa gccctcccgg gaacacccag cagccgctgc | 840 |
| ctggcctgcc actggcttcc ccgccagggg tcccgcccgt ctccttgcac acccaggtcc | 900 |
| agagtgtggt cccccagcag ctactgacag tcacagctgc ccccacggca gccctgtaa | 960 |
| cgaccactgt gacctcgcag atccagcagg tcccggtcct gctgcagccc cacttcatca | 1020 |
| aggcagactc gctgcttctg acagccatga agacagacgg agccactgtg aaggcggcag | 1080 |
| gtctcagtcc cctggtctct ggcaccactg tgcagacagg gcctttgccg accctggtga | 1140 |
| gtggcggaac catcttggca acagtccac tggtcgtaga gcggagaag ctgcctatca | 1200 |
| accggctcgc agctggcagc aaggcccgg cctctgccca gagccgtgga gagaagcgca | 1260 |
| cagcccacaa cgccattgag aagcgctacc gctcctccat caatgacaaa atcattgagc | 1320 |
| tcaaggatct ggtggtgggc actgaggcaa agctgaataa atctgctgtc ttgcgcaagg | 1380 |
| ccatcgacta cattcgcttt ctgcaacaca gcaaccagaa actcaagcag gagaacctaa | 1440 |
| gtctgcgcac tgctgtccac aaaagcaaat ctctgaagga tctggtgtcg gcctgtggca | 1500 |
| gtggagggaa cacagacgtg ctcatggagg gcgtgaagac tgaggtggag gacacactga | 1560 |
| cccccacccc ctcggatgct ggctcacctt ccagagcag cccttgtcc cttggcagca | 1620 |
| ggggcagtgg cagcggtggc agtggcagtg actcggagcc tgacagccca gtctttgagg | 1680 |

```
acagcaaggc aaagccagag cagcggccgt ctctgcacag ccggggcatg ctggaccgct    1740
cccgcctggc cctgtgcacg ctcgtcttcc tctgcctgtc ctgcaacccc ttggcctcct    1800
tgctgggggc ccgggggctt cccagcccct cagataccac cagcgtctac catagccctg    1860
ggcgcaacgt gctgggcacc gagagcagag atggccctgg ctgggcccag tggctgctgc    1920
ccccagtggt ctggctgctc aatgggctgt tggtgctcgt ctccttggtg cttctctttg    1980
tctacggtga gccagtcaca cggccccact caggccccgc cgtgtacttc tggaggcatc    2040
gcaagcaggc tgacctggac ctggcccggg agactttgc ccaggctgcc cagcagctgt     2100
ggctggccct gcgggcactg gccggcccc tgcccacctc ccacctggac ctggcttgta     2160
gcctcctctg gaacctcatc cgtcacctgc tgcagcgtct ctgggtgggc cgctggctgg    2220
caggccgggc aggggggcctg cagcaggact gtgctctgcg agtggatgct agcgccagcg    2280
cccgagacgc agccctggtc taccataagc tgcaccagct gcacaccatg gggaagcaca    2340
caggcgggca cctcactgcc accaacctgg cgctgagtgc cctgaacctg cagagtgtg     2400 caggggatgc cgtgtctgtg gcgacgctgg ccgagatcta tgtggcggct gcattgagag    2460
tgaagaccag tctcccacgg gccttgcatt ttctgacacg cttcttcctg agcagtgccc    2520
gccaggcctg cctggcacag agtggctcag tgcctcctgc catgcagtgg ctctgccacc    2580
ccgtgggcca ccgtttcttc gtggatgggg actggtccgt gctcagtacc ccatgggaga    2640
gcctgtacag cttggccggg aacccagtgg accccctggc ccaggtgact cagctattcc    2700
gggaacatct cttagagcga gcactgaact gtgtgaccca gcccaacccc agccctgggt    2760
cagctgatgg ggacaaggaa ttctcggatg ccctcgggta cctgcagctg ctgaacagct    2820
gttctgatgc tgcgggggct cctgcctaca gcttctccat cagttccagc atggccacca    2880
ccaccggcgt agaccggtg gccaagtggt gggcctctct gacagctgtg gtgatccact     2940
ggctgcggcg ggatgaggag gcggctgagc ggctgtgccc gctggtggag cacctgcccc    3000
gggtgctgca ggagtctgag agaccctgc ccagggcagc tctgcactcc ttcaaggctg     3060
cccgggccct gctgggctgt gccaaggcag agtctggtcc agccagcctg accatctgtg    3120
agaaggccag tgggtacctg caggacagcc tggctaccac accagccagc agctccattg    3180
acaaggccgt gcagctgttc ctgtgtgacc tgcttcttgt ggtgcgcacc agcctgtggc    3240
ggcagcagca gccccggcc ccggcccag cagcccaggg caccagcagc aggccccagg      3300
cttccgccct tgagctgcgt ggcttccaac gggacctgag cagcctgagg cggctggcac    3360
agagcttccg gcccgccatg cggagggtgt tcctacatga ggccacggcc cggctgatgg    3420 cggggggccag ccccacacgg acacaccagc tcctcgaccg cagtctgagg cggcgggcag   3480 gcccccggtgg caaaggaggc gcggtggcgg agctggagcc gcggcccacg cggcgggagc   3540
acgcggaggc cttgctgctg gcctcctgct acctgccccc cggcttcctg tcggcgcccg    3600
ggcagcgcgt gggcatgctg gctgaggcgg cgcgcacact cgagaagctt ggcgatcgcc    3660
ggctgctgca cgactgtcag cagatgctca tgcgcctggg cggtgggacc actgtcactt    3720
ccagctagac cccgtgtccc cggcctcagc acccctgtct ctagccactt tggtcccgtg    3780
cagcttctgt cctgcgtcga agctttgaag gccgaaggca gtgcaagaga ctctggcctc    3840
cacagttcga cctgcggctg ctgtgtgcct tcgcggtgga aggcccgagg ggcgcgatct    3900
tgaccctaag accggcggcc atgatggtgc tgacctctgg tggccgatcg ggcactgca     3960 ggggccgagc cattttgggg ggcccccctc cttgctctgc aggcacctta gtggcttttt    4020
tcctcctgtg tacagggaag agaggggtac atttccctgt gctgacggaa gccaacttgg    4080
```

```
cttteccgga ctgcaagcag ggctctgccc cagaggcctc tctctccgtc gtgggagaga    4140
gacgtgtaca tagtgtaggt cagcgtgctt agcctcctga cctgaggctc ctgtgctact    4200
ttgccttttg caaactttat tttcatagat tgagaagttt tgtacagaga attaaaaatg    4260
aaattattta taatctggaa aaaa                                           4284

<210> SEQ ID NO 12
<211> LENGTH: 1536
<212> TYPE: DNA
<213> ORGANISM: Homo sapiens

<400> SEQUENCE: 12 ggggggggggg ggaccacttg gcctgcctcc gtcccgccgc gccacttggc ctgcctccgt    60
cccgccgcgc cacttcgcct gcctccgtcc ccgccccgcc gcgccatgcc tgtggccggc    120
tcggagctgc cgcgccggcc cttgcccccc gccgcacagg agcgggacgc cgagccgcgt    180
ccgccgcacg gggagctgca gtacctgggg cagatccaac acatcctccg ctgcggcgtc    240
aggaaggacg accgcacggg caccggcacc ctgtcggtat tcggcatgca ggcgcgctac    300
agcctgagag atgaattccc tctgctgaca ccaaacgtg tgttctggaa gggtgttttg     360
gaggagttgc tgtggtttat caagggatcc acaaatgcta aagagctgtc ttccaaggga    420
gtgaaaatct gggatgccaa tggatcccga gacttttggg acagcctggg attctccacc    480
agagaagaag gggacttggg cccagtttat ggcttccagt ggaggcattt tggggcagaa    540
tacagagata tggaatcaga ttattcagga cagggagttg accaactgca aagagtgatt    600
gacaccatca aaaccaaccc tgacgacaga agaatcatca tgtgcgcttg gaatccaaga    660
gatcttcctc tgatggcgct gcctccatgc catgccctct gccagttcta tgtggtgaac    720
agtgagctgt cctgccagct gtaccagaga tcgggagaca tgggcctcgg tgtgcctttc    780
aacatcgcca gctacgccct gctcacgtac atgattgcgc acatcacggg cctgaagcca    840
ggtgacttta tacacacttt gggagatgca catatttacc tgaatcacat cgagccactg    900
aaaattcagc ttcagcgaga acccagacct ttcccaaagc tcaggattct tcgaaaagtt    960
gagaaaattg atgacttcaa agctgaagac tttcagattg aagggtacaa tccgcatcca   1020
actattaaaa tggaaatggc tgtttagggt gctttcaaag gagcttgaag gatattgtca   1080
gtctttaggg gttgggctgg atgccgaggt aaaagttctt tttgctctaa aagaaaaagg   1140
aactaggtca aaaatctgtc cgtgacctat cagttattaa ttttttaagga tgttgccact   1200 ggcaaatgta actgtgccag ttcttttccat aataaaaggc tttgagttaa ctcactgagg   1260
gtatctgaca atgctgaggt tatgaacaaa gtgaggagaa tgaaatgtat gtgctcttag   1320
caaaaacatg tatgtgcatt tcaatcccac gtacttataa agaaggttgg tgaatttcac   1380
aagctatttt tggaatattt ttagaatatt ttaagaattt cacaagctat tccctcaaat   1440
ctgagggagc tgagtaacac catcgatcat gatgtagagt gtggttatga actttatagt   1500
tgttttatat gttgctataa taaagaagtg ttctgc                             1536

<210> SEQ ID NO 13
<211> LENGTH: 3849
<212> TYPE: DNA
<213> ORGANISM: Homo sapiens

<400> SEQUENCE: 13
ggggtcgagt cagtgccgtt tgcgccagtt ggaatcgaag cctcttaaaa tggcagatga    60
```

```
tttggacttc gagacaggag atgcaggggc ctcagccacc ttcccaatgc agtgctcagc    120
attacgtaag aatggctttg tggtgctcaa aggctggcca tgtaagatcg tggagatgtc    180
tgcttcgaag actggcaagc acggccacgc caaggtccat ctggttggta ttgacatctt    240
tactgggaag aaatatgaag atatctgccc gtcaactcat aatatggatg tccccaacat    300
caaaaggaat gacttccagc tgattggcat ccaggatggg tacctatcac tgctccagga    360
cagcggggag gtaccagagg accttcgtct ccctgaggga gaccttggca aggagattga    420
gcagaagtac gactgtggag aagagatcct gatcacggtg ctgtctgcca tgacagagga    480
ggcagctgtt gcaatcaagg ccatggcaaa ataactggct cccaaggtgg cagtggtggc    540
agcagtgatc ctccgaacct gcagaggccc cctcccccag cctggcctgg ctctggcctg    600
gtcctaggtt ggactcctcc tacacaattt atttgacgtt ttattttggt tttcccacc     660 ccctcaatct gtcagggagc ccctgccctt cacctagctc ccttggccag gagcgagcga    720
agccatggcc ttggtgaagc tgccctcctc ttctcccctc acactacagc cctggtgggg    780
gagaaggggg tgggtgctgc ttgtggttta gtcttttttt ttttttaaa ttcaatctgg     840 aatcagaaag cggtggattc tggcaaatgg tccttgtgcc ctccccactc atccttggtc    900
tggtcccctg ttgcccatag cccttacccc tgagcaccac ccaacagact ggggaccagc    960
cccctcgcct gcctgtgtct ctccccaaac cctttagat ggggagggaa gaagaggaga    1020
ggggagggga cctgccccct cctcaggcat ctggaaggg cctgccccca tgggctttac    1080
ccttccctgc gggctctctc cccgacacat ttgttaaaat caaacctgaa taaaactaca    1140
agtttaatat gaaaaaaaaa aaaaagaaa gaaagacgtg taaaatgcca agaactctag    1200
gaaacaggga caaaaacact tcaaagagaa agttcatgca cttgtttctg accacccagg    1260
gcacccttca gcacacgctg tctggagtgg cctgaagcaa ggagtgtctt gtgaggtgca    1320
gaggatgcaa tgggagcagg gtcctgtccc caccctaaag gagttcacag tttaacgcaa    1380
atgagaagcc agtgaggaca tcactactcc tgctgtgaac ttgggaacta gaaacacaaa    1440
acctgagtct ggagggaagc taaggaagca ttctgctctg gagtagacat gagtgcgtgt    1500
gaagcttctg atctcccatg agagcaatgg ggacatgggg cagaatctaa acccatgac     1560 tgaaagcacc aaattgctaa aatggcaata agagacatg aggccaagat ggagaagaag    1620
gaacccagga cgagggtcag cctcacattt ggggctcatt tccctcagtt tcctcactga    1680
atttcagaag ggactaactg agatgcaaag aagcagagca gcttttgcac catgtggagg    1740
actagatgga aaacaagtag actgagggtc tgctagtgaa ggtgacccct actgaagtcc    1800
actggctttg gttgggaccc agaagagtca cacgccagga atagaggtgg acaggaaaca    1860
ccctgacttt tgtagggact gaacctcact gataacctca attgcggatg gtatggaggg    1920
tgtctaggtg tgctaggacc cctgcccatt ccccagaaat agactcccat cttttctaca    1980
gcaagataac gtgctagtag gcctcaattc attgctaaat atttttaacg agtgtcttac    2040
atttagccaa aaagactagt catgtggcag gaaaaataca atgtcatatg accaaaagct    2100
aaaagactgt gaaatgaat ccagaggtga cccaagcatt gaatttaaca atgccagtac     2160
ctggacctcc gcttgcccct aaaacattac aatcaagaat gtaggaaggg aaaggaaaca    2220
cgaagattaa tcaagcagga aggacaagct cagttttgca cccactgaat ttgccacaaa    2280
tattgtggaa aatattctcg gggacattgc agttgtctac tttggttggc acatggttca    2340
tacaacagtg tttgtgtcag tgaacatctt actcttcctc ggcagtcttt ctttgcccag    2400
agatttcgca atgactgttg accttcatca tcaccttttg gactttggct tgcactttag    2460
```

```
cttctgtaga tctccatgat gtaaagaagt attttaggtc cattttaatt cctgcaaagg    2520
ataaaatcct tctatttgtg tgcatataag tggacctgag cccttggtta gggtgtagag    2580
aggagaaggg gagaaacctg agggccagaa gctgttcttt cccttaaaag ggcaaactca    2640
tttccacact atggggactc tgacagatag catacctttcc tgtctatggc tattggacct   2700
gcaggctttc ccctgtaaat ccgtgttctg tcattgacat tttgtgactg taagacagac    2760
ttgagataag acatctagaa aacaataatt gaacaatgat gtgaatatat ttcacacaac    2820
tgaactgtac atttcaacaa ggttaagatg gtaattatca cgttatacat tttttaccgc    2880
aggttaaaat gtttcacagg ttgaaaggaa agcaactacc ttcagttctc tgagttcaag    2940
aatttgtaac atttcacccc ctgctccttc ctgatcttct gtggagcatc ttttttccat    3000
ccatgctcta ctcagagccc actttccctt ccctgacacc agcttcactg aggctggttg    3060
gaacctaaca caaacattc tcagtaatga ctgaattccc acaagaatt ccatatagac      3120 tgcatatgag ttgaatcttc taagacatga aatatttgtt ctcttcttgg ctaatatgca    3180
atgcaaatcc tgttgcagat gtacgtcata tacctctgaa attcctgatg tattcaatga    3240
aataacatct ttaaagttct gtgtagaatg ttttttttct gatttcttca catacgatag    3300
aaaaaaaaac ccaaaaaaac atgtactagg atttcaatag aagcaatggg tgatctaaaa    3360
agatgaaaga gcaaccgcat gcgccctaca gctaccgcta gattttatgg ggaaagcagc    3420
tggcccagtt tgcagctagg agaaatgtca aacacatgaa gaaatgagaa gcaaagaaaa    3480
accatgaggc atgaacattt catggcaatc acgatgtcct ggtttgtgag ataatgggat    3540
agaggagtag aaaacaagga gaaagatgag aaggtacaaa gtggttcaag tcaaacagct    3600
caactgaact tttcttaatg gaatatttaa aaagtggtac attaaaaaac ttcccccagt    3660
tcacatcaaa aattctctct tcaggactaa gttgggtaga gactgttcaa tgtgcctaga    3720
tatcttcaga acttatatat tttctgtttt ctacgtatgt tgaagggcag tgccaaatga    3780
tgtgtaatta tctaggttgt aaaaataaaa catactcccc cttcccttga ggataaaaaa    3840
aaaaaaaaa                                                           3849
```

<210> SEQ ID NO 14
<211> LENGTH: 4037
<212> TYPE: DNA
<213> ORGANISM: Homo sapiens

<400> SEQUENCE: 14

```
ctgctctggc gctgcggccg ctggggatct gagtgggctc cgccccgcct cggacccgcc      60
cctcccggcc tcccgccgca atcttggcgg gaaggcgccg gccgctaaga agccgaaaga    120
tgtccaggtc gggcgcggcg gctgagaagg cggactccag acagcgaccc cagatgaagg    180
taaatgaata taaagaaaat caaaacatcg cttatgtgtc tctgagacca gcacagacta    240
cagttttaat aaaaacagct aaggtctatc ttgccccctt ttcactcagt aattaccagc    300
tagaccagct tatgtgcccc aaatccctat cagaaaagaa ttctaacaat gaagtggcgt    360
gtaagaagac taaataaag aaaacttgca gaaggattat acctccaaag atgaaaaaca    420
catcttccaa ggcagaatcc acgctgcaaa attcatcctc agctgttcat actgaaagta    480
acaagctaca acccaagaga acggcagatg cgatgaatct cagtgttgat gtggaaagta    540
gtcaggatgg agacagtgat gaagatacca ccatccct ggattttcg ggattgtcac        600 cctacgaaag gaagagactg aagaacatat cagaaacgc agactttttt gcttctcttc      660
```

```
agttgtctga gtctgctgca agactccgtg aaatgataga gaagagacag cctcctaaat    720
ccaaaagaaa gaagcctaag agagaaaatg ggattggatg tagaaggtca atgcgattac    780
taaaagttga tccttcggga gtttcattac cagcagctcc aacaccgccg acattagtag    840
cagatgaaac tcctttgtta cctcctgggc ctttagaaat gacttctgaa aatcaagaag    900
acaacaatga acgatttaaa ggatttctgc acacatgggc aggaatgagc aagccaagta    960
gtaagaacac tgagaaggga ttatctagca ttaaaagcta caaagccaat ttaaatggca   1020
tggtcattag tgaagatacc gtttacaaag ttaccacagg cccaatattc tctatggctc   1080
tccatccatc agaaactaga actttggtag cagttgggc caaatttggg caagttggac    1140
tttgtgattt gacccagcaa cctaaagaag atggagttta tgtttttcat ccccatagtc   1200
agccagttag ctgtctttac ttctcacccg ccaatccggc ccacatactg tcactgagct   1260
atgatggcac gttacgctgt ggggattttt ccagggctat ttttgaagag gtgtatagaa   1320
atgaagaag tagcttttcc tccttcgact tcttggcaga agatgcctcc actttaatag    1380
taggacactg ggatggaaat atgtcactgg tggatagacg gacacctgga acttcttatg   1440
agaaacttac cagttcttct atgggaaaaa taagaactgt tcatgtccac ccagtgcata   1500
gacagtattt tatcactgcc ggattgaggg atactcatat ttatgatgca aggcgattga   1560
attccaggag aagtcagcct ttgatttctt tgactgaaca tacaaagagc attgcttccg   1620
cctatttttc acctcttact ggtaacagag tggtgaccac atgtgctgat tgtaatctga   1680
gaattttttga cagcagctgt atatcttcta agattccgct cctcaccacc atcaggcaca   1740
acactttcac tgggcgatgg ctgaccaggt tccaagccat gtgggatcct aaacaagaag   1800
actgtgtcat agttggcagc atggcccatc cacgacgggt agaaatcttc catgagacag   1860
gaaagagggt gcattcgttt ggtggagaat accttgtctc tgtgtgttcc atcaatgcca   1920
tgcacccaac tcggtatatt ttggctggag gtaattccag cgggaagata catgttttta   1980
tgaatgaaaa aagctgctga gttttttggtt taggaacatc aatttgttca aattgaccac   2040
tgtctaagga gcctagtaat cggcgtgcct tagtgtgttt atgtggtaat gtgttacatt   2100
tagcaattat aacattgttt tattaataag actataagaa gagtgtactt ttagtaaggg   2160
agaagtcttg gagggttgct tctgcaggac ggggagggaa tttgagggga ggctgaggtg   2220
ccgtcaggac ttttttttttt ttttttttttt tgagatggag ttttgctctt gttgcccagg   2280
ctggagtgca atagcgcgat cttggctcac cgcaacctcc gcctcccagg ttcaagcgat   2340
tctcctgcct cagactccta agtagctggg attacaggca cctgccacca cgcctggcta   2400
tttttttgta tttttagtag agatgggggtt tcatcatgtt ggccaggctg gtctcgagct   2460
cctgacctca ggtgatctgc ccgcctcggc ctccaaaagt gctggaatta caggcgtgag   2520
ccaccatgcc tggccatcag aacttgtaat caagacagta tgttgagaaa ttctaacatt   2580
ataaattaca aagctttgac tattaaagtt tttgtgatct aatgatacag ttttgattct   2640
atagtaattt gtggcttatt ttatagttta taatgaatac ttatttctag actcatacac   2700
tggaagggga cccggaaagg taatgtaact cagtgatttt aaaacttgat tttttttaact   2760
gagaactttt tttgccccct gcctgtaggt taagtcttac gtgaaatgcc aagataattg   2820
ctgagcagct ttggttaccc agggcggggt ctgggtctgt ctgtactttg cctttactct   2880
agatggctcc tgagacacag gcaggactcc caagcaccgg gttgggatct gccctggtcc   2940
cggcattcca gtataagatt gcctcagacc tgtgtttttc agactgggtt tttgctcttc   3000
acatgaaatc aagttagatg acaatgactg gtgttgaaaa aaatgaaaag gaaagaattt   3060
```

```
gtaaagaaca gaaatatat ttgagtaagt attgtttggt aaaacttagt tacatatgca    3120
tatatatttg ttaggtatat atgtttatgt gtattctgat gtaaaatata tatatatata    3180
tattttatta ctatagtacc atgggtaatg gataaagaag ttaaagctac tgcttagaat    3240
gaagaaggcc ccaggcttac ctgtcccgat ctttaaactg tccgaaggaa attcaatagc    3300
ctgttaagtg aataccttca ttcttacttg tatttggggg aatattatga aatactcacc    3360
acttttggta ttttatgaaa atgttttctt ttcagaagtt atggtaattt caatgtgttt    3420
gttgttggga ggggagctgc caaatcagtt actaatatta ctgtgtgaca tctatccaac    3480 tttttttcatt attcttcatt gccaaatact gaaagacttg taaatggctt tggcaatatg    3540
tttgaattct aagaggaaat attttcccat aattgtatat cagagaaata tagtgatata    3600
caatttcctt gaaaaccaat ttctaaataa ttttcttctc tgtaatctaa gtgtaaaaag    3660
gtttagtttt ttaataggtt taggtgttta taagcaatag ttctctattt tctagttgat    3720
ataagtagaa gaattgacaa gtgagatgga aatgttaatt tataaaggga agaaaaagct    3780
aggtgaggtt gagttataat taaactgttc aggaaacatc gtaaaggctt taggctccct    3840
ttttcatttc tataccaatt aatctcatgg gttctagagt ggttagttct acgggaattg    3900
tttttgtttt tgttttaaa gatgctgaaa actactctca atcaaattag taccatcatt    3960
taagctttga atacttggca gtaattgcct gggctcgtca ataaatgtta gcaaattctt    4020
gatgttcaaa aaaaaaa                                                    4037

<210> SEQ ID NO 15
<211> LENGTH: 1237
<212> TYPE: DNA
<213> ORGANISM: Homo sapiens

<400> SEQUENCE: 15
gctgcagagg attcctgcag aggatcaaga cagcacgtgg acctcgcaca gcctctccca      60
caggtaccat gaaggtctcc gcggcagccc tcgctgtcat cctcattgct actgccctct     120
gcgctcctgc atctgcctcc ccatattcct cggacaccac accctgctgc tttgcctaca     180
ttgcccgccc actgccccgt gcccacatca aggagtattt ctacaccagt ggcaagtgct     240
ccaacccagc agtcgtcttt gtcacccgaa agaaccgcca agtgtgtgcc aacccagaga     300
agaaatgggt tcgggagtac atcaactctt tggagatgag ctaggatgga gagtccttga     360
acctgaactt acacaaattt gcctgttct gcttgctctt gtcctagctt gggaggcttc     420
ccctcactat cctaccccac ccgctccttg aagggcccag attctaccac acagcagcag     480
ttacaaaaac cttccccagg ctggacgtgg tggctcacgc ctgtaatccc agcactttgg     540
gaggccaagt gggtggatc acttgaggtc aggagttcga ccagcctg ccaacatga         600 tgaaacccca tctctactaa aaatacaaaa aattagccgg gcgtggtagc gggcgcctgt     660
agtcccagct actcgggagg ctgaggcagg agaatggcgt gaacccggga ggcggagctt     720
gcagtgagcc gagatcgcgc cactgcactc cagcctgggc gacagagcga gactccgtct     780
caaaaaaaaa aaaaaaaaa aaaatacaaa aattagccgg gcgtggtggc ccacgcctgt     840
aatcccagct actcgggagg ctaaggcagg aaaattgttt gaacccagga ggtggaggct     900
gcagtgagct gagattgtgc cacttcactc cagcctgggt gacaaagtga gactccgtca     960
caacaacaac aacaaaaagc ttccccaact aaagcctaga agagcttctg aggcgctgct    1020
ttgtcaaaag gaagtctcta ggttctgagc tctggctttg ccttggcttt gccagggctc    1080
```

| | |
|---|---|
| tgtgaccagg aaggaagtca gcatgcctct agaggcaagg aggggaggaa cactgcactc | 1140 |
| ttaagcttcc gccgtctcaa cccctcacag gagcttactg gcaaacatga aaaatcggct | 1200 |
| taccattaaa gttctcaatg caaccataaa aaaaaaa | 1237 |

<210> SEQ ID NO 16
<211> LENGTH: 1320
<212> TYPE: DNA
<213> ORGANISM: Homo sapiens

<400> SEQUENCE: 16

| | |
|---|---|
| cggaaggggga aggggggtgga ggttgctgct atgagagaga aaaaaaaaac agccacaata | 60 |
| gagattctgc cttcaaaggt tggcttgcca cctgaagcag ccactgccca ggggggtgcaa | 120 |
| agaagagaca gcagcgccca gcttggaggt gctaactcca gaggccagca tcagcaactg | 180 |
| ggcacagaaa ggagccgcct gggcagggac catggcacgg ccacatccct ggtggctgtg | 240 |
| cgttctgggg accctggtgg ggctctcagc tactccagcc cccaagagct gcccagagag | 300 |
| gcactactgg gctcagggaa agctgtgctg ccagatgtgt gagccaggaa cattcctcgt | 360 |
| gaaggactgt gaccagcata gaaaggctgc tcagtgtgat ccttgcatac cgggggtctc | 420 |
| cttctctcct gaccaccaca cccggcccca ctgtgagagc tgtcggcact gtaactctgg | 480 |
| tcttctcgtt cgcaactgca ccatcactgc caatgctgag tgtgcctgtc gcaatggctg | 540 |
| gcagtgcagg gacaaggagt gcaccgagtg tgatcctctt ccaaacccctt cgctgaccgc | 600 |
| tcggtcgtct caggccctga gcccacaccc tcagcccacc cacttacctt atgtcagtga | 660 |
| gatgctggag gccaggacag ctgggcacat gcagactctg gctgacttca ggcagctgcc | 720 |
| tgcccggact ctctctaccc actggccacc ccaaagatcc ctgtgcagct ccgattttat | 780 |
| tcgcatcctt gtgatcttct ctggaatgtt ccttgttttc accctggccg gggccctgtt | 840 |
| cctccatcaa cgaaggaaat atagatcaaa caaggagaa agtcctgtgg agcctgcaga | 900 |
| gccttgtcgt tacagctgcc cagggagga ggagggcagc accatcccca tccaggagga | 960 |
| ttaccgaaaa ccggagcctg cctgctcccc ctgagccagc acctgcggga gctgcactac | 1020 |
| agccctggcc tccaccccca ccccgccgac catccaaggg agagtgagac ctggcagcca | 1080 |
| caactgcagt cccatcctct tgtcagggcc cttttcctgtg tacacgtgac agagtgcctt | 1140 |
| ttcgagactg gcagggacga ggacaaatat ggatgaggtg gagagtggga agcaggagcc | 1200 |
| cagccagctg cgcctgcgct gcaggagggc gggggctctg gttgtaaaac acacttcctg | 1260 |
| ctgcgaaaga cccacatgct acaagacggg caaaataaag tgacagatga ccaccctgca | 1320 |

<210> SEQ ID NO 17
<211> LENGTH: 3691
<212> TYPE: DNA
<213> ORGANISM: Homo sapiens

<400> SEQUENCE: 17

| | |
|---|---|
| ggcgcaacgc tgagcagctg gcgcgtcccg cgcggcccca gttctgcgca gcttcccgag | 60 |
| gctccgcacc agccgcgctt ctgtccgcct gcagggcatt ccagaaagat gaggatattt | 120 |
| gctgtctttta tattcatgac ctactggcat ttgctgaacg catttactgt cacggttccc | 180 |
| aaggacctat atgtggtaga gtatggtagc aatatgacaa ttgaatgcaa attcccagta | 240 |
| gaaaaacaat tagaccctgg ctgcactaatt gtctattggg aaatggagga taagaacatt | 300 |
| attcaatttg tgcatggaga ggaagacctg aaggttcagc atagtagcta cagacagagg | 360 |
| gcccggctgt tgaaggacca gctctccctg ggaaatgctg cacttcagat cacagatgtg | 420 |

```
aaattgcagg atgcaggggt gtaccgctgc atgatcagct atggtggtgc cgactacaag    480
cgaattactg tgaaagtcaa tgccccatac aacaaaatca accaaagaat tttggttgtg    540
gatccagtca cctctgaaca tgaactgaca tgtcaggctg agggctaccc caaggccgaa    600
gtcatctgga caagcagtga ccatcaagtc ctgagtggta agaccaccac caccaattcc    660
aagagagagg agaagctttt caatgtgacc agcacactga gaatcaacac aacaactaat    720
gagattttct actgcacttt taggagatta gatcctgagg aaaaccatac agctgaattg    780
gtcatcccag aactacctct ggcacatcct ccaaatgaaa ggactcactt ggtaattctg    840
ggagccatct tattatgcct tggtgtagca ctgacattca tcttccgttt aagaaaaggg    900
agaatgatgg atgtgaaaaa atgtggcatc caagatacaa actcaaagaa gcaaagtgat    960
acacatttgg aggagacgta atccagcatt ggaacttctg atcttcaagc agggattctc   1020
aacctgtggt ttaggggttc atcggggctg agcgtgacaa gaggaaggaa tgggcccgtg   1080
ggatgcaggc aatgtgggac ttaaaaggcc caagcactga aatggaacc tggcgaaagc    1140 agaggaggag aatgaagaaa gatggagtca acagggagc ctggagggag accttgatac    1200
tttcaaatgc ctgaggggct catcgacgcc tgtgacaggg agaaaggata cttctgaaca   1260
aggagcctcc aagcaaatca tccattgctc atcctaggaa gacgggttga gaatccctaa   1320
tttgagggtc agttcctgca gaagtgccct tgcctccac tcaatgcctc aatttgtttt    1380
ctgcatgact gagagtctca gtgttggaac gggacagtat ttatgtatga gttttcctga   1440 tttatttga gtctgtgagg tcttcttgtc atgtgagtgt ggttgtgaat gatttctttt    1500
gaagatatat tgtagtagat gttacaattt tgtcgccaaa ctaaacttgc tgcttaatga   1560
tttgctcaca tctagtaaaa catggagtat tgtaaggtg cttggtctcc tctataacta    1620
caagtataca ttggaagcat aaagatcaaa ccgttggttg cataggatgt caccttatt    1680 taacccatta atactctggt tgacctaatc ttattctcag acctcaagtg tctgtgcagt   1740
atctgttcca tttaaatatc agctttacaa ttatgtggta gcctacacac ataatctcat   1800
ttcatcgctg taaccaccct gttgtgataa ccactattat tttacccatc gtacagctga   1860
ggaagcaaac agattaagta acttgcccaa accagtaaat agcagacctc agactgccac   1920
ccactgtcct tttataatac aatttacagc tatattttac tttaagcaat tcttttattc   1980
aaaaaccatt tattaagtgc ccttgcaata tcaatcgctg tgccaggcat tgaatctaca   2040
gatgtgagca agacaaagta cctgtcctca aggagctcat agtataatga ggagattaac   2100
aagaaaatgt attattacaa tttagtccag tgtcatagca taaggatgat gcgaggggaa   2160
aacccgagca gtgttgccaa gaggaggaaa taggccaatg tggtctggga cggttggata   2220
tacttaaaca tcttaataat cagagtaatt ttcatttaca aagagaggtc ggtacttaaa   2280
ataaccctga aaaataacac tggaattcct tttctagcat tatatttatt cctgatttgc   2340
ctttgccata taatctaatg cttgtttata tagtgtctgg tattgtttaa cagttctgtc   2400 tttttctattt aaatgccact aaattttaaa ttcataccctt tccatgattc aaaattcaaa   2460
agatcccatg ggagatggtt ggaaaatctc cacttcatcc tccaagccat tcaagtttcc   2520
tttccagaag caactgctac tgcctttcat tcatatgttc ttctaaagat agtctacatt   2580
tggaaatgta tgttaaaagc acgtattttt aaaatttttt tcctaaatag taacacattg   2640
tatgtctgct gtgtactttg ctattttat ttatttagt gtttcttata tagcagatgg     2700
aatgaatttg aagttcccag gctgaggat ccatgccttc tttgtttcta agttatcttt    2760
```

| | |
|---|---|
| cccatagctt tteattatct tteatatgat ccagtatatg ttaaatatgt cctacatata | 2820 |
| catttagaca accaccattt gttaagtatt tgctctagga cagagtttgg atttgtttat | 2880 |
| gtttgctcaa aaggagaccc atgggctctc cagggtgcac tgagtcaatc tagtcctaaa | 2940 |
| aagcaatctt attattaact ctgtatgaca gaatcatgtc tggaacttt gttttctgct | 3000 |
| ttctgtcaag tataaacttc actttgatgc tgtacttgca aaatcacatt ttctttctgg | 3060 |
| aaattccggc agtgtacctt gactgctagc taccctgtgc cagaaaagcc tcattcgttg | 3120 |
| tgcttgaacc cttgaatgcc accagctgtc atcactacac agccctccta agaggcttcc | 3180 |
| tggaggtttc gagattcaga tgccctggga gatcccagag tttcctttcc ctcttggcca | 3240 |
| tattctggtg tcaatgacaa ggagtacctt ggctttgcca catgtcaagg ctgaagaaac | 3300 |
| agtgtctcca acagagctcc ttgtgttatc tgtttgtaca tgtgcatttg tacagtaatt | 3360 |
| ggtgtgacag tgttctttgt gtgaattaca ggcaagaatt gtggctgagc aaggcacata | 3420 |
| gtctactcag tctattccta agtcctaact cctccttgtg gtgttggatt tgtaaggcac | 3480 |
| tttatccctt ttgtctcatg tttcatcgta aatggcatag gcagagatga tacctaattc | 3540 |
| tgcatttgat tgtcactttt tgtacctgca ttaatttaat aaaatattct tatttatttt | 3600 |
| gttacttggt acaccagcat gtccatttc ttgtttattt tgtgtttaat aaaatgttca | 3660 |
| gtttaacatc ccagtggaga aagttaaaaa a | 3691 |

<210> SEQ ID NO 18
<211> LENGTH: 3419
<212> TYPE: DNA
<213> ORGANISM: Homo sapiens

<400> SEQUENCE: 18

| | |
|---|---|
| ccggcctcag ggacgcaccg gagccgcctt tccgggcctc aggcggattc tccggcgcgg | 60 |
| cccgccccgc ccctcggact ccccgggccg ccccggccc ccattcgggc cgggcctcgc | 120 |
| tgcggcggcg actgagccag gctgggccg gtccctgagt cccagagtcg gcgcggcgcg | 180 |
| gcagggcag ccttccacca cggggagccc agctgtcagc cgcctcacag gaagatgctg | 240 |
| cgtcggcggg gcagccctgg catggtgtgt catgtgggtg cagccctggg agcactgtgg | 300 |
| ttctgcctca caggagccct ggaggtccag gtccctgaag acccagtggt ggcactggtg | 360 |
| ggcaccgatg ccaccctgtg ctgctccttc tcccctgagc ctggcttcag cctggcacag | 420 |
| ctcaacctca tctggcagct gacagatacc aaacagctgg tgcacagctt tgctgagggc | 480 |
| caggaccagg gcagcgccta tgccaaccgc acggccctct tccggacct gctggcacag | 540 |
| ggcaacgcat ccctgaggct gcagcgcgtg cgtgtggcgg acgagggcag cttcacctgc | 600 |
| ttcgtgagca tccgggattt cggcagcgct gccgtcagcc tgcaggtggc cgctccctac | 660 |
| tcgaagccca gcatgaccct ggagcccaac aaggacctgc ggccagggga cacggtgacc | 720 |
| atcacgtgct ccagctacca gggctacccc gaggctgagg tgttctggca ggatgggcag | 780 |
| ggtgtgcccc tgactggcaa cgtgaccacg tcgcagatgg ccaacgagca gggcttgttt | 840 |
| gatgtgcaca gcatcctgcg ggtggtgctg ggtgcaaatg gcacctacag ctgcctggtg | 900 |
| cgcaaccccg tgctgcagca ggatgcgcac agctctgtca ccatcacacc ccagagaagc | 960 |
| cccacaggag ccgtggaggt ccaggtccct gaggacccgg tggtggccct agtgggcacc | 1020 |
| gatgccaccc tgcgctgctc cttctccccc gagcctggct tcagcctggc acagctcaac | 1080 |
| ctcatctggc agctgacaga caccaaacag ctggtgcaca gtttcaccga aggccgggac | 1140 |
| cagggcagcg cctatgccaa ccgcacggcc ctcttcccgg acctgctggc acaaggcaat | 1200 |

```
gcatccctga ggctgcagcg cgtgcgtgtg gcggacgagg gcagcttcac ctgcttcgtg    1260
agcatccggg atttcggcag cgctgccgtc agcctgcagg tggccgctcc ctactcgaag    1320
cccagcatga ccctggagcc caacaaggac ctgcggccag ggacacggt gaccatcacg    1380 tgctccagct accggggcta ccctgaggct gaggtgttct ggcaggatgg gcagggtgtg    1440
cccctgactg gcaacgtgac cacgtcgcag atggccaacg agcagggctt gtttgatgtg    1500
cacagcgtcc tgcgggtggt gctgggtgcg aatggcacct acagctgcct ggtgcgcaac    1560
cccgtgctgc agcaggatgc gcacggctct gtcaccatca cagggcagcc tatgacattc    1620
cccccagagg ccctgtgggt gaccgtgggg ctgtctgtct gtctcattgc actgctggtg    1680
gccctggctt tcgtgtgctg agaaagatc aaacagagct gtgaggagga aatgcagga    1740 gctgaggacc aggatgggga gggagaaggc tccaagacag ccctgcagcc tctgaaacac    1800
tctgacagca agaagatga tggacaagaa atagcctgac catgaggacc agggagctgc    1860 taccctccc tacagctcct accctctggc tgcaatgggg ctgcactgtg agccctgccc    1920
ccaacagatg catcctgctc tgacaggtgg gctccttctc caaaggatgc gatacacaga    1980
ccactgtgca gccttatttc tccaatggac atgattccca agtcatcctg ctgccttttt    2040
tcttatagac acaatgaaca gaccacccac aaccttagtt ctctaagtca tcctgcctgc    2100
tgccttattt cacagtacat acatttctta gggacacagt acactgacca catcaccacc    2160
ctcttcttcc agtgctgcgt ggaccatctg gctgcctttt ttctccaaaa gatgcaatat    2220
tcagactgac tgaccccctg ccttatttca ccaaagacac gatgcatagt caccccggcc    2280
ttgtttctcc aatggccgtg atacactagt gatcatgttc agccctgctt ccacctgcat    2340
agaatctttt cttctcagac agggacagtg cggcctcaac atctcctgga gtctagaagc    2400
tgtttccttt cccctccttc ctcctcttgc tctagcctta atactggcct tttccctccc    2460
tgccccaagt gaagacaggg cactctgcgc ccaccacatg cacagctgtg catggagacc    2520
tgcaggtgca cgtgctggaa cacgtgtggt tccccctgg cccagcctcc tctgcagtgc    2580
ccctctcccc tgcccatcct ccccacgaa gcatgtgctg gtcacactgg ttctccaggg    2640
gtctgtgatg gggcccctgg gggtcagctt ctgtccctct gccttctcac ctctttgttc    2700 cttcttttc atgtatccat tcagttgatg tttattgagc aactacagat gtcagcactg    2760
tgttaggtgc tggggggccct gcgtgggaag ataaagttcc tccctcaagg actccccatc    2820
cagctgggag acagacaact aactacactg caccctgcgg tttgcagggg gctcctgcct    2880
ggctccctgc tccacacctc ctctgtggct caaggcttcc tggatacctc accccctcc    2940 caccccataat tcttacccag agcatggggt tggggcggaa acctggagag agggacatag    3000
cccctcgcca cggctagaga atctggtggt gtccaaaatg tctgtccagg tgtgggcagg    3060
tgggcaggca ccaaggccct ctggaccttt catagcagca gaaaaggcag agcctggggc    3120
agggcagggc caggaatgct ttggggacac cgaggggact gccccccacc ccaccatgg    3180 tgctattctg gggctggggc agtctttttcc tggcttgcct ctggccagct cctggcctct    3240
ggtagagtga gacttcagac gttctgatgc cttccggatg tcatctctcc ctgccccagg    3300
aatggaagat gtgaggactt ctaatttaaa tgtgggactc ggagggattt tgtaaactgg    3360
gggtatattt tggggaaaat aaatgtcttt gtaaaaagct taaaaaaaaa aaaaaaaa    3419
```

<210> SEQ ID NO 19
<211> LENGTH: 2325
<212> TYPE: DNA

<213> ORGANISM: Homo sapiens

<400> SEQUENCE: 19

| | | | | | |
|---|---|---|---|---|---|
| cgaaaaggag | ggtgactctc | ctcggcgggg | gcttcgggtg | acatcacatc | ctccaaatgc | 60 |
| gaaatcaggc | tccgggccgg | ccgaagggcg | caactttccc | ccctcggcgc | ccaccggct | 120 |
| cccgcgcgcc | tccctcgcg | cccgagcttc | gagccaagca | gcgtcctggg | gagcgcgtca | 180 |
| tggccttacc | agtgaccgcc | ttgctcctgc | cgctggcctt | gctgctccac | gccgccaggc | 240 |
| cgagccagtt | ccgggtgtcg | ccgctggatc | ggacctggaa | cctgggcgag | acagtggagc | 300 |
| tgaagtgcca | ggtgctgctg | tccaacccga | cgtcgggctg | ctcgtggctc | ttccagccgc | 360 |
| gcggcgccgc | cgccagtccc | accttcctcc | tatacctctc | ccaaaacaag | cccaaggcgg | 420 |
| ccgaggggct | ggacacccag | cggttctcgg | gcaagaggtt | gggggacacc | ttcgtcctca | 480 |
| ccctgagcga | cttccgccga | gagaacgagg | gctactattt | ctgctcggcc | ctgagcaact | 540 |
| ccatcatgta | cttcagccac | ttcgtgccgg | tcttcctgcc | agcgaagccc | accacgacgc | 600 |
| cagcgccgcg | accaccaaca | ccggcgccca | ccatcgcgtc | gcagcccctg | tccctgcgcc | 660 |
| cagaggcgtg | ccggccagcg | gcgggggggcg | cagtgcacac | gaggggggctg | gacttcgcct | 720 |
| gtgatatcta | catctgggcg | cccttggccg | ggacttgtgg | ggtccttctc | ctgtcactgg | 780 |
| ttatcaccct | ttactgcaac | cacaggaacc | gaagacgtgt | tgcaaatgt | ccccggcctg | 840 |
| tggtcaaatc | gggagacaag | cccagccttt | cggcgagata | cgtctaaccc | tgtgcaacag | 900 |
| ccactacatt | acttcaaact | gagatccttc | cttttgaggg | agcaagtcct | tcccttcat | 960 |
| tttttccagt | cttcctccct | gtgtattcat | tctcatgatt | attattttag | tgggggcggg | 1020 |
| gtgggaaaga | ttacttttttc | tttatgtgtt | tgacgggaaa | caaaactagg | taaaatctac | 1080 |
| agtacaccac | aagggtcaca | atactgttgt | gcgcacatcg | cggtagggcg | tggaaagggg | 1140 |
| caggccagag | ctacccgcag | agttctcaga | atcatgctga | gagagctgga | ggcacccatg | 1200 |
| ccatctcaac | ctcttccccg | cccgttttac | aaggggggag | gctaaagccc | agagacagct | 1260 |
| tgatcaaagg | cacacagcaa | gtcagggttg | gagcagtagc | tggagggacc | ttgtctccca | 1320 |
| gctcagggct | ctttcctcca | caccattcag | gtctttcttt | ccgaggcccc | tgtctcaggg | 1380 |
| tgaggtgctt | gagtctccaa | cggcaaggga | acaagtactt | cttgatacct | gggatactgt | 1440 |
| gcccagagcc | tcgaggaggt | aatgaattaa | agaagagaac | tgcctttggc | agagttctat | 1500 |
| aatgtaaaca | atatcagact | tttttttttt | ataatcaagc | ctaaaattgt | atagacctaa | 1560 |
| aataaaatga | agtggtgagc | ttaaccctgg | aaaatgaatc | cctctatctc | taaagaaaat | 1620 |
| ctctgtgaaa | cccctatgtg | gaggcggaat | tgctctccca | gcccttgcat | tgcagagggg | 1680 |
| cccatgaaag | aggacaggct | acccctttac | aaatagaatt | tgagcatcag | tgaggttaaa | 1740 |
| ctaaggcccct | cttgaatctc | tgaatttgag | atacaaacat | gttcctggga | tcactgatga | 1800 |
| cttttttatac | tttgtaaaga | caattgttgg | agagcccctc | acacagccct | ggcctctgct | 1860 |
| caactagcag | atacagggat | gaggcagacc | tgactctctt | aaggaggctg | agagcccaaa | 1920 |
| ctgctgtccc | aaacatgcac | ttccttgctt | aaggtatggt | acaagcaatg | cctgcccatt | 1980 |
| ggagagaaaa | aacttaagta | gataaggaaa | taagaaccac | tcataattct | tcaccttagg | 2040 |
| aataatctcc | tgttaatatg | gtgtacattc | ttcctgatta | ttttctacac | atacatgtaa | 2100 |
| aatatgtctt | tcttttttaa | atagggttgt | actatgctgt | tatgagtggc | tttaatgaat | 2160 |
| aaacatttgt | agcatcctct | ttaatgggta | aacagcatcc | gaaaaaaaaa | aaaaaaaaa | 2220 |
| aaaaaaaaaa | aaaaaaaaaa | aaaaaaaaaa | aaaaaaaaaa | aaaaaaaaaa | aaaaaaaaaa | 2280 | aaaaaaaaaa aaaaaaaaaa aaaaaaaaaa aaaaaaaaaa aaaaa           2325

<210> SEQ ID NO 20
<211> LENGTH: 1900
<212> TYPE: DNA
<213> ORGANISM: Homo sapiens

<400> SEQUENCE: 20
gaattcggca cgagtcaggg aagcagcccc ggcggccagc agggagctca ggacagagca      60
ggctccctgg gaagcctccg ggtgataggg gtgttccagc tgcggcgctc tgggggttca     120 gaggggatc ttgaatgaac aaatgaatga actgctttct gggcaaacag ccacagccag     180
aggagcctgt gattggcaga aagaagccag ggtgtgcaag tctccccaac agcctcgagt     240
ggcctgcagt cacagggaac cctcaggaag accttccggg cagagaccag agggaagccc     300
atctctccag cagaactgct tggattttc taccaggagg ctcagggctc tgcaacaatg     360
atagcagaag ctgatggcat ctagagatct aggctgggac tagcacagca tcacttctac     420
cactttctgt tggtcacagc aactcaccat gccagtgcag attcaagggg aggagaaata     480
gagtccactt cttgatggga ggcgtgacat agaatggagg atgaagatta caacacttcc     540
atcagttacg gtgatgaata ccctgattat ttagactcca ttgtggtttt ggaggactta     600 tccccttgg aagccagggt gaccaggatc ttcctggtgg tggtctacag catcgtctgc     660
ttcctcggga ttctgggcaa tggtctggtg atcatcattg ccaccttcaa gatgaagaag     720
acagtgaaca tggtctggtt cctcaacctg gcagtggcag atttcctgtt caacgtcttc     780
ctcccaatcc atatcaccta tgccgccatg gactaccact gggttttcgg acagccatg     840 tgcaagatca gcaacttcct tctcatccac aacatgttca ccagcgtctt cctgctgacc     900
atcatcagct ctgaccgctg catctctgtg ctcctccctg tctggtccca gaaccaccgc     960
agcgttcgcc tggcttacat ggcctgcatg gtcatctggg tcctggcttt cttcttgagt    1020
tccccatctc tcgtcttccg ggacacagcc aacctgcatg ggaaaatatc ctgcttcaac    1080
aacttcagcc tgtccacacc tgggtcttcc tcgtggccca ctcactccca aatggaccct    1140
gtggggtata gccggcacat ggtggtgact gtcacccgct tcctctgtgg cttcctggtc    1200
ccagtcctca tcatcacagc ttgctacctc accatcgtgt gcaaactgca gcgcaaccgc    1260
ctggccaaga ccaagaagcc cttcaagatt attgtgacca tcatcattac cttcttcctc    1320
tgctggtgcc cctaccacac actcaacctc ctagagctcc accacactgc catgcctggc    1380
tctgtcttca gcctgggttt gcccctggcc actgcccttg ccattgccaa cagctgcatg    1440
aaccccattc tgtatgtttt catgggtcag gacttcaaga agttcaaggt ggccctcttc    1500
tctcgcctgg tcaatgctct aagtgaagat acaggccact cttcctaccc cagccataga    1560
agctttacca agatgtcatc aatgaatgag aggacttcta tgaatgagag ggagaccggc    1620
atgctttgat cctcactgtg gaaccctca atggactctc tcaacccagg acacccaag    1680 gatatgtctt ctgaagatca aggcaagaac ctctttagca tccaccaatt ttcactgcat    1740
tttgcatggg atgaacagtg ttttatgctg ggaatctagg gcctggaacc cctttcttct    1800
agtggacaga acatgctgtg ttccatacag ccttggacta gcaatttatg cttcttggga    1860
ggccagcctt gactgactca aagcaaaaaa ggaagaattc                          1900

<210> SEQ ID NO 21
<211> LENGTH: 2545
<212> TYPE: DNA

<213> ORGANISM: Homo sapiens

<400> SEQUENCE: 21

```
atccaataca ggagtgactt ggaactccat tctatcacta tgaagaaaag tggtgttctt      60
ttcctcttgg gcatcatctt gctggttctg attggagtgc aaggaacccc agtagtgaga     120
aagggtcgct gttcctgcat cagcaccaac caagggacta tccacctaca atccttgaaa     180
gaccttaaac aatttgcccc aagcccttcc tgcgagaaaa ttgaaatcat tgctacactg     240
aagaatggag ttcaaacatg tctaaaccca gattcagcag atgtgaagga actgattaaa     300
aagtgggaga acaggtcagc caaaagaaa aagcaaaaga atgggaaaaa acatcaaaaa      360
aagaaagttc tgaaagttcg aaaatctcaa cgttctcgtc aaaagaagac tacataagag     420
accacttcac caataagtat tctgtgttaa aaatgttcta tttttaattat accgctatca     480
ttccaaagga ggatggcata taatacaaag gcttattaat ttgactagaa aatttaaaac      540
attactctga aattgtaact aaagttagaa agttgatttt aagaatccaa acgttaagaa     600
ttgttaaagg ctatgattgt ctttgttctt ctaccaccca ccagttgaat ttcatcatgc      660
ttaaggccat gattttagca atacccatgt ctacacagat gttcacccaa ccacatccca     720
ctcacaacag ctgcctggaa gagcagccct aggcttccac gtactgcagc tccagagag      780
tatctgaggc acatgtcagc aagtcctaag cctgttagca tgctggtgag ccaagcagtt     840
tgaaattgag ctggacctca ccaagctgct gtggccatca acctctgtat ttgaatcagc     900
ctacaggcct cacacacaat gtgtctgaga gattcatgct gattgttatt gggtatcacc     960
actggagatc accagtgtgt ggctttcaga gcctcctttc tggctttgga agccatgtga    1020
ttccatcttg cccgctcagg ctgaccactt tatttctttt tgttccccctt tgcttcattc    1080
aagtcagctc ttctccatcc taccacaatg cagtgccttt cttctctcca gtgcacctgt    1140
catatgctct gatttatctg agtcaactcc tttctcatct tgtccccaac accccacaga    1200
agtgctttct tctcccaatt catcctcact cagtccagct tagttcaagt cctgcctctt    1260
aaataaacct ttttggacac acaaattatc ttaaaactcc tgtttcactt ggttcagtac    1320
cacatgggtg aacactcaat ggttaactaa ttccttgggtg tttatcctat ctctccaacc   1380
agattgtcag ctccttgagg gcaagagcca cagtatattt ccctgtttct tccacagtgc    1440
ctaataatac tgtggaacta ggttttaata atttttttaat tgatgttgtt atgggcagga    1500
tggcaaccag accattgtct cagagcaggt gctggctctt tcctggctac tccatgttgg    1560
ctagcctctg gtaacctctt acttattatc ttcaggacac tcactacagg gaccagggat    1620
gatgcaacat ccttgtcttt ttatgacagg atgtttgctc agcttctcca acaataagaa    1680
gcacgtggta aaacacttgc ggatattctg gactgttttt aaaaaatata cagtttaccg    1740
aaaatcatat aatcttacaa tgaaaaggac tttatagatc agccagtgac caacctttc     1800
ccaaccatac aaaaattcct tttcccgaag gaaaagggct ttctcaataa gcctcagctt    1860
tctaagatct aacaagatag ccaccgagat cttatcgaa actcatttta ggcaaatatg     1920
agttttattg tccgtttact tgtttcagag tttgtattgt gattatcaat taccacacca    1980
tctcccatga agaaagggaa cggtgaagta ctaagcgcta gaggaagcag ccaagtcggt    2040
tagtggaagc atgattggtg cccagttagc ctctgcagga tgtggaaacc tccttccagg    2100
ggaggttcag tgaattgtgt aggagaggtt gtctgtggcc agaatttaaa cctatactca    2160
cttccccaaa ttgaatcact gctcacactg ctgatgattt agagtgctgt ccggtggaga    2220
tcccacccga acgtcttatc taatcatgaa actccctagt tccttcatgt aacttccctg    2280
```

```
aaaaatctaa gtgtttcata aatttgagag tctgtgaccc acttaccttg catctcacag    2340
gtagacagta taactaac  aaccaaagac tacatattgt cactgacaca cacgttataa    2400
tcatttatca tatatataca tacatgcata cactctcaaa gcaaataatt tttcacttca    2460
aaacagtatt gacttgtata ccttgtaatt tgaaatattt tctttgttaa aatagaatgg    2520
tatcaataaa tagaccatta atcag                                         2545

<210> SEQ ID NO 22
<211> LENGTH: 1953
<212> TYPE: DNA
<213> ORGANISM: Homo sapiens

<400> SEQUENCE: 22
gcagaccttg cttcatgagc aagctcatct ctggaacaaa ctggcaaagc atctctgctg      60
gtgttcatca gaacagacac catggcagag catgattacc atgaagacta tgggttcagc     120
agtttcaatg acagcagcca ggaggagcat caagacttcc tgcagttcag caaggtcttt     180
ctgccctgca tgtacctggt ggtgtttgtc tgtggtctgg tggggaactc tctggtgctg     240
gtcatatcca tcttctacca taagttgcag agcctgacgg atgtgttcct ggtgaaccta     300
cccctggctg acctggtgtt tgtctgcact ctgcccttct gggcctatgc aggcatccat     360
gaatgggtgt ttggccaggt catgtgcaag agcctactgg catctacac tattaacttc     420 tacacgtcca tgctcatcct cacctgcatc actgtggatc gtttcattgt agtggttaag     480
gccaccaagg cctacaacca gcaagccaag aggatgacct ggggcaaggt caccagcttg     540
ctcatctggg tgatatccct gctggtttcc ttgccccaaa ttatctatgg caatgtcttt     600
aatctcgaca agctcatatg tggttaccat gacgaggcaa tttccactgt ggttcttgcc     660
acccagatga cactggggtt cttcttgcca ctgctcacca tgattgtctg ctattcagtc     720
ataatcaaaa cactgcttca tgctggaggc ttccagaagc acagatctct aaagatcatc     780
ttcctggtga tggctgtgtt cctgctgacc cagatgccct tcaacctcat gaagttcatc     840
cgcagcacac actggggaata ctatgccatg accagcttc actacaccat catggtgaca     900
gaggccatcg catacctgag ggcctgcctt aaccctgtgc tctatgcctt tgtcagcctg     960
aagtttcgaa agaacttctg gaaacttgtg aaggacattg gttgcctccc ttaccttggg    1020
gtctcacatc aatggaaatc ttctgaggac aattccaaga cttttttctgc ctcccacaat    1080 gtggaggcca ccagcatgtt ccagttatag gccttgccag ggtttcgaga agctgctctg    1140
gaatttgcaa gtcatggctg tgccctcttg atgtggtgag gcaggctttg tttatagctt    1200
gcgcattctc atggagaagt tatcagacac tctggctggt ttggaatgct tcttctcagg    1260
catgaacatg tactgttctc ttcttgaaca ctcatgctga aagcccaagt agggggtcta    1320 aaattttaa ggactttcct tcctccatct ccaagaatgc tgaaaccaag ggggatgaca    1380
tgtgactcct atgatctcag gttctccttg attgggactg gggctgaagg ttgaagaggt    1440
gagcacggcc aacaaagctg ttgatggtag gtggcacact gggtgcccaa gctcagaagg    1500
ctcttctgac tactgggcaa agagtgtaga tcagagcagc agtgaaaaca agtgctggca    1560
ccaccaggca cctcacagaa atgagatcag gctctgcctc accttgggc ttgactttg     1620 tataggtaga tgttcagatt gctttgatta atccagaata actagcacca gggactatga    1680
atgggcaaaa ctgaattata agaggctgat aattccagtg gtccatggaa tgcttgaaaa    1740
atgtgcaaaa cagcgtttaa gactgtaatg aatctaagca gcatttctga agtggactct    1800
```

```
ttggtggctt tgcattttaa aaatgaaatt ttccaatgtc tgccacacaa acgtatgtaa    1860
atgtatatac ccacacacat acacacatat gtcatatatt actagcatat gagtttcata    1920
gctaagaaat aaaactgtta aagtctccaa act                                 1953

<210> SEQ ID NO 23
<211> LENGTH: 1542
<212> TYPE: DNA
<213> ORGANISM: Homo sapiens

<400> SEQUENCE: 23
acaattactc tacagctcag aacaccaact gctgaggctg ccttgggaag aggatgatcc      60
taaacaaagc tctgctgctg ggggccctcg ctctgaccac cgtgatgagc ccctgtggag     120
gtgaagacat tgtggctgac cacgttgcct cttgtggtgt aaacttgtac cagttttacg     180
gtccctctgg ccagtacacc catgaatttg atggagatga gcagttctac gtggacctgg     240
agaggaagga gactgcctgg cggtggcctg agttcagcaa atttggaggt tttgaccccg     300
agggtgcact gagaaacatg gctgtggcaa aacacaactt gaacatcatg attaaacgct     360
acaactctac cgctgctacc aatgaggttc ctgaggtcac agtgttttcc aagtctcccg     420
tgacactggg tcagcccaac accctcattt gtcttgtgga caacatcttt cctcctgtgg     480
tcaacatcac atggctgagc aatgggcagt cagtcacaga aggtgtttct gagaccagct     540
tcctctccaa gagtgatcat tccttcttca agatcagtta cctcaccttc ctcccttctg     600
ctgatgagat ttatgactgc aaggtggagc actggggcct ggaccagcct cttctgaaac     660
actgggagcc tgagattcca gcccctatgt cagagctcac agagactgtg gtctgtgccc     720
tggggttgtc tgtgggcctc atgggcattg tggtgggcac tgtcttcatc atccaaggcc     780
tgcgttcagt tggtgcttcc agacaccaag ggccattgtg aatcccatcc tggaagggaa     840
ggtgcatcgc catctacagg agcagaagaa tggacttgct aaatgaccta gcactattct     900
ctggcccgat ttatcatatc ccttttctcc tccaaatatt tctcctctca cctttttctct     960 gggacttaag ctgctatatc ccctcagagc tcacaaatgc ctttacattc tttccctgac    1020
ctcctgattt ttttttttctt ttctcaaatg ttacctacaa agacatgcct ggggtaagcc    1080
acccggctac ctaattcctc agtaacctcc atctaaaatc tccaaggaag caataaattc    1140
cttttatgag atctatgtca aattttttcca tctttcatcc agggctgact gaaactatgg    1200
ctaataattg gggtactctt atgtttcaat ccaatttaac ctcatttccc agatcatttt    1260
tcatgtccag taacacagaa gccaccaagt acagtatagc ctgataatat gttgatttct    1320
tagctgacat taatatttct tgcttccttg tgttcccacc cttggcactg ccacccaccc    1380
ctcaattcag gcaacaatga aattaatgga taccgtctgc ccttggccca gaattgttat    1440
agcaaaaatt ttagaaccaa aaaataagtc tgtactaatt tcaatgtggc ttttaaaagt    1500
atgacagaga aataagttag gataaaggaa atttgaatct ca                       1542

<210> SEQ ID NO 24
<211> LENGTH: 1182
<212> TYPE: DNA
<213> ORGANISM: Homo sapiens

<400> SEQUENCE: 24
tagttctccc tgagtgagac ttgcctgctt ctctggcccc tggtcctgtc ctgttctcca      60
gcatggtgtg tctgaagctc cctggaggct cctgcatgac agcgctgaca gtgacactga     120
tggtgctgag ctccccactg gctttggctg gggacacccg accacgtttc ttgtggcagc     180
```

```
ttaagtttga atgtcatttc ttcaatggga cggagcgggt gcggttgctg gaaagatgca        240
tctataacca agaggagtcc gtgcgcttcg acagcgacgt gggggagtac cgggcggtga        300
cggagctggg gcggcctgat gccgagtact ggaacagcca aaggacctc ctggagcaga        360 ggcgggccgc ggtggacacc tactgcagac acaactacgg ggttggtgag agcttcacag       420
tgcagcggcg agttgagcct aaggtgactg tgtatccttc aaagacccag ccctgcagc        480 accacaacct cctggtctgc tctgtgagtg gtttctatcc aggcagcatt gaagtcaggt       540
ggttccggaa cggccaggaa gagaaggctg gggtggtgtc cacaggcctg atccagaatg      600
gagattggac cttccagacc ctggtgatgc tggaaacagt tcctcggagt ggagaggttt      660
acacctgcca agtggagcac ccaagtgtga cgagccctct cacagtggaa tggagagcac      720
ggtctgaatc tgcacagagc aagatgctga gtggagtcgg gggcttcgtg ctgggcctgc      780
tcttccttgg ggccgggctg ttcatctact tcaggaatca gaaaggacac tctggacttc      840
agccaacagg attcctgagc tgaaatgcag atgaccacat tcaaggaaga accttctgtc      900
ccagctttgc agaatgaaaa gctttcctgc ttggcagtta ttcttccaca agagagggct      960
ttctcaggac ctggttgcta ctggttcggc aactgcagaa aatgtcctcc cttgtggctt     1020
cctcagctcc tgcccttggc ctgaagtccc agcattgatg acagcgcctc atcttcaact     1080
tttgtgctcc cctttgccta aaccgtatgg cctcccgtgc atctgtactc accctgtacg     1140
acaaacacat tacattatta aatgtttctc aaagatggag tt                        1182

<210> SEQ ID NO 25
<211> LENGTH: 1701
<212> TYPE: DNA
<213> ORGANISM: Homo sapiens

<400> SEQUENCE: 25
cggactcaag aagttctcag gactcagagg ctgggatcat ggtagatgga accctccttt        60
tactcctctc ggaggccctg gcccttaccc agacctgggc gggctcccac tccttgaagt       120
atttccacac ttccgtgtcc cggcccggcc gcggggagcc ccgcttcatc tctgtgggct       180
acgtggacga cacccagttc gtgcgcttcg acaacgacgc cgcgagtccg aggatggtgc      240
cgcgggcgcc gtggatggag caggaggggt cagagtattg ggaccgggag acacggagcg      300
ccagggacac cgcacagatt ttccgagtga acctgcggac gctgcgcggc tactacaatc      360
agagcgaggc cgggtctcac accctgcagt ggatgcatgg ctgcgagctg gggcccgacg     420
ggcgcttcct ccgcgggtat gaacagttcg cctacgacgg caaggattat ctcaccctga      480
atgaggacct gcgctcctgg accgcggtgg acacggcggc tcagatctcc gagcaaaagt      540
caaatgatgc ctctgaggcg gagcaccaga gagcctacct ggaagacaca tgcgtggagt      600
ggctccacaa atacctggag aaggggaagg agacgctgct tcacctggag cccccaaaga    660
cacacgtgac tcaccacccc atctctgacc atgaggccac cctgaggtgc tgggccctgg      720
gcttctaccc tgcggagatc acactgacct ggcagcagga tggggagggc catacccagg    780
acacggagct cgtggagacc aggcctgcag gggatggaac cttccagaag tgggcagctg    840
tggtggtgcc ttctgagag gagcagagat acacgtgcca tgtgcagcat gaggggctac    900
ccgagcccgt cacctgaga tggaagccgg cttcccagcc caccatcccc atcgtgggca      960
tcattgctgg cctggttctc cttgatctg tggtctctgg agctgtggtt gctgctgtga     1020
tatggaggaa gaagagctca ggtggaaaag gagggagcta ctctaaggct gagtggagcg   1080
```

| | |
|---|---:|
| acagtgccca ggggtctgag tctcacagct tgtaaagcct gagacagctg ccttgtgtgc | 1140 |
| gactgagatg cacagctgcc ttgtgtgcga ctgagatgca ggatttcctc acgcctcccc | 1200 |
| tatgtgtctt aggggactct ggcttctctt tttgcaaggg cctctgaatc tgtctgtgtc | 1260 |
| cctgttagca caatgtgagg aggtagagaa acagtccacc tctgtgtcta ccatgacccc | 1320 |
| cttcctcaca ctgacctgtg ttccttccct gttctctttt ctattaaaaa taagaacctg | 1380 |
| ggcagagtgc ggcagctcat gcctgtaatc ccagcactta gggaggccga ggagggcaga | 1440 |
| tcacgaggtc aggagatcga accatcctg gctaacacgg tgaaaccccg tctctactaa | 1500 |
| aaaatacaaa aaattagctg gcgcagagg cacgggcctg tagtcccagc tactcaggag | 1560 |
| gcggaggcag gagaatggcg tcaacccggg aggcggaggt tgcagtgagc caggattgtg | 1620 |
| cgactgcact ccagcctggg tgacagggtg aaacgccatc tcaaaaaata aaaattgaaa | 1680 |
| aataaaaaaa aaaaaaaaa a | 1701 |

<210> SEQ ID NO 26
<211> LENGTH: 1655
<212> TYPE: DNA
<213> ORGANISM: Homo sapiens

<400> SEQUENCE: 26

| | |
|---|---:|
| aatttctcac tgcccctgtg ataaactgtg tcactggct gtggcagcaa ctattataag | 60 |
| atgctctgaa aactcttcag acactgaggg gcaccagagg agcagactac aagaatggca | 120 |
| cacgctatgg aaaactcctg acaatcagt aaagagtacc atattgatga agaagtgggc | 180 |
| tttgctctgc caaatccaca ggaaaatcta cctgattttt ataatgactg gatgttcatt | 240 |
| gctaaacatc tgcctgatct catagagtct ggccagcttc gagaaagagt tgagaagtta | 300 |
| aacatgctca gcattgatca tctcacagac cacaagtcac agcgccttgc acgtctagtt | 360 |
| ctgggatgca tcaccatggc atatgtgtgg ggcaaaggtc atggagatgt ccgtaaggtc | 420 |
| ttgccaagaa atattgctgt tccttactgc caactctcca gaaactgga actgcctcct | 480 |
| attttggttt atgcagactg tgtcttggca aactggaaga aaaaggatcc taataagccc | 540 |
| ctgacttatg agaacatgga cgttttgttc tcatttcgtg atggagactg cagtaaagga | 600 |
| ttcttcctgg tctctctatt ggtggaaata gcagctgctt ctgcaatcaa agtaattcct | 660 |
| actgtattca aggcaatgca aatgcaagaa cgggacactt tgctaaaggc gctgttggaa | 720 |
| atagcttctt gcttggagaa agcccttcaa gtgtttcacc aaatccacga tcatgtgaac | 780 |
| ccaaaagcat ttttcagtgt tcttcgcata tatttgtctg gctggaaagg caaccccag | 840 |
| ctatcagacg gtctggtgta tgaagggttc tgggaagacc caaggagtt tgcagggggc | 900 |
| agtgcaggcc aaagcagcgt ctttcagtgc ttttgacgtcc tgctgggcat ccagcagact | 960 |
| gctggtggag gacatgctgc tcagttcctc caggacatga aagatatat gccaccagct | 1020 |
| cacaggaact tcctgtgctc attagagtca aatccctcag tccgtgagtt tgtcctttca | 1080 |
| aaaggtgatg ctggcctgcg ggaagcttat gacgcctgtg tgaaagctct ggtctccctg | 1140 |
| aggagctacc atctgcaaat cgtgactaag tacatcctga ttcctgcaag ccagcagcca | 1200 |
| aaggagaata gacctctga agacccttca aaactggaag ccaaggaac tggaggcact | 1260 |
| gatttaatga atttcctgaa gactgtaaga agtacaactg agaaatccct tttgaaggaa | 1320 |
| ggttaatgta acccaacaag agcacatttt atcatagcag agacatctgt atgcattcct | 1380 |
| gtcattaccc attgtaacag agccacaaac taatactatg caatgttta ccaataatgc | 1440 |
| aatacaaaag acctcaaaat acctgtgcat ttcttgtagg aaaacaacaa aaggtaatta | 1500 |

```
tgtgtaatta tactagaagt tttgtaatct gtatcttatc attggaataa aatgacattc      1560
aataaataaa aaaaaaaaaa aaaaaaaaaa aaaaaaaaaa aaaaaaaaaa aaaaaaaaaa      1620
aaaaaaaaaa aaaaaaaaaa aaaaaaaaaa aaaaa                                 1655

<210> SEQ ID NO 27
<211> LENGTH: 1995
<212> TYPE: DNA
<213> ORGANISM: Homo sapiens

<400> SEQUENCE: 27 acagggtga  aggcccagag  accagcagaa  cggcatccca  gccacgacgg  ccactttgct     60
ctgtctgctc  tccgccacgg  ccctgctctg  ttccctggga  caccccgcc   cccacctcct   120 caggctgcct  gatctgccca  gctttccagc  tttcctctgg  attccggcct  ctggtcatcc   180
ctccccaccc  tctctccaag  gccctctcct  ggtctccctt  cttctagaac  cccttcctcc   240
acctccctct  ctgcagaact  tctcctttac  ccccaccccc  caccactgc   cccctttcct   300 tttctgacct  ccttttggag  ggctcagcgc  tgcccagacc  ataggagaga  tgtgggaggc   360
tcagttcctg  ggcttgctgt  ttctgcagcc  gctttgggtg  gctccagtga  agcctctcca   420
gccaggggct  gaggtcccgg  tggtgtgggc  ccaggagggg  gctcctgccc  agctcccctg   480
cagccccaca  atcccctcc   aggatctcag  ccttctgcga  agagcagggg  tcacttggca   540
gcatcagcca  gacagtggcc  cgcccgctgc  cgccccggcc  catcccctgg  cccccggccc   600
tcacccggcg  gcgccctcct  cctgggggcc  caggccccgc  cgctacacgg  tgctgagcgt   660
gggtcccgga  ggcctgcgca  gcgggaggct  gccccctgcag  ccccgcgtcc  agctggatga   720
gcgcggccgg  cagcgcgggg  acttctcgct  atggctgcgc  ccagcccggc  gcgcggacgc   780
cggcgagtac  cgcgccgcgg  tgcacctcag  ggaccgcgcc  ctctcctgcc  gcctccgtct   840
gcgcctgggc  caggcctcga  tgactgccag  cccccccagga  tctctcagag  cctccgactg   900
ggtcattttg  aactgctcct  tcagccgccc  tgaccgccca  gcctctgtgc  attggttccg   960 gaaccgggggc  cagggccgag  tccctgtccg  ggagtccccc  catcaccact  tagcggaaag  1020
cttcctcttc  ctgccccaag  tcagcccccat  ggactctggg  ccctggggct  gcatcctcac  1080
ctacagagat  ggcttcaacg  tctccatcat  gtataacctc  actgttctgg  gtctggagcc  1140
cccaactccc  ttgacagtgt  acgctggagc  aggttccagg  gtggggctgc  cctgccgcct  1200
gcctgctggt  gtggggaccc  ggtctttcct  cactgccaag  tggactcctc  ctggggagg   1260 ccctgacctc  ctggtgactg  gagacaatgg  cgactttacc  cttcgactag  aggatgtgag  1320
ccaggcccag  gctgggacct  acacctgcca  tatccatctg  caggaacagc  agctcaatgc  1380
cactgtcaca  ttggcaatca  tcacagtgac  tcccaaatcc  tttgggtcac  ctggatccct  1440
ggggaagctg  ctttgtgagg  tgactccagt  atctggacaa  gaacgctttg  tgtggagctc  1500
tctggacacc  ccatcccaga  ggagtttctc  aggaccttgg  ctgaggcac   aggaggccca  1560 gctccttccc  cagccttggc  aatgccagct  gtaccagggg  gagaggcttc  ttggagcagc  1620
agtgtacttc  acagagctgt  ctagcccagg  tgcccaacgc  tctgggagag  ccccaggtgc  1680
cctcccagca  ggccacctcc  tgctgttcct  catccttggt  gtccttctc   tgctcctttt  1740 ggtgactgga  gcctttggct  ttcacctttg  gagaagacag  tggcgaccaa  gacgattttc  1800
tgccttagag  caagggattc  accctccgca  ggctcagagc  aagatagagg  agctggagca  1860
agaaccggag  ccggagccgg  agccggaacc  ggagcccgag  cccgagcccg  agccggagca  1920
```

-continued

| | |
|---|---|
| gctctgacct ggagctgagg cagccagcag atctcagcag cccagtccaa ataaactccc | 1980 |
| tgtcagcagc aaaaa | 1995 |

<210> SEQ ID NO 28
<211> LENGTH: 826
<212> TYPE: DNA
<213> ORGANISM: Homo sapiens

<400> SEQUENCE: 28

| | |
|---|---|
| tcatgtgaca aagcgcagga cccctcactg ccccaactgc ttgctgttct ctctttcttg | 60 |
| ggctctaagg acccaggagt ctgggtgcac agcctccttc tctctgagat caagagtct | 120 |
| gatcagcagc ctcttcctcc tccaggaccc agaagccctg agcttatccc catggagctc | 180 |
| tgccggtccc tggccctgct gggggggctcc ctgggcctga tgttctgcct gattgctttg | 240 |
| agcaccgatt tctggtttga ggctgtgggt cccacccact cagctcactc gggcctctgg | 300 |
| ccaacagggc atggggacat catatcaggc tacatccacg tgacgcagac cttcagcatt | 360 |
| atggctgttc tgtgggccct ggtgtccgtg agcttcctgg tcctgtcctg cttcccctca | 420 |
| ctgttccccc caggccacgg cccgcttgtc tcaaccaccg cagcctttgc tgcagccatc | 480 |
| tccatggtgg tggccatggc ggtgtacacc agcgagcggt gggaccagcc tccacacccc | 540 |
| cagatccaga ccttcttctc ctggtccttc tacctgggct gggtctcagc tatcctcttg | 600 |
| ctctgtacag gtgccctgag cctgggtgct cactgtggcg gtccccgtcc tggctatgaa | 660 |
| accttgtgag cagaaggcaa gagcggcaag atgagttttg agcgttgtat tccaaaggcc | 720 |
| tcatctggag cctcgggaaa gtctggtccc acatctgccc gcccttccag cccttcccca | 780 |
| gccccctcctc ttgtttcttc attcattcaa caaaatttgg ctggaa | 826 |

<210> SEQ ID NO 29
<211> LENGTH: 2418
<212> TYPE: DNA
<213> ORGANISM: Homo sapiens

<400> SEQUENCE: 29

| | |
|---|---|
| gcaaaccta agctgaatga caacttttc ttctcttgaa tatatcttaa cgccaaattt | 60 |
| tgagtgcttt tttgttaccc atcctcatat gtcccagcta gaaagaatcc tgggttggag | 120 |
| ctactgcatg ttgattgttt tgttttttcct tttggctgtt cattttggtg gctactataa | 180 |
| ggaaatctaa cacaaacagc aactgttttt tgttgtttac ttttgcatct ttacttgtgg | 240 |
| agctgtggca gtcctcata tcaaatacag aacatgatct tcctcctgct aatgttgagc | 300 |
| ctggaattgc agcttcacca gatagcagct ttattcacag tgacagtccc taaggaactg | 360 |
| tacataatag agcatggcag caatgtgacc ctggaatgca actttgacac tggaagtcat | 420 |
| gtgaaccttg gagcaataac agccagtttg caaaaggtgg aaaatgatac atccccacac | 480 |
| cgtgaaagag ccactttgct ggaggagcag ctgcccctag ggaaggcctc gttccacata | 540 |
| cctcaagtcc aagtgaggga cgaaggacag taccaatgca ataatcatcta tggggtcgcc | 600 |
| tgggactaca agtacctgac tctgaaagtc aaagcttcct acaggaaaat aaacactcac | 660 |
| atcctaaagg ttccagaaac agatgaggta gagctcacct gccaggctac aggttatcct | 720 |
| ctggcagaag tatcctggcc aaacgtcagc gttcctgcca acaccagcca ctccaggacc | 780 |
| cctgaaggcc tctaccaggt caccagtgtt ctgcgcctaa agccaccccc tggcagaaac | 840 |
| ttcagctgtg tgttctggaa tactcacgtg agggaactta ctttggccag cattgacctt | 900 |
| caaagtcaga tggaacccag gacccatcca acttggctgc ttcacatttt catcccctc | 960 |

```
tgcatcattg ctttcatttt catagccaca gtgatagccc taagaaaaca actctgtcaa    1020
aagctgtatt cttcaaaaga cacaacaaaa agacctgtca ccacaacaaa gagggaagtg    1080
aacagtgcta tctgaacctg tggtcttggg agccagggtg acctgatatg acatctaaag    1140
aagcttctgg actctgaaca agaattcggt ggcctgcaga gcttgccatt tgcacttttc    1200
aaatgccttt ggatgaccca gcactttaat ctgaaacctg caacaagact agccaacacc    1260
tggccatgaa acttgcccct tcactgatct ggactcacct ctggagccta tggctttaag    1320
caagcactac tgcactttac agaattaccc cactggatcc tggacccaca gaattccttc    1380
aggatccttc ttgctgccag actgaaagca aaaggaatta tttcccctca agttttctaa    1440
gtgatttcca aaagcagagg tgtgtggaaa tttccagtaa cagaaacaga tgggttgcca    1500
atagagttat tttttatcta tagcttcctc tgggtactag aagaggctat tgagactatg    1560
agctcacaga cagggcttcg cacaaactca aatcataatt gacatgtttt atggattact    1620
ggaatcttga tagcataatg aagttgttct aattaacaga gagcatttaa atatacacta    1680
agtgcacaaa ttgtggagta aagtcatcaa gctctgtttt tgaggtctaa gtcacaaagc    1740
atttgtttta acctgtaatg gcaccatgtt taatggtggt ttttttttg aactacatct    1800 ttcctttaaa aattattggt ttcttttat ttgttttac cttagaaatc aattatatac    1860
agtcaaaaat atttgatatg ctcatacgtt gtatctgcag caatttcaga taagtagcta    1920
aaatggccaa agccccaaac taagcctcct tttctggccc tcaatatgac tttaaatttg    1980
acttttcagt gcctcagttt gcacatctgt aatacagcaa tgctaagtag tcaaggcctt    2040
tgataattgg cactatggaa atcctgcaag atcccactac atatgtgtgg agcagaaggg    2100
taactcggct acagtaacag cttaattttg ttaaatttgt tctttatact ggagccatga    2160
agctcagagc attagctgac ccttgaacta ttcaaatggg cacattagct agtataacag    2220
acttacatag gtgggcctaa agcaagctcc ttaactgagc aaaatttggg gcttatgaga    2280
atgaaagggt gtgaaattga ctaacagaca aatcatacat ctcagtttct caattctcat    2340
gtaaatcaga gaatgccttt aaagaataaa actcaattgt tattcttcaa cgttctttat    2400
atattctact tttgggta                                                  2418

<210> SEQ ID NO 30
<211> LENGTH: 1009
<212> TYPE: DNA
<213> ORGANISM: Homo sapiens

<400> SEQUENCE: 30
agacgtgaag cctagcagag gacttttag ctgctcactg gccccgcttg tctggccgac      60
tcatccgccc gcgaccccta atccctctg cctgccccaa gatgctgaag ccagccctgg     120
agccccgagg gggcttctcc ttcgagaact gccaaagaaa tgcatcattg gaacgcgtcc     180
tcccggggct caaggtccct cacgcacgca agaccgggac caccatcgcg ggcctggtgt     240
tccaagacgg ggtcattctg ggcgccgata cgcgagccac taacgattcg gtcgtggcgg     300
acaagagctg cgagaagatc cacttcatcg cccccaaaat ctactgctgt ggggctggag     360
tagccgcgga cgccgagatg accacacgga tggtggcgtc caagatggag ctacacgcgt     420
tatctacggg ccgcgagccc gcgtggccca cggtcactcg catcctgcgc cagacgctct     480
tcaggtacca gggccacgtg ggtgcatcgc tgatcgtggg cggcgtagac ctgactggac     540
cgcagctcta cggcgtgcat ccccatggct cctacagccg tctgcccttc acagccctgg     600
```

| | |
|---|---|
| gctctggtca ggacgcggcc ctggcggtgc tagaagaccg gttccagccg aacatgacgc | 660 |
| tggaggctgc tcaggggctg ctggtggaag ccgtcaccgc cgggatcttg ggtgacctgg | 720 |
| gctccggggg caatgtggac gcatgtgtga tcacaaagac tggcgccaag ctgctgcgga | 780 |
| cactgagctc acccacagag cccgtgaaga ggtctggccg ctaccacttt gtgcctggaa | 840 |
| ccacagctgt cctgacccag acagtgaagc cactaaccct ggagctagtg gaggaaactg | 900 |
| tgcaggctat ggaggtggag taagctgagg cttagagctt ggaacaaggg ggaataaacc | 960 |
| cagaaaatac agttaaacaa aaaaaaaaaa aaaaaaaaa aaaaaaaa | 1009 |

<210> SEQ ID NO 31
<211> LENGTH: 4157
<212> TYPE: DNA
<213> ORGANISM: Homo sapiens

<400> SEQUENCE: 31

| | |
|---|---|
| agcggggcgg ggcgccagcg ctgccttttc tcctgccggg tagtttcgct ttcctgcgca | 60 |
| gagtctgcgg aggggctcgg ctgcaccggg gggatcgcgc ctggcagacc ccagaccgag | 120 |
| cagaggcgac ccagcgcgct cgggagaggc tgcaccgccg cgccccgcc tagcccttcc | 180 |
| ggatcctgcg cgcagaaaag tttcatttgc tgtatgccat cctcgagagc tgtctaggtt | 240 |
| aacgttcgca ctctgtgtat ataacctcga cagtcttggc acctaacgtg ctgtgcgtag | 300 |
| ctgctccttt ggttgaatcc ccaggccctt gttggggcac aaggtggcag gatgtctcag | 360 |
| tggtacgaac ttcagcagct tgactcaaaa ttcctggagc aggttcacca gctttatgat | 420 |
| gacagttttc cctatgaaat cagacagtac ctggcacagt ggttagaaaa gcaagactgg | 480 |
| gagcacgctg ccaatgatgt ttcatttgcc accatccgtt ttcatgaccct cctgtcacag | 540 |
| ctggatgatc aatatagtcg cttttctttg gagaataact tcttgctaca gcataacata | 600 |
| aggaaaagca agcgtaatct tcaggataat tttcaggaag acccaatcca gatgtctatg | 660 |
| atcatttaca gctgtctgaa ggaagaaagg aaaattctgg aaaacgccca gagatttaat | 720 |
| caggctcagt cggggaatat tcagagcaca gtgatgttag acaaacagaa agagcttgac | 780 |
| agtaaagtca gaaatgtgaa ggacaaggtt atgtgtatag agcatgaaat caagagcctg | 840 |
| gaagatttac aagatgaata tgacttcaaa tgcaaaacct tgcagaacag agaacacgag | 900 |
| accaatggtg tggcaaagag tgatcagaaa caagaacagc tgttactcaa gaagatgtat | 960 |
| ttaatgcttg acaataagag aaaggaagta gttcacaaaa taatagagtt gctgaatgtc | 1020 |
| actgaactta cccagaatgc cctgattaat gatgaactag tggagtggaa gcggagacag | 1080 |
| cagagcgcct gtattggggg gccgcccaat gcttgcttgg atcagctgca gaactggttc | 1140 |
| actatagttg cggagagtct gcagcaagtt cggcagcagc ttaaaaagtt ggaggaattg | 1200 |
| gaacagaaat acacctacga acatgaccct atcacaaaaa acaaacaagt gttatgggac | 1260 |
| cgcaccttca gtctttttcca gcagctcatt cagagctcgt ttgtggtgga agacagccc | 1320 |
| tgcatgccaa cgcacccctca gaggccgctg gtcttgaaga caggggtcca gttcactgtg | 1380 |
| aagttgagac tgttggtgaa attgcaagag ctgaattata atttgaaagt caaagtctta | 1440 |
| tttgataaag atgtgaatga gagaaataca gtaaaaggat ttaggaagtt caacattttg | 1500 |
| ggcacgcaca caaaagtgat gaacatggag gagtccacca atggcagtct ggcggctgaa | 1560 |
| tttcggcacc tgcaattgaa agaacagaaa aatgctggca ccagaacgaa tgagggtcct | 1620 |
| ctcatcgtta ctgaagagct tcactccctt agttttgaaa cccaattgtg ccagcctggt | 1680 |
| ttggtaattg acctcgagac gacctctctg cccgttgtgg tgatctccaa cgtcagccag | 1740 |

```
ctcccgagcg gttgggcctc catcctttgg tacaacatgc tggtggcgga acccaggaat    1800
ctgtccttct tcctgactcc accatgtgca cgatgggctc agctttcaga agtgctgagt    1860
tggcagtttt cttctgtcac caaaagaggt ctcaatgtgg accagctgaa catgttggga    1920
gagaagcttc ttggtcctaa cgccagcccc gatggtctca ttccgtggac gaggttttgt    1980
aaggaaaata taaatgataa aaattttccc ttctggcttt ggattgaaag catcctagaa    2040
ctcattaaaa aacacctgct ccctctctgg aatgatgggt gcatcatggg cttcatcagc    2100
aaggagcgag agcgtgccct gttgaaggac cagcagccgg gaccttcct gctgcggttc     2160
agtgagagct cccgggaagg ggccatcaca ttcacatggg tggagcggtc ccagaacgga    2220
ggcgaacctg acttccatgc ggttgaaccc tacacgaaga agaactttc tgctgttact     2280
ttccctgaca tcattcgcaa ttacaaagtc atggctgctg agaatattcc tgagaatccc    2340
ctgaagtatc tgtatccaaa tattgacaaa gaccatgcct ttggaaagta ttactccagg    2400
ccaaaggaag caccagagcc aatgaacttg atggcccta aaggaactgg atatatcaag     2460
actgagttga tttctgtgtc tgaagttcac ccttctagac ttcagaccac agacaacctg    2520
ctccccatgt ctcctgagga gtttgacgag gtgtctcgga gtgggctc tgtagaattc      2580
gacagtatga tgaacacagt atagagcatg aattttttc atcttctctg gcgacagttt    2640
tccttctcat ctgtgattcc ctcctgctac tctgttcctt cacatcctgt gtttctaggg    2700
aaatgaaaga aaggccagca aattcgctgc aacctgttga tagcaagtga attttctct    2760
aactcagaaa catcagttac tctgaagggc atcatgcatc ttactgaagg taaaattgaa    2820
aggcattctc tgaagagtgg gtttcacaag tgaaaaacat ccagatacac ccaaagtatc    2880
aggacgagaa tgagggtcct ttgggaaagg agaagttaag caacatctag caaatgttat    2940
gcataaagtc agtgcccaac tgttataggt tgttggataa atcagtggtt atttagggaa    3000
ctgcttgacg taggaacggt aaatttctgt gggagaattc ttacatgttt tctttgcttt    3060
aagtgtaact ggcagttttc cattggttta cctgtgaaat agttcaaagc caagtttata    3120
tacaattata tcagtcctct ttcaaaggta gccatcatgg atctggtagg gggaaaatgt    3180
gtattttatt acatctttca cattggctat ttaaagacaa agacaaattc tgtttcttga    3240
gaagagaata ttagctttac tgtttgttat ggcttaatga cactagctaa tatcaataga    3300
aggatgtaca tttccaaatt cacaagttgt gtttgatatc caaagctgaa tacattctgc    3360
tttcatcttg gtcacataca attatttta cagttctccc aagggagtta ggctattcac    3420
aaccactcat tcaaaagttg aaattaacca tagatgtaga taaactcaga aatttaattc    3480
atgtttctta aatgggctac tttgtccttt ttgttattag ggtggtattt agtctattag    3540
ccacaaaatt gggaaaggag tagaaaaagc agtaactgac aacttgaata atacaccaga    3600
gataatatga gaatcagatc atttcaaaac tcatttccta tgtaactgca ttgagaactg    3660
catatgtttc gctgatatat gtgtttttca catttgcgaa tggttccatt ctctctcctg    3720
tacttttttcc agacactttt ttgagtggat gatgtttcgt gaagtatact gtattttttac  3780
cttttttcctt ccttatcact gacacaaaaa gtagattaag agatgggttt gacaaggttc   3840
ttccctttta catactgctg tctatgtggc tgtatcttgt ttttccacta ctgctaccac   3900
aactatatta tcatgcaaat gctgtattct tctttggtgg agataaagat ttcttgagtt   3960
ttgttttaaa attaaagcta aagtatctgt attgcattaa atataaatatg cacacagtgc  4020
tttccgtggc actgcataca atctgaggcc tcctctctca gttttttatat agatggcgag  4080
```

```
aacctaagtt tcagttgatt ttacaattga aatgactaaa aaacaaagaa gacaacatta    4140
aaacaatatt gtttcta                                                    4157

<210> SEQ ID NO 32
<211> LENGTH: 2139
<212> TYPE: DNA
<213> ORGANISM: Homo sapiens

<400> SEQUENCE: 32
acatctgctt cctgtaggcc ctctgggcag aagcatgcgc tggtgtctcc tcctgatctg      60
ggcccagggg ctgaggcagg ctcccctcgc ctcaggaatg atgacaggca caatagaaac     120 aacgggaac atttctgcag agaaaggtgg ctctatcatc ttacaatgtc acctctcctc      180
caccacggca caagtgaccc aggtcaactg ggagcagcag gaccagcttc tggccatttg     240
taatgctgac ttggggtggc acatctcccc atccttcaag gatcgagtgg ccccaggtcc     300
cggcctgggc cttaccctcc agtcgctgac cgtgaacgat acaggggagt acttctgcat     360
ctatcacacc taccctgatg gggcgtacac tgggagaatc ttcctggagg tcctagaaag     420
ctcagtggct gagcacggtg ccaggttcca gattccattg cttggagcca tggccgcgac     480
gctggtggtc atctgcacag cagtcatcgt ggtggtcgcg ttgactagaa agaagaaagc     540
cctcagaatc cattctgtgg aaggtgacct caggagaaaa tcagctggac aggaggaatg     600
gagccccagt gctccctcac ccccaggaag ctgtgtccag gcagaagctg cacctgctgg     660
gctctgtgga gagcagcggg gagaggactg tgccgagctg catgactact tcaatgtcct     720
gagttacaga agcctgggta actgcagctt cttcacagag actggttagc aaccagaggc     780
atcttctgga agatacactt ttgtctttgc tattatagat gaatatataa gcagctgcac     840
tctccatcag tgctgcgtgt gtgtgtgtgt gtgtatgtgt gtgtgtgttc agttgagtga     900
ataaatgtca tcctcttctc catcttcatt tccttggcct tttcgttcta ttccattttg     960
cattatggca ggcctagggt gagtaacgtg gatcttgatc ataaatgcaa aattaaaaaa    1020
tatcttgacc tggttttaaa tctggcagtt tgagcagatc ctatgtctct gagagacaca    1080
ttcctcataa tggccagcat tttgggctac aaggttttgt ggttgatgat gaggatggca    1140
tgactgcaga gccatcctca tctcattttt tcacgtcatt ttcagtaact ttcactcatt    1200
caaaggcagg ttataagtaa gtcctggtag cagcctctat ggggagattt gagagtgact    1260
aaatcttggt atctgccctc aagaacttac agttaaatgg ggagacaatg ttgtcatgaa    1320
aaggtattat agtaaggaga gaaggagaca tacacaggcc ttcaggaaga gacgacagtt    1380
tggggtgagg tagttggcat aggcttatct gtgatgaagt ggcctgggag caccaagggg    1440
atgttgaggc tagtctggga ggagcaggag ttttgtctag ggaacttgta ggaaattctt    1500
ggagctgaaa gtcccacaaa gaaggccctg gcaccaaggg agtcagcaaa cttcagattt    1560
tattctctgg gcaggcattt caagtttcct tttgctgtga catactcatc cattagacag    1620
cctgatacag gcctgtagcc tcttccggcc gtgtgtgctg gggaagcccc aggaaacgca    1680
catgcccaca cagggagcca agtcgtagca tttgggcctt gatctacctt ttctgcatca    1740
atacactctt gagcctttga aaaagaacg tttcccacta aaaagaaaat gtggattttt    1800 aaaatagga ctcttcctag gggaaaaagg ggggctggga gtgatagagg gtttaaaaaa    1860
taaacacctt caaactaact tcttcgaacc cttttattca ctccctgacg actttgtgct    1920
ggggttgggg taactgaact gcttattct gtttaattgc attcaggctg gatcttagaa     1980 gactttatc cttccaccat ctctctcaga ggaatgagcg gggaggttgg atttactggt    2040
```

```
gactgatttt ctttcatggg ccaaggaact gaaagagaat gtgaagcaag gttgtgtctt    2100
gcgcatggtt aaaaataaag cattgtcctg cttcctaag                           2139

<210> SEQ ID NO 33
<211> LENGTH: 3360
<212> TYPE: DNA
<213> ORGANISM: Homo sapiens

<400> SEQUENCE: 33
gcgccagctt ggagagccag ccccatcggg gttccccgcc gccggaagcg gaaatagcac      60
cgggcgccgc cacagtagct gtaactgcca ccgcgatgcc gaaggcgccc aagcagcagc     120
cgccggagcc cgagtggatc ggggacggag agagcacgag cccatcagac aaagtggtga     180
agaaagggaa gaaggacaag aagatcaaaa aaacgttctt tgaagagctg gcagtagaag     240
ataaacaggc tggggaagaa gagaaagtgc tcaaggagaa ggagcagcag cagcagcaac     300
agcaacagca gcaaaaaaaa aagcgagata cccgaaaagg caggcggaag aaggatgtgg     360
atgatgatgg agaagagaaa gagctcatgg agcgtcttaa gaagctctca gtgccaacca     420
gtgatgagga ggatgaagta cccgccccaa aaccccgcgg agggaagaaa accaaggggtg     480 gtaatgtttt tgcagccctg attcaggatc agagtgagga gaggaggag gaagaaaaac     540 atcctcctaa gcctgccaag ccggagaaga atcggatcaa taaggccgta tctgaggaac     600
agcagcctgc actcaagggc aaaaagggaa aggaagagaa gtcaaaaggg aaggctaagc     660
ctcaaaataa attcgctgct ctggacaatg aagaggagga taagaagaa gaaattataa     720 aggaaaagga gcctcccaaa caagggaagg agaaggccaa aaggcagag cagatggagt     780 atgagcgcca agtggcttca ttaaaagcag ccaatgcagc tgaaaatgac ttctccgtgt     840
cccaggcgga gatgtcctcc cgccaagcca tgttagaaaa tgcatctgac atcaagctgg     900
agaagttcag catctccgct catggcaagg agctgttcgt caatgcagac ctgtacattg     960
tagccggccg ccgctacggg ctggtaggac ccaatggcaa gggcaagacc acactcctca    1020
agcacattgc caaccgagcc ctgagcatcc ctcccaacat tgatgtgttg ctgtgtgagc    1080
aggaggtggt agcagatgag acaccagcag tccaggctgt tcttcgagct gacaccaagc    1140
gattgaagct gctggaagag gagcggcggc ttcagggaca gctggaacaa ggggatgaca    1200
cagctgctga gaggctagag aaggtgtatg aggaattgcg ggccactggg gcggcagctg    1260
cagaggccaa agcacggcgg atcctggctg gcctgggctt tgaccctgaa atgcagaatc    1320
gacccacaca gaagttctca gggggctggc gcatgcgtgt ctccctggcc agggcactgt    1380
tcatggagcc cacactgctg atgctggatg agcccaccaa ccacctggac ctcaacgctg    1440
tcatctggct taataactac ctccagggct ggcggaagac cttgctgatc gtctcccatg    1500
accagggctt cttggatgat gtctgcactg atatcatcca cctcgatgcc cagcggctcc    1560
actactatag gggcaattac atgaccttca aaaagatgta ccagcagaag cagaaagaac    1620
tgctgaaaca gtatgagaag caagagaaaa agctgaagga gctgaaggca ggcgggaagt    1680
ccaccaagca ggcggaaaaa caaacgaagg aagccctgac tcggaagcag cagaaatgcc    1740
gacgaaaaaa ccaagatgag gaatcccagg aggcccctga gctcctgaag cgccctaagg    1800
agtacactgt gcgcttcact tttccagacc ccccaccact cagccctcca gtgctgggtc    1860
tgcatggtgt gacattcggc taccagggac agaaaccact cttttaagaac ttggattttg    1920 gcatcgacat ggattcaagg atttgcattg tgggccctaa tggtgtgggg aagagtacgc    1980
```

```
tactcctgct gctgactggc aagctgacac cgacccatgg ggaaatgaga agaaccacc      2040 ggctgaaaat tggcttcttc aaccagcagt atgcagagca gctgcgcatg gaggagacgc    2100
ccactgagta cctgcagcgg ggcttcaacc tgccctacca ggatgcccgc aagtgcctgg    2160
gccgcttcgg cctggagagt cacgcccaca ccatccagat ctgcaaactc tctggtggtc    2220
agaaggcgcg agttgtgttt gctgagctgg cctgtcggga acctgatgtc ctcatcttgg    2280
acgagccaac caataacctg gacatagagt ctattgatgc tctaggggag gccatcaatg    2340
aatacaaggg tgctgtgatc gttgtcagcc atgatgcccg actcatcaca gaaaccaatt    2400
gccagctgtg ggtggtggag gagcagagtg ttagccaaat cgatggtgac tttgaagact    2460
acaagcggga ggtgttggag gccctgggtg aagtcatggt cagccggccc cgagagtgag    2520
ctttccttcc cagaagtctc ccgagagaca tatttgtgtg cctagaagt cctctgtggt     2580 ctcccctcct ctgaagactg cctctggcct gcagctgacc tggcaaccat tcaggcacat    2640
gaaggtggag tgtgaccttg atgtgaccgg gatcccactc tgattgcatc catttctctg    2700
aaagacttgt ttgttctgct tctcttcata taactgagct ggccttatcc ttggcatccc    2760
cctaaacaaa caagaggtga ccaccttatt gtgaggttcc atccagccaa gtttatgtgg    2820
cctattgtct caggactctc atcactcaga agcctgcctc tgatttaccc tacagcttca    2880
ggcccagctg cccccagtc tttgggtggt gctgttcttt tctggtggat ttaatgctga     2940
ctcactggta caaacagctg ttgaagctca gagctggagg tgagcttctg aggcctttgc    3000
cattatccag cccaagattt ggtgcctgca gcctcttgtc tggttgagga cttggggcag    3060
gaaaggaatg ctgctgaact tgaatttccc tttacaaggg gaagaaataa aggaaaggag    3120
ttgctgccga cctgtcactg tttggagatt gatgggagtt ggaactgttc tcagtcttga    3180
tttgctttat tcagttttct agcagctttt aatagtcccc tcttccccac taaatggatc    3240
ttgtttgcag tcttgctgac agtgtttgct gtttaaggat cataggattc cttcccccca    3300
acccttcacg caaggaaaaa gcaaagtgat tcataccttc tatcttggaa aaaaaaaaa    3360
```

<210> SEQ ID NO 34
<211> LENGTH: 4026
<212> TYPE: DNA
<213> ORGANISM: Homo sapiens

<400> SEQUENCE: 34

```
cccccttggcc ccgccccacc ctgctttgcc ctgcctctcc ctgccccgcc gcgcccccagt   60 cccttgacga ccctcctctc tgggcccgcg ccctcccgct tcggggtcaa gccccagaga    120
gcgccgcgaa aaccacattt cccagagtgc accgcgacgg caggggtcct cagaccggcg    180
ctcgctcgcc ggcgccatcc ctatagagaa gaacggaggc acggcctgtg gtcatggcgc    240
tgttcccagc cttttgcgggg cttagtgagg ctcccgatgg cgggagctcc aggaaagagt    300
tagactggct gagcaaccca agcttttgtg ttggatccat aacgtccctg agccaacaaa    360
ctgaagcagc tccagcccat gtttctgaag ggttaccgct gacaaggagt catctgaaat    420
cagagtcttc agatgaaagt gacactaaca aaaagctcaa acaaacaagt agaaaaaaga    480
agaaagagaa aaagaaaaaa aggaagcatc agcatcataa gaaaacaaag aggaagcatg    540
ggccgtcgag tagcagcagg tctgagacag acaccgattc tgaaaaggac aaaccttcca    600
gaggcgttgg aggcagtaaa aaggaatctg aggaaccgaa tcaaggaaat aatgctgcag    660
ctgatactgg acatcgcttt gtttggcttg aggacattca ggctgtgacg ggagaaacct    720
tcagaacaga taagaaacca gatcctgcga actgggagta caagtctctc taccgagggg    780
```

| | |
|---|---|
| atatagcaag atacaagagg aaaggagact cctgccttgg cattaaccct aagaagcagt | 840 |
| gcatatcttg ggaagggact tccacagaga agaagcattc acgcaagcag gttgaacgct | 900 |
| attttactaa gaagagtgtg ggattaatga acatcgatgg agttgccatt agcagtaaaa | 960 |
| ctgaacctcc ctcatctgag cccatctcct ttataccagt gaaggacttg gaagatgcgg | 1020 |
| ctcctgttac aacctggttg aatcctctgg ggatttatga tcagtcaacc acacattggc | 1080 |
| tacaaggaca gggtcctcca gagcaggaat caaagcagcc agacgcacag ccagacagcg | 1140 |
| agagtgcggc tctcaaggcc aaggtggagg agtttaacag gagggtgcgg gagaatcctc | 1200 |
| gggatacgca gctgtggatg gcatttgttg cttttcagga cgaggtcatg aaaagtcctg | 1260 |
| gcctgtatgc catcgaggaa ggagagcagg aaaagcgaaa gaggtccctg aagctcattc | 1320 |
| tggagaagaa gctggccatt ctggagcggg ccattgagga caaccagagc agtgtggatc | 1380 |
| tgaaactggc caagctgaag ctctgcacag agttctggga gccctccact ctggtcaaag | 1440 |
| agtggcagaa actgatattt ttgcatccca ataatacagc cctttggcag aaataccttt | 1500 |
| tattttgcca gagccagttt agtaccttt cgatatcaaa aattcacagt ctttatggaa | 1560 |
| aatgcttgag cactttgtct gctgttaagg acggcagcat cttatctcac cctgcgttgc | 1620 |
| ctggcacgga agaggccatg tttgcactct ttcttcagca gtgccacttt ctgcggcagg | 1680 |
| ctggccactc tgagaaggcc atctcattgt tccaggccat ggtggacttc accttcttca | 1740 |
| aacccgacag cgtgaaagat ctgcctacca aaggacaggt ggaattcttt gaacccttt | 1800 |
| gggacagtgg agagcccgg gctggggaga agggagcccg aggctggaag gcgtggatgc | 1860 |
| accagcagga acgaggtggc tgggtggtca tcaacccaga tgaggatgac gatgaaccag | 1920 |
| aagaggatga ccaggaaata aaagataaga ctctgcccag gtggcagatc tggcttgctg | 1980 |
| ctgagcgttc ccgtgaccag aggcactggc ggccctggcg ccctgataag accaagaagc | 2040 |
| aaaccgagga agactgtgag gatcccgaga cacaggtgtt gtttgatgat attgggcaat | 2100 |
| cttttgatcag actttccagc catgatcttc agttccagct ggtggaggcc ttcctgcagt | 2160 |
| tcttgggtgt gccttctggc tttactcctc cagcctcctg tctttatctg gccatggatg | 2220 |
| agaacagcat ctttgataat ggactttatg atgaaaagcc cttgactttt ttcaacccctt | 2280 |
| tgttttctgg ggctagctgt gttggccgca tggataggtt gggctatcct cgctggacca | 2340 |
| ggggtcagaa ccgagagggc gaggagttca tccgcaatgt cttccacctt gtcatgcctt | 2400 |
| tattttcagg caaagagaag tcccagctct gcttctcctg gttacagtat gagattgcaa | 2460 |
| aggtcatttg gtgcctgcac actaaaaaca agaagagatt aaagtctcaa gggaagaact | 2520 |
| gcaaaaaact agccaagaat ctccttaagg agccagaaaa ctgcaacaac ttttgcctgt | 2580 |
| ggaagcagta tgcacatctg gagtggttgc ttggcaacac ggaggatgcc agaaaagttt | 2640 |
| ttgacacagc acttggcatg gcaggaagca gagaactgaa agactctgac ctctgtgagc | 2700 |
| tcagtctgct ctatgctgag ctggaggtgg agctgtcgcc agaagtgaga agggctgcca | 2760 |
| cagctcgagc tgttcacata ttaaccaagc tgactgagag cagcccctat gggccctaca | 2820 |
| ctggacaggt gttggctgtt cacattttga aagcgcgaaa ggcttatgag cacgcactgc | 2880 |
| aggactgttt gggtgacagc tgtgtctcca atccagctcc caccgattcc tgtagccgcc | 2940 |
| taattagcct ggctaaatgc ttcatgctct tccagtattt gaccataggg attgatgctg | 3000 |
| ctgtgcagat atacgaacag gtgtttgtaa aactgaacag ttctgttttc ccagaaggct | 3060 |
| ctggcgaggg ggacagtgcc agctcccaga gttggaccag tgttctcgaa gccatcacac | 3120 |

| | |
|---|---|
| tgatgcacac gagcctgctg agattccaca tgaaagtgag tgtttacccg ctggcccctc | 3180 |
| tgcgagaggc actctcacag gctttaaagt tgtatccagg caaccaggtt ctttggaggt | 3240 |
| cctatgtaca gattcagaat aagtcccaca gtgccagcaa aaccaggaga ttttttgaca | 3300 |
| caatcaccag gtctgccaaa cccttggagc cttggttgtt tgcaattgaa gctgagaaac | 3360 |
| tgaggaagag actggtggaa actgtccaga ggttagacgg tagagagatc cacgccacaa | 3420 |
| ttcctgagac cggcttaatg catcggatcc aagccctgtt tgaaaatgcc atgcgcagcg | 3480 |
| acagtggcag ccagtgcccc ttgctgtgga ggatgtattt gaactttctg gtttccttag | 3540 |
| gaaataaaga aagaagcaaa ggtgtattct acaaagcact tcagaattgc ccttgggcaa | 3600 |
| aggtgttgta cctggacgcc gtggagtatt tcccccgatga gatgcaggag atcctggacc | 3660 |
| tgatgactga gaaggagctc cgggtgcgcc tgccgctgga ggagctggag ctgctgctgg | 3720 |
| aggattagag agcagcggga aaacgggctg tgcctgcgag gccaagttgc ccaccctgcg | 3780 |
| gagctaggag gcgcgagcag agaacgtgtg tgttaggaga actcggcttt tgaaatgttc | 3840 |
| tttctcgata gtaataatgt gggctgccag cctctcacat cttgcacact tttgggtgt | 3900 |
| gtaaatgaca caaaagttat ttacatatta tatatgtgaa tatgtgtata tatgtacata | 3960 |
| gccagagagt catgccacgt ggtcattaaa ccgatgatga ttgaggcgtg aaaaaaaaaa | 4020 |
| aaaaaa | 4026 |

<210> SEQ ID NO 35
<211> LENGTH: 2650
<212> TYPE: DNA
<213> ORGANISM: Homo sapiens

<400> SEQUENCE: 35

| | |
|---|---|
| agggacagcc cagaggaggc gtggccacgc tgccggcgga agtggagccc tccgcgagcg | 60 |
| cgcgaggccg ccggggcagg cggggaaacc ggacagtagg ggcggggccg ggccggcgat | 120 |
| ggggatgcgg gagcactacg cggagctgca cccgtgcccg ccggaattgg ggatgcagag | 180 |
| cagcggcagc gggtatggca gcagccggc gggccggcct ccagcgcagg tgcccgagag | 240 |
| gcagggctg gcctgggatg cgcgcgcacc tgccctcgcc ccgccccgcc cgcacgaggg | 300 |
| gtggtggccg aggccccgcc ccgcacgcct cgcctgaggc gggtccgctc agcccaggcg | 360 |
| cccgcccccg ccccgccga ttaaatgggc cggcggggct cagcccccgg aaacggtcgt | 420 |
| aacttcgggg ctgcgagcgc ggagggcgac gacgacgaag cgcagacagc gtcatggcag | 480 |
| agcaggtggc cctgagccgg acccaggtgt gcgggatcct gcgggaagag ctttttccagg | 540 |
| gcgatgcctt ccatcagtcg gatacacaca tattcatcat catgggtgca tcgggtgacc | 600 |
| tggccaagaa gaagatctac cccaccatct ggtggctgtt ccgggatggc cttctgcccg | 660 |
| aaaacacctt catcgtgggc tatgcccgtt cccgcctcac agtggctgac atccgcaaac | 720 |
| agagtgagcc cttcttcaag gccaccccag aggagaagct caagctggag gacttctttg | 780 |
| cccgcaactc ctatgtggct ggccagtacg atgatgcagc ctcctaccag cgcctcaaca | 840 |
| gccacatgga tgccctccac ctggggtcac aggccaaccg cctcttctac ctggccttgc | 900 |
| ccccgaccgt ctacgaggcc gtcaccaaga acattcacga gtcctgcatg agccagatag | 960 |
| gctggaaccg catcatcgtg gagaagccct cgggaggga cctgcagagc tctgaccggc | 1020 |
| tgtccaacca catctcctcc ctgttccgtg aggaccagat ctaccgcatc gaccactacc | 1080 |
| tgggcaagga gatggtgcag aacctcatgg tgctgagatt tgccaacagg atcttcggcc | 1140 |
| ccatctggaa ccgggacaac atcgcctgcg ttatcctcac cttcaaggag ccctttggca | 1200 |

```
ctgagggtcg cggggctat ttcgatgaat ttgggatcat ccgggacgtg atgcagaacc    1260
acctactgca gatgctgtgt ctggtggcca tggagaagcc cgcctccacc aactcagatg    1320
acgtccgtga tgagaaggtc aaggtgttga aatgcatctc agaggtgcag gccaacaatg    1380
tggtcctggg ccagtacgtg gggaaccccg atggagaggg cgaggccacc aaagggtacc    1440
tggacgaccc cacggtgccc cgcgggtcca ccaccgccac ttttgcagcc gtcgtcctct    1500
atgtggagaa tgagaggtgg gatggggtgc ccttcatcct gcgctgcggc aaggccctga    1560
acgagcgcaa ggccgaggtg aggctgcagt ccatgatgt ggccggcgac atcttccacc    1620
agcagtgcaa gcgcaacgag ctggtgatcc gcgtgcagcc caacgaggcc gtgtacacca    1680
agatgatgac caagaagccg ggcatgttct tcaaccccga ggagtcggag ctggacctga    1740
cctacggcaa cagatacaag aacgtgaagc tccctgacgc ctacgagcgc ctcatcctgg    1800
acgtcttctg cgggagccag atgcacttcg tgcgcagcga cgagctccgt gaggcctggc    1860 gtatttcac cccactgctg caccagattg agctggagaa gcccaagccc atcccctata    1920
tttatggcag ccgaggcccc acggaggcag acgagctgat gaagagagtg ggtttccagt    1980
atgagggcac ctacaagtgg gtgaaccccc acaagctctg agccctgggc acccactcc    2040 accccgcca cggccaccct ccttcccgcc gcccgaccc gagtcgggag gactccggga    2100
ccattgacct cagctgcaca ttcctggccc gggctctgg ccaccctggc ccgccctcg    2160 ctgctgctac tacccgagcc cagctacatt cctcagctgc aagcactcg agaccatcct    2220 ggccccctcca gaccctgcct gagcccagga gctgagtcac ctcctccact cactccagcc    2280
caacagaagg aaggaggagg gcgcccattc gtctgtccca gagcttattg gccactgggt    2340
ctcactcctg agtggggcca gggtggggag gagggacaag gggaaggaa gggcgagca    2400 cccacgtgag agaatctgcc tgtggccttg cccgccagcc tcagtgccac ttgacattcc    2460
ttgtcaccag caacatctcg agcccctggg atgtcccctg tcccaccaac tctgcactcc    2520
atggccaccc cgtgccaccc gtaggcagcc tctctgctat aagaaaagca gacgcagcag    2580
ctgggacccc tcccaacctc aatgccctgc cattaaatcc gcaaacagcc aaaaaaaaa    2640 aaaaaaaaaa                                                           2650
```

<210> SEQ ID NO 36
<211> LENGTH: 1146
<212> TYPE: DNA
<213> ORGANISM: Homo sapiens

<400> SEQUENCE: 36

```
ttttgcgaac ggcgagcagc ggcggcggcg cggagagacg cagcggaggt tttcctggtt     60
tcggacccca gcgccggat ggtgaaatcc tccctgcagc ggatcctcaa tagccactgc    120
ttcgccagag agaaggaagg ggataaaccc agcgccacca tccacgccag ccgcaccatg    180
ccgctcctaa gcctgcacag ccgcggcgg agcagcagtg agagttccag ggtctccctc    240
cactgctgta gtaacccggg tccggggcct cggtggtgct cctgatgccc ctcacccacc    300
cctgaagatc ccaggtgggc gagggaatag tcagagggat cacaatcttt cagctaactt    360
attctactcc gatgatcggc tgaatgtaac agaggaacta acgtccaacg acaagacgag    420
gattctcaac gtccagtcca ggctcacaga cgccaaacgc attaactggc gaacagtgct    480
gagtggcggc agcctctaca tcgagatccc gggcggcgcg ctgccgagg ggagcaagga    540 cagctttgca gttctcctgg agttcgctga ggagcagctg cgagccgacc atgtcttcat    600
```

```
ttgcttccac aagaaccgcg aggacagagc cgccttgctc cgaaccttca gcttttgggg      660
ctttgagatt gtgagaccgg ggcatcccct tgtccccaag agacccgacg cttgcttcat      720
ggcctacacg ttcgagagag agtcttcggg agaggaggag gagtagggcc gcctcggggc      780
tgggcatccg gcccctgggg ccacccctcg tcagccgggt gggtaggaac cgtagactcg      840
ctcatctcgc ctgggtttgt ccgcatgttg taatcgtgca aataaacgct cactccgaat      900
tagcggtgta tttcttgaag tttaatattg tgtttgtgat actgaagtat ttgctttaat      960
tctaaataaa aatttatatt ttactttttt attgctggtt taagatgatt cagattatcc     1020
ttgtactttg aggagaagtt tcttatttgg agtcttttgg aaacagtctt agtcttttaa     1080
cttggaaaga tgaggtatta atcccctcca ttgctctcca aaagccaata aagtgattac     1140
acccga                                                                1146

<210> SEQ ID NO 37
<211> LENGTH: 6732
<212> TYPE: DNA
<213> ORGANISM: Homo sapiens

<400> SEQUENCE: 37
gagagcgcgg ccgggacggt tggagaagaa ggcggctccc cggaaggggg agagacaaac       60
tgccgtaacc tctgccgttc aggaacccgg ttacttattt attcgttacc cttttttctc     120
ttcctccccc aaaaacccttt tccttttccc ttctttttttt ttccttttttg ggagctgaaa    180 aatttccggt aagggaaaga agggctcctt tcgctcctta tttcgccgcc tccttccctc      240
cgccaccttc ccctcctccg gcttttttcct cccaactcgg ggaggtcctt cccggtggcc     300
gccctgacga ggtctgagca cctaggcgga ggcggcgcag gctttttgta gtgaggtttg      360
cgcctgcgca ggcgcctgcc tccgccatgc acggggtgg ccccccctcg ggggacagcg      420
catgcccgct gcgcaccatc aagagagtcc agttcggagt cctgagtccg gatgaactga      480
agcgaatgtc tgtgacggag ggtggcatca aatacccaga gacgactgag ggaggccgcc      540
ccaagcttgg ggggctgatg gacccgaggc aggggggtgat tgagcggact ggccgctgcc     600
aaacatgtgc aggaaacatg acagagtgtc ctggccactt tggccacatt gaactggcca      660
agcctgtgtt tcacgtgggc ttcctggtga agacaatgaa agttttgcgc tgtgtctgct      720
tcttctgctc caaactgctt gtggactcta caacccaaa gatcaaggat atcctggcta      780
agtccaaggg acagcccaag aagcggctca cacatgtcta cgacctttgc aagggcaaaa      840
acatatgcga gggtggggag gagatggaca caagttcgg tgtggaacaa cctgagggtg      900
acgaggatct gaccaaagaa aagggccatg gtggctgtgg gcggtaccag cccaggatcc      960
ggcgttctgg cctagagctg tatgcggaat ggaagcacgt taatgaggac tctcaggaga     1020
agaagatcct gctgagtcca gagcgagtgc atgagatctt caaacgcatc tcagatgagg     1080
agtgttttgt gctgggcatg gagccccgct atgcacggcc agagtggatg attgtcacag     1140
tgctgcctgt gccccgctc tccgtgcggc ctgctgttgt gatgcagggc tctgcccgta     1200
accaggatga cctgactcac aaactggctg acatcgtgaa gatcaacaat cagctgcggc     1260
gcaatgagca gaacggcgca gcggcccatg tcattgcaga ggatgtgaag ctcctccagt     1320
tccatgtggc caccatggtg gacaatgagc tgcctggctt gccccgtgcc atgcagaagt     1380
ctgggcgtcc cctcaagtcc ctgaagcagc ggttgaaggg caaggaaggc cgggtgcgag     1440
ggaacctgat gggcaaaaga gtggacttct cggcccgtac tgtcatcacc cccgacccca     1500
acctctccat tgaccaggtt ggcgtgcccc gctccattgc tgccaacatg acctttgcgg     1560
```

```
agattgtcac cccottcaac attgacagac ttcaagaact agtgcgcagg gggaacagtc    1620
agtacccagg cgccaagtac atcatccgag acaatggtga tcgcattgac ttgcgtttcc    1680
accccaagcc cagtgacctt cacctgcaga ccggctataa ggtggaacgg cacatgtgtg    1740
atggggacat tgttatcttc aaccggcagc caactctgca caaaatgtcc atgatggggc    1800
atcgggtccg cattctccca tggtctacct ttcgcttgaa tcttagcgtg caactccgt     1860 acaatgcaga ctttgacggg gatgagatga acttgcacct gccacagtct ctggagacgc    1920
gagcagagat ccaggagctg gccatggttc ctcgcatgat tgtcaccccc cagagcaatc    1980
ggcctgtcat gggtattgtg caggacacac tcacagcagt gcgcaaattc accaagagag    2040
acgtcttcct ggagcggggt gaagtgatga acctcctgat gttcctgtcg acgtgggatg    2100
ggaaggtccc acagccggcc atcctaaagc cccggcccct gtggacaggc aagcaaatct    2160
tctccctcat catacctggt cacatcaatt gtatccgtac ccacagcacc catcccgatg    2220
atgaagacag tggcccttac aagcacatct ctcctgggga caccaaggtg gtggtggaga    2280
atggggagct gatcatgggc atcctgtgta agaagtctct gggcacgtca gctggctccc    2340
tggtccacat ctcctaccta gagatgggtc atgacatcac tcgcctcttc tactccaaca    2400
ttcagactgt cattaacaac tggctcctca tcgagggtca tactattggc attggggact    2460
ccattgctga ttctaagact taccaggaca ttcagaacac tattaagaag gccaagcagg    2520
acgtaataga ggtcatcgag aaggcacaca acaatgagct ggagcccacc ccagggaaca    2580
ctctgcggca gacgtttgag aatcaggtga accgcattct taacgatgcc cgagacaaga    2640
ctggctcctc tgctcagaaa tccctgtctg aatacaacaa cttcaagtct atggtcgtgt    2700
ccggagctaa aggttccaag attaacatct cccaggtcat tgctgtcgtt ggacagcaga    2760
acgtcgaggg caagcggatt ccatttggct tcaagcaccg gactctgcct cacttcatca    2820
aggatgacta cggcctgag agccgtggct ttgtggagaa ctcctaccta gccggcctca    2880
cacccactga gttcttttc cacgccatgg ggggtcgtga ggggctcatt gacacggctg    2940
tcaagactgc tgagactgga tacatccagc ggcggctgat caagtccatg gagtcagtga    3000
tggtgaagta cgacgcgact gtgcggaact ccatcaacca ggtggtgcag ctgcgctacg    3060
gcgaagacgg cctggcaggc gagagcgttg agttccagaa cctggctacg cttaagcctt    3120
ccaacaaggc ttttgagaag aagttccgct ttgattatac caatgagagg gccctgcggc    3180
gcactctgca ggaggacctg gtgaaggacg tgctgagcaa cgcacacatc cagaacgagt    3240
tggagcggga atttgagcgg atgcgggagg atcgggaggt gctcagggtc atcttcccaa    3300
ctggagacag caaggtcgtc ctcccctgta acctgctgcg gatgatctgg aatgctcaga    3360
aaatcttcca catcaaccca cgccttccct ccgacctgca ccccatcaaa gtggtggagg    3420
gagtcaagga attgagcaag aagctggtga ttgtgaatgg ggatgaccca ctaagtcgac    3480
aggcccagga aaatgccacg ctgctcttca acatccacct gcggtccacg ttgtgttccc    3540
gccgcatggc agaggagttt cggctcagtg gggaggcctt cgactggctg cttggggaga    3600
ttgagtccaa gttcaaccaa gccattgcgc atcccgggga aatggtgggg gctctggctg    3660
cgcagtccct tggagaacct gccacccaga tgaccttgaa taccttccac tatgctggtg    3720
tgtctgccaa gaatgtgacg ctgggtgtgc cccgacttaa ggagctcatc aacatttcca    3780
agaagccaaa gactccttcg cttactgtct tcctgttggg ccagtccgct cgagatgctc    3840
agagagccaa ggatattctg tgccgtctgg agcatacaac gttgaggaag gtgactgcca    3900
```

```
acacagccat ctactatgac cccaaccccc agagcacggt ggtggcagag gatcaggaat    3960
gggtgaatgt ctactatgaa atgcctgact ttgatgtggc ccgaatctcc ccctggctgt    4020
tgcgggtgga gctggatcgg aagcacatga ctgaccggaa gctcaccatg gagcagattg    4080
ctgaaaagat caatgctggt tttggtgacg acttgaactg catctttaat gatgacaatg    4140
cagagaagct ggtgctccgt attcgcatca tgaacagcga tgagaacaag atgcaagagg    4200
aggaagaggt ggtggacaag atggatgatg atgtcttcct gcgctgcatc gagtccaaca    4260
tgctgacaga tatgaccctg cagggcatcg agcagatcag caaggtgtac atgcacttgc    4320
cacagacaga caacaagaag aagatcatca tcacggagga tggggaattc aaggccctgc    4380
aggagtggat cctggagacg gacggcgtga gcttgatgcg ggtgctgagt gagaaggacg    4440
tggaccccgt acgcaccacg tccaatgaca ttgtggagat cttcacggtg ctgggcattg    4500
aagccgtgcg gaaggccctg gagcgggagc tgtaccacgt catctccttt gatggctcct    4560
atgtcaatta ccgacacttg gctctcttgt gtgataccat gacctgtcgt ggccacttga    4620
tggccatcac ccgacacgga gtcaaccgcc aggacacagg accactcatg aagtgttcct    4680
ttgaggaaac ggtggacgtg cttatggaag cagccgcaca cggtgagagt gaccccatga    4740
aggggtctc tgagaatatc atgctgggcc agctggctcc ggccggcact ggctgctttg    4800
acctcctgct tgatgcagag aagtgcaagt atggcatgga gatccccacc aatatcccg    4860
gcctggggc tgctgacccc accggcatgt tctttggttc agcacccagt ccatgggtg    4920
gaatctctcc tgccatgaca ccttggaacc agggtgcaac ccctgcctat ggcgcctggt    4980
cccccagtgt tgggagtgga atgacccag gggcagccgg cttctctccc agtgctgcgt    5040
cagatgccag cggcttcagc ccaggttact ccctgcctg gtctcccaca ccgggctccc    5100
cggggtcccc aggtccctca agccctaca tcccttcacc aggtggtgcc atgtctccca    5160
gctactcgcc aacgtcacct gcctacgagc ccgctctcc tgggggctac acacccccaga    5220
gtccctctta ttcccccact tcaccctcct actcccctac ctctccatcc tattctccaa    5280
ccagtcccaa ctatagtccc acatcaccca gctattcgcc aacgtcaccc agctactcac    5340
cgacctctcc cagctactca cccacctctc ccagctactc gcccacctct cccagctatt    5400
cgcccacctc tcccagctac tcacccactt ccctagcta ttcgcccact tccctagct    5460
actcgccaac gtctcccagc tactcgccga catctcccag ctactcgcca acttcaccca    5520
gctattctcc cacttctccc agctactcac ctacctctcc aagctattca cccacctccc    5580
ccagctactc acccacttcc ccaagttact cacccaccag cccgaactat tctccaacca    5640
gtcccaatta caccccaaca tcacccagct acagcccgac atcacccagc tattccccta    5700
ctagtcccaa ctacacacct accagcccta actacagccc aacctctcca agctactctc    5760
caacatcacc cagctattcc ccgacctcac caagttactc ccttccagc ccacgataca    5820
caccacagtc tccaacctat accccaagct caccccagcta cagccccagt cgcccagct    5880
acagcccaac ctcacccaag tacaccccaa ccagtccttc ttatagtccc agctccccag    5940
agtataccc aacctctccc aagtactcac ctaccagtcc caaatattca cccacctctc    6000
ccaagtactc gctaccagt cccacctatt caccaccac cccaaaatac tccccaacat    6060
ctcctactta ttccccaacc tctccagtct acaccccaac ctctcccaag tactcaccta    6120
ctagccccac ttactcgccc acttccccca gtactcgcc caccagcccc acctactcgc    6180
ccacctcccc caaaggctca acctactctc ccacttcccc tggttactcg cccaccagcc    6240
ccacctacag tctcacaagc ccggctatca gcccggatga cagtgacgag gagaactgag    6300
```

```
ggcacgtggg gtgcggcagc gggctagggc ccagggcagc ttgcccgtgc tgccgtgcag    6360
ttcttgcctc cctcacgggg cgtcaccccc agcccagctc cgttgtacat aaataccttg    6420
tgacagagct cccggtgaac ttctggatcc cgtttctgat gcagattctt gtcttgttct    6480
ccacttgtgc tgttagaact cactggccca gtggtgttct acctcctacc ccacccaccc    6540
cctgcctgtc cccaaattga agatccttcc ttgcctgtgg cttgatgcgg ggcgggtaaa    6600
gggtatttta acttaggggt agttcctgct gtgagtggtt acagctgatc ctcgggaaga    6660
acaaagctaa agctgccttt tgtctgttat tttattttt tgaagtttaa ataaagttta    6720
ctaattttga cc                                                         6732
```

<210> SEQ ID NO 38
<211> LENGTH: 2277
<212> TYPE: DNA
<213> ORGANISM: Homo sapiens

<400> SEQUENCE: 38

```
gactgcgcgg cggcaacagc agacatgtcg ggggtccggg gcctgtcgcg gctgctgagc      60
gctcggcgcc tggcgctggc caaggcgtgg ccaacagtgt tgcaaacagg aacccgaggt     120
tttcacttca ctgttgatgg gaacaagagg gcatctgcta aagtttcaga ttccatttct     180
gctcagtatc cagtagtgga tcatgaattt gatgcagtgg tggtaggcgc tggaggggca     240
ggcttgcgag ctgcatttgg cctttctgag gcagggttta atacagcatg tgttaccaag     300
ctgtttccta ccaggtcaca cactgttgca gcgcagggag gaatcaatgc tgctctgggg     360
aacatggagg aggacaactg gaggtggcat ttctacgaca ccgtgaaggg ctccgactgg     420 ctggggacc aggatgccat ccactacatg acggagcagg ccccgccgc cgtggtcgag      480 ctagaaaatt atggcatgcc gtttagcaga actgaagatg ggaagattta tcagcgtgca     540
tttggtggac agagcctcaa gtttggaaag ggcgggcagg cccatcggtg ctgctgtgtg     600
gctgatcgga ctggccactc gctattgcac accttatatg acggtctct gcgatatgat     660 accagctatt ttgtggagta ttttgccttg gatctcctga tggagaacgg ggagtgccgt     720
ggtgtcatcg cactgtgcat agaggacggg tccatccatc gcataagagc aaagaacact     780
gttgttgcca caggaggcta cgggcgcacc tacttcagct gcacgtctgc ccacaccagc     840
actggcgacg gcacggccat gatcaccagg gcaggccttc cttgccagga cctagagttt     900
gttcagttcc accccacagg catatatggt gctggttgtc tcattacgga aggatgtcgt     960
ggagagggag gcattctcat taacagtcaa ggcgaaaggt ttatggagcg atacgccccc    1020
gtcgcgaagg acctggcgtc tagagatgtg gtgtctcggt cgatgactct ggagatccga    1080
gaaggaagag gctgtggccc tgagaaagat cacgtctacc tgcagctgca ccacctacct    1140
ccagagcagc tggccacgcg cctgcctggc atttcagaga cagccatgat cttcgctggc    1200
gtggacgtca cgaaggagcc gatccctgtc ctccccaccg tgcattataa catgggcggc    1260
attcccacca actacaaggg gcaggtcctg aggcacgtga atggccagga tcagattgtg    1320
cccggcctgt acgcctgtgg ggaggccgcc tgtgcctcgg tacatggtgc caaccgcctc    1380 ggggcaaaact cgctcttgga cctggttgtc tttggtcggg catgtgccct gagcatcgaa    1440
gagtcatgca ggcctggaga taaagtccct ccaattaaac caaacgctgg ggaagaatct    1500
gtcatgaatc ttgacaaatt gagatttgct gatggaagca agaacatc ggaactgcga     1560 ctcagcatgc agaagtcaat gcaaaatcat gctgccgtgt tccgtgtggg aagcgtgttg    1620
```

| | |
|---|---|
| caagaaggtt gtgggaaaat cagcaagctc tatggagacc taaagcacct gaagacgttc | 1680 |
| gaccggggaa tggtctggaa cacagacctg gtggagaccc tggagctgca gaacctgatg | 1740 |
| ctgtgtgcgc tgcagaccat ctacggagca gaggcgcgga aggagtcacg gggcgcgcat | 1800 |
| gccagggaag actacaaggt gcggattgat gagtacgatt actccaagcc catccagggg | 1860 |
| caacagaaga agcccttttga ggagcactgg aggaagcaca ccctgtcctt tgtggacgtt | 1920 |
| ggcactggga aggtcactct ggaatataga cccgtaatcg acaaaacttt gaacgaggct | 1980 |
| gactgtgcca ccatcccgcc agccattcgc tcctactgat gagacaagat gtggtgatga | 2040 |
| cagaatcagc ttttgtaatt atgtataata gctcatgcat gtgtccatgt cataactgtc | 2100 |
| ttcatacgct tctgcactct ggggaagaag gagtacattg aagggagatt ggcacctagt | 2160 |
| ggctgggagc ttgccaggaa cccagtggcc agggagcgtg gcacttacct ttgtcccttg | 2220 |
| cttcattctt gtgagatgat aaaactgggc acagctctta aataaaatat aaatgag | 2277 |

<210> SEQ ID NO 39
<211> LENGTH: 3602
<212> TYPE: DNA
<213> ORGANISM: Homo sapiens

<400> SEQUENCE: 39

| | |
|---|---|
| gataggcgcc gggcagctga gctggtagga ggaccagacg gggatgttcg gctccgcccc | 60 |
| ccagcgtccc gtggccatga cgaccgctca gagggactcc ctgttgtgga agctcgcggg | 120 |
| gttgctgcgg gagtccgggg atgtggtcct gtctggctgt agcaccctga gcctgctgac | 180 |
| tcccacactg caacagctga accacgtatt tgagctgcac ctggggccat ggggccctgg | 240 |
| ccagacaggc tttgtggctc tgccctccca tcctgccgac tcccctgtta ttcttcagct | 300 |
| tcagtttctc ttcgatgtgc tgcagaaaac actttcactc aagctggtcc atgttgctgg | 360 |
| tcctggcccc acagggccca tcaagatttt ccccttcaaa tcccttcggc acctggagct | 420 |
| ccgaggtgtt cccctccact gtctgcatgg cctccgaggc atctactccc agctggagac | 480 |
| cctgatttgc agcaggagcc tccaggcatt agaggagctc ctctcagcct gcggcggcga | 540 |
| cttctgctct gccctccctt ggctggctct gctttctgcc aacttcagct acaatgcact | 600 |
| gaccgcctta gacagctccc tgcgcctctt gtcagctctg cgtttcttga acctaagcca | 660 |
| caatcaagtc caggactgtc agggattcct gatggatttg tgtgagctcc accatctgga | 720 |
| catctcctat aatcgcctgc atttggtgcc aagaatggga ccctcagggg ctgctctggg | 780 |
| ggtcctgata ctgcgaggca atgagcttcg gagcctgcat ggcctagagc agctgaggaa | 840 |
| tctgcggcac ctggatttgg catacaacct gctggaagga caccgggagc tgtcaccact | 900 |
| gtggctgctg gctgagctcc gcaagctcta cctggagggg aaccctcttt ggttccaccc | 960 |
| tgagcaccga gcagccactg cccagtactt gtcaccccgg gccagggatg ctgctactgg | 1020 |
| cttccttctc gatggcaagg tcttgtcact gacagatttt cagactcaca catccttggg | 1080 |
| gctcagcccc atgggcccac ctttgccctg gccagtgggg agtactcctg aaacctcagg | 1140 |
| tggccctgac ctgagtgaca gcctctcctc agggggtgtt gtgacccagc cctgcttca | 1200 |
| taaggttaag agccgagtcc gtgtgaggcg ggcaagcatc tctgaaccca gtgatacgga | 1260 |
| cccggagccc cgaactctga ccctctcc ggctggatgg ttcgtgcagc agcacccgga | 1320 |
| gctggagctc atgagcagct tccgggaacg gttcggccgc aactggctgc agtacaggag | 1380 |
| tcacctggag ccctccggaa accctctgcc ggccaccccc actacttctg cacccagtgc | 1440 |
| acctccagcc agctcccagg gccccgacac tgcacccaga ccttcacccc cgcaggagga | 1500 |

```
agccagaggc ccccaggagt caccacagaa aatgtcagag gaggtcaggg cggagccaca   1560
ggaggaggaa gaggagaagg aggggaagga ggagaaggag gaggggggaga tggtggaaca   1620 gggagaagag gaggcaggag aggaggaaga agaggagcag gaccagaagg aagtggaagc   1680
ggaactctgt cgcccttgt tggtgtgtcc cctggagggg cctgagggcg tacggggcag    1740
ggaatgcttt ctcagggtca cttctgccca cctgtttgag gtggaactcc aagcagctcg   1800
caccttggag cgactggagc tccagagtct ggaggcagct gagatagagc cggaggccca   1860
ggcccagagg tcgcccaggc ccacgggctc agatctgctc cctggagccc ccatcctcag   1920
tctgcgcttc tcctacatct gccctgaccg gcagttgcgt cgctatttgg tgctggagcc   1980
tgatgcccac gcagctgtcc aggagctgct tgccgtgttg accccagtca ccaatgtggc   2040
tcgggaacag cttggggagg ccagggacct cctgctgggg agattccagt gtctacgctg   2100
tggccatgag ttcaagccag aggagcccag gatgggatta gacagtgagg aaggctggag   2160
gcctctgttc caaagacag aatctcctgc tgtgtgtcct aactgtggta gtgaccacgt    2220
ggttctcctc gctgtgtctc ggggaacccc caacagggag cggaaacagg gagagcagtc   2280
tctggctcct tctccgtctg ccagcccgt ctgccaccct cctggccatg gtgaccacct     2340
tgacagggcc aagaacagcc cacctcaggc accgagcacc cgtgaccatg gtagttggag   2400
cctcagtccc cccctgagc gctgtggcct ccgctctgtg gaccaccgac tccggctctt     2460
cctggatgtt gaggtgttca gcgatgccca ggaggagttc cagtgctgcc tcaaggtgcc   2520
agtggcattg gcaggccaca ctggggagtt catgtgccct gtggttgtgt ctgaccgcag   2580
gctgtacctg ttgaaggtga ctggggagat gcgtgagcct ccagctagct ggctgcagct   2640
gaccctggct gttcccctgc aggatctgag tggcatagag ctgggcctgg caggccagag   2700
cctgcggcta gagtgggcag ctggggcggg ccgctgtgtg ctgctgcccc gagatgccag   2760
gcattgccgg gccttcctag aggagctcct tgatgtcttg cagtctctgc cccctgcctg   2820
gaggaactgt gtcagtgcca cagaggagga ggtcaccccc cagcaccggc tctggccatt   2880
gctgaaaaaa gactcatcct tggaggctcg ccagttcttc taccttcggg cgttcctggt   2940
tgaaggccct tccacctgcc tcgtatccct gttgctgact ccgtccaccc tgttcctgtt   3000
agatgaggat gctgcagggt ccccggcaga gccctctcct ccagcagcat ctggcgaagc   3060
ctctgagaag gtgcctccct cggggccggg ccctgctgtg cgtgtcaggg agcagcagcc   3120
actcagcagc ctgagctccg tgctgctcta ccgctcagcc cctgaggact gcggctgct    3180 cttctacgat gaggtgtccc ggctggagag cttttgggca ctccgtgtgg tgtgtcagga   3240
gcagctgaca gccctgcttg cctggatccg ggaaccatgg gaggagctgt tttccatcgg   3300
actccggaca gtgatccaag aggcgctggc ccttgaccga tgagggtccc acgctgacct   3360
tggccctgac ctcaggagcc acgctgtaga cattccctct cctggtctct gggtctggct   3420
tccaggctct ggctgtggat gtcttcagcc tctgggtgct ggccagtgag gtcccaaatg   3480
acccagggct taagggagag gcgagagaat gatctggcct caggggacag gccacctggt   3540
caggaggaat atttttcctg cacttttcct caggtatcaa taaagttgtt ccaactcat    3600 aa                                                                  3602

<210> SEQ ID NO 40
<211> LENGTH: 3326
<212> TYPE: DNA
<213> ORGANISM: Homo sapiens
```

<400> SEQUENCE: 40

```
gaggggcggc cgcggccat ggagacgggc acggcgcccc tggtggcccc gccgcgccgt        60
catggcgccc ccgcggcccc ctcgccgccg ccccggggtt cccgggccgg gcccgtcgtg       120
gtggtggctc cggaccctcc agtgactacg gccacttcgg cccccgtcac cctggtggcc       180
cccggggagg cgcggcccgc ctgggtcccg gggtcggccg agacctctgc tccggccccg       240
gccccagccc cggccccagc cccggctgtc acgggcagca cggtggtggt gctgaccctg       300
gaggcctcgc ccgaagcccc aaagccgcag ctcccctccg gcccggaatc cccagagccc       360
gcggcagtgg ctggagttga gcatcgagg gctctggccg caggggcaga ctcgccgaag        420
acagaggagg ctcgaccctc acccgcccca ggaccaggga cccccaccgg gaccoctacc       480
aggaccoctt ccagaacggc tcctggtgcc ctgaccgcca accccccgct gccoccaag        540
ccgggaacca cagtggcctc aggagtgact gcacggagtg catcaggaca agtgacaggt       600
gggcatggag ctgccgcagc aacatcagca tcagcaggac aggctcctga ggaccoctca       660
ggccctggca caggcccctc tgggacttgt gaggctccgg tagctgtcgt gaccgtgacc       720
ccagctccgg agcctgctga aaactctcaa gacctgggct ccacgtccag cctgggacct       780
ggcatctctg ggcctcgagg gcaggccccg gacacgctga gttacttgga ctccgtgagc       840
ctcatgtctg gaccttgga gtccttggcg gatgatgtga gctccatggg ctcagattca       900
gagataaacg ggctggccct gcgcaagacg acaagtatg gcttccttgg gggcagccag        960
tactcgggca gcctagagag ctccattccc gtggacgtgg ctcggcagcg ggagctcaaa      1020
tggctggaca tgttcagtaa ctgggataag tggctgtcac ggcgattcca gaaggtgaag      1080
ctgcgctgcc ggaaggggat cccctcctct ctcagagcca aagcctggca gtacctgtct      1140
aatagcaagg aacttctgga gcagaaccca ggaaagtttg aggagctgga acgggctcct      1200
ggggacccca gtggctgga tgtgattgag aaggacctgc accgccagtt cccttttccac      1260
gagatgtttg ctgctcgagg ggggcatggg caacaggacc tgtaccgaat cctgaaggcc      1320
tacaccatct accggcctga cgagggttac tgccaggccc aggccccgt ggctgcggtc        1380
ctgctcatgc acatgcctgc ggagcaagcc ttttggtgcc tggtgcagat ctgcgacaag      1440
tacctcccag gttactacag tgcagggctg gaggccattc agctggacgg ggagatcttt      1500
tttgcactcc tgcgccgggc ctcccgctg gcgcatcgcc acctgcggcg gcagcgcatt       1560
gaccctgtgc tctacatgac ggagtggttc atgtgcatct tcgcccgcac cctgccctgg      1620
gcgtcggtgc tgcgtgtctg ggacatgttt ttctgtgaag gcgttaagat catcttccgg      1680
gtggccctgg tcctgctgcg ccacacgctg ggctcagtgg agaagctgcg ctcctgccaa      1740
ggcatgtatg agaccatgga gcagctgcgt aacctgcccc agcagtgcat gcaggaagac      1800
ttcctggtgc atgaggtgac caatctgccg gtgacagaag cactgattga gcgggagaat      1860
gcagcccagc tcaagaagtg gcgggaaacg cggggggagc tgcagtatcg gccctcacgg      1920
cgactgcatg ggtcccgggc catccacgag gagcgccggc ggcaacagcc accctgggc      1980
ccctcctcca gctcctcag cctccctggc ctcaagagcc gaggctcccg ggcagctgga      2040
ggggcccgt cccgccgcc ccccgtccgc agagccagtg ctgggcctgc ccagggcct       2100
gtggtcactg ctgagggact gcatccatcc cttccctcac ccactggcaa tagcaccccc      2160
ttgggttcca gcaaggagac ccggaagcag agaaggagc ggcagaaaca ggagaaggag       2220
cggcagaaac aggagaagga gcgggagaag gagcggcaga gcaggagaa agagcgagag       2280
aagcaggaaa aggagcgaga gaagcaggag aaggagcggc agaagcagga gaagaaggct      2340
```

-continued

```
caaggccgga agctttcgct gcgtcgaaag gcagatgggc ccccaggccc ccatgatggt      2400
ggggacaggc cctcagccga ggcccggcag gacgcttact tctgacctct gccctggggc      2460
tggactgcat ggccccccte tttccctcag ccaagaacag gcctggccca aggtgccacc      2520
ccctagcacc ttgtcaggct gtcccttgct ggggaaagtg gcttggttcc ccatctcctc      2580
gccagctgct gatccctaca cgggcaggac agatgggcag ctgcaaatga gtctggagcc      2640
tctcatctcc catgaggctc agctggggtc tctgtcgctc ctgccccagt tccctctggg      2700 tccccteeta ggtgctgtcc tgaatggccc gttgtcatcc caggggtgac tcctggtgat      2760
gggagtcagc agtttcagat tcttacactc catagctccc cttaccatga ggtggagctg      2820
gcttcctttt ccctgtcttc agccctccct gtctccccca cttcctggcc agggctctca      2880
ttctggacct gtgttgtaat tgtgtacaga ggatggcgtt ggcctggggt ggggtgctc       2940 gctttgtctt ctgtccttttg gttctccttc cataatgctc ctgtacccag tttatttaag     3000
gggacatgca ctggaatagg aaatgtcccc catctccctt cctgcaccct gctgtgctcc      3060
ctccaaaccc accttgctct gtgttctcag gccccctgc ttttgtctca ccaggaccca       3120
tacctttcac cttgttccct tccacccctc cagttagtcc ctatctgggt aagggtcttc      3180
ccttgagctc caggggtgg aacccaatgt ttacattctc ttctgtctct gccccacccc       3240
catgcagcgc tttgaggaat tggaaaagaa cctgctgttg tacctgggaa aaaaaaaaa       3300 aaaaaaaaaa aaaaaaaaa aaaaaa                                            3326
```

<210> SEQ ID NO 41
<211> LENGTH: 1719
<212> TYPE: DNA
<213> ORGANISM: Homo sapiens

<400> SEQUENCE: 41

```
ggcggaagtg acattatcaa cgcgcgccag gggttcagtg aggtcgggca ggttcgctgt        60
ggcgggcgcc tgggccgccg gctgtttaac ttcgcttccg ctggcccata gtgatctttg       120
cagtgaccca gggtgccatg actcccggaa tccctatctt tagtccaatg atgccttatg       180
gcactggact gaccccacag cctattcaga acaccaatag tctgtctatt ttggaagagc       240
aacaaaggca gcagcagcaa caacaacagc agcagcagca gcagcagcag caacagcaac       300
agcagcagca gcagcagcag cagcagcagc agcagcagca gcagcagcag cagcagcaac       360
aggcagtggc agctgcagcc gttcagcagt caacgtccca gcaggcaaca cagggaacct       420
caggccaggc accacagctc ttccactcac agactctcac aactgcaccc ttgccgggca       480
ccactccact gtatccctcc cccatgactc ccatgacccc catcactcct gccacgccag       540
cttcggagag ttctgggatt gtaccgcagc tgcaaaatat tgtatccaca gtgaatcttg       600
gttgtaaact tgacctaaag accattgcac ttcgtgcccg aaacgccgaa tataatccca       660
agcggtttgc tgcggtaatc atgaggataa gagagccacg aaccacggca ctgattttca       720
gttctgggaa aatggtgtgc acaggagcca agagtgaaga acagtccaga ctggcagcaa       780
gaaaatatgc tagagttgta cagaagttgg gttttccagc taagttcttg gacttcaaga       840
ttcagaatat ggtggggagc tgtgatgtga gtttcctat aaggttagaa ggccttgtgc        900
tcacccacca acaatttagt agttatgagc cagagttatt tcctggttta atctacagaa       960
tgatcaaacc cagaattgtt ctccttattt ttgtttctgg aaaagttgta ttaacaggtg      1020
ctaaagtcag agcagaaatt tatgaagcat ttgaaaacat ctaccctatt ctaaagggat      1080
```

| | |
|---|---|
| tcaggaagac gacgtaatgg ctctcatgta cccttgcctc ccccacccec ttcttttttt | 1140 |
| tttttaaac aaatcagttt gttttggtac ctttaaatgg tggtgttgtg agaagatgga | 1200 |
| tgttgagttg cagggtgtgg caccaggtga tgcccttctg taagtgccca ccgcgggatg | 1260 |
| ccgggaaggg gcattatttg tgcactgaga acaccgcgca gcgtgactgt gagttgctca | 1320 |
| taccgtgctg ctatctgggc agcgctgccc atttatttat atgtagattt taaacactgc | 1380 |
| tgttgacaag ttggtttgag ggagaaaact ttaagtgtta aagccacctc tataattgat | 1440 |
| tggactttt aattttaatg ttttccca tgaaccacag ttttatatt tctaccagaa | 1500 |
| aagtaaaaat ctttttaaa agtgttgttt ttctaattta taactcctag gggttatttc | 1560 |
| tgtgccagac acattccacc tctccagtat tgcaggacag aatatatgtg ttaatgaaaa | 1620 |
| tgaatggctg tacatatttt tttctttctt cagagtactc tgtacaataa atgcagttta | 1680 |
| taaaagtgtt agattgttgt taaaaaaaaa aaaaaaaa | 1719 |

<210> SEQ ID NO 42
<211> LENGTH: 971
<212> TYPE: DNA
<213> ORGANISM: Homo sapiens

<400> SEQUENCE: 42

| | |
|---|---|
| cactcgttgc ataaatttgc gctccgccag cccggagcat ttaggggcgg ttggctttgt | 60 |
| tgggtgagct tgtttgtgtc cctgtgggtg gacgtggttg gtgattggca ggatcctggt | 120 |
| atccgctaac aggtcaaaat gcagatcttc gtgaaaaccc ttaccggcaa gaccatcacc | 180 |
| cttgaggtgg agcccagtga caccatcgaa aatgtgaagg ccaagatcca ggataaggaa | 240 |
| ggcattcccc ccgaccagca gaggctcatc tttgcaggca gcagctggaa gatggccgt | 300 |
| actcttctg actacaacat ccagaaggag tcgaccctgc acctggtcct gcgtctgaga | 360 |
| ggtggtatgc agatcttcgt gaagaccctg accggcaaga ccatcaccct ggaagtggag | 420 |
| cccagtgaca ccatcgaaaa tgtgaaggcc aagatccagg ataaagaagg catccctccc | 480 |
| gaccagcaga ggctcatctt tgcaggcaag cagctggaag atggccgcac tctttctgac | 540 |
| tacaacatcc agaaggagtc gaccctgcac ctggtcctgc gtctgagagg tggtatgcag | 600 |
| atcttcgtga agaccctgac cggcaagacc atcactctgg aggtggagcc cagtgacacc | 660 |
| atcgaaaatg tgaaggccaa gatccaagat aaagaaggca tccccccga ccagcagagg | 720 |
| ctcatctttg caggcaagca gctggaagat ggccgcactc tttctgacta caacatccag | 780 |
| aaagagtcga ccctgcacct ggtcctgcgc ctgaggggtg gctgttaatt cttcagtcat | 840 |
| ggcattcgca gtgcccagtg atggcattac tctgcactat agccatttgc cccaacttaa | 900 |
| gtttagaaat tacaagtttc agtaatagct gaacctgttc aaaatgttaa taaaggtttc | 960 |
| gttgcatggt a | 971 |

<210> SEQ ID NO 43
<211> LENGTH: 6577
<212> TYPE: DNA
<213> ORGANISM: Homo sapiens

<400> SEQUENCE: 43

| | |
|---|---|
| cggggactgg cctggcgccg gcggcggcgg agggggcgcc gcggcgggc gatgtgagcg | 60 |
| cggcgctctg gacagagtac gcttcatgtc agtagaaatg gacagcagca gttttattca | 120 |
| gtttgatgtg cccgagtaca gcagcaccgt tctgagccca ctaaacgaac tccgcctgca | 180 |
| ggggaaacta tgtgacatca ttgtacacat tcagggtcag ccattccgag cccacaaagc | 240 |

```
agtccttgct gccagctccc catatttccg ggaccattca gcgttaagta ccatgagtgg    300
cttgtcaata tcagtgatta aaatcccaa tgtgtttgag cagttgcttt cttttttgtta    360 cactggaaga atgtccttgc agctgaagga tgttgtcagt tttctgactg cagccagctt    420
tcttcagatg cagtgtgtca ttgacaagtg cacgcagatc ctagagagca tccattccaa    480
aatcagcgtt ggagatgttg actctgttac cgtcggtgct gaagagaatc ccgagagtcg    540
aaacggagtg aaagacagca gcttctttgc caacccagtg gagatctctc ctccatattg    600
ctctcaggga cggcagccca ccgcaagcag tgacctccgg atggagacga cccccagcaa    660
agctttgcgc agccgcttac aggaggaggg gcactcagac cgcggagca gtgggagcgt    720 ttctgaatat gagattcaga tagagggaga ccatgagcaa ggagacctat tggtgaggga    780
gagccagatc accgaggtga aagtgaagat ggagaagtcc gaccggccca gctgttccga    840
cagctcctcc ctgggtgacg atgggtacca caccgagatg gttgatgggg aacaagttgt    900
ggcagtgaat gtgggctcct atggttctgt gctccagcac gcatactcct attcccaagc    960
agcctcacag ccaaccaatg tatcagaagc ttttggaagt ttgagtaatt ccagcccatc   1020
caggtccatg ctgagctgtt tccgaggagg gcgtgcccgc cagaagcggg ctttgtctgt   1080
ccacctgcac agtgacctgc agggcctggt gcagggctct gacagtgaag ccatgatgaa   1140
caaccccggg tatgagagca gtccccggga gaggagtgcg agagggcatt ggtacccgta   1200
caatgagagg ttgatctgta tttactgtgg aaagtccttc aaccagaaag aagccttga   1260 taggcacatg cgactccata tgggaatcac cccctttgtg tgcaagttct gtgggaagaa   1320
gtacacacgg aaggaccaac tggagtacca catccggggc catacagatg ataaaccatt   1380
ccgctgtgag atctgcggga agtgctttcc attccaaggt accctcaacc agcacttgcg   1440
gaaaaaccac ccaggcgttg ctgaagtcag gagtcgcatt gagtcccccg agagaacaga   1500
tgtgtacgtg gaacagaaac tagaaaatga cgcatcggcc tcagagatgg gcctagattc   1560
ccggatggaa attcacacag tgtctgatgc tcccgattaa gatggtaaag aagtgcaccc   1620
aaacaaagca cattaatcaa tgcatatttg tgatttgctt tgttgtaatc tttggttttc   1680
ccaaccatct ggaaatctct tggtctcttg gcagtttttc taaagtttct ggatggaaca   1740
cttcgttgtg tttatccttt cccctgccct ccctccccga aggagctcaa agcatgaagg   1800
gcaacgcatc cagggaaaac acaggctgac agtattcctc tttggctgaa ctcttaatcc   1860
aaaatctgcc agtgatttag ctatgccaac tggttgaccc tccattctct gccaagaggc   1920
atactctttc tcattgtgtg cgctggcagc agtgcacttc cacggaggga gattaggatg   1980
ccgtcagctg atacaaatgg gtaaccttt ctaatttaaa attccttta gggggtagtt   2040 agacaattta tatatatata taataaaact attattatat atagtata tatacatttt   2100 caaatttgat tttattctgg ttgaggtgaa tgtaagagga atatataatt taatacaatg   2160
tgaacagggc ttctgagtct atctcatccc tacctaatat gttagggttt tgccccttca   2220
tttcccttac aaaagaatgt tagtaggttt atattaatca ttgtgtccaa aagcaagcaa   2280
agcaaatcac agtgttcaca gctctgcttc ataacaaata cataaccaa atgccataaa   2340 atttcttcaa ctctagttgg aaaccgtttg gaatttttgt tagttgtcca gcaggtaagc   2400
tggatgacct gtggtgctga cctttttaca tagtgtagtg ttatattagc caaccccaaa   2460
ggagcagtgg ttttcaaggt ttttactggc ctacaaatct accttcattc cgtactgtag   2520
aaacatacat accaggtaac taaatcgaat cactctctat catgagttag tactcactcg   2580
```

```
cacttaagga aagggatttg tagttctgtc tacaaaattc tccaagcagt gttgtggttt    2640
tttttgtttt tgttttttttt ctttctcttt tcaaacagcc agttcaggtg cacagcaact    2700
ttttctacat gcagttccca gggaaactgc agaacttaga atttgtactt tttgtaaagc    2760
tatactctat gggaattgca agcaatatat ctatcttagt attgtgtgtg ctaatgagag    2820
cctcagtggc tcccccactc tctcagtgtt tcctgcttaa agaaccaaca gtttaaaagc    2880
cctctaagat actctgtgtg tcaccaaatc tgtgtgtcac cattttttgg tcatgtggtg    2940 ctattttgt taagtgtctt tttaggtcag tatagttgta gaaaatgtga aatctgatgg      3000
taataatgaa ttataattgt tttcctctct tgagttcata gcttgaaaag agacctcaaa    3060
agcatgtgct ggcaaacacg ttactgtatg aaaacatacc tgagtccatt tgaataatgt    3120
tttattagta ctttcggaaa tgtcttcagt tctgtattgt gttcacatac acaaacaggc    3180
tttacaagat tgcttcggta ctgtaaactc tggcagagag taattttgta ggcagtttgg    3240
tggtgagttt gtgctgcagg ctgcctgtgg gatgtcagcg ttctggtatc tgcctgagaa    3300
cctgggctct gagacgcaca accagtgcac ctccatagga gaacagtgca gccacctaaa    3360
agaaaaacga acgaaggacc agcctcagag gctagaagtt aaaggaatac agaattagat    3420
gtttgctggt ttttctgtgct ttttttggctc ctaaaatacc aatggtggat ttgttttttgt   3480 ttttgttttt tgttttgaga aataaaaagt cattcaagcc ctttgtgtgt aatagccccc    3540
aggggtggca gctgtgcagt cgcatctctt tggcacacag gatctgttca cgtgtgaact    3600
gctgcgctac acatcagtgt taactcccta cagattacac tctaatcccg ctgctcccga    3660
ggagcggctt tgctaaatcg ggtatatagt atatgccttt ttcctcgtca aactgcctaa    3720
gtaggggttc gttctctccc tgaagcactt gttcaactcc tgttaaagcc gcgtgcctca    3780
aggggaggct ggaccccaag tgtttaccca cttaaatatg ttctgggggtt tcaggtaaat    3840 gtttgtgggt ttttttttcc ttacatgaat aagtttggtt ttgatttttt tttaattgaa    3900
tgcaaaaaat ttgtgttgtg atacaaatta agtttgtgac aagaaatgcc caaatccaag    3960
gacataagag gtcaagctca gggaaggaac ctccttttca ctcaggcttg gggcctccag    4020
cgaggtttcc agagcattcc atggtatgag agacagtgag gagggagggc acctggcgcg    4080
ggcacttcca gcgtcctggc tcttggcatt gtccgtctta accttatta catggagttc      4140 tttgtatttg tgaatctgtt taactggttt gagtttacca aagagtgact tatccaaaat    4200
tgtctttgac aaaaatatcc attgctttga ttgtacagtt caggttcaaa cattgtaatg    4260
ggactgttaa ggggcagaaa attgattgag tttctctcta agaatcatga ttccacattt    4320
tgcaagttcc acttgctccc attcgtgttg ctaacacttt acccttttcca ctgctcgcag    4380 tgttaagaat gaattctcaa gccataacac agtactgtaa agttccgcag gcttcgaggg    4440
gaggcagcgc ctaggccagc acggagctgt gtagcctctc tgagcgttcg cactgtcatg    4500
cttcccaggg gtgtgactgg tgagagatta actccattca gatcgggcag cagcaattaa    4560
ttgtgccttg ccgcatgagg atgtgtcagg aggattaaca tgaccacaga accgaaacat    4620
tctctccctg aagttcactt cacgtctccg cagacgaagt acgctgtgta actccttaga    4680
gcaactcttt ttgaaaagca aagtcccttat ttctgtacag ttttaggtta ggtgtttcat   4740
ttataacaga tgcagaaatc aattaagata aagtgatatg tgaagaaatc ttttacagta    4800
aaatatatcc tgaattcata taggcttgtt cataattgag tctcttcttg agctacctttt    4860 tcaatattag acaatgtgaa gacagtgaca gcgtcccttt ctagagatat ttagcctgtt    4920
attacaaact gtgaagacaa agaattttat acttttacta atgtttgtgg ttttaaacag    4980
```

```
ttattttcat tctaatcagt tctctaccct ctaatttcta ctaaagctgt aaatacattt      5040
agaaattata tttgtaaata cagtatatgg agacaagtta attttttggt cagtggaaaa      5100
agcctcccaa ccaattggcc ctgccttggc agttgtgttt tttgttgttg ttgttgttgt      5160
tttagtttag tttttttttt taaacagcag aaaggatact gtcggttcac tgttgagcag      5220
aatatactgt agaacgaaaa tgataatttt taaatcttcc agagcatgag taaatgtctt      5280
ttctaatgat agcaaatata accaactctt tgttttccc ttagcccaga ccatatagac       5340
ctgcgtattt tgtgtgtggt tttgttttta tttttgttct tacagcctag accctaggaa      5400
aaatttgcag gaacacgaaa caagggctgg ggggaaaatc atctatgtga atgagcttta      5460 cttttaaagag atcaatgtat tttatttat caacttttc tcttagttac tgtgattttt       5520
gttgttgttg tcctcgttat tgttaaattc tgtaatggtt tcctgtgaag cctccactga      5580
aagggactca aatatgcaac acctaaacta ttttccaagg gcacatgccc cttgaatggt      5640
gcttctagac tggtcagggt tatttattaa atttatata tgaaagtatt ggggaattat       5700
gtaaattctt tatatgaaac tatctagttc ataaatcata gatttcatat tactcagtgc      5760
aactgaacta aaagttcaga aaagtcattc acattgttcc aaatttgtaa tggttgtcac      5820
atgtcacatg cgtctttttc agtaagtgcc agagtgttcc cactgtttct gcccagtgct      5880
tgacttctcg gcccggaaga gaacctgctt tctctggttt ccttcctgag tctggcacag      5940
acggggctat tgtagttctt gatcaagtcc tggagtcagc cttgcctggc tctccttgta      6000
gcagattcag tccacagacc tcttgctgcc cctcagtgac aagtatgctg tgaattcaac      6060
ctttggactt gctgcccaag cctttggttg ctgccctgac tattgtaaga ggtaaactta      6120
cctggtttgt ttgagaatga ccatttttcct aatgtgaaaa ccatctctct caccacttt     6180 attagtaggg ctaacatttt tttccgttat aaatggttga gcaatttgaa tgacttaaca      6240
cagtgtcatt atcttgcaat ataaactggt aacctcacaa ctccacactt catcaccata      6300
tgaagtaaat gaagctagct aagcggatgc tgtatcaact agtaacttgc cattaaggat      6360 tatttatag catgaattta agactattta ttcaaatgat attttactct tgtattcact       6420 ttgtttaga tttgtgacat gaatatttca gtgctgctta attttgttct gaattcttgt       6480
ttcttgcttg taaatggctt ttttatggta taaataaagt caatggacat tgctgtttgt      6540
aaataaaaat gctgctagag caaaaaaaaa aaaaaaa                               6577
```

<210> SEQ ID NO 44
<211> LENGTH: 100
<212> TYPE: DNA
<213> ORGANISM: Homo sapiens

<400> SEQUENCE: 44

```
cagggacatg aggttctccg ggagatgttg cataaccact ccttcgtggg ctgtgtgaat       60
cctcagtggg ccttggcaca gcatcaaacc aagttatacc                            100
```

<210> SEQ ID NO 45
<211> LENGTH: 100
<212> TYPE: DNA
<213> ORGANISM: Homo sapiens

<400> SEQUENCE: 45

```
aggtgaagaa aggtgtctgt gatcaaagtt ttgggattca tgttgcagag cttgctaatt       60
tccctaagca tgtaatagag tgtgctaaac agaaagccct                            100
```

```
<210> SEQ ID NO 46
<211> LENGTH: 100
<212> TYPE: DNA
<213> ORGANISM: Homo sapiens

<400> SEQUENCE: 46
aggcctgaac agccctgtca aagttgctcg aaagcggaag agaatggtga ctggaaatgg      60
ctctcttaaa aggaaaagct ctaggaagga aacgccctca                          100

<210> SEQ ID NO 47
<211> LENGTH: 100
<212> TYPE: DNA
<213> ORGANISM: Homo sapiens

<400> SEQUENCE: 47
tcaggtttca tttcacaatg cacgcatgga gttggaagga gttcaacaga cagacagttt      60
ttctttatca accggcggcc ttgtgaccca gcaaaggtct                          100

<210> SEQ ID NO 48
<211> LENGTH: 100
<212> TYPE: DNA
<213> ORGANISM: Homo sapiens

<400> SEQUENCE: 48
ggggcaacaa cagtccactt ctcagacaaa caatggcttt gtgactttgg cttcttggtg      60
gacattatgg aacaccttcg agaactcagt gaagaattac                          100

<210> SEQ ID NO 49
<211> LENGTH: 100
<212> TYPE: DNA
<213> ORGANISM: Homo sapiens

<400> SEQUENCE: 49
tgccctcaag caacaattgc tagagtaaca tctttgtata agcaagtaac cccagataga      60
gttgacgttt cagctttggg ctgtcaaaag ggtatgtcat                          100

<210> SEQ ID NO 50
<211> LENGTH: 100
<212> TYPE: DNA
<213> ORGANISM: Homo sapiens

<400> SEQUENCE: 50
gaaaagctgc agaagaaaga tcagcaactg gagcctaaaa aaagtaccag ccctaaaaaa      60
gctgcggagc ccactgtgga tcttttagga cttgatggcc                          100

<210> SEQ ID NO 51
<211> LENGTH: 100
<212> TYPE: DNA
<213> ORGANISM: Homo sapiens

<400> SEQUENCE: 51
ctcttttatg aagctggtac gaagattgat gtcccttggg ctgggcagta catcaccagt      60
aatccctgca tacgcttcgt ctccattgat aataagaagc                          100

<210> SEQ ID NO 52
<211> LENGTH: 100
<212> TYPE: DNA
<213> ORGANISM: Homo sapiens

<400> SEQUENCE: 52
```

```
ctctgcttgt gaattccaga tgccaggcat gggaggcggc ttgtgctttg ccttcacttg    60
gaagccacca ggaacagaag gtctggccac cctggaagga                         100
```

<210> SEQ ID NO 53
<211> LENGTH: 100
<212> TYPE: DNA
<213> ORGANISM: Homo sapiens

<400> SEQUENCE: 53

```
ctaccaccaa acattaacat caaggaacct cgatgggatc aaagcacttt cattggacga    60
gccaatcatt tcttcactgt aactgacccc aggaacattc                         100
```

<210> SEQ ID NO 54
<211> LENGTH: 100
<212> TYPE: DNA
<213> ORGANISM: Homo sapiens

<400> SEQUENCE: 54

```
ttcgctttct gcaacacagc aaccagaaac tcaagcagga gaacctaagt ctgcgcactg    60
ctgtccacaa aagcaaatct ctgaaggatc tggtgtcggc                         100
```

<210> SEQ ID NO 55
<211> LENGTH: 99
<212> TYPE: DNA
<213> ORGANISM: Homo sapiens

<400> SEQUENCE: 55

```
tgctaaagag ctgtcttcca agggagtgaa atctgggat gccaatgatc ccgagacttt     60
ttggacagcc tgggattctc caccagagaa gaaggggac                          99
```

<210> SEQ ID NO 56
<211> LENGTH: 100
<212> TYPE: DNA
<213> ORGANISM: Homo sapiens

<400> SEQUENCE: 56

```
aaaggaaaca cgaagattaa tcaagcagga aggacaagct cagttttgca cccactgaat    60
ttgccacaaa tattgtggaa atattctcg gggacattgc                          100
```

<210> SEQ ID NO 57
<211> LENGTH: 100
<212> TYPE: DNA
<213> ORGANISM: Homo sapiens

<400> SEQUENCE: 57

```
cgtttggtgg agaataccttt gtctctgtgt gttccatcaa tgccatgcac ccaactcggt    60
atattttggc tggaggtaat tccagcggga agatacatgt                         100
```